US012703739B2

(12) United States Patent
Crowe, Jr.

(10) Patent No.: US 12,703,739 B2
(45) Date of Patent: Aug. 11, 2026

(54) HUMAN ANTIBODIES TO RIFT VALLEY FEVER VIRUS

(71) Applicant: Vanderbilt University, Nashville, TN (US)

(72) Inventor: James E. Crowe, Jr., Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 911 days.

(21) Appl. No.: 17/791,997

(22) PCT Filed: Jan. 8, 2021

(86) PCT No.: PCT/US2021/012720

§ 371 (c)(1),
(2) Date: Jul. 11, 2022

(87) PCT Pub. No.: WO2021/142276

PCT Pub. Date: Jul. 15, 2021

(65) Prior Publication Data

US 2023/0063625 A1 Mar. 2, 2023

Related U.S. Application Data

(60) Provisional application No. 62/960,072, filed on Jan. 12, 2020.

(51) Int. Cl.

| | |
|---|---|
| ***C07K 16/00*** | (2006.01) |
| ***A61P 31/14*** | (2006.01) |
| ***C07K 16/10*** | (2006.01) |
| ***G01N 33/569*** | (2006.01) |
| *A61K 39/00* | (2006.01) |

(52) U.S. Cl.

CPC .............. *C07K 16/10* (2013.01); *A61P 31/14* (2018.01); *G01N 33/56983* (2013.01); *A61K 2039/545* (2013.01); *A61K 2039/55* (2013.01); *C07K 2317/52* (2013.01); *C07K 2317/76* (2013.01); *C07K 2317/92* (2013.01); *G01N 2333/175* (2013.01); *G01N 2469/10* (2013.01)

(58) Field of Classification Search

CPC ................ C07K 16/10; C07K 2317/52; C07K 2317/76; A61P 31/14; G01N 2333/175; G01N 2469/10; A61K 2039/505; Y02A 50/30

See application file for complete search history.

(56) References Cited

U.S. PATENT DOCUMENTS

| | | | |
|---|---|---|---|
| 2009/0203538 A1 | 8/2009 | Sugioka et al. |
| 2017/0081409 A1 | 3/2017 | Gijk et al. |

FOREIGN PATENT DOCUMENTS

| | | |
|---|---|---|
| CN | 109734800 A | 5/2019 |

OTHER PUBLICATIONS

Allen, Elizabeth R., et al. "A protective monoclonal antibody targets a site of vulnerability on the surface of Rift Valley fever virus." *Cell Reports* 25.13 (2018): 3750-3758.
Extended European Search Report issued in European Application No. 21738978.2, mailed Apr. 15, 2024.
Machine translation of CN 109734800 A, dated Jan. 19, 2024.
Partial European Search Report issued in European Application No. 21738978.2, mailed Jan. 25, 2024.
Wang, Qihui, et al. "Neutralization mechanism of human monoclonal antibodies against Rift Valley fever virus." *Nature Microbiology* 4.7 (2019): 1231-1241.
Faburay, B. et al., "Evaluation of an Indirect ELISA Based on Recombinant Baculovirus-Expressed Rift Valley Fever Virus Nucleoprotein as the Diagnostic Antigen," *J. Clin. Microbiol.*, (2019): 1-38.
Gutjahr, B. et al., "Generation and characterization of antibodies against Rift Valley fever phlebovirus and evaluation of their therapeutic efficacy in a mouse model," *Doctoral Dissertation at University of Veterinary Medicine Hannover*, (2019): 1-115.
PCT International Search Report and Written Opinion issued in International Patent Application No. PCT/US2021/012720, mailed May 20, 2021.
PCT International Preliminary Report on Patentability issued in International Patent Application No. PCT/US2021/012720, mailed Jul. 21, 2022.
Chapman, Nathaniel S., et al. "Multifunctional human monoclonal antibody combination mediates protection against Rift Valley fever virus at low doses." *Nature Communications* 14.1 (Sep. 2023): 5650.
Chapman, Nathaniel S., et al. "Potent neutralization of Rift Valley fever virus by human monoclonal antibodies through fusion inhibition." *Proceedings of the National Academy of Sciences* 118.14 (Apr. 2021): e2025642118.
Connors, Kaleigh A., et al. "Potent neutralizing human monoclonal antibodies protect from Rift Valley fever encephalitis." *JCI insight* 9.18 (Aug. 2024): e180151.
McMillen, Cynthia M., et al. "A highly potent human neutralizing antibody prevents vertical transmission of Rift Valley fever virus in a rat model." *Nature Communications* 14.1 (Jul. 2023): 4507.

*Primary Examiner* — Jeanette M Lieb

(74) *Attorney, Agent, or Firm* — pH IP Law

(57) ABSTRACT

The present disclosure is directed to antibodies binding to and neutralizing Rift Valley Fever Virus and methods for use thereof.

11 Claims, 12 Drawing Sheets

Specification includes a Sequence Listing.

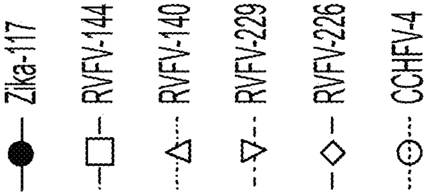
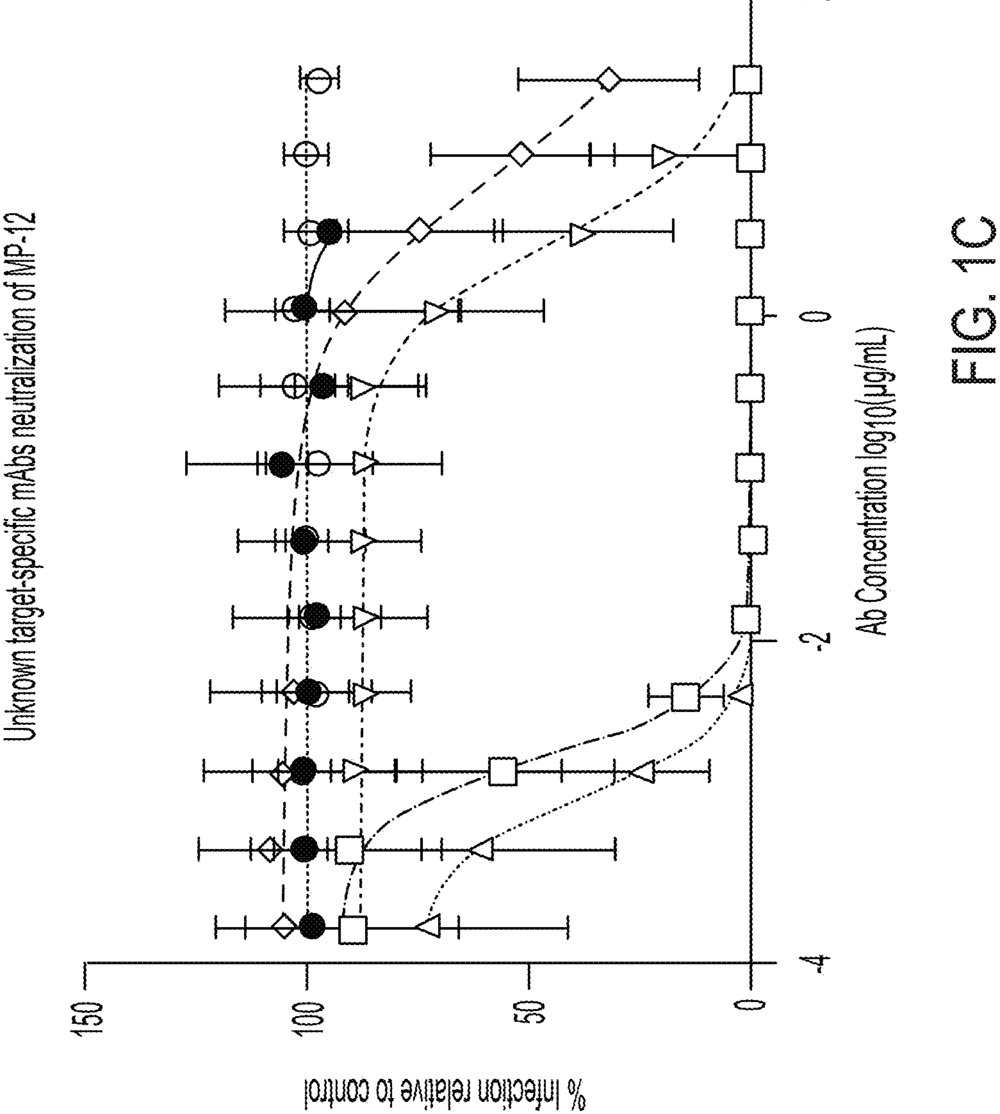
FIG. 1C

Second Antibody (Labeled)

First Antibody (Unlabeled)

| mAb | RVFV-142 | RVFV-379 | RVFV-368 | RVFV-296 | RVFV-381 | RVFV-226 |
|---|---|---|---|---|---|---|
| RVFV-142 | 13 | 11 | 13 | 16 | 153 | 157 |
| RVFV-379 | 88 | 0 | 3 | 9 | 97 | 86 |
| RVFV-368 | 104 | 42 | 7 | 38 | 95 | 113 |
| RVFV-296 | 99 | 79 | 77 | 5 | 93 | 105 |
| RVFV-381 | 135 | 75 | 83 | 6 | 18 | 112 |
| RVFV-226 | 134 | 87 | 129 | 80 | 76 | 31 |

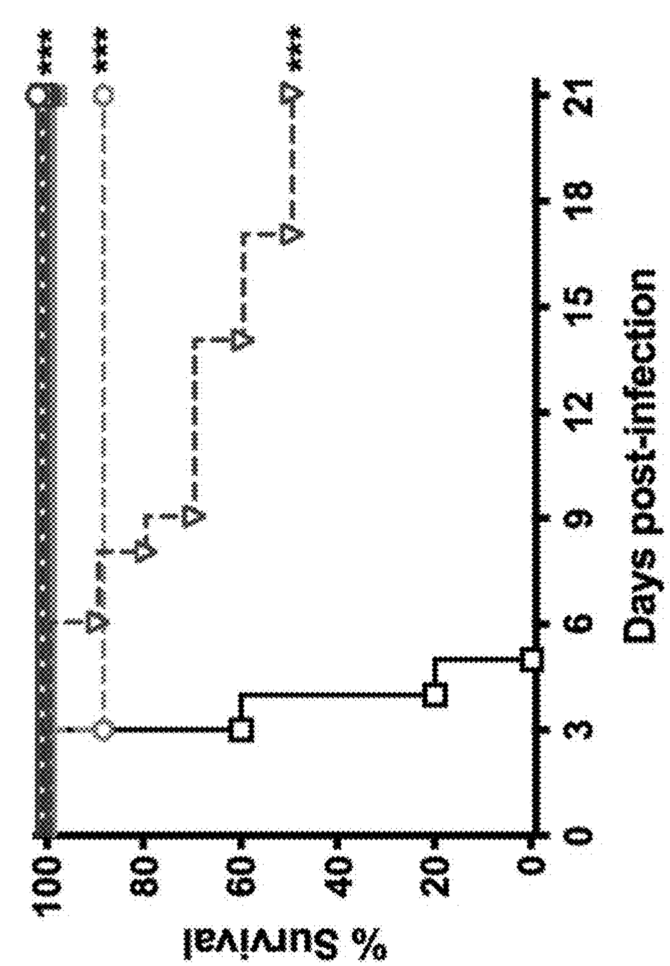
FIG. 5A

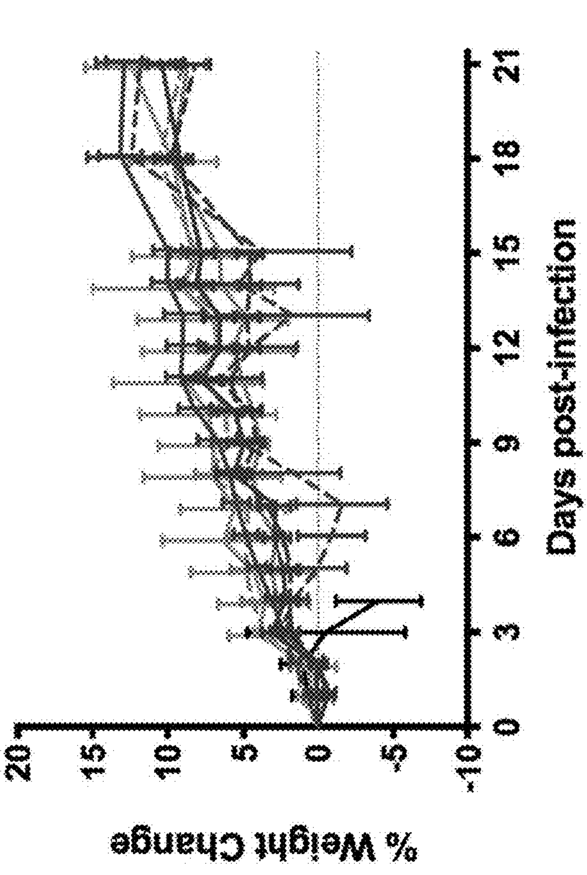
FIG. 5B

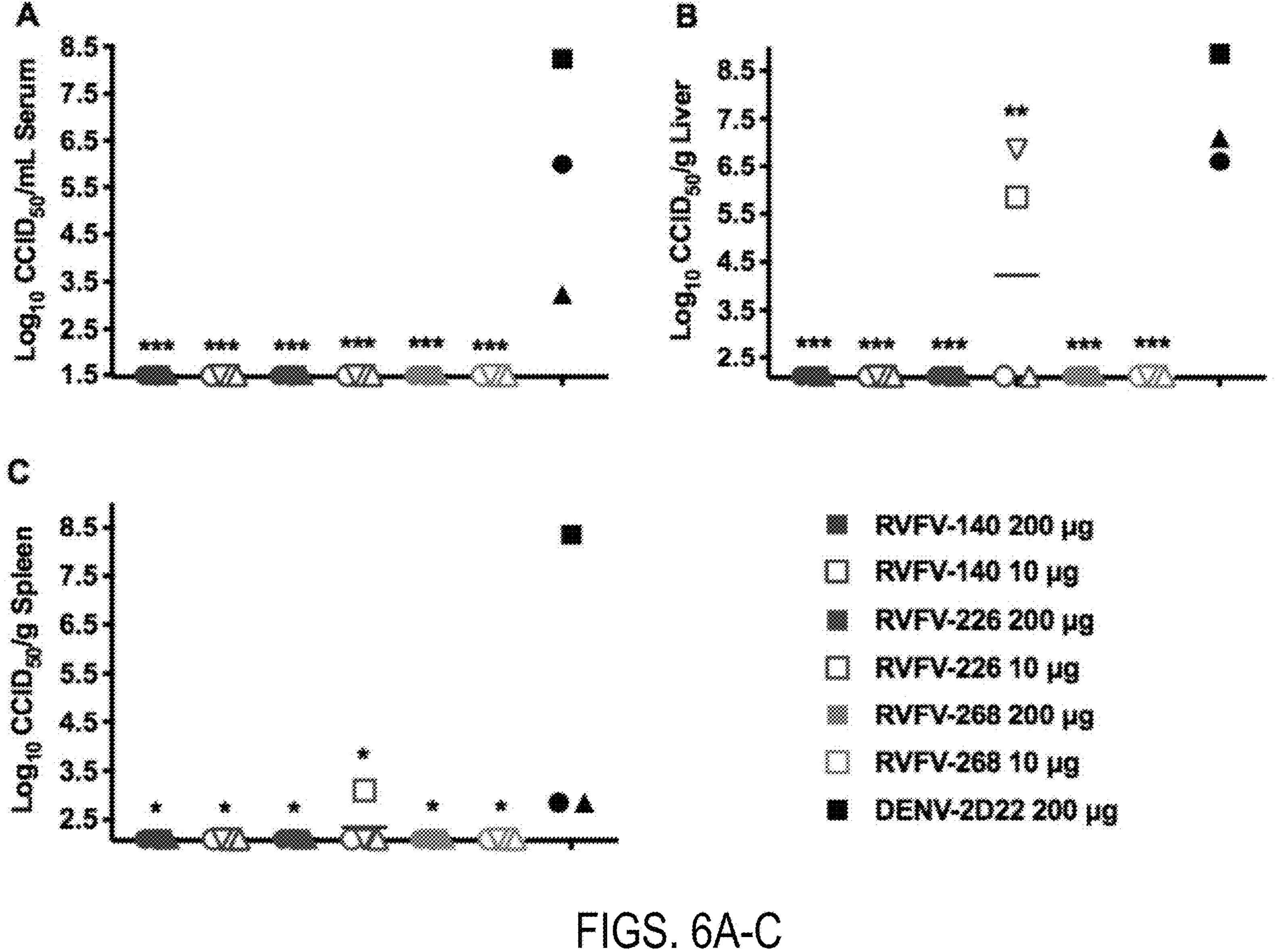
FIGS. 6A-C

SEQUENCE LISTING

<160> NUMBER OF SEQ ID NOS: 825

<210> SEQ ID NO 1
<211> LENGTH: 348
<212> TYPE: DNA
<213> ORGANISM: Artificial sequence
<220> FEATURE:
<223> OTHER INFORMATION: Synthetic antibody

<400> SEQUENCE: 1
cagatgcagc tgcaggagtc gggcccagga ctggtgaagc cttcggggac cctgtccctc 60
acctgcgctg tctctggtga ctccatcagc actagtacct ggtggagttg ggtccgccag 120
tccccaggga aggggctgga gtggattggg gaaatctatc atagtgagag caccaactac 180
aacccgtccc tcaagagtcg agtcagctta tcactagaca agtccaaaaa ccagttgtcc 240
ctgaggctga gctctgtgac cgccgcggac acgggcgtgt attactgtgc gagaggaagc 300
ttagtctttg actactgggg ccagggagcc caggtcgtcg tctcctca 348

<210> SEQ ID NO 2
<211> LENGTH: 321
<212> TYPE: DNA
<213> ORGANISM: Artificial sequence
<220> FEATURE:
<223> OTHER INFORMATION: Synthetic antibody

<400> SEQUENCE: 2
gaaatagtga tgacgcagtc tccagccacc ctgtctgtgt ctccagggga aagagccacc 60
ctctcctgta gggccagtca gagtgttagc agtaatttag cctggtacca gcagaaacct 120
ggccaggctc ccaggctcct catctatgct gcatccacca gggccactgg tatcccagcc 180
aggttcagtg gcagtgggtc tgggacagag ttcactctca ccatcagcag cctgcagtct 240
gaagattttg cagtttatta ctgtcagcag tttaataact ggcctaggac gttcggccaa 300
gggaccaagg tggaaatcaa a 321

<210> SEQ ID NO 3
<211> LENGTH: 366
<212> TYPE: DNA
<213> ORGANISM: Artificial sequence
<220> FEATURE:
<223> OTHER INFORMATION: Synthetic antibody

<400> SEQUENCE: 3
caggtgcagc tgcaggagtc gggcccagga ctggtgaagc cttcggagac cctgtccctc 60
acctgcactg tctctggtga ctccgtcaga aattactact ggagctggat ccggcagccc 120
ccaggggagg gactggagtg gattgggtat atctattaca gtgggagcac cgacttcaac 180
ccctccctca agagtcgagt caccatgtca gtggacacgt ccaagaacca cttctccctg 240
aagctgaggt ctgtgaccgc tgcggacacg gccatgtatt actgtgcgag agtcgctata 300
cgtacagatg gctacatacg ggcttttgat atctggggcg cagggacaat ggtcaccgtc 360
tcttca 366

<210> SEQ ID NO 4
<211> LENGTH: 321
<212> TYPE: DNA
<213> ORGANISM: Artificial sequence
<220> FEATURE:
<223> OTHER INFORMATION: Synthetic antibody

<400> SEQUENCE: 4

```
gacatccaga tgacccagtc tccatcctcc ccgtctgcat ctgtaggaga cagagtcacc     60

gtcacttgcc gggcaagtca gagcattagg aactacttaa attggtatca gcagaaacca    120

gggaaagccc ctaagctcct gatatatgct gcatccagtt tacaaagtgg ggtcccatca    180

aggttcagtg gcagtggatc tgggacagaa ttcactctca ccatcagcag tctgcaacct    240

gaagattttg caacgtacta ctgtcaacag acgtacagta ccgcgtggac gttcggccaa    300

gggaccaagg tggaaatcaa a                                              321
```

<210> SEQ ID NO 5
<211> LENGTH: 369
<212> TYPE: DNA
<213> ORGANISM: Artificial sequence
<220> FEATURE:
<223> OTHER INFORMATION: Synthetic antibody

<400> SEQUENCE: 5

```
caggtgcagc tgcaggagtc gggcccagga ctggtgaagc cttcacagac cctgtccctc     60

acctgcactg tctctggtgg ctccatcagc agtggtgatt acttctggag ttggatccgc    120

cagcccccag ggaagggcct ggagtggatt gggtacatct attacagtgg gagcacctac    180

tacaacccgt ccctcaagag tcgaattacc atatcagtag acacgtccaa gaaccagttt    240

tccctgaagc tgagctctgt gactgccgca gacacggccg tgttttactg tgccagagtc    300

cagactccgg ggagtgatac ttactacttt gactactggg gccagggaac cctggtcacc    360

gtctcctca                                                            369
```

<210> SEQ ID NO 6
<211> LENGTH: 324
<212> TYPE: DNA
<213> ORGANISM: Artificial sequence
<220> FEATURE:
<223> OTHER INFORMATION: Synthetic antibody

<400> SEQUENCE: 6

```
gacatccaga tgacccagtc tccatcctcc ctgtctgctt ctgtaggaga cagagtcacc     60

atcacttgcc gggcaagtca gagcattagc agctatttaa attggtatca gcagaaacca    120

gggaaagccc ctaagctcct gatctatgct gcatccagtt tgcaaagtgg ggtcccatca    180

aggttcagtg gcagtggatc tgggacagat ttcactctca ccatcagcag tctgcaacct    240

gaagattttg caacttactt ctgtcaacag agttacagta cccctatgta cacttttggc    300

caggggacca agctggagat caaa                                           324
```

<210> SEQ ID NO 7
<211> LENGTH: 369
<212> TYPE: DNA
<213> ORGANISM: Artificial sequence
<220> FEATURE:
<223> OTHER INFORMATION: Synthetic antibody

<400> SEQUENCE: 7

```
cagctgcagc tgcaggagtc gggcccagga ctggtgaagc catcggagac cctgtccctc     60

acctgcactg tctctggtgg ctccatcagc agtagtagtt accactgggg ctggatccgc    120

cagcccccag ggaaggggct ggagtggatt ggcagtattt attatactgg gagcacctac    180

tacaacccgt ccctcaagag tcgagtcatc atatccgtag acgcgtccaa gaaccagttc    240

tccctgaagc tgagctctgt gaccgccgca gacacggctg tctattactg tgcgagacgg    300
```

```
tcgcttagga gtggctgggc cgccgctatt gacttctggg gccagggaac cctggtcacc    360

gtctcctca                                                            369


<210> SEQ ID NO 8
<211> LENGTH: 324
<212> TYPE: DNA
<213> ORGANISM: Artificial sequence
<220> FEATURE:
<223> OTHER INFORMATION: Synthetic antibody

<400> SEQUENCE: 8

gacatccaga tgacccagtc tccatcctcc ctgtctgctt ctgtaggaga cagagtcacc     60

atcacttgcc gggcaagtca gagcattagc agctatttaa attggtatca gcagaaacca    120

gggaaagccc ctaagctcct gatctatgct gcatccagtt tgcaaagtgg ggtcccatca    180

aggttcagtg gcagtggatc tgggacagat ttcactctca ccatcagcag tctgcaacct    240

gaagattttg caacttactt ctgtcaacag agttacagta cccctatgta cacttttggc    300

caggggacca agctggagat caaa                                           324


<210> SEQ ID NO 9
<211> LENGTH: 378
<212> TYPE: DNA
<213> ORGANISM: Artificial sequence
<220> FEATURE:
<223> OTHER INFORMATION: Synthetic antibody

<400> SEQUENCE: 9

caggtgcagc tgcaggagtc gggcccagga ctggtgaagc cttcggagac cctgtccctc     60

acctgcactg tctctggtgg ctccgtcagc agtggtagtt actactggag ctggatccgg    120

cagcccccag ggaagggact ggagtggatt gggtatatct attacagtgg gagcaccaac    180

tacaacccct ccctcaagag tcgagtcacc atatcagtag acacgtccaa gaaccagttc    240

tccctgaagc tgagctctgt gaccgctgcg gacacggccg tgtattactg tgcgagagat    300

tatcgcgtga ctacggggaa ctactactac tacggtatgg acgtctgggg ccaagggacc    360

acggtcaccg tctcctca                                                  378


<210> SEQ ID NO 10
<211> LENGTH: 330
<212> TYPE: DNA
<213> ORGANISM: Artificial sequence
<220> FEATURE:
<223> OTHER INFORMATION: Synthetic antibody

<400> SEQUENCE: 10

cagtctgtgc tgactcagcc accctcagcg tctgggaccc ccgggcagag ggtcaccatc     60

tcttgttctg gaagcagctc caacatcgga agtaatactg taaactggta ccagcagctc    120

ccaggaacgg cccccaaact cctcatctat agtaataatc agcggccctc aggggtccct    180

gaccgattct ctggctccaa gtctggcacc tcagcctccc tggccatcag tgggctccag    240

tctgaggatg aggctgatta ttactgtgca gcatgggatg acagcctgaa tggttgggtg    300

ttcggcggag ggaccaagct gaccgtccta                                     330


<210> SEQ ID NO 11
<211> LENGTH: 381
<212> TYPE: DNA
<213> ORGANISM: Artificial sequence
<220> FEATURE:
<223> OTHER INFORMATION: Synthetic antibody
```

<400> SEQUENCE: 11

```
tcaacgcaga gtacatgggc gggcccagga ctggtgaagc cttcacagac cctgtccctc     60
acctgcactg tctctggtgg ctccgtcagc agtggtgatt actactggag ttggatccgc    120
cagcccccag ggaggggcct ggagtggatt gggtacatct cttacagtgg gagcacctat    180
tacaacccgt ccctcgagag tcgaattacc atgtcaggcg acacgtccaa gcagcagttc    240
tccctgaagc tgagctctgt gactgtcgcg gacacggccg tctattactg tgccaccaat    300
tacttccatt tacatgactt cggtgacctc tactggtact tcgatctctg gggccgtggc    360
accctggtca ctgtctcctc a                                               381
```

<210> SEQ ID NO 12
<211> LENGTH: 330
<212> TYPE: DNA
<213> ORGANISM: Artificial sequence
<220> FEATURE:
<223> OTHER INFORMATION: Synthetic antibody

<400> SEQUENCE: 12

```
cagtctgccc tgactcagcc tgcctccgtg tctgggtctc ctggacagtc gatcaccatc     60
tcctgcactg gaaccagcag tgacattggt gcttataact ttgtctcctg gtaccaacaa    120
cacccaggca cagcccccaa actcctgatt tatgatgtca ctaatcggcc ctcaggggtt    180
tctaatcgct tctctggctc caagtctggc aacacggcct ccctgaccat ctctgggctc    240
caggctgagg acgaggctaa ttattactgc aactcatata caagcagcag tcatgtggtc    300
ttcggcggcg ggaccaagct gaccgtccta                                      330
```

<210> SEQ ID NO 13
<211> LENGTH: 369
<212> TYPE: DNA
<213> ORGANISM: Artificial sequence
<220> FEATURE:
<223> OTHER INFORMATION: Synthetic antibody

<400> SEQUENCE: 13

```
cagttgcagc tgcaggagtc gggcccagga ctggcgaggc cttcggagac cccgtccctc     60
acctgcactg tctctggtgg ctccatcagt agtagtgttt actattgggg ctggatccgc    120
cagcccccag ggaaggggct ggagtggatt gggagtatct attatagtgg gtacaccaac    180
tacaacccgt ccctcaagag tcgagtctcc atatctgtag acacgtccaa gaaccagttc    240
tccctgcaac tgaactctgt gaccgccgca gacacggctg tttattactg tgcgagacat    300
tcggattgtg gtaatgattg ctattacttt gactactggg gccagggaac cctggtcacc    360
gtctcctca                                                             369
```

<210> SEQ ID NO 14
<211> LENGTH: 321
<212> TYPE: DNA
<213> ORGANISM: Artificial sequence
<220> FEATURE:
<223> OTHER INFORMATION: Synthetic antibody

<400> SEQUENCE: 14

```
tcctatgagc tgactcagcc accctcagtg tccgtgtccc caggacagac agccagcatc     60
acctgctctg gagatagatt gggggataaa tatgcttcct ggtatcagca gaagccaggc    120
cagtcccctg tgctggtcat ctatcaagat tacaagcggc cctcagggat ccctgagcga    180
```

```
ttctctggct ccaactctgg gcacacagcc actctgacca tcagcgggac ccaggctatg    240

gatgaggctg actatttctg tcaggcgtgg gacagcagtg atggttctgt cttcggaact    300

gggaccaagg tcaccgtcct g                                              321
```

<210> SEQ ID NO 15
<211> LENGTH: 381
<212> TYPE: DNA
<213> ORGANISM: Artificial sequence
<220> FEATURE:
<223> OTHER INFORMATION: Synthetic antibody

<400> SEQUENCE: 15

```
caggtgcagc tgcaggagtc gggcccagga ctggtgaagc cttcacagac cctgtccctc     60

acctgcactg tctctggtgg ctccgtcagc agtggtgatt actactggag ttggatccgc    120

cagcccccag ggaggggcct ggagtggatt gggtacatct cttacagtgg gagcacctat    180

tacaacccgt ccctcgagag tcgaattacc atgtcaggcg acacgtccaa gcagcagttc    240

tccctgaagc tgagctctgt gactgtcgcg gacacggccg tctattactg tgccaccaat    300

tacttccatt tacatgactt cggtgacctc tactggtact tcgatctctg gggccgtggc    360

accctggtca ctgtctcctc a                                              381
```

<210> SEQ ID NO 16
<211> LENGTH: 330
<212> TYPE: DNA
<213> ORGANISM: Artificial sequence
<220> FEATURE:
<223> OTHER INFORMATION: Synthetic antibody

<400> SEQUENCE: 16

```
cagtctgccc tgactcagcc tgcctccgtg tctgggtctc ctggacagtc gatcaccatc     60

tcctgcactg gaaccagcag tgacattggt gcttataact ttgtctcctg gtaccaacaa    120

cacccaggca cagcccccaa actcctgatt tatgatgtca ctaatcggcc ctcaggggtt    180

tctaatcgct tctctggctc caagtctggc aacacggcct ccctgaccat ctctgggctc    240

caggctgagg acgaggctaa ttattactgc aactcatata caagcagcag tcatgtggtc    300

ttcggcggcg ggaccaagct gaccgtccta                                     330
```

<210> SEQ ID NO 17
<211> LENGTH: 357
<212> TYPE: DNA
<213> ORGANISM: Artificial sequence
<220> FEATURE:
<223> OTHER INFORMATION: Synthetic antibody

<400> SEQUENCE: 17

```
gaggtgcagc tggtggagtc tgggggaggc ttggtccagc ctggggggtc cctgagactc     60

tcctgtgcag cctctggatt catgtttagt cggtattgga tgagctgggt ccgccaggct    120

ccagggaagg ggctggagtg ggtggccaac ataaagcaag atggaagtga gaaaaactat    180

gtggactctg tgaagggccg attcaccatc tccagagaca acgccaagaa ctcactgtat    240

ctgcaaatga acaccctgag agccgaggac acggctgtgt attactgtgc gagaggagaa    300

tactatggtt cagggagtta ttcctggggc caggggaccc tggtcaccgt ctcctca       357
```

<210> SEQ ID NO 18
<211> LENGTH: 321
<212> TYPE: DNA
<213> ORGANISM: Artificial sequence
<220> FEATURE:
<223> OTHER INFORMATION: Synthetic antibody

<400> SEQUENCE: 18

```
gacatccaga tgacccagtc tccttccacc ctgtctgcat ctgtaggaga cagagtcacc      60

atcacttgcc gggccagtca gagtattagt agctggttgg cctggtatca gcagaaacca     120

gggaaagccc ctaagctcct gatctataag gcgtctagtt tagaaagtgg ggtcccatca     180

aggttcagcg gcagtggatc tgggacagaa ttcactctca ccatcagcag cctgcagcct     240

gatgattttg caacttatta ctgccaacag tataatagtt acccgctcac tttcggcgga     300

gggaccaagg tggagatcaa a                                               321
```

<210> SEQ ID NO 19
<211> LENGTH: 369
<212> TYPE: DNA
<213> ORGANISM: Artificial sequence
<220> FEATURE:
<223> OTHER INFORMATION: Synthetic antibody

<400> SEQUENCE: 19

```
cagttgcagc tgcaggagtc gggcccagga ctggcgaggc cttcggagac cccgtccctc      60

acctgcactg tctctggtgg ctccatcagt agtagtgttt actattgggg ctggatccgc     120

cagcccccag ggaaggggct ggagtggatt gggagtatct attatagtgg gtacaccaac     180

tacaacccgt ccctcaagag tcgagtctcc atatctgtag acacgtccaa gaaccagttc     240

tccctgcaac tgaactctgt gaccgccgca gacacggctg tttattactg tgcgagacat     300

tcggattgtg gtaatgattg ctattacttt gactactggg gccagggaac cctggtcacc     360

gtctcctca                                                             369
```

<210> SEQ ID NO 20
<211> LENGTH: 321
<212> TYPE: DNA
<213> ORGANISM: Artificial sequence
<220> FEATURE:
<223> OTHER INFORMATION: Synthetic antibody

<400> SEQUENCE: 20

```
tcctatgagc tgactcagcc accctcagtg tccgtgtccc caggacagac agccagcatc      60

acctgctctg gagatagatt gggggataaa tatgcttcct ggtatcagca gaagccaggc     120

cagtcccctg tgctggtcat ctatcaagat tacaagcggc cctcagggat ccctgagcga     180

ttctctggct ccaactctgg gcacacagcc actctgacca tcagcgggac ccaggctatg     240

gatgaggctg actatttctg tcaggcgtgg gacagcagtg atggttctgt cttcggaact     300

gggaccaagg tcaccgtcct g                                               321
```

<210> SEQ ID NO 21
<211> LENGTH: 363
<212> TYPE: DNA
<213> ORGANISM: Artificial sequence
<220> FEATURE:
<223> OTHER INFORMATION: Synthetic antibody

<400> SEQUENCE: 21

```
caggtgcacc tgcaggagtc gggcccagga ctggtgaagc cttcggagac cctgtccctc      60

acctgcactg tctctggtgg ctccatcggc acttactact ggagctggat ccggcagccc     120

ccagggaagg gactggagtg gattgggtat gtctatcaca gtggggccac caacgacaac     180
```

```
ccctccctca tgagtcgact caccatgtca gtagacacgt ccaagaacca gttctccctg    240

gacctgaggt ctgtgaccgc tgcggacacg gccatatatt actgtgcgag agaaggctcc    300

aatggtgact tccgagggca ttttgactcc tggggccagg gaaccctggt caccgtctcc    360

tca                                                                  363
```

<210> SEQ ID NO 22
<211> LENGTH: 330
<212> TYPE: DNA
<213> ORGANISM: Artificial sequence
<220> FEATURE:
<223> OTHER INFORMATION: Synthetic antibody

<400> SEQUENCE: 22

```
cagtctgccc tgactcagcc tgcctccgtg tctgggtctc ctggacagtc gatcaccatc     60

tcctgcactg gaaccagcag tgacgttggt ggctttaact ttgtctcctg gtaccaacaa    120

cacccaggca aagcccccaa actcatgatt tatgatgtca gtaaccggcc ctcaggggtt    180

tctaatcgct tctctggctc caagtctggc aacacggcct ccctgaccat ctctgggctc    240

cggactgacg acgagggtga ttattactgc acttcataca caagcagcag cactgttgtg    300

ttcggcggag ggaccaagct gaccgtccta                                     330
```

<210> SEQ ID NO 23
<211> LENGTH: 387
<212> TYPE: DNA
<213> ORGANISM: Artificial sequence
<220> FEATURE:
<223> OTHER INFORMATION: Synthetic antibody

<400> SEQUENCE: 23

```
caggtgcagc tacaacagtg gggcgcagga ctgttgaagc cttcggagac cctgtccctc     60

acctgcgctg tctatggtgg gtccttcagt ggttactact ggagttggat ccgccagccc    120

ccagggaagg ggctggagtg gattggggaa atcaatcata gtggaagaac caagtacaat    180

ccgtccctct cgagtgggct caccttgtcg gtggacaagt ccaagaacca gttctccctg    240

aaactgaggt ctgtgaccgc cgcggacacg gctgtgtatt actgtgcgag aggacatgtc    300

gttgtgacac ctgctactct ctttcaccgg gtcggcgaac actactttga cttctggggc    360

cagggaaccc tggtctccgt ctcctca                                        387
```

<210> SEQ ID NO 24
<211> LENGTH: 324
<212> TYPE: DNA
<213> ORGANISM: Artificial sequence
<220> FEATURE:
<223> OTHER INFORMATION: Synthetic antibody

<400> SEQUENCE: 24

```
tcttctgagc tgactcagga ccctgctgtg tctgtggcct tgggacagac agtcaggatc     60

acatgccaag gagacagcct caaaaactat tatgcaagct ggtaccagca gaagccaggt    120

cgggcccctt tacttgtcat gtctggtaaa aacaaccggc cctcagggat cccagatcga    180

ttctctggct ccagctcagg aaacacagct tccttgacca tcactggggc tcaggcggag    240

gatgaggctg actattactg tagctcccgg gacagaagtg ataagtattg ggttttcggc    300

ggagggacca aggtgaccgt ccta                                           324
```

<210> SEQ ID NO 25
<211> LENGTH: 390

<212> TYPE: DNA
<213> ORGANISM: Artificial sequence
<220> FEATURE:
<223> OTHER INFORMATION: Synthetic antibody

<400> SEQUENCE: 25
caggtccaac ttgtgcagtc tggggctgag gtgaagaggc ctggggcctc agtgaaggtt 60
tcctgcaagg cttctggata caccttcact acctatgcaa tacactgggt gcgccaggcc 120
cccggacaaa ggcttgagtg gatgggatgg atcaacgctg gcaacggaga cacaaaatac 180
tcacagaggt tccagggcag agtcaccgtc accagggaca catccgcgaa cacagcctac 240
atggaactga ccagcctgac atccgaagac acggctgtgt attactgtgc gagaggttgg 300
gtgggttgta ttggtaaaag gggtaaaacc tgttacgcga atttaccaga tgactactgg 360
ggccagggaa ccctggtcac cgtctcctca 390

<210> SEQ ID NO 26
<211> LENGTH: 327
<212> TYPE: DNA
<213> ORGANISM: Artificial sequence
<220> FEATURE:
<223> OTHER INFORMATION: Synthetic antibody

<400> SEQUENCE: 26
cagtctgccc tgactcagcc tgcctccgtg tctgggtctc gtggacagtc gatcaccatc 60
acctgcactg gaaccagcag tgacgttggt gcttacaagt ttgtctcctg gtaccaacaa 120
cacccaggca aagcccccaa tctcattatt tatgatgtca atagtcggcc ctcaggggtt 180
tctgatcgct tctctggctc caagtctggc tacacggcct ccctgaccat ctctgggctc 240
caggctgagg acgaggctga ttattactgc agctcatata caaggggccc ttatatcttc 300
ggaactggga ccaaggtcac cgtccta 327

<210> SEQ ID NO 27
<211> LENGTH: 375
<212> TYPE: DNA
<213> ORGANISM: Artificial sequence
<220> FEATURE:
<223> OTHER INFORMATION: Synthetic antibody

<400> SEQUENCE: 27
caggtgaagc tggtggagtc tgggggaggc gtggtccagc ctgggaggtc cctgagactc 60
tcctgtgaag cctctagatt caccttcaat acctacggca tgcactgggt ccgccaggct 120
ccaggcaagg ggctggagtg ggtggcagtt atatcatatg atggaaagaa gaaatactat 180
gcagactccg cgaagggccg attcaccatc tccagagacg actccaggaa cacactgtat 240
ctggagatga acagcctgcg agttgaggac acggctgtgt attattgtgc gagagattta 300
aggagatttt atagcaatgg ctggttcacg gggtcggact tttggggcca gggaaccctg 360
gtcaccgtct cctca 375

<210> SEQ ID NO 28
<211> LENGTH: 324
<212> TYPE: DNA
<213> ORGANISM: Artificial sequence
<220> FEATURE:
<223> OTHER INFORMATION: Synthetic antibody

<400> SEQUENCE: 28
gaaattgtgt tgacgcagtc tccagccacc ctgtctttgt ctccagggga gagagccacc 60

```
ctctcctgcg gggccagtca aactattagc agcaacaact tagcctggta tcagcagaaa    120

cctggcctgg cgcccaggct cctcatctat gatgcttcca ccagggccgc tggcatccca    180

cgcagattca gtggcagtgg gtctgggaca aacttcactc tcaccgtcac cagactggac    240

cctgaagatt ttgcactgta ttcctgtcag cagtatggtc gctcaccgat caccttcggc    300

caagggacac gactggagat taaa                                           324
```

```
<210> SEQ ID NO 29
<211> LENGTH: 363
<212> TYPE: DNA
<213> ORGANISM: Artificial sequence
<220> FEATURE:
<223> OTHER INFORMATION: Synthetic antibody

<400> SEQUENCE: 29

caggtggagc tgcgggagtc gggcccagga ctggtgaagc cttcggggac cctgtccctc     60

acctgcgctg tctctggtgt gtccatcacc agtagtaact ggtggaattg ggtccgccag    120

tccccaggga aggggctgga gtggattggg caagtctatc atagtgggag caccaagtac    180

aacccatccc tcaggagtcg actcaccata tcagtggaca agtccaagaa ccagttctcc    240

ctgaagatga aatatgtgcg cgccgcggac acggccgtat acttctgtgc gagagacgga    300

tttagtggtt acgatgttgc acttgacaag tggggccagg gaaccctggt caccgtctct    360

tca                                                                  363
```

```
<210> SEQ ID NO 30
<211> LENGTH: 336
<212> TYPE: DNA
<213> ORGANISM: Artificial sequence
<220> FEATURE:
<223> OTHER INFORMATION: Synthetic antibody

<400> SEQUENCE: 30

cagtctgtgt tgacgcagcc gccctcagtg tctgcggccc caggacagag ggtcaccatc     60

tcctgctctg gaagcagctc caacattggg aatagttatg tatcctggta ccagcacctc    120

ccgggaacag cccccaaact cctcatttat gacaataata agcgaccctc agggattcct    180

gaccgattct ctgcctccaa gtctggcacg tcagccaccc tgggcatcac cggactccgg    240

actggggacg aggccgatta ttactgcgca acatgggaga gccgcctgag tgctggccat    300

gtggtcttcg gcggagggac caagctgacc gtcctc                              336
```

```
<210> SEQ ID NO 31
<211> LENGTH: 387
<212> TYPE: DNA
<213> ORGANISM: Artificial sequence
<220> FEATURE:
<223> OTHER INFORMATION: Synthetic antibody

<400> SEQUENCE: 31

cagatcacct tgcaggagtc tggtcctacg ctggtgaaac ccacacggac cctcacgctg     60

acctgcaccc tctctggggt ctcactcagt agtagtggag tgggtgtggg ctggatccgc    120

cagcccccg gaagggccct ggagtggctt gcagtcatct attgggatga tgataagcac    180

tacaggccat ctctgaagag caggctcacc atcaccaagg acacctccaa aaaccaggtg    240

gtccttacaa tgaccaacat ggaccctgtg gacacagcca catattactg tgcacaccga    300

aatattgtgg tagtacgagc tgatccgcac cgttgggcgg ggacctttga ctactggggc    360

cagggagccc tggtcaccgt ctcggca                                        387
```

<210> SEQ ID NO 32
<211> LENGTH: 324
<212> TYPE: DNA
<213> ORGANISM: Artificial sequence
<220> FEATURE:
<223> OTHER INFORMATION: Synthetic antibody

<400> SEQUENCE: 32

```
gaaattgtgt tgacgcagtc tccaggcacc ctgtctttgt ctccagggga aagagccacc     60

ctctcctgca gggccagtca gagtgttacc agcaactact tagcctggta ccagcagaag    120

cctggccagg ctcccagact cctcatctat ggtgcatcca gcagggccgc tggcatccca    180

gacaggttca gtggcagtgg gtctgggaca gacttcactc tcaccatcag caggctggag    240

cctgaagatc ttggagtgta ttcctgtcag cagtacgctg gttcaccgtt cactttcggc    300

cctgggacca aagtggaaat caaa                                           324
```

<210> SEQ ID NO 33
<211> LENGTH: 381
<212> TYPE: DNA
<213> ORGANISM: Artificial sequence
<220> FEATURE:
<223> OTHER INFORMATION: Synthetic antibody

<400> SEQUENCE: 33

```
gaggtgcagc tgttggagtc tgggggaggc ttggtacagc ctggggggtc cctgagactc     60

tcctgtgcag cctctggatt cacctttagc agctatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcaaatga acagcctgag agccgaggac acggccgtat attactgtgc gaaagatcaa    300

ggaactatga tagtagtggt tacactcccc cctggtgctt ttgatatctg gggccaaggg    360

acaatggtca ccgtctcttc a                                              381
```

<210> SEQ ID NO 34
<211> LENGTH: 357
<212> TYPE: DNA
<213> ORGANISM: Artificial sequence
<220> FEATURE:
<223> OTHER INFORMATION: Synthetic antibody

<400> SEQUENCE: 34

```
gaggtgcagc tggtggagtc tgggggaggc ttggtccagc ctggggggtc cctgagactc     60

tcctgtgcag cctctggatt catgtttagt cggtattgga tgagctgggt ccgccaggct    120

ccagggaagg ggctggagtg ggtggccaac ataaagcaag atggaagtga gaaaaactat    180

gtggactctg tgaagggccg attcaccatc tccagagaca acgccaagaa ctcactgtat    240

ctgcaaatga acaccctgag agccgaggac acggctgtgt attactgtgc gagaggagaa    300

tactatggtt cagggagtta ttcctggggc caggggaccc tggtcaccgt ctcctca       357
```

<210> SEQ ID NO 35
<211> LENGTH: 336
<212> TYPE: DNA
<213> ORGANISM: Artificial sequence
<220> FEATURE:
<223> OTHER INFORMATION: Synthetic antibody

<400> SEQUENCE: 35

```
gatattgtga tgactcagtc tccactctcc ctgcccgtca cccctggaga gccggcctcc     60

atctcctgca ggtctagtca gagcctcctg catagtaatg gatacaacta tttggattgg    120

tacctgcaga agccagggca gtctccacag ctcctgatct atttgggttc taatcgggcc    180

tccggggtcc ctgacaggtt cagtggcagt ggatcaggca cagattttac actgaaaatc    240

agcagagtgg aggctgagga tgttggagtt tattactgcg tgcaagctct acaaattcct    300

ctcactttcg gcggagggac caaggtggag atcaag                              336
```

<210> SEQ ID NO 36
<211> LENGTH: 369
<212> TYPE: DNA
<213> ORGANISM: Artificial sequence
<220> FEATURE:
<223> OTHER INFORMATION: Synthetic antibody

<400> SEQUENCE: 36

```
caggtgcatc tgcaggagtc gggcccagga ctggtgaagc cttcacaggc cctgtccctc     60

acctgcactg tctctggtgg ctccatcaac ggtgataatt actactggag ttggatccgc    120

cagcccccag ggaagggcct ggagtggatt gggtacatct attacagtgg gagcacctac    180

tacaacccgt ccctcaagag tcgaattagc atatcagtag acacgtccaa gaaccagttc    240

tccctgaaac tgagctctgt gactgccgca gacacggccg tgtattactg tgccagaggt    300

gcggattgcg gtaatgattg ctattacttt gactactggg gccagggagc cctggtcacc    360

gtctcctca                                                            369
```

<210> SEQ ID NO 37
<211> LENGTH: 321
<212> TYPE: DNA
<213> ORGANISM: Artificial sequence
<220> FEATURE:
<223> OTHER INFORMATION: Synthetic antibody

<400> SEQUENCE: 37

```
tcctatgagc tgactcagcc accctcagtg tccgtgtccc caggacagac agccagcatc     60

acctgctctg gagataaatt gggacataaa tatgcttgct ggtatcagca gaggccaggc    120

cagtcccctg tgctggtcat ctatcaagat agtaagcggc cctcagggat ccctgagcga    180

ttctctggct ccaattctgg gaacacagcc actctgacca tcagcgggac ccaggctgtg    240

gatgaggctg actattactg tcaggcgtgg gacagcagct ccttctatgt cttcggaact    300

gggaccaagg tcaccgtcct a                                              321
```

<210> SEQ ID NO 38
<211> LENGTH: 363
<212> TYPE: DNA
<213> ORGANISM: Artificial sequence
<220> FEATURE:
<223> OTHER INFORMATION: Synthetic antibody

<400> SEQUENCE: 38

```
gaagtgcagc tggtggagtc tgggggaggc ttggtacagc ctggcaggtc cctgagactc     60

tcctgtgcag cctctggatt cacctttgat gattatgcca tgcactgggt ccggcaagct    120

ccagggaagg gcctggagtg ggtctcaggt attagttgga atagtggtag cataggctat    180

gtggactctg tgaagggccg attcaccatc tccagagaca acgccaagaa ctccctgtat    240

ctgcaaatga acagtctgag agctgaggac acggccttgt attactgtgc aaaaggtcta    300

gtgggagcta ttcacgatgc ttttgatatc tggggccaag ggacaatggt caccgtctct    360
```

tca 363

<210> SEQ ID NO 39
<211> LENGTH: 321
<212> TYPE: DNA
<213> ORGANISM: Artificial sequence
<220> FEATURE:
<223> OTHER INFORMATION: Synthetic antibody

<400> SEQUENCE: 39
gacatccaga tgacccagtc tccttccacc ctgtctgcat ctgtaggaga cagagtcacc 60
atcacttgcc gggccagtca gagtattagt agctggttgg cctggtatca gcagaaacca 120
gggaaagccc ctaagctcct gatctataag gcgtctagtt tagaaagtgg ggtcccatca 180
aggttcagcg gcagtggatc tgggacagaa ttcactctca ccatcagcag cctgcagcct 240
gatgattttg caacttatta ctgccaacag tataatagtt acccgctcac tttcggcgga 300
gggaccaagg tggagatcaa a 321

<210> SEQ ID NO 40
<211> LENGTH: 369
<212> TYPE: DNA
<213> ORGANISM: Artificial sequence
<220> FEATURE:
<223> OTHER INFORMATION: Synthetic antibody

<400> SEQUENCE: 40
caggtgcagc tgcaggagtc gggcccagga ctggtgaagc cttcacagac cctgtccctc 60
acctgcactg tctctggtgg ctccatcagc agtggtgatt acttctggag ttggatccgc 120
cagcccccag ggaagggcct ggagtggatt gggtacatct attacagtgg gagcacctac 180
tacaacccgt ccctcaagag tcgaattacc atatcagtag acacgtccaa gaaccagttt 240
tccctgaagc tgagctctgt gactgccgca gacacggccg tgttttactg tgccagagtc 300
cagactccgg ggagtgatac ttactacttt gactactggg gccagggaac cctggtcacc 360
gtctcctca 369

<210> SEQ ID NO 41
<211> LENGTH: 318
<212> TYPE: DNA
<213> ORGANISM: Artificial sequence
<220> FEATURE:
<223> OTHER INFORMATION: Synthetic antibody

<400> SEQUENCE: 41
tcctatgagc tgactcagcc accctcagtg tccgtgtccc cagggcagac agccagcatc 60
acctgctctg gagataaatt gggggataaa tatgcttgct ggtatcagca gaagccaggc 120
cagtcccctg tgctggtcat ctatcaagat accaagcggc cctcagggat ccctgagcga 180
ttctctggct ccaactctgg gaacacagcc actctgacca tcagcgggac ccaggctatg 240
gatgaggctg actattactg tcaggcgtgg gacagcagca ctgtggtatt cggcggaggg 300
accgagctga ccgtccta 318

<210> SEQ ID NO 42

<400> SEQUENCE: 42

000

<210> SEQ ID NO 43
<211> LENGTH: 387
<212> TYPE: DNA
<213> ORGANISM: Artificial sequence
<220> FEATURE:
<223> OTHER INFORMATION: Synthetic antibody

<400> SEQUENCE: 43
caggtgcaga tggtgcagtc tggggctgag gtgaagaagc ctggggcctc agtgaaggtc 60
tcctgcaagg cttctggata caccttcacc ggctactata tgcactgggt gcgacaggcc 120
cctggacaag gccttgagtg gatgggatgg atcaacccta acagtggtgg aacaaactat 180
gcacagaaac ttcagggcag ggtcaccatg accagggaca cgtccatcag cacagcctac 240
atggagctga gcaggctgag atctgacgac acagccgtgt attactgtgc gagaggccgt 300
tattgtgata gtgccagttg ctatgtccgt aactacttct actacatgga cgtctggggc 360
aaagggacca cggtcaccgt ctcctca 387

<210> SEQ ID NO 44
<211> LENGTH: 318
<212> TYPE: DNA
<213> ORGANISM: Artificial sequence
<220> FEATURE:
<223> OTHER INFORMATION: Synthetic antibody

<400> SEQUENCE: 44
gaaattgtgt tgacacagtc tccagccacc ctgtctttgt ctccagggga aagagccacc 60
ctctcctgca gggccagtca gagtgttagc aggtacttag cctggtacca acagaaactt 120
ggccaggctc ccaggctcct catctatgat gcatccaaca gggccactgg catcccagcc 180
aggttcagtg gcagtgggtc tgggacagac ttcactctca ccatcagcag cctagagcct 240
gaagattttg cagtttatta ctgtcagcaa cgtagcaact ggcccacctt cggccaaggg 300
acacgactgg acattaaa 318

<210> SEQ ID NO 45
<211> LENGTH: 345
<212> TYPE: DNA
<213> ORGANISM: Artificial sequence
<220> FEATURE:
<223> OTHER INFORMATION: Synthetic antibody

<400> SEQUENCE: 45
ggagtggagt tggtggagtc cgggggaggg gcagctcagc cggggggggtc cctgagactc 60 tactgtgcag cctctggatt caccttcagt aactactgga tgaactgggt tcgccaaggt 120
ccaggaaagg gtctgacctg gatcgcacgt attaatgatc atgggaatta tacaagttat 180
gaggactccg tgaagggccg attcaccatc tccagagaca acaccaagaa tacagtgttt 240
ttgcaaatga acagtctgag actcgacgac tcggctgtct attactgtgt acgagccttc 300 gggggggggct actggggcca gggaaccccg gtcaccgtct cctca 345

<210> SEQ ID NO 46
<211> LENGTH: 336
<212> TYPE: DNA
<213> ORGANISM: Artificial sequence
<220> FEATURE:
<223> OTHER INFORMATION: Synthetic antibody

<400> SEQUENCE: 46
gatgttgtga tgactcagtc tccactctcc ctgcccgtct cccttggaca gccggcctcc 60
atctcctgca agtctggtca gagtctcgta tatagagatg gaaacaccta cttgagttgg 120
tttttccaga ggccaggcca atctccaagg cgcctaattt atcaggtttt taagcgggac 180
tctggggtcc cagacagatt caccggcagt gggtcaggct ccgatttcac actgcaaatc 240
agcagggtgc agtctgagga tgttggaatt tattactgca tgcaatctac acactggccg 300
tggacgttcg gccaagggac caaggtggaa atcaaa 336

<210> SEQ ID NO 47
<211> LENGTH: 372
<212> TYPE: DNA
<213> ORGANISM: Artificial sequence
<220> FEATURE:
<223> OTHER INFORMATION: Synthetic antibody

<400> SEQUENCE: 47
caggtgcagc tggtggagtc tgggggaggc gtggtccagc ctgggaggtc cctgagactc 60
tcctgtgcag cgtctggatt caccttcagt agctatggca tgcactgggt ccgccaggct 120
ccaggcaagg ggctggagtg ggtggcagtt atatggtatg atggaagtaa taaatactat 180
gcagactccg tgaagggccg attcaccatc tccagagaca attccaagaa cacgctgtat 240
ctgcaaatga acagcctgag agccgaggac acggctgtgt attactgtgc gagagaacgg 300
agtatagcag ctcgtcagaa ccgggggtac tttgactact ggggccaggg aaccctggtc 360
accgtctcct ca 372

<210> SEQ ID NO 48
<211> LENGTH: 321
<212> TYPE: DNA
<213> ORGANISM: Artificial sequence
<220> FEATURE:
<223> OTHER INFORMATION: Synthetic antibody

<400> SEQUENCE: 48
gacatccaga tgacccagtc tccatcctcc ctgtctgcat ctgtaggaga cagagtcacc 60
atcacttgcc gggcaagtca gggcattaga aatgatttag gctggtatca gcagaaacca 120
gggaaagccc ctaagcgcct gatctatgct gcatccagtt tgcaaagtgg ggtcccatca 180
aggttcagcg gcagtggatc tgggacagaa ttcactctca caatcagcag cctgcagcct 240
gaagattttg caacttatta ctgtctacag cataatagtt acccgtggac gttcggccaa 300
gggaccaagg tggaaatcaa a 321

<210> SEQ ID NO 49
<211> LENGTH: 348
<212> TYPE: DNA
<213> ORGANISM: Artificial sequence
<220> FEATURE:
<223> OTHER INFORMATION: Synthetic antibody

<400> SEQUENCE: 49
gaggtgcagc tggtggagtc cgggggaggc ttagttcagc cggggggggtc cctgagactc 60 tcctgtgcag cctccggatt caccttcagc aggtactata tgcactgggt ccgccaagct 120
ccagggaagg ggccggtgtg gatctcacgt attaacactg atgggagcac cacagcgtat 180
gccgactccg tgaagggccg attcaccatc tccagagaca acgccaagaa cacattgtat 240
ttgcaaatga acagtctgag agtcgaagat acggctgtgt attattgtgc aaggccctat 300
agtgggtact tccactgggg ccggggagcc ctggtcaccg tctcctca 348

<210> SEQ ID NO 50
<211> LENGTH: 333
<212> TYPE: DNA
<213> ORGANISM: Artificial sequence
<220> FEATURE:
<223> OTHER INFORMATION: Synthetic antibody

<400> SEQUENCE: 50
gatatcgtga tgacccagac tccactctcc tcatctgtaa cccttggaca gccggcctcc 60
atctcctgca ggtctagtca aagcctcgta cacagtgatg gaaacaccta cttgaattgg 120
cttcaccaga ggccaggcca gcctccaaga ctcctaattt ataagatttc taatcggttc 180
tctggggtcc cagatagatt cagtggcagt ggggcaggga cagatttcac actgaaaatc 240
agcagggtgg aagctgagga tgtcggggtt tattactgca tgcaaggtac acgattgtac 300
acttttggcc aggggaccaa gctggagatc aaa 333

<210> SEQ ID NO 51
<211> LENGTH: 336
<212> TYPE: DNA
<213> ORGANISM: Artificial sequence
<220> FEATURE:
<223> OTHER INFORMATION: Synthetic antibody

<400> SEQUENCE: 51
gaggtgctgc tgctggagtc tgggggaggc ttagtccagc ctggggggtc cctgagactc 60
tcctgtacag tctctggatt caccttcact aactcctgga tgcactgggt ccgccaagct 120
ccagggaagg ggctggtgtg ggtctcaggt attaatcctg atgggagcaa aatagaccac 180
gcggagtccg tgcagggccg attcaccatc tccagagaca acgccaagaa cacgctttat 240
ctgcaaatgg acagtctgag agacgaggac acggctgttt attactgcgc aaggtggcta 300
tcctggggcc agggagccct ggtcaccgtc acctca 336

<210> SEQ ID NO 52
<211> LENGTH: 315
<212> TYPE: DNA
<213> ORGANISM: Artificial sequence
<220> FEATURE:
<223> OTHER INFORMATION: Synthetic antibody

<400> SEQUENCE: 52
accatctctt gttctggaag cagctccaac atcggaagta atcatgttta ttggtaccaa 60
caactcccag gatcggcccc ccaactcctc atttctaaga ataatcagcg gccctcaggg 120
gtccctgacc gattctctgg ctccaagtct ggcacctcag gttccctggc catcagtggg 180
ctccggtccg aggatgaggc tgcttattat tgtgcagcat gggatgacag cctgcgtggt 240
tgggaattcg gcggagggac ccaggtgacc gtcctaggtc agcccaaggc tgccccctcg 300
gtcactctgt tccca 315

<210> SEQ ID NO 53
<211> LENGTH: 336
<212> TYPE: DNA
<213> ORGANISM: Artificial sequence
<220> FEATURE:
<223> OTHER INFORMATION: Synthetic antibody

<400> SEQUENCE: 53
gaggtgctgc tgctggagtc tgggggaggc ttagtccagc ctggggggtc cctgagactc 60
tcctgtacag tctctggatt caccttcact aactcctgga tgcactgggt ccgccaagct 120
ccagggaagg ggctggtgtg ggtctcaggt attaatcctg atgggagcaa aatagaccac 180
gcggagtccg tgcagggccg attcaccatc tccagagaca acgccaagaa cacgctttat 240
ctgcaaatgg acagtctgag agacgaggac acggctgttt attactgcgc aaggtggcta 300
tcctggggcc agggagccct ggtcaccgtc acctca 336

<210> SEQ ID NO 54
<211> LENGTH: 318
<212> TYPE: DNA
<213> ORGANISM: Artificial sequence
<220> FEATURE:
<223> OTHER INFORMATION: Synthetic antibody

<400> SEQUENCE: 54
gaaattgtgt tgacacagtc tccagccacc ctgtctttgt ctccagggga aagagccacc 60
ctctcctgca gggccagtca gagtgttagc aggaaattag cctggttcca gcagagactt 120
ggccaggctc ccagactcct catctatgat gcatccacca gggccactgg tgtcccagcc 180
aagttcagtg gcagtgggtc tgggacagac ttcactctca ccatcagcag cctagagcct 240
gaagattttg cagtttatta ctgtcaccag cgtagcaact ggtggacgtt cggccaaggg 300
accaaggtgg aagtcaag 318

<210> SEQ ID NO 55
<211> LENGTH: 354
<212> TYPE: DNA
<213> ORGANISM: Artificial sequence
<220> FEATURE:
<223> OTHER INFORMATION: Synthetic antibody

<400> SEQUENCE: 55
caggtgcttc tggtacagtc tgaggctgag gtgcggaagc ctggggcctc agttaaaatt 60
tcctgcaaga catctggata caccttcacc acctacttta tgcactgggt gcgacaggcc 120
cctggacaag ggcttgagtg ggtggcaatt gtcgacccta gtactggaaa cacaggctac 180
gcacagaggt tccagggcag agtcaccgtg accagggaca cgtccacggg aacactcttc 240
atggaactga ccagcctgac aacagaggac acggccatgt actactgtgg tagagatcgt 300
ggctcccggg cggttgactc ctggggccaa ggaaccctgg tcaccgtctt ttca 354

<210> SEQ ID NO 56
<211> LENGTH: 333
<212> TYPE: DNA
<213> ORGANISM: Artificial sequence
<220> FEATURE:
<223> OTHER INFORMATION: Synthetic antibody

<400> SEQUENCE: 56
cagtctgtgc tgactcagcc accctcagtg tctggggccc ccgggcagag ggtcactatc 60
tcttgttctg gaagcagctc caacgtcgga cctaatactg taagctggta ccaacaactc 120
ccaggagtgg cccccaaact cctcatctat cgtaataatc agcgcccctc aggggtccct 180
gaccgatttt ctggctccaa atttggcacc tcagcctccc tggtcatcgg tgggctccag 240
tctgaggatg aggctgacta ttattgtgca gcatgggatg acagcctgaa tggccatatg 300
gtgttcggcg gagggaccaa agtggccgtc cta 333

<210> SEQ ID NO 57
<211> LENGTH: 345
<212> TYPE: DNA
<213> ORGANISM: Artificial sequence
<220> FEATURE:
<223> OTHER INFORMATION: Synthetic antibody

<400> SEQUENCE: 57
caggtgcagc tgcaggagtc gggcccagga ctggcgaagc cttcggagac cctgtccctc 60
acctgcactg tctctggtgg ctccatcagt agttactttt ggagctggat ccggcagccc 120
gccgggaagg gactggagtg gattgggcgt atccatacca ctgggagcac caactacaac 180
ccctccctca agaatcgagt catcatgtca gtagacacgt ccaagaacca gttctccctg 240
aacctgagct ctgtgaccgc cgcggacacg gccgtgtatt actgtgcgag agaagggacg 300
gcttttgata tctggggcca agggacaatg gtcaccgtct cttca 345

<210> SEQ ID NO 58
<211> LENGTH: 321
<212> TYPE: DNA
<213> ORGANISM: Artificial sequence
<220> FEATURE:
<223> OTHER INFORMATION: Synthetic antibody

<400> SEQUENCE: 58
tcctatgagc tgactcagtc accctcagtg tccgtgtccc caggacagac agccagcatc 60
ccctgctctg gagataaatt gggggataaa tatgcttgct ggtatcagca gaagccaggc 120
cagtcccctg tgctggtcat ctatcaagat accaagcggc cctcagggat ccctgagcga 180
ttctctggct ccaactctgg gaacacagcc actctgacca tcagcgagac ccaggctatg 240
gatgaggctg actattactg tcaggcgtgg gacagcagca ctccatgggt gttcggcgga 300
gggaccaagc tgaccgtcct a 321

<210> SEQ ID NO 59
<211> LENGTH: 354
<212> TYPE: DNA
<213> ORGANISM: Artificial sequence
<220> FEATURE:
<223> OTHER INFORMATION: Synthetic antibody

<400> SEQUENCE: 59
caggtgcacc tggtggagtc tgggggaggc ttggtcaagc ctggagggtc cctgagactc 60
tcctgtgcag cctctggatt caccttcagt gactactaca tgagctggat ccgccaggct 120
ccagggaagg ggctggagtg ggtttcatac attagtggta ctggtagttt catatactac 180
gcagactctg tgaagggccg attcaccatc tccagggaca acgccaagaa ctcactgtat 240
ctgcagatca acagcctgag agccgaggac acggccgtgt attactgtgc gagaggaatc 300
agggctgact gctttgacca gtggggccac ggaaccctgg tcaccgtctc ctca 354

<210> SEQ ID NO 60
<211> LENGTH: 324
<212> TYPE: DNA
<213> ORGANISM: Artificial sequence
<220> FEATURE:
<223> OTHER INFORMATION: Synthetic antibody

<400> SEQUENCE: 60
tcctatgtgc tgactcagcc accctcggtg tcagtggccc caggacagac ggccaggatt 60
acctgtgggg gaaacaacat tggagataaa agtgtgcact ggtaccagca gaagccaggc 120
caggcccctg tgctggtcgt ctatgatgat agcgaccggc cctcagggat ccctgagcga 180
ttctctggct ccaactctgg gaacacggcc accctgacca tcagcagggt cgaagccggg 240
gatgaggccg actattactg tcaggtgtgg gatagtagta gtgatcatct tgtcttcgga 300
actgggacca aggtcaccgt ccta 324

<210> SEQ ID NO 61
<211> LENGTH: 357
<212> TYPE: DNA
<213> ORGANISM: Artificial sequence
<220> FEATURE:
<223> OTHER INFORMATION: Synthetic antibody

<400> SEQUENCE: 61
caggtgcagc tggtgcagtc tggggctgag gtgaagaagc ctggggcctc agtgaaggtt 60
tcctgcaagg catctggata caccttcacc agctactata tgcactgggt gcgacaggcc 120
cctggacaag ggcttgagtg gatgggaata atcaacccta gtggtggtag cacaagctac 180
gcacagaagt tccagggcag agtcaccatg accagggaca cgtccacgag cacagtctac 240
atggagctga gcagcctgag atctgaggac acggccgtgt attactgtgc gagagcccgt 300
ggggggagct actcccttga ctactggggc cagggaaccc tggtcaccgt ctcctca 357

<210> SEQ ID NO 62
<211> LENGTH: 324
<212> TYPE: DNA
<213> ORGANISM: Artificial sequence
<220> FEATURE:
<223> OTHER INFORMATION: Synthetic antibody

<400> SEQUENCE: 62
tcctatgtgc tgactcagcc accctcggtg tcagtggccc caggacagac ggccaggatt 60
acctgtgggg gaaacaacat tggaagtaaa agtgtgcact ggtaccagca gaagccaggc 120
caggcccctg tgctggtcgt ctatgatgat agcgaccggc cctcagggat ccctgagcga 180
ttctctggct ccaactctgg gaacacggcc accctgacca tcagcagggt cgaagccggg 240
gatgaggccg actattactg tcaggtgtgg gatagtagta gtgatcattg ggtgttcggc 300
ggagggacca agctgaccgt ccta 324

<210> SEQ ID NO 63
<211> LENGTH: 360
<212> TYPE: DNA
<213> ORGANISM: Artificial sequence
<220> FEATURE:
<223> OTHER INFORMATION: Synthetic antibody

<400> SEQUENCE: 63
caggttcacc tggtggagtc tgggggaggc gtggtccagc ctgggaagtc cctgagactc 60
tcctgtgcag cgtctggatt catcttcaat cattttggca tccactgggt ccgccagtct 120
ccaggcaagg ggctggagtg ggtggcagtc atatggtatg atggaagtaa aaaatacttt 180
gcagactccg tgaagggccg attcagcatc tccagagaca attcccagaa cactgtgtat 240
ctacaaatga acagcctgag aaccgaggac acggctgtgt attactgtgc gagagagaga 300
tggagtggtc attcgtacct tgactactgg ggccatggag ccctggtcac cgtctcctca 360

<210> SEQ ID NO 64
<211> LENGTH: 324
<212> TYPE: DNA
<213> ORGANISM: Artificial sequence
<220> FEATURE:
<223> OTHER INFORMATION: Synthetic antibody

<400> SEQUENCE: 64

```
tccaatgtgc tgactcagcc accctcggtg tctgtggccc caggacagac ggccaggatt     60

tcctgtgggg gaaacaacct tgaaagtaaa tatgtgcact ggtaccagca gaagccaggc    120

caggcccctg tgctagtcgt ctatgaagat agcggccggc cctcggggat ccctgagcga    180

ttctctggct ccaactctgg gggtacggcc accctgacca tcagcagggt cgaagccggg    240

gatgaggccg actattactg tcaggagtgg gatactagta gtgattatcc ggtgttcggc    300

ggagggacca aggtgaccgt ccta                                           324
```

<210> SEQ ID NO 65
<211> LENGTH: 357
<212> TYPE: DNA
<213> ORGANISM: Artificial sequence
<220> FEATURE:
<223> OTHER INFORMATION: Synthetic antibody

<400> SEQUENCE: 65

```
caggtgcagg tggcggagtc tgggggaggc gtggtccagc ctgggaggtc tctgagactc     60

tcctgtgtag cctctggatt cacctttagg actaaaacca tgcattgggt ccgccaggct    120

ccaggcaagg ggctggagtg ggtggcgttt atttcgggta gtggaaaaga taaatcctac    180

gcagactccg tgaagggcca attcaccatc tccagagaca actccaagaa cacgctgttt    240

ctgcaattgg atagcctgag acctgaggac acggctgtct attactgtgt gaaagataga    300

gaggggactt ggtcctttga ccactggggc cagggagccc tggtcaccgt ctcctca       357
```

<210> SEQ ID NO 66
<211> LENGTH: 330
<212> TYPE: DNA
<213> ORGANISM: Artificial sequence
<220> FEATURE:
<223> OTHER INFORMATION: Synthetic antibody

<400> SEQUENCE: 66

```
cagtctgccc tgactcagcc tgcctccgtg tctgggtctc ctggacagtc gatcaccatc     60

tcctgcactg gaaccaacaa tgacgttggt ctttatgact atgtctcctg gtaccaacaa    120

cacccaggca gagcccccaa actcatcatt tatgaggtca ctaatcggcc ctcaggggtt    180

tctgatcgct tctctgcttc caagtctggc aacacggcct ccctgaccat ctctgggctc    240

caggctgagg acgaggctga ttattactgc agctcatata caagaagcat cacttgggtg    300

ttcggcgggg ggaccaaggt gaccgtcctg                                     330
```

<210> SEQ ID NO 67
<211> LENGTH: 375
<212> TYPE: DNA
<213> ORGANISM: Artificial sequence
<220> FEATURE:
<223> OTHER INFORMATION: Synthetic antibody

<400> SEQUENCE: 67

```
gaggtgcagc tgttggagtc tgggggaggc ttggtacagc ctggggggtc cctgagactc     60

tcctgtgcag cctctggatt cacctttagc agctatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcaaatga acagcctgag agccgaggac acggccgtat attactgtgc gaaaaagtat    300

tacgattttt ggagtggtta ttacccgaac tggttcgacc cctggggcca gggaaccctg    360
```

gtcaccgtct cctca 375

<210> SEQ ID NO 68
<211> LENGTH: 324
<212> TYPE: DNA
<213> ORGANISM: Artificial sequence
<220> FEATURE:
<223> OTHER INFORMATION: Synthetic antibody

<400> SEQUENCE: 68
gaaatagtga tgacgcagtc tccagccacc ctgtctgtgt ctccagggga aagagccacc 60
ctctcctgca gggccagtca gagtgttagc agcaacttag cctggtacca gcagaaacct 120
ggccaggctc ccaggctcct catctatggt gcatccacca gggccactgg tatcccagcc 180
aggttcagtg gcagtgggtc tgggacagag ttcactctca ccatcagcag cctgcagtct 240
gaagattttg cagtttatta ctgtcagcag tataataact ggcctcagcg gacgttcggc 300
caagggacca aggtggaaat caaa 324

<210> SEQ ID NO 69
<211> LENGTH: 348
<212> TYPE: DNA
<213> ORGANISM: Artificial sequence
<220> FEATURE:
<223> OTHER INFORMATION: Synthetic antibody

<400> SEQUENCE: 69
caggtgcagc tggtgcaatc tgggtctgag ttgaagaagt ctggggcctc cgtgaaggtt 60
tcctgtaggg cttctggata caccttcact acctatgtta tgaattgggt gcgacaggcc 120
cctggacaag ggcttgagtg gatgggatgg atcaacacca acactgggaa cccaacgtat 180
gcccagggct tcacaggacg ctttgtcttc tccttagaca cctctgtcag cacggcatat 240
ctacagatca acagcctaaa ggctgaggac actgccgtgt attattgtgc gagggagtac 300
aatagctttg actattgggg ccagggaacc ctggtcaccg tctcctca 348

<210> SEQ ID NO 70
<211> LENGTH: 333
<212> TYPE: DNA
<213> ORGANISM: Artificial sequence
<220> FEATURE:
<223> OTHER INFORMATION: Synthetic antibody

<400> SEQUENCE: 70
cagtctgtgc tgacgcagcc gccctcagtg tctggggccc cagggcagag ggtcaccatc 60
tcctgcactg ggagcagctc caacatcggg gcaggttatg atgtacactg gtaccagcag 120
cttccaggaa cagcccccaa actcctcatc tatgataaca acaatcggcc ctcaggggtc 180
cctgaccgat tctctggctc caggtctggc acctcaacct ccctggccat cactgggctc 240
caggctgaag atgaggctga ttattactgc cagtcctatg atttcaggct gagtggttcg 300
gtattcggcg gagggaccaa agtcaccgtc cta 333

<210> SEQ ID NO 71
<211> LENGTH: 357
<212> TYPE: DNA
<213> ORGANISM: Artificial sequence
<220> FEATURE:
<223> OTHER INFORMATION: Synthetic antibody

<400> SEQUENCE: 71
caggtgcagc tggtgcagtc tggggctgag gtgaagaagc ctggggcctc agtgaaggtt 60

```
tcctgcaagg catctggata caccttcacc agctactata tgcactgggt gcgacaggcc    120

cctggacaag ggcttgagtg gatgggaata atcagcccta gtggtggtag cacagactac    180

gcacagaagt tccagggcag agtcaccatg accagggaca cgtccacgag cacagtctac    240

atggaactga gcagcctgag atctgaggac acggccgtgt attactgtgc gagacaagtg    300

cagactgatt actactttga ctactggggc cagggaaccc tggtcaccgt ctcctca       357


<210> SEQ ID NO 72
<211> LENGTH: 327
<212> TYPE: DNA
<213> ORGANISM: Artificial sequence
<220> FEATURE:
<223> OTHER INFORMATION: Synthetic antibody

<400> SEQUENCE: 72

tcctatgtgc tgactcagcc accctcggtg tcagtggccc caggacagac ggccaggatt     60

acctgtggga gaaacaacat tggaagtaaa agtgtgcact ggtaccagca gaagccaggc    120

caggcccctg tgctggtcgt ctatgatgat agcgaccggc cctcagggat ccctgagcga    180

ttctctggct ccaactctgg gaacacggcc accctgacca tcagcagggt cgaagccggg    240

gatgaggccg actattactg tcaggtgtgg gatagtagta gtgatcactc ttgggtgttc    300

ggcggaggga ccaagctgac cgtcctg                                        327


<210> SEQ ID NO 73
<211> LENGTH: 360
<212> TYPE: DNA
<213> ORGANISM: Artificial sequence
<220> FEATURE:
<223> OTHER INFORMATION: Synthetic antibody

<400> SEQUENCE: 73

caggtgcagc tggtggagtc tgggggaggc gtggtccagc ctgggaggtc cctgagactc     60

tcctgtgcag cctctggatt caccttcagt agctatgcta tgcactgggt ccgccaggct    120

ccaggcaagg ggctggagtg ggtagcagct atatcatatg atggaagtga taaatactac    180

gcagactccg tgaagggccg attcaccatc tccagagaca attccaagaa cacggtgtat    240

ctgcaaatgg acagcctgag agctgaggac acggctgtgt attactgtgc gagagatcgg    300

agtgggagct actactggtt cgacccctgg ggccagggaa ccctggtcac cgtctcctca    360


<210> SEQ ID NO 74
<211> LENGTH: 330
<212> TYPE: DNA
<213> ORGANISM: Artificial sequence
<220> FEATURE:
<223> OTHER INFORMATION: Synthetic antibody

<400> SEQUENCE: 74

aattttatgc tgactcagcc ccactctgtg tcggagtctc cggggaggac ggtaaccatc     60

tcctgcaccc gcagcagtgg cagcattgcc aacaactttg tgcagtggta ccagcagcgc    120

ccgggcagtt cccccaccac tgtgatctat gaggatgacc aaagaccctc tggggtccct    180

gatcggttct ctggctccat cgacagctcc tccaactctg cctccctcac catctctgga    240

ctgaagactg aggacgaggc tgactactac tgtcagtctt atgatagcag caatcaggtg    300

ttcggcggag ggaccaagct gaccgtccta                                     330


<210> SEQ ID NO 75
```

<211> LENGTH: 366
<212> TYPE: DNA
<213> ORGANISM: Artificial sequence
<220> FEATURE:
<223> OTHER INFORMATION: Synthetic antibody

<400> SEQUENCE: 75
caggtccagc ttgtgcagtc tggggctgag gtgaagaagc ctggggcctc agtgaaggtt 60
tcctgcaagg cttctggata caccttcact aactatgcta tacattgggt gcgccaggcc 120
cccggacaaa ggcttgagtg gatgggatgg atcaacgctg gcaatggtga cacaaaatat 180
tcacagaagt tccagggcag agtcaccatt accagggaca catccgcgag cacagcctac 240
atggagctga gcagcctgag atctgaagac acggctgtgt attactgtgc gagacccggg 300
tatagcagca gctgggatga gggctttgac tactggggcc agggaaccct ggtcaccgtc 360
tcctca 366

<210> SEQ ID NO 76
<211> LENGTH: 318
<212> TYPE: DNA
<213> ORGANISM: Artificial sequence
<220> FEATURE:
<223> OTHER INFORMATION: Synthetic antibody

<400> SEQUENCE: 76
tcgtatgagc tgactcagcc accctcagtg tccgtgtccc caggacagac agccagcatc 60
acctgctctg gagataaatt gggggataaa tatgcttgct ggtatcagca gaagtcaggc 120
cagtcccctg tgctggtcat caatctagat agcaagcggc cctcagggat ccctgagcga 180
ttctctggct ccaactctgg gaacacagcc actctgacca tcagcgggac ccaggctatg 240
gatgaggctg actattactg tcaggcgtgg gacagcagca ctggggtttt cggcggaggg 300
accaagctga ccgtccta 318

<210> SEQ ID NO 77
<211> LENGTH: 363
<212> TYPE: DNA
<213> ORGANISM: Artificial sequence
<220> FEATURE:
<223> OTHER INFORMATION: Synthetic antibody

<400> SEQUENCE: 77
gaggtgcagc tggtggagtc cgggggaggc ttagttcagc ctggggggtc cctgagactc 60
tcctgtgcag cctctggatt caccttcagt agctactgga tgcactgggt ccgccaagct 120
ccagggaagg ggctggtgtg ggtctcacgt attaatagtg atgggagtag cacaagctac 180
gcggactccg tgaagggccg attcaccatc tccagagaca acgccaagaa cacgctgtat 240
ctgcaaatga acagtctgag agccgaggac acggctgtgt attactgtgc aagtggggat 300
agcagtggct ggtacatgcc atttgactac tggggccagg gaaccctggt caccgtctcc 360
tca 363

<210> SEQ ID NO 78
<211> LENGTH: 333
<212> TYPE: DNA
<213> ORGANISM: Artificial sequence
<220> FEATURE:
<223> OTHER INFORMATION: Synthetic antibody

<400> SEQUENCE: 78
cagtctgccc tgactcagcc tgcctccgtg tctgggtctc ctggacagtc gatcaccatc 60

```
tcctgcactg gaaccagcag tgacgttggt ggttataact atgtctcctg gtaccaacag    120

cacccaggca aagcccccaa actcatgatt tatgatgtca gtaatcggcc ctcaggggtt    180

tctaatcgct tctctggctc caagtctggc aacacggcct ccctgaccat ctctgggctc    240

caggctgagg acgaggctga ttattactgc agctcatata caagcagcag cactaatgtg    300

gtattcggcg gagggaccaa gctgaccgtc cta                                 333


<210> SEQ ID NO 79
<211> LENGTH: 369
<212> TYPE: DNA
<213> ORGANISM: Artificial sequence
<220> FEATURE:
<223> OTHER INFORMATION: Synthetic antibody

<400> SEQUENCE: 79

caggtgcagc tgcaggagtc gggcccagga ctggtgaagc cttcggagac cctgtccctc     60

acctgcactg tctctggtgg ctccatcagt agttactact ggagctggat ccggcagccc    120

ccagggaagg gactggagtg gattgggtat atctattaca gtgggagcac caactacaac    180

ccctccctca agagtcgagt caccatatca gtagacacgt ccaagaacca gttctccctg    240

aagctgagct ctgtgaccgc cgcagacacg gccgtgtatt actgtgcgag acatggggat    300

attttgactg gtttcttgta ctggtacttc gatctctggg gccgtggcac cctggtcact    360

gtctcctca                                                            369


<210> SEQ ID NO 80
<211> LENGTH: 333
<212> TYPE: DNA
<213> ORGANISM: Artificial sequence
<220> FEATURE:
<223> OTHER INFORMATION: Synthetic antibody

<400> SEQUENCE: 80

cagtctgccc tgactcagcc tgcctccgtg tctgggtctc ctggacagtc gatcaccatc     60

tcctgcactg gaaccagcag tgacgttggt ggttataact atgtctcctg gtaccaacag    120

cacccaggca aagcccccaa actcatgatt tatgatgtca gtaatcggcc ctcaggggtt    180

tctaatcgct tctctggctc caagtctggc aacacggcct ccctgaccat ctctgggctc    240

caggctgagg acgaggctga ttattactgc agctcatata caagcagcag cactctagtg    300

gtattcggcg gagggaccaa gctgaccgtc cta                                 333


<210> SEQ ID NO 81
<211> LENGTH: 363
<212> TYPE: DNA
<213> ORGANISM: Artificial sequence
<220> FEATURE:
<223> OTHER INFORMATION: Synthetic antibody

<400> SEQUENCE: 81

gaagtgcagc tggtgcagtc tggagcagag gtgaaaaagc ccggggagtc tctgaggatc     60

tcctgtaagg gttctggata cagctttacc agctactgga tcagctgggt gcgccagatg    120

cccgggaaag gcctggagtg gatggggagg attgatccta gtgactctta taccaactac    180

agcccgtcct tccaaggcca cgtcaccatc tcagctgaca agtccatcag cactgcctac    240

ctgcagtgga gcagcctgaa ggcctcggac accgccatgt attactgtgc gagacatgga    300

gagggtggga gctacgagga gttcgacccc tggggccagg gaaccctggt caccgtctcc    360
```

tca 363

<210> SEQ ID NO 82
<211> LENGTH: 321
<212> TYPE: DNA
<213> ORGANISM: Artificial sequence
<220> FEATURE:
<223> OTHER INFORMATION: Synthetic antibody

<400> SEQUENCE: 82
gacatccaga tgacccagtc tccatcctcc ctgtctgcat ctgtaggaga cagagtcacc 60
atcacttgcc gggcaagtca gagcattagc agctatttaa attggtatca gcagaaacca 120
gggaaagccc ctaagctcct gatctatgct gcatccagtt tgcaaagtgg ggtcccatca 180
aggttcagtg gcagtggatc tgggacagat ttcactctca ccatcagcag tctgcaacct 240
gaagattttg caacttacta ctgtcaacag agttacagta ccccgtggac gttcggccaa 300
gggaccaagg tggaaatcaa a 321

<210> SEQ ID NO 83
<211> LENGTH: 378
<212> TYPE: DNA
<213> ORGANISM: Artificial sequence
<220> FEATURE:
<223> OTHER INFORMATION: Synthetic antibody

<400> SEQUENCE: 83
gaggtgcagc tggtgcagtc tggagcagag gtgaaaaagg ccggggagtc tctgaagatc 60
tcctgtaagg gttctggata cagctttacc agctactgga tcggctgggt gcgccagatg 120
cccgggaaag gccaggagtg gatgggaatc atctatcctg gtgactctga taccacatac 180
agcccgtcct tccaaggcca ggtcaccatc tcagccgaca agtccctcag caccgcctac 240
ctgcagtgga gcagcctgaa ggcctcggac accgccatgt attactgtgc gagaggggca 300
tattgtggtg gtgattgctt tgggggcgct gaatacttcc agcactgggg ccagggcacc 360
ctggtcaccg tctcctca 378

<210> SEQ ID NO 84
<211> LENGTH: 339
<212> TYPE: DNA
<213> ORGANISM: Artificial sequence
<220> FEATURE:
<223> OTHER INFORMATION: Synthetic antibody

<400> SEQUENCE: 84
gacatcgtga tgacccagtc tccagactcc ctggctgtgt ctctgggcga gagggccacc 60
atcaactgca agtccagcca gagtgtttta tacagctcca acaataagaa ctacttagct 120
tggtaccagc agaaaccagg acagcctcct aagctgctca tttactgggc atctacccgg 180
gaatccgggg tccctgaccg attcagtggc agcgggtctg ggacagattt cactctcacc 240
atcagcagcc tgcaggctga agatgtggca gtttattact gtcagcagta ttatagtact 300
ccgctcactt tcggcggagg gaccaaggtg gagatcaaa 339

<210> SEQ ID NO 85
<211> LENGTH: 357
<212> TYPE: DNA
<213> ORGANISM: Artificial sequence
<220> FEATURE:
<223> OTHER INFORMATION: Synthetic antibody

<400> SEQUENCE: 85

```
caggtgcagc tggtgcagtc tggggctgag gtgaagaggc ctggggcctc agtgaaggtt     60

tcctgcaagg catctggata taccttcacc aactactata tgcactgggt gcgacaggcc    120

cctggacaag ggcttgagtg gatgggaata atcaacccta gtggtgttag cacaatgtac    180

gcacagaagt tccagggcag agtcaccatg accagggaca cgtccacgag cacagtctac    240

atggagctga gcagcctgag atctgaggac acggccgtgt attcctgtgc gagaatggat    300

actgaatact actactttga ctactggggc cagggaaccc tggtcaccgt ctcctca       357
```

```
<210> SEQ ID NO 86
<211> LENGTH: 324
<212> TYPE: DNA
<213> ORGANISM: Artificial sequence
<220> FEATURE:
<223> OTHER INFORMATION: Synthetic antibody

<400> SEQUENCE: 86

tcctatgtgc tgactcagcc accctcggtg tcagtggccc caggacagac ggccaggatt     60

acctgtgggg gaaacaacat tggaagtaaa agtgtgcact ggtaccagca gaggccaggc    120

caggcccctg tgctggtcgt ctatgatgat agcgaccggc cctcagggat ccctgagcga    180

ttctctggct ccaactctgg gaacacggcc accctgacca tcaacagggt cgaagccggg    240

gatgaggccg actattactg tcaggtgtgg gatagtagta gtgatcattg ggtgttcggc    300

ggagggacca agctgaccgt ccta                                           324
```

```
<210> SEQ ID NO 87
<211> LENGTH: 357
<212> TYPE: DNA
<213> ORGANISM: Artificial sequence
<220> FEATURE:
<223> OTHER INFORMATION: Synthetic antibody

<400> SEQUENCE: 87

gaggtgcagc tgcaggagtc gggcccagga ctggtgcagc cttcggggac cctgtccctc     60

acctgcgctg tctctggtgg ctccatcagc agtagtaact ggtggagttg ggtccgccag    120

cccccaggga aggggctgga gtggattggg gaaatctatc atagtgggag caccaactac    180

aacccgtccc tcaagagtcg agtcaccata tcagtagaca agtccaagaa ccagttctcc    240

ctgaagctga gctctgtgac cgccgcggac acggccgtgt actactgtgc gagacgctcc    300

tactactact actacatgga cgtctggggc aaagggacca cggtcaccgt ctcctca       357
```

```
<210> SEQ ID NO 88
<211> LENGTH: 324
<212> TYPE: DNA
<213> ORGANISM: Artificial sequence
<220> FEATURE:
<223> OTHER INFORMATION: Synthetic antibody

<400> SEQUENCE: 88

tcctatgtgc tgactcagcc accctcggtg tcagtggccc caggacagac ggccaggatt     60

acctgtgggg gaaacaacat tggaagtaaa agtgtgcact ggtaccagca gaagccaggc    120

caggcccctg tgctggtcgt ctatgatgat agcgaccggc cctcagggat ccctgagcga    180

ttctctggct ccaactctgg gaacacggcc accctgacca tcagcagggt cgaagccggg    240

gatgaggccg actattactg tcaggtgtgg gatagtagta gtgattatgt ggtattcggc    300

ggagggacca agctgaccgt ccta                                           324
```

<210> SEQ ID NO 89
<211> LENGTH: 366
<212> TYPE: DNA
<213> ORGANISM: Artificial sequence
<220> FEATURE:
<223> OTHER INFORMATION: Synthetic antibody

<400> SEQUENCE: 89
gaggtgcagc tgttggagtc tgggggaggc ttggtacagc cggggggggtc cctgagactc 60 tcctgtgcag cctctggatt cacctttagt agttatgcca tgagctgggt ccgccaggct 120
ccagggaagg ggctggagtg ggtctcagtt attagtggta gtggtggtag cacatactac 180
gcagactccg tgaagggccg gttcaccatc tccagagaca attccaagaa cacactgtat 240
ctgcaaatga gtagcctgag agccgaggac acggcccttt attactgtgc gaaatgtatc 300
gataactact actactactg ctacatggac gtctggggca aagggaccac ggtcaccgtc 360
tcctca 366

<210> SEQ ID NO 90
<211> LENGTH: 330
<212> TYPE: DNA
<213> ORGANISM: Artificial sequence
<220> FEATURE:
<223> OTHER INFORMATION: Synthetic antibody

<400> SEQUENCE: 90
cagtctgccc tgactcagcc tgcctccgtg tctgggtctc ctggacagtc gatcaccatc 60
tcctgcactg gaaccagcag tgacgttggt ggttatgact atgtctcctg gtaccaacac 120
cacccaggca aagcccccaa actcatgatt tatgctgtca gtaatcggcc ctcaggggtt 180
tctaatcgct tctctggctc caagtctggc aacacggcct ccctgaccat ctctgggctc 240
cagcctgagg acgaatctga ttattactgc agctcatata caagcagcag cacttgggtg 300
ttcggcggag ggaccaagct gaccgtccta 330

<210> SEQ ID NO 91
<211> LENGTH: 354
<212> TYPE: DNA
<213> ORGANISM: Artificial sequence
<220> FEATURE:
<223> OTHER INFORMATION: Synthetic antibody

<400> SEQUENCE: 91
caggttcagc tggtgcagtc tggagctgag gtgaagaagc ctggggcctc agtgaaggtc 60
tcctgcaagg cttctggtta cacctttact agctatggta tcacctgggt gcgactggcc 120
cctggacaag ggcttgagtg gatgggatgg atcagcgctt acaatggtaa cacaaactat 180
gcacagaagc tccagggcag agtcaccatg accacagaca catccacgag cacagcctac 240
atggagctga ggagcctgag atctgacgac acggccgtgt attactgtgc gagagatggg 300
gttcagggtg cttttgatat ctggggccaa gggacaatgg tcaccgtctc ttca 354

<210> SEQ ID NO 92
<211> LENGTH: 324
<212> TYPE: DNA
<213> ORGANISM: Artificial sequence
<220> FEATURE:
<223> OTHER INFORMATION: Synthetic antibody

<400> SEQUENCE: 92
tcctatgtgc tgactcagcc accctcggtg tcagtggccc caggacagac ggccaggatt 60

```
acctgtgggg gaaacaacat tggaagtaaa agtgtgcact ggtaccagca gaagccaggc    120

caggcccctg tgctggtcgt ctatgatgat agcgaccggc cctcagggat ccctgagcga    180

ttctctggct ccaactctgg gaacacggcc accctgacca tcagcagggt cgaagccggg    240

gatgaggccg actattactg tcaggtgtgg gatagtagta gtgatcaaag ggtcttcgga    300

actgggacca aggtcaccgt ccta                                           324
```

```
<210> SEQ ID NO 93
<211> LENGTH: 384
<212> TYPE: DNA
<213> ORGANISM: Artificial sequence
<220> FEATURE:
<223> OTHER INFORMATION: Synthetic antibody

<400> SEQUENCE: 93

caggtgcagc tggtggagtc tgggggaggc gtggtccagc ctgggaggtc cctgagactc     60

tcctgtgcag cctctggatt caccttcagt agctatggca tgcactgggt ccgccaggct    120

ccaggcaagg ggctggagtg ggtggcagtt atatcatatg atggaagtaa taaatactat    180

gcagactccg tgaagggccg attcaccatc tccagagaca attccaagaa cacgctgtat    240

ctgcaaatga acagcctgag agctgaggac acggctgtgt attactgtgc gaattggggc    300

aattactatg atagtagtgg ttacagctac tactactact acatggacgt ctggggcaaa    360

gggaccacgg tcaccgtctc ctca                                           384
```

```
<210> SEQ ID NO 94
<211> LENGTH: 330
<212> TYPE: DNA
<213> ORGANISM: Artificial sequence
<220> FEATURE:
<223> OTHER INFORMATION: Synthetic antibody

<400> SEQUENCE: 94

cagtctgtgc tgactcagcc accctcagcg tctgggaccc ccgggcagag ggtcaccatc     60

tcttgttctg gaagcagctc caacatcgga agtaatactg taaactggta ccagcagctc    120

ccaggaacgg cccccaaact cctcatctat agtaataatc agcggccctc aggggtccct    180

gaccgattct ctggctccaa gtctggcacc tcagcctccc tggccatcag tgggctccag    240

tctgaggatg aggctgatta ttactgtgca gcatgggatg acagcctgaa tggttgggtg    300

ttcggcggag ggaccaagct gaccgtccta                                     330
```

```
<210> SEQ ID NO 95
<211> LENGTH: 363
<212> TYPE: DNA
<213> ORGANISM: Artificial sequence
<220> FEATURE:
<223> OTHER INFORMATION: Synthetic antibody

<400> SEQUENCE: 95

gaggtgcagc tggtggagtc cgggggaggc ttagttcagc ctggggggtc cctgagactc     60

tcctgtgcag cctctggatt caccttcagt agctactgga tgcactgggt ccgccaagct    120

ccagggaagg ggctggtgtg ggtctcacgt attaatagtg atgggagtag cacaagctac    180

gcggactccg tgaagggccg attcaccatc tccagagaca acgccaagaa cacgctgtat    240

ctgcaaatga acagtctgag agccgaggac acggctgtgt attactgtgc aagtggggat    300

agcagtggct ggtacatgcc atttgactac tggggccagg gaaccctggt caccgtctcc    360
```

tca 363

<210> SEQ ID NO 96
<211> LENGTH: 333
<212> TYPE: DNA
<213> ORGANISM: Artificial sequence
<220> FEATURE:
<223> OTHER INFORMATION: Synthetic antibody

<400> SEQUENCE: 96
cagtctgccc tgactcagcc tgcctccgtg tctgggtctc ctggacagtc gatcaccatc 60
tcctgcactg gaaccagcag tgacgttggt ggttataact atgtctcctg gtaccaacag 120
cacccaggca aagcccccaa actcatgatt tatgatgtca gtaatcggcc ctcaggggtt 180
tctaatcgct tctctggctc caagtctggc aacacggcct ccctgaccat ctctgggctc 240
caggctgagg acgaggctga ttattactgc agctcatata caagcagcag cactaatgtg 300
gtattcggcg gagggaccaa gctgaccgtc cta 333

<210> SEQ ID NO 97
<211> LENGTH: 363
<212> TYPE: DNA
<213> ORGANISM: Artificial sequence
<220> FEATURE:
<223> OTHER INFORMATION: Synthetic antibody

<400> SEQUENCE: 97
gaggtgcagc tggtggagtc cgggggaggc ttagttcagc ctggggggtc cctgagactc 60
tcctgtgcag cctctggatt caccttcagt agctactgga tgcactgggt ccgccaagct 120
ccagggaagg ggctggtgtg ggtctcacgt attaatagtg atgggagtag cacaagctac 180
gcggactccg tgaagggccg attcaccatc tccagagaca acgccaagaa cacgctgtat 240
ctgcaaatga acagtctgag agccgaggac acggctgtgt attactgtgc aagtggggat 300
agcagtggct ggtacatgcc atttgactac tggggccagg gaaccctggt caccgtctcc 360
tca 363

<210> SEQ ID NO 98
<211> LENGTH: 333
<212> TYPE: DNA
<213> ORGANISM: Artificial sequence
<220> FEATURE:
<223> OTHER INFORMATION: Synthetic antibody

<400> SEQUENCE: 98
cagtctgccc tgactcagcc tgcctccgtg tctgggtctc ctggacagtc gatcaccatc 60
tcctgcactg gaaccagcag tgacgttggt ggttataact atgtctcctg gtaccaacag 120
cacccaggca aagcccccaa actcatgatt tatgatgtca gtaatcggcc ctcaggggtt 180
tctaatcgct tctctggctc caagtctggc aacacggcct ccctgaccat ctctgggctc 240
caggctgagg acgaggctga ttattactgc agctcatata caagcagcag cactaatgtg 300
gtattcggcg gagggaccaa gctgaccgtc cta 333

<210> SEQ ID NO 99
<211> LENGTH: 363
<212> TYPE: DNA
<213> ORGANISM: Artificial sequence
<220> FEATURE:
<223> OTHER INFORMATION: Synthetic antibody

<400> SEQUENCE: 99

```
caggtgcagc tgcaggagtc gggcccagga ctggtgaagc cttcggggac cctgtccctc     60

acctgcgctg tctctggtgg ctccatcagc agtagtaact ggtggagttg ggtccgccag    120

cccccaggga aggggctgga gtggattggg gaaatctatc atagtgggag caccaactac    180

aacccgtccc tcaagagtcg agtcaccata tcagtagaca agtccaagaa ccagttctcc    240

ctgaagctga gctctgtgac cgccgcggac acggccgtgt attactgtgc gagagattcg    300

cggcagtggc tggtacgggg ttttgactac tggggccagg gaaccctggt caccgtctcc    360

tca                                                                  363

<210> SEQ ID NO 100
<211> LENGTH: 381
<212> TYPE: DNA
<213> ORGANISM: Artificial sequence
<220> FEATURE:
<223> OTHER INFORMATION: Synthetic antibody

<400> SEQUENCE: 100

gaggcacagc tggtggagtc tgggggaggc ttggtaaagc cggggggggtc ccttagactc     60

tcctgtgcag cctctgggtt cagtttcagt tacgcctgga tgagttgggt ccgccgactt    120

ccagggaagg ggctggagtg ggttggccgt attaaaggca aggctgatgg tgagacaact    180

gactacgctg cacccgtgaa aggcagattc accatctcga gagatgattc aaagaccacg    240

gtgtatctgc aaatgaacac cctgaaaatc gaggacacag gcgtctatta ctgtaccaca    300

gatattggcg atttctatga cagtattgga tactcttata ctgactactg gggccaggga    360

accctggtca ccgtctcctc a                                              381

<210> SEQ ID NO 101
<211> LENGTH: 321
<212> TYPE: DNA
<213> ORGANISM: Artificial sequence
<220> FEATURE:
<223> OTHER INFORMATION: Synthetic antibody

<400> SEQUENCE: 101

gaaattgtgt tgacacagtc tccagccacc ctgtctttgt ctccggggga aagagccacc     60

ctctcctgca gggccagtca gagtgtttcc agttacttag cctggtacca acagaaacct    120

ggccaggctc ccaggctcct catctatgat gcatccaaca gggccactgg catcccagtc    180

aggttcagtg gcagtgggtc tgggacagac ttcactctca ccatcagcag cctagagcct    240

gaagattttg cccttttatta ctgtcagcag cgtagcgact ggcctccgac gttcggccaa    300

gggaccaagg tggaaatcaa a                                              321

<210> SEQ ID NO 102
<211> LENGTH: 357
<212> TYPE: DNA
<213> ORGANISM: Artificial sequence
<220> FEATURE:
<223> OTHER INFORMATION: Synthetic antibody

<400> SEQUENCE: 102

caggtgcagc tggtgcagtc tggggctgag gtgaagaagc ctggggcctc agtgaaggtt     60

tcctgcaagg catctggata caccttcacc agctactata tgcactgggt gcgacaggcc    120

cctggacaag ggcttgagtg gatgggaata atcaacccta gtggtggtag cacaagctac    180

gcacagaagt tccagggcag agtcaccatg accagggaca cgtccacgag cacagtctac    240
```

```
atggagctga gcagcctgag atctgaggac acggccgtgt attactgtgc gagagttggg    300

aactactact actacatgga cgtctggggc aaagggacca cggtcaccgt ctcctca       357


<210> SEQ ID NO 103
<211> LENGTH: 324
<212> TYPE: DNA
<213> ORGANISM: Artificial sequence
<220> FEATURE:
<223> OTHER INFORMATION: Synthetic antibody

<400> SEQUENCE: 103

tcctatgtgc tgactcagcc accctcggtg tcagtggccc caggacagac ggccaggatt     60

acctgtgggg gaaacaacat tggaagtaaa agtgtgcact ggtaccagca gaagccaggc    120

caggcccctg tgctggtcgt ctatgatgat agcgaccggc cctcagggat ccctgagcga    180

ttctctggct ccaactctgg gaacacggcc accctgacca tcagcagggt cgaagccggg    240

gatgaggccg actattactg tcaggtgtgg gatagtagta gtgatcattg ggtgttcggc    300

ggagggacca agctgaccgt ccta                                           324


<210> SEQ ID NO 104
<211> LENGTH: 372
<212> TYPE: DNA
<213> ORGANISM: Artificial sequence
<220> FEATURE:
<223> OTHER INFORMATION: Synthetic antibody

<400> SEQUENCE: 104

gaggtgcagc tggtggagtc tgggggaggc ttggtacagc cagggcggtc cctgagactc     60

tcctgtacag cttctggatt cacctttggt gattatgcta tgagctgggt ccgccaggct    120

ccagggaagg ggctggagtg ggtaggtttc attagaagca aagcttatgg tgggacaaga    180

gaatacgccg cgtctgtgaa aggcagattc accatctcaa gagatgattc caaaagcatc    240

gcctatctgc aaatgaacag cctgaaaacc gaggacacag ccgtgtatta ttgtactaac    300

catcgtggca gcagctggta cccggatgct tttgatatct ggggccaagg gacaatggtc    360

accgtctctt ca                                                        372


<210> SEQ ID NO 105
<211> LENGTH: 327
<212> TYPE: DNA
<213> ORGANISM: Artificial sequence
<220> FEATURE:
<223> OTHER INFORMATION: Synthetic antibody

<400> SEQUENCE: 105

tcctatgtgc tgactcagcc accctcggtg tcagtggccc caggaaagac ggccaggatt     60

acctgtgggg gaaacaacat tggaagtaaa agtgtgcact ggtaccagca gaagccaggc    120

caggcccctg tgctggtcgt ctatgatgat agcgaccggc cctcagggat ccctgagcga    180

ttctctggct ccaactctgg gaacacggcc accctgacca tcagcagggt cgaagccggg    240

gatgaggccg actattactg tcaggtgtgg gatagtagta gtgatcccga tgtggtattc    300

ggcggaggga ccaagctgac cgtccta                                        327


<210> SEQ ID NO 106
<211> LENGTH: 351
<212> TYPE: DNA
<213> ORGANISM: Artificial sequence
<220> FEATURE:
<223> OTHER INFORMATION: Synthetic antibody
```

<400> SEQUENCE: 106
caggtgcagc tggtggagtc tgggggaggc gtggtccagc ctgggaggtc cctgagactc 60
tcctgtgcag cctctggatt caccttcagt agttatgcta tgcactgggt ccgccaggct 120
ccaggcaggg ggctggagtg ggtggcagtt atatcatatg atggaagtaa taaatactac 180
gcagactccg tgaagggccg attcaccatc tccagagaca attccaagaa cacgctgtat 240
ctgcaaatga acagcctgag agctgaggac acggctgtgt attactgtgc taaagatata 300
actgggagac ttgactactg gggccaggga accctggtca ccgtctcctc a 351

<210> SEQ ID NO 107
<211> LENGTH: 324
<212> TYPE: DNA
<213> ORGANISM: Artificial sequence
<220> FEATURE:
<223> OTHER INFORMATION: Synthetic antibody

<400> SEQUENCE: 107
tcctatgggc tgactcagcc accctcggtg tcagtggccc caggacagac ggccaggatt 60
acctgtgggg gaaacaacat tggaagtaaa agtgtgaact ggtaccagca gaagccaggc 120
caggcccctg tgctggtcgt ctatgatgat agcgaccggc ccttagggat ccctgagcga 180
ttctctggct ccaactctgg gaacacggcc accctgacca tcagcagggt cgaagccggg 240
gatgaggccg actataactg tcaggtgtgg gatagtagta gtgatcattg ggtgttcggc 300
ggagggacca agctgaccgt ccta 324

<210> SEQ ID NO 108
<211> LENGTH: 348
<212> TYPE: DNA
<213> ORGANISM: Artificial sequence
<220> FEATURE:
<223> OTHER INFORMATION: Synthetic antibody

<400> SEQUENCE: 108
gaggtgcagc tggtggagtc tgggggaggc ttggtacagc ctggggggtc cctgagactc 60
tcctgtgcag cctctggatt caccttcagt agctacgaca tgcactgggt ccgccaagct 120
acaggaaaag gtctggaatg ggtctcagct attggtactg ctggtgacac atactatcca 180
ggctccgtga agggccgatt caccatctcc agagaaagtg ccaagaactc cttgtatctt 240
caaatgaaca gcctgagagc cggggacacg gctgtgtatt actgtgcaag aggtcttgga 300
ggggggtttg actactgggg ccagggaacc ctggtcaccg tctcctca 348

<210> SEQ ID NO 109
<211> LENGTH: 324
<212> TYPE: DNA
<213> ORGANISM: Artificial sequence
<220> FEATURE:
<223> OTHER INFORMATION: Synthetic antibody

<400> SEQUENCE: 109
tcctatgtgc tgactcagcc accctcggtg tcagtggccc caggaaagac ggccaggatt 60
acctgtgggg gaaacaacat tggaagtaaa agtgtgcact ggtaccagca gaagccaggc 120
caggcccctg tgctggtcgt ctatgatgat agcgaccggc cctcagggat ccctgagcga 180
ttctctggct ccaactctgg gaacacggcc accctgacca tcagcagggt cgaagccggg 240
gatgaggccg actattactg tcaggtgtgg gatagtagta gcgatcatta tgtcttcgga 300
actgggacca aggtcaccgt ccta 324

<210> SEQ ID NO 110
<211> LENGTH: 363
<212> TYPE: DNA
<213> ORGANISM: Artificial sequence
<220> FEATURE:
<223> OTHER INFORMATION: Synthetic antibody

<400> SEQUENCE: 110
gaggtgcagc tgttggagtc tggggggaggc ttggtacagc cggggggggtc cctgagactc 60 tcctgcgtag cctctggatt cacctttagc aactatgcca tgagctgggt ccgccaggct 120
ccagggaagg ggctggagtg ggtctccgcg attagcggta atgttgataa cacacactac 180
gcagactccg tgaagggccg gttcaccatc tccagagaca attccaagag cacactgttt 240
ctgcaaatgc acagcctgag agccgaggac acggccgtat atttctgtgc gaaagtgggc 300
caatattgga gtggtcatta tctggactac tggggccagg gaaccctggt caccgtctcc 360
tca 363

<210> SEQ ID NO 111
<211> LENGTH: 324
<212> TYPE: DNA
<213> ORGANISM: Artificial sequence
<220> FEATURE:
<223> OTHER INFORMATION: Synthetic antibody

<400> SEQUENCE: 111
tcctatgtgc tgactcagcc accctcggtg tcagtggccc caggacagac ggccaggatg 60
acctgtgggg gaaacaatat tggaagtaaa agtgtgcact ggtatcagca gaagccaggc 120
caggcccctg tactggtcgt ctatgatgat agcgaccggc cctcggggat ccctgagcga 180
ttctctggct ccaactctgg gaacacggcc accctgacca tcaacagggt cgaagccggg 240
gatgaggccg actattactg tcaggtgtgg catagtgata gtgatcaata tgtcttcgga 300
actgggacga aggtcaccgt ccta 324

<210> SEQ ID NO 112
<211> LENGTH: 363
<212> TYPE: DNA
<213> ORGANISM: Artificial sequence
<220> FEATURE:
<223> OTHER INFORMATION: Synthetic antibody

<400> SEQUENCE: 112
gaggtgcagc tgttggagtc tggggggaggc ttggtacacc ctggggggtc cctgagactc 60
tcctgtgcag cctctggatt cacctttagc agctatgcca tgagctgggt ccgccaggct 120
ccagggaagg ggctggagtg ggtctcagct attagtggta gtggtggcag cacatactac 180
gcagactccg tgaagggccg gttcaccatc tccagagaca atttcaagaa cacactgtat 240
gtgcaaatga acagcctgag agccgaggac acggccgtat attactgtgc gacagagaac 300
gacttttgga gtggtcacca gtttgactac tggggccagg gaaccctggt cactgtctcc 360
tca 363

<210> SEQ ID NO 113
<211> LENGTH: 324
<212> TYPE: DNA
<213> ORGANISM: Artificial sequence
<220> FEATURE:
<223> OTHER INFORMATION: Synthetic antibody

<400> SEQUENCE: 113
tcctatgtgc tgactcagcc accctcggtg tcagtggccc caggacagac ggccaggatg 60
acctgtgggg gaaacaatat tggaagtaaa agtgtgcagt ggtaccagca gaagccaggc 120
caggcccctg tgctggtcgt ccatgatgat agcgaccggc cctcagggat ccctgagcga 180
ttctctggct ccaactctgg gaacacggcc accctgacca tcagcagggt cgaagccggg 240
gatgaggccg actattactg tcaggtgtgg gatagtagta gtgatcattg ggtgttcggc 300
ggagggacca agctgaccgt ccta 324

<210> SEQ ID NO 114
<211> LENGTH: 348
<212> TYPE: DNA
<213> ORGANISM: Artificial sequence
<220> FEATURE:
<223> OTHER INFORMATION: Synthetic antibody

<400> SEQUENCE: 114
gaggtgcagc tggtggagtc tgggggaggc ttggtacagc ctggggggtc cctgagactc 60
tcctgtgcag cctctggatt caccttcagt agctacgaca tgcactgggt ccgccaagct 120
acaggaaaag gtctggagtg ggtctcagct attggtactg ctggtgacac atactatcca 180
ggctccgtga agggccgatt caccatctcc agagaaaatg ccaagaactc cttgtatctt 240
caaatgaaca gcctgagagc cggggacacg gctgtgtatt actgtgcaag agcggtgggg 300
ggggggtttg actactgggg ccagggaacc ctggtcaccg tctcctca 348

<210> SEQ ID NO 115
<211> LENGTH: 324
<212> TYPE: DNA
<213> ORGANISM: Artificial sequence
<220> FEATURE:
<223> OTHER INFORMATION: Synthetic antibody

<400> SEQUENCE: 115
tcctatgtgc tgactcagcc accctcggtg tcagtggccc caggaaagac ggccaggatt 60
acctgtgggg gaaacaacat tggaagtaaa agtgtgcact ggtaccagca gaagccaggc 120
caggcccctg tgctggtcgt ctatgatgat agcgaccggc cctcagggat ccctgagcga 180
ttctctggct ccaactctgg gaacacggcc accctgacca tcagcagggt cgaagccggg 240
gatgaggccg actattactg tcaggtgtgg gatagtagta gtgatcttta tgtcttcgga 300
actgggacca aggtcaccgt ccta 324

<210> SEQ ID NO 116
<211> LENGTH: 369
<212> TYPE: DNA
<213> ORGANISM: Artificial sequence
<220> FEATURE:
<223> OTHER INFORMATION: Synthetic antibody

<400> SEQUENCE: 116
caggtgcagc tgcaggagtc gggcccagga ctggtgaagc cttcggagac cctgtccctc 60
acctgcactg tctctggtgg ctccatcagt agttactact ggagctggat ccggcagccc 120
ccagggaagg gactggagtg gattgggtat atctattaca gtgggagcac caactacaac 180
ccctccctca agagtcgagt caccatatca gtagacacgt ccaagaacca gttctccctg 240
aagctgagct ctgtgaccgc tgcggacacg gccgtgtatt actgtgcgag agggtcaagg 300

```
gcaattttga ctggttaccc caactggttc gacccctggg gccagggaac cctggtcacc    360

gtctcctca                                                            369


<210> SEQ ID NO 117
<211> LENGTH: 321
<212> TYPE: DNA
<213> ORGANISM: Artificial sequence
<220> FEATURE:
<223> OTHER INFORMATION: Synthetic antibody

<400> SEQUENCE: 117

gacatccaga tgacccagtc tccatcctcc ctgtctgcat ctgtaggaga cagagtcacc     60

atcacttgcc gggcaagtca gagcattagc agctatttaa attggtatca gcagaaacca    120

gggaaagccc ctaagctcct gatctatgct gcatccagtt tgcaaagtgg ggtcccatca    180

aggttcagtg gcagtggatc tgggacagat ttcactctca ccatcagcag tctgcaacct    240

gaagattttg caacttacta ctgtcaacag agttacagta ctccgtacac ttttggccag    300

gggaccaagc tggagatcaa a                                              321


<210> SEQ ID NO 118
<211> LENGTH: 369
<212> TYPE: DNA
<213> ORGANISM: Artificial sequence
<220> FEATURE:
<223> OTHER INFORMATION: Synthetic antibody

<400> SEQUENCE: 118

gaagtgcagc tggtggagtc tgggggaggc ttggtacagc ctggcaggtc cctgagactc     60

tcctgtgcag cctctggatt cacctttgat gactatgcca tgcactgggt ccggcaagct    120

ccagggaagg gcctggagtg ggtctcaggt attagttgga atagtggtag cataggctat    180

gcggactctg tgaagggccg attcaccatc tccagagaca acgccaagaa ctccctgtat    240

ctgcaaatga acagtctgag aactgaggac acggccttct attactgtgc aaaagataaa    300

ggagatggtt cggggagttt ctactacatg gacgtctggg gcaaagggac cacggtcacc    360

gtctcctca                                                            369


<210> SEQ ID NO 119
<211> LENGTH: 321
<212> TYPE: DNA
<213> ORGANISM: Artificial sequence
<220> FEATURE:
<223> OTHER INFORMATION: Synthetic antibody

<400> SEQUENCE: 119

gacatccaga tgacccagtc tccatcctcc ctgtctgcat ctgtaggaga cagagtcacc     60

atcacttgcc aggcgagtca ggacattagc aactatttaa attggtatca gcagaaacca    120

gggaaagccc ctaagctcct gatctacgat gcatccaatt tggaaacagg ggtcccatca    180

aggttcagtg gaagtggatc tgggacagat tttactttca ccatcagcag cctgcagcct    240

gaagatattg caacatattc ctgtcaacag tatgataatc tcccgctcac tttcggcgga    300

gggaccaagg tggagatcaa a                                              321


<210> SEQ ID NO 120
<211> LENGTH: 348
<212> TYPE: DNA
<213> ORGANISM: Artificial sequence
<220> FEATURE:
<223> OTHER INFORMATION: Synthetic antibody
```

<400> SEQUENCE: 120
caggtgcagc tgcaggagtc gggcccagga ctggtgaagc cttcggagac cctgtccctc 60
acctgcactg tctctggtgg ctccatcagt agttactact ggagctggat ccggcagccc 120
ccagggaagg gactggagtg gattgggtat atctattaca gtgggagcac caactacaac 180
ccctccctca agagtcgagt caccatatca gtagacacgt ccaagaacca gttctccctg 240
aagctgagct ctgtgaccgc tgcggacacg gccgtgtatt actgtgcgag agggttgggg 300
gtagtagtct ggccctgggg ccagggaacc ctggtcaccg tctcctca 348

<210> SEQ ID NO 121
<211> LENGTH: 345
<212> TYPE: DNA
<213> ORGANISM: Artificial sequence
<220> FEATURE:
<223> OTHER INFORMATION: Synthetic antibody

<400> SEQUENCE: 121
cagcctgtgc tgactcagcc accttcctcc tccgcatctc ctggagaatc cgccagactc 60
acctgcacct tgcccagtga catcaatgtt ggtagctaca acatatactg gtaccagcag 120
aagccaggga gccctcccag gtatctcctg tactactact cagactcaga taagggccag 180
ggctctggag tccccagccg cttctctgga tccaaagatg cttcagccaa tacagggatt 240
ttactcatct ccgggctcca gtctgaggat gaggctgact attactgtat gatttggcca 300
agcaatgcct gggtgttcgg cggagggacc aagctgaccg tccta 345

<210> SEQ ID NO 122
<211> LENGTH: 351
<212> TYPE: DNA
<213> ORGANISM: Artificial sequence
<220> FEATURE:
<223> OTHER INFORMATION: Synthetic antibody

<400> SEQUENCE: 122
caggtgcagc tggtggagtc tgggggaggc gtggtccagc ctgggaggtc cctgagactc 60
tcctgtgcag cctctggatt caccttcagt agctatggca tgcactgggt ccgccaggct 120
ccaggcaagg ggctggagtg ggtggcagtt atatcatatg atggaagtaa taaatactat 180
gcagactccg tgaagggccg attcaccatc tccagagaca attccaagaa cacgctgtat 240
ctgcaaatga acagcctgag agctgaggac acggctgtgt attactgtgc gaaagctttg 300
agcagtggct ggtacgaatg gggccaggga accctggtca ccgtctcctc a 351

<210> SEQ ID NO 123
<211> LENGTH: 324
<212> TYPE: DNA
<213> ORGANISM: Artificial sequence
<220> FEATURE:
<223> OTHER INFORMATION: Synthetic antibody

<400> SEQUENCE: 123
tcctatgtgc tgactcagcc accctcggtg tcagtggccc caggacagac ggccaggatt 60
acctgtgggg gaaacaacat tggaagtaaa agtgtgcact ggtaccagca gaagccaggc 120
caggcccctg tgctggtcgt ctatgatgat agcgaccggc cctcagggat ccctgagcga 180
ttctctggct ccaactctgg gaacacggcc accctgacca tcagcagggt cgaagccggg 240
gatgaggccg actattactg tcaggtgtgg gatagtagta gtgatcatta tgtcttcgga 300
actgggacca aggtcaccgt ccta 324

<210> SEQ ID NO 124
<211> LENGTH: 351
<212> TYPE: DNA
<213> ORGANISM: Artificial sequence
<220> FEATURE:
<223> OTHER INFORMATION: Synthetic antibody

<400> SEQUENCE: 124
caggtgcagc tgcaggagtc gggcccagga ctggtgaagc cttcggagac cctgtccctc 60
acctgcactg tctctggtgg ctccatcagt agttactact ggagctggat ccggcagccc 120
ccagggaagg gactggagtg gatcgggtat atctattaca gtgggagcac caactacaac 180
ccctccctca agagtcgagt caccatatca ttagacacgt ccaagaacca gttctccctg 240
aagctgagct ctgtgaccgc tgcggacacg gccgtgtatt actgtgcgag gggactccgg 300
ccggatgctt ttgatatctg gggccaaggg acaatggtca ccgtctcttc a 351

<210> SEQ ID NO 125
<211> LENGTH: 324
<212> TYPE: DNA
<213> ORGANISM: Artificial sequence
<220> FEATURE:
<223> OTHER INFORMATION: Synthetic antibody

<400> SEQUENCE: 125
tcctatgtgc tgactcagcc accctcggtg tcagtggccc caggacagac ggccaggatt 60
acctgtgggg gaaacaacat tggaagtaaa agtgtgcact ggtaccagca gaagccaggc 120
caggcccctg ggctggtcgt ctatgatgat agcgaccggc cctcagggat ccctgagcga 180
ttctctggct ccaactctgg gaacacggcc accctgacca tcagcagggt cgaagccggg 240
gatgaggccg actattactg tcaggtgtgg gatagtagta gtgatcatgt ggtattcggc 300
ggagggacca agctgaccgt ccta 324

<210> SEQ ID NO 126
<211> LENGTH: 363
<212> TYPE: DNA
<213> ORGANISM: Artificial sequence
<220> FEATURE:
<223> OTHER INFORMATION: Synthetic antibody

<400> SEQUENCE: 126
gaagtgcagc tggtgcagtc tggagcagag gtgaaaaagc ccggggagtc tctgaggatc 60
tcctgtaagg gttctggata cagctttacc agctactgga tcagctgggt gcgccagatg 120
cccgggaaag gcctggaatg gatggggagg attgagccta gtgactctta taccaactac 180
agcccgtcct tccaaggcca cgtcaccatc tcagctgaca agtccatcag cactgcctac 240
ctgcagtgga gcagcctgaa ggcctcggac accgccatgt attattgtgc gagactaggt 300
gatagtagtg gttacgggga gattgactac tggggccagg gaaccctggt caccgtctcc 360
tca 363

<210> SEQ ID NO 127
<211> LENGTH: 321
<212> TYPE: DNA
<213> ORGANISM: Artificial sequence
<220> FEATURE:
<223> OTHER INFORMATION: Synthetic antibody

<400> SEQUENCE: 127
gacatccaga tgacccagtc tccatcctcc ctgtctgcat ctgtaggaga cagagtcacc 60
atcacttgcc gggcaagtca gagcattagc agctatttaa attggtatca gcagaaacca 120
gggaaagccc ctaagctcct gatctatgct gcatccagtt tgcaaagtgg ggtcccatca 180
aggttcagtg gcagtggatc tgggacagat ttcactctca ccatcagcag tctgcaacct 240
gaagattttg caacttacta ctgtcaacag agttacagta cccctcagac gttcggccaa 300
gggaccaagg tggaaatcaa a 321

<210> SEQ ID NO 128
<211> LENGTH: 351
<212> TYPE: DNA
<213> ORGANISM: Artificial sequence
<220> FEATURE:
<223> OTHER INFORMATION: Synthetic antibody

<400> SEQUENCE: 128
caggtgcagc tgatgcagtc tggggctgag gtgaagaagc ctggggcctc agtgaaggtt 60
tcctgcaggg catctggaaa caccttcacc agctactata tgcactgggt gcgacaggcc 120
cctggacaag ggcttgagtg gatgggaata atcaacccta gtggtggtag cacaatctac 180
gcacagaagt tccagggcag agtcaccatg accagggaca cgtccacgag cacagtatac 240
atggagttga gcagcctgaa atctgaggac acggccgtgt attactgtgc gagaggcgaa 300
tcgtactact ttgactactg gggccaggga accctggtca ccgtctcctc a 351

<210> SEQ ID NO 129
<211> LENGTH: 324
<212> TYPE: DNA
<213> ORGANISM: Artificial sequence
<220> FEATURE:
<223> OTHER INFORMATION: Synthetic antibody

<400> SEQUENCE: 129
tcctatgtgc tgactcagcc accctcggtg tcagtggccc caggaaagac ggccaggatt 60
acctgtgggg gaaacaacat tgaaagtaaa agtgtgcact ggtaccagca gaagccaggc 120
caggcccctg tgctggtcgt ctatgatgat accgaccggc cctcagggat ccctgagcga 180
ttctctggct ccaactctgg gaacacggcc accctgacca tcagcagggt cgaagccggg 240
gatgaggccg actattactg tcaggtgtgg gatagtagta gtgatcattg cgtgttcggc 300
ggagggacca agctgaccgt ccta 324

<210> SEQ ID NO 130
<211> LENGTH: 354
<212> TYPE: DNA
<213> ORGANISM: Artificial sequence
<220> FEATURE:
<223> OTHER INFORMATION: Synthetic antibody

<400> SEQUENCE: 130
gaggtgcagc tggtggagtc tgggggaggc ttggtacagc ctggggggtc cctgagactc 60
tcctgtgcag cctctggatt caccttcagt agctatagca tgaactgggt ccgccaggct 120
ccagggaagg ggctggagtg ggtttcatac attagtagta gtagtagtac catatactac 180
gcagactctg tgaagggccg attcaccatc tccagagaca atgccaagaa ctcactgtat 240
ctgcaaatga acagcctgag agacgaggac acggctgtgt attactgtgc gagagatttt 300
tacccagctg ctatggacgt ctggggcaaa gggaccacgg tcaccgtctc ctca 354

<210> SEQ ID NO 131
<211> LENGTH: 324
<212> TYPE: DNA
<213> ORGANISM: Artificial sequence
<220> FEATURE:
<223> OTHER INFORMATION: Synthetic antibody

<400> SEQUENCE: 131

```
tcctatgtgc tgactcagcc accctcggtg tcagtggccc caggacagac ggccaggatt     60

acctgtgggg gaaacaacat tggaagtaaa agtgtgcact ggtaccagca gaagccaggc    120

caggcccctg tgctggtcgt ctatgatgat agcgaccggc cctcagggat ccctgagcga    180

ttctctggct ccaactctgg gaacacggcc accctgacca tcagcagggt cgaagccggg    240

gatgaggccg actattactg tcaggtgtgg gatagtagta gtgatcatcg ggtgttcggc    300

ggagggacca agctgaccgt ccta                                           324
```

<210> SEQ ID NO 132
<211> LENGTH: 363
<212> TYPE: DNA
<213> ORGANISM: Artificial sequence
<220> FEATURE:
<223> OTHER INFORMATION: Synthetic antibody

<400> SEQUENCE: 132

```
gaggtgcagc tggtgcagtc tggagcagag gtgaaaaagc ccggggagtc tctgaggatc     60

tcctgtaagg gttctggata cagctttacc agctactgga tcagctgggt gcgccagatg    120

cccgggaaag gcctggaatg gatggggagg attgagccta gtgactctta taccaactac    180

agcccgtcct tccaaggcca cgtcaccatc tcagctgaca agtccatcag cactgcctac    240

ctgcagtgga gcagcctgaa ggcctcggac accgccatgt attattgtgc gagactaggt    300

gatagtagtg gttacgggga gattgactac tggggccagg gaaccctggt caccgtctcc    360

tca                                                                  363
```

<210> SEQ ID NO 133
<211> LENGTH: 321
<212> TYPE: DNA
<213> ORGANISM: Artificial sequence
<220> FEATURE:
<223> OTHER INFORMATION: Synthetic antibody

<400> SEQUENCE: 133

```
gacatccaga tgacccagtc tccatcctcc ctgtctgcat ctgtaggaga cagagtcacc     60

atcacttgcc gggcaagtca gagcattagc agctatttaa attggtatca gcagaaacca    120

gggaaagccc ctaagctcct gatctatgct gcatccagtt tgcaaagtgg ggtcccatca    180

aggttcagtg gcagtggatc tgggacagat ttcactctca ccatcagcag tctgcaacct    240

gaagattttg caacttacta ctgtcaacag agttacagta cccctcagac gttcggccaa    300

gggaccaagg tggaaatcaa a                                              321
```

<210> SEQ ID NO 134
<211> LENGTH: 360
<212> TYPE: DNA
<213> ORGANISM: Artificial sequence
<220> FEATURE:
<223> OTHER INFORMATION: Synthetic antibody

<400> SEQUENCE: 134

```
caggtgcagc tgcaggagtc gggcccagga ctggtgaagc cttcacagac cctgtccctc     60
```

acctgcactg tctctggtga ctccatcagc ggtggtgatt attactggag ttggatccgg 120
cggcccgccg gggagggcct ggagtggatt gggcgtgttc atactactgg gagtaccgac 180
tacaacccct ccctcaggac tcgagtcacc atatcaatag acacgtccaa gaaccacttc 240
tttctgaaga tgacctctgt gaccgccgca gacacggccg tgtattactg tgcgagagag 300
ggggattata gtgcctggtt cgacccctgg ggccagggag ccctggtcac cgtctcctca 360

<210> SEQ ID NO 135
<211> LENGTH: 324
<212> TYPE: DNA
<213> ORGANISM: Artificial sequence
<220> FEATURE:
<223> OTHER INFORMATION: Synthetic antibody

<400> SEQUENCE: 135
gacatccaga tgacccagtc tccttcctcc ctgtctgcat ctataggaga cagagtcacc 60
atcacttgcc gggcaagtca gcacattgag agttttttaa attggtatca gcagaaacca 120
gggaaagccc ctaaactcct aatctatatt gcatccactt tgcaaggtgg ggtcccatca 180
aggttcagtg gccgtggatt tgggacagat ttcactctca ccatcaacag tctgcaacct 240
gaagattttg caacttacta ctgtcagcag agttacacta tctctccgat caccttcggc 300
caggggacac gactggaaat taaa 324

<210> SEQ ID NO 136
<211> LENGTH: 372
<212> TYPE: DNA
<213> ORGANISM: Artificial sequence
<220> FEATURE:
<223> OTHER INFORMATION: Synthetic antibody

<400> SEQUENCE: 136
caggagcagt tggttgagtc tgggggaggc gtggtccagc ctgggaggtc cctgagactc 60
tcctgtgcag cctctggatt caccctcagg ggctatggaa tttactgggt ccgccaggct 120
ccaggcaagg ggctggagtg ggtggcagtt atatcacatg atggcaaaaa tgaatcttac 180
acagactccg tgaagggccg attctccatc tccagagaca aaagtaagaa tacggtcttt 240
ctgcaaatga acagcctgac aactcaagac acttctgtct attactgtgc gagatggact 300
gagggatcag aggaattcta ctaccatggt ctggacgtct ggggccaagg gaccacggtc 360
accgtctccc ca 372

<210> SEQ ID NO 137
<211> LENGTH: 327
<212> TYPE: DNA
<213> ORGANISM: Artificial sequence
<220> FEATURE:
<223> OTHER INFORMATION: Synthetic antibody

<400> SEQUENCE: 137
tcctatgagc tgacacagcc accgtcggtg tcagtgtccc caggacagac ggccaggatc 60
acctgctctg gacatctact gccaaaacaa tatgcttatt ggtaccagca gaagccaggc 120
caggccccga cactggtgat atatgcagac tataacaggg cctcagggat ccctgagcga 180
ttctctggcg ccagctcagg gaccacagtc accttgacca tcactggggt caaggcagaa 240
gaccaggctg actattattg tcaatcaata gacaatcgtt ttcattatcc tatgatattc 300
ggcggcggga ccaaactgac cgtccta 327

<210> SEQ ID NO 138
<211> LENGTH: 390
<212> TYPE: DNA
<213> ORGANISM: Artificial sequence
<220> FEATURE:
<223> OTHER INFORMATION: Synthetic antibody

<400> SEQUENCE: 138
cagatcacct tcaaggagtc tggtcctacg ctggtgaaac ccacacagac cctcacgctg 60
acctgcacct tctctgggtt ctcactcagc actagtggag tgggtgtggg ctggatccgt 120
cagcccccag gaaaggccct ggagtggctt gccctccttt attggaatga tgataagcgc 180
tacaccccat ctctgaggag caggctcacc atcaccaagg acacctccaa aaaccaggtg 240
gtcctcacaa tgaccgacat ggaccctgtt gacacagcca catattattg tgcacgcaag 300
cctagggacg acttcttacg tcttactatg atgggggggg gggattactt tgactactgg 360
ggccagggaa ccctggtcac cgtctcctca 390

<210> SEQ ID NO 139
<211> LENGTH: 327
<212> TYPE: DNA
<213> ORGANISM: Artificial sequence
<220> FEATURE:
<223> OTHER INFORMATION: Synthetic antibody

<400> SEQUENCE: 139
tcctatgagc tgacacagcc accctcggtg tcagtgtccc caggacagac ggccaggatc 60
acctgctctg gagatgcatt gccagaccaa tatgcttatt ggtaccagca gaagccaggc 120
caggcccctg tcctggtgtt atataaagac aatgagaggc cctcagggat ccctgagcga 180
ttctctggct ccacctcagg gacaacagtc acgttgacca tcagtggagt ccaggcagaa 240
gacgaggctg actattactg tcaatcagca gacaccagta ctgcttacca tgttatattc 300
ggcggaggga ccaagctgac cgtccta 327

<210> SEQ ID NO 140
<211> LENGTH: 363
<212> TYPE: DNA
<213> ORGANISM: Artificial sequence
<220> FEATURE:
<223> OTHER INFORMATION: Synthetic antibody

<400> SEQUENCE: 140
gaggtgcagc tggtggagtc tgggggaggg ttggtgcagc ctggagggtc cctgagactc 60
tcctgtgcag cctctggatt caccttcagt agttttgaaa tgaactgggt ccgccaggct 120
ccagggaagg gcctggagtg ggtttcatac attagtagga gtggtactac caaacactac 180
gcagactctg tgaagggccg attcgccatc tccagagacg acgccaagaa ctcactttat 240
ctgcaaatga acagtctgag agccgaggac acggctgttt attactgtgc gagaggggga 300
gcccgggtgc tacaggcccc tcttgactac tggggccagg gaaccctggt caccgtctcc 360
tca 363

<210> SEQ ID NO 141
<211> LENGTH: 324
<212> TYPE: DNA
<213> ORGANISM: Artificial sequence
<220> FEATURE:
<223> OTHER INFORMATION: Synthetic antibody

<400> SEQUENCE: 141

```
tcctatgagc tgactcagcc accctcagtg tcagtggccc caggagagac ggccaggatt     60

acctgtggtg gaaccaacat tggaaataaa agtgtgcgct ggtaccagca gaagccaggc    120

caggcccctg tgttggtcat ctattatgat aacgaccggc cgtcagggat ccctgagcga    180

ttctctggct ccaactctgg gaacacggcc accctgacca tcagcagggt cgaagccggg    240

gatgaggccg actactactg tcaggtgtgg gataatagta gtgatcacgc ggtattcggc    300

ggagggacca agctgaccgt ccta                                           324
```

<210> SEQ ID NO 142
<211> LENGTH: 363
<212> TYPE: DNA
<213> ORGANISM: Artificial sequence
<220> FEATURE:
<223> OTHER INFORMATION: Synthetic antibody

<400> SEQUENCE: 142

```
caggtgcagc tggtgcagtc tggggctgag gtgaagaagc ctggggcctc agtgaaggtt     60

tcctgcaagg catctggata caccttcacc gactattata tgcactgggt gcgacaggcc    120

cctggacaag ggcttgagtg gatgggaata atcaacccta gtggtggcag cacaaactac    180

gcacagaatt tccagggcag agtcaccatg accagggaca cgtccacgac cacagtctac    240

atggagctga gcagcctgag atctgaggac acggccgtgt attactgtgc gagagcaatt    300

tactggaacg tcccgtacta ttttgactac tggggccagg gaaccctggt caccgtctcc    360

tca                                                                  363
```

<210> SEQ ID NO 143
<211> LENGTH: 321
<212> TYPE: DNA
<213> ORGANISM: Artificial sequence
<220> FEATURE:
<223> OTHER INFORMATION: Synthetic antibody

<400> SEQUENCE: 143

```
gaaactgtgt tgacgcagtc tccaggcact ctgtctttgt ctccagggga aagagccacc     60

ctctcctgca gggccagtca gagtgttagc agcagctggt tagcctggta ccagcagaaa    120

cctggccagg ctcccaggct cctcatctat gatgcatcca gggccactgg catcccagac    180

aggttcagtg gcagtgggtc tgggacagac ttcactctca ccatcagcag attggagcct    240

gaagatttag cagtgtatta ctgtcagcag tatggtaact cacctacaac gttcggccaa    300

gggaccaagg tggaaatcaa a                                              321
```

<210> SEQ ID NO 144
<211> LENGTH: 369
<212> TYPE: DNA
<213> ORGANISM: Artificial sequence
<220> FEATURE:
<223> OTHER INFORMATION: Synthetic antibody

<400> SEQUENCE: 144

```
caggtgcagc tgcaggagtc gggcccagga ctgctgaagc cttcacagac cctgtccctc     60

acctgcggtg tctctggtga ctccatcacc agtactggtg actcctggac ctggatccgg    120

cagccaccag ggaaggggct ggagtggatt gggtatatct attacagtgg gagcgcctac    180

tataacccgt ccctcaagag tcgagtcacc atttcagtag acacgtccaa gaaccagttc    240

tccctgaggc tgaggtctgt gaccgccgcg gacacggccg tctattattg tgccagagcc    300
```

```
ttggagtatg gtgcagggag ttgggcggcg gccttctggg gccagggaat actagtcacc    360

gtctcctca                                                             369


<210> SEQ ID NO 145
<211> LENGTH: 318
<212> TYPE: DNA
<213> ORGANISM: Artificial sequence
<220> FEATURE:
<223> OTHER INFORMATION: Synthetic antibody

<400> SEQUENCE: 145

tcctatgagg tgactcaacc accctcagtg tccgtgtccc caggacagac agccagcatc     60

acctgttctg gagataaatt ggtggagaga tatgtttcct ggtatcagca gaagcctggc    120

cagtcccctc tactagtcat ctatcatgat atcaaacggc cctcagggat ccctgagcga    180

ttctctggct ccaactctgg gaacacagcc actctgacca tcagcgggac ccagcctatg    240

gatgaggccg actattactg tcaggcgtgg gacagcagca ctgtgctctt cggcggaggg    300

accaagctga ccgtccta                                                   318


<210> SEQ ID NO 146
<211> LENGTH: 372
<212> TYPE: DNA
<213> ORGANISM: Artificial sequence
<220> FEATURE:
<223> OTHER INFORMATION: Synthetic antibody

<400> SEQUENCE: 146

caggtccagc tggtgcagtc tggggctgag gtgaagaagc ctgggtcctc ggtgaaggtc     60

tcctgcaggg cttctggagg cacattcagc agctatacta tcagctgggt gcgacaggcc    120

cctggccaag gacttgagtg gatgggggg atcatcccta tccttggtct aacaaagttc    180

gcacagaagt tccaggacag agtcaccatt accgcggaca tatccgcgac cacaacctac    240

atggaactga gtagcctgac atctgaggac acggccgtct attactgtgc gagaaatggg    300

gagcagctcg agtggagcta ctactacggt atggacgtct ggggccaagg gaccacggtc    360

accgtctcct ca                                                         372


<210> SEQ ID NO 147
<211> LENGTH: 339
<212> TYPE: DNA
<213> ORGANISM: Artificial sequence
<220> FEATURE:
<223> OTHER INFORMATION: Synthetic antibody

<400> SEQUENCE: 147

gacatcgtga tgacccagtc tccagactcc ctggctgtgt ctctgggcga gagggccacc     60

atcaactgca agcccagcca gagtatttta tacagctcca acaataagaa ctacttagct    120

tggtaccagc agaaaccagg acagcctcct aaactgctca ttaactgggc atctacccgg    180

gaatccgggg tccctgaccg attcagtggc agcgggtctg ggacagactt cactctcacc    240

atcagcagcc tgcaggctga agatgtggca gttttttact gtcaacaata ttatactatt    300

cccccgacgt tcggccaagg gaccaaggtg gaaatcaaa                            339


<210> SEQ ID NO 148
<211> LENGTH: 369
<212> TYPE: DNA
<213> ORGANISM: Artificial sequence
<220> FEATURE:
<223> OTHER INFORMATION: Synthetic antibody
```

<400> SEQUENCE: 148
caggtgcagc tacagcagtg gggcgcagga ctattgaagc cttcggagac cctgtccctc 60
acctgcactg tctatggtgg gtccttcact ctttactact ggacctggat ccgccagccc 120
ccagggaagg ggctggagtg gattggggaa atcaatcaga gtggaagcac caactacaac 180
ccgtccctca ggagtcgact caccatatca gtagacacgt ccaagagcca gttctccctg 240
aaggtgacct ctgtgaccgc cgcggacacg gctgtgtatt actgtgcgag aggccatgat 300
agtagtggtt attatatcga ctactacttg gacgtctggg gcaaagggac cacggtcacc 360
gtctcctca 369

<210> SEQ ID NO 149
<211> LENGTH: 324
<212> TYPE: DNA
<213> ORGANISM: Artificial sequence
<220> FEATURE:
<223> OTHER INFORMATION: Synthetic antibody

<400> SEQUENCE: 149
tcttctgagc tgactcagga ccctgctgtg tctgtggcct tgggacagac agtcaggatc 60
acatgccaag gagacagcct cagaaactat tatgcaggct ggtaccagca gaggccagga 120
caggcccctg ttcttgtctt ctatggtaaa gacaaccggc cctcagggat cccagaccga 180
ttctctggct ccagctcagg aaacacagct tccttgacca tcactggggc tcaggcggaa 240
gatgaggctg actattactg taactcccgg gacagcagtg gtgacgttgt ggtattcggc 300
ggagggacca agctgaccgt ccta 324

<210> SEQ ID NO 150
<211> LENGTH: 366
<212> TYPE: DNA
<213> ORGANISM: Artificial sequence
<220> FEATURE:
<223> OTHER INFORMATION: Synthetic antibody

<400> SEQUENCE: 150
caggtgcagc tgcacgagtc gggcccagga ctggtgaagc cttcggagac cctgtccctc 60
acctgcggtg tctctggtta caccataagc agtgattact actggggctg gatccggcag 120
cccccaggga aggggctgga gtggattggg agtatctatc aaaatgggca cacctactac 180
aacccgtccc tcaagagtcg agtcaccatt tcggtagaca cgtccaagaa ccaattctcc 240
ctagagctga gctctgtgac cgccgcagac acggccgtat attactgtgc gagaaggggg 300
gattgtggtg ctgattgcta ccactttgac tattggggcc ggggaacggc ggtcaccgtc 360
tcctca 366

<210> SEQ ID NO 151
<211> LENGTH: 324
<212> TYPE: DNA
<213> ORGANISM: Artificial sequence
<220> FEATURE:
<223> OTHER INFORMATION: Synthetic antibody

<400> SEQUENCE: 151
tcctatgagg tgactcagcc actctcagtg tccgtgtccc caggacagac agccagcatc 60
acctgctctg gagaaaaatt ggaaaataaa tatgtttcct ggtatcagca gaagccaggc 120
cagtcccctg tactggttat gtatcaagat ttcaagcggc cctcagggat ccctgagcga 180
ttctctggct ccaactctgg gaacacagcc actctgacca tcagcgggac ccaggctatg 240
gatgaggctg actattactg tcaggcgtgg gacaggagca ccttttatgt cttcggaact 300
gggaccaagg tcaccgtcgt aggt 324

<210> SEQ ID NO 152
<211> LENGTH: 369
<212> TYPE: DNA
<213> ORGANISM: Artificial sequence
<220> FEATURE:
<223> OTHER INFORMATION: Synthetic antibody

<400> SEQUENCE: 152
cagttgcagc tgcaggagtc gggcccagga ctggtgaagc cttcggagac cctgtccctc 60
acttgctttg tccctggtga cttcctcagc agtactaatt tctactgggg ctggatccgc 120
cagcccccag gaaagggact ggagtggatt gggagtattt atgacagtgg gaacacttac 180
tacaacccgt ccctcaagag tcgagtcacc atgtcaatag acacgcccaa gaaccagttc 240
tccctgcagc tgagttctgt gaccgccgcg gacacggccg tatattactg cgcgcgagtc 300
ggggattgtg gtgcagactg ctactacttt gaccactggg gccagggaac cctggtcacc 360
gtctcctca 369

<210> SEQ ID NO 153
<211> LENGTH: 321
<212> TYPE: DNA
<213> ORGANISM: Artificial sequence
<220> FEATURE:
<223> OTHER INFORMATION: Synthetic antibody

<400> SEQUENCE: 153
tcctatgaac tgactcagcc accctcagtg tccgtgtccc caggacagac agccagcatc 60
tcttgttctg gagataggtt gcgggataga tatgtttcct ggtatcagca gaagccaggc 120
cagtcccctg tggtagtcat ctatcaagac ttcaagcggc cctcagggat ccctgcgcga 180
ttctctgcct ccaactctgg caacacagcc actctgacca tcatcgggac ccaggctatg 240
gatgaggctg actattactg tcaggcgtgg gacagcttca cttatgtctt cggagctggg 300
accaaggtca ccgtccttgg t 321

<210> SEQ ID NO 154
<211> LENGTH: 357
<212> TYPE: DNA
<213> ORGANISM: Artificial sequence
<220> FEATURE:
<223> OTHER INFORMATION: Synthetic antibody

<400> SEQUENCE: 154
gaggtgcatc tggtggagtc tgggggaggc ttggtccagc ctggggggtc cctgagactc 60
tcctgtgcag cctctggatt cacctttagt agttattgga tgagctgggt ccgccaggct 120
ccagggaagg ggctggagtg ggtggccaac ataaagcaag atggaagtga gaaatattat 180
gtggactctg tgaagggccg attcaccatc tccagagaca acgccaagaa ctcactgtat 240
ctgcaaatga acagcctgag agccgaggac acggctgtgt attactgtgc gagggggtcg 300
atcgggtggt tatcccctga ctactggggc cagggaacgc tggtcaccgt ctcctca 357

<210> SEQ ID NO 155
<211> LENGTH: 324
<212> TYPE: DNA
<213> ORGANISM: Artificial sequence
<220> FEATURE:
<223> OTHER INFORMATION: Synthetic antibody

<400> SEQUENCE: 155

```
tcttctgagc tgactcagga ccctgctgtg tctgtggcct tgggacagac agtcaggatc     60
acatgccaag gagacagcct cagaagcttt tatgcaagct ggtaccagca gaagccagga    120
caggccccta tacttgtctt ctatggtcaa aacaaccggc cctcagggat cccagaccga    180
ttctctggct ccagttcagg aaacacagct tccttgacca tcactggggc tcaggcggaa    240
gatgaggctg actattactg taactcccgg gacagcggtg gttaccatct ggtgttcggc    300
ggagggacca agctgaccgt ccta                                           324
```

<210> SEQ ID NO 156
<211> LENGTH: 330
<212> TYPE: DNA
<213> ORGANISM: Artificial sequence
<220> FEATURE:
<223> OTHER INFORMATION: Synthetic antibody

<400> SEQUENCE: 156

```
cagcctgtgc tgactcagcc accctctgca tcagcctccc tgggagcctc ggtcacactc     60
acctgcaccc tgagcagcgg ctacagtaat tataaactgg actgatacca ccagagacca    120
gggaagggcc cccgatttga gatgcgagtg ggcactggtg ggattgtgac atccacgggg    180
gatggcatcc ctgatcgctt cgcagtcttg ggctcaggcc tgaatcggtt cctgaccatc    240
aagaacatcc aggaagagga tgagagtgac taccactgtg ggccagacca tgggcgtggg    300
tgttcggcgg agggaccaag gtgaccgtcc                                     330
```

<210> SEQ ID NO 157
<211> LENGTH: 321
<212> TYPE: DNA
<213> ORGANISM: Artificial sequence
<220> FEATURE:
<223> OTHER INFORMATION: Synthetic antibody

<400> SEQUENCE: 157

```
tcctatgagt tgactcagcc accctcagtg tccgtgtccc caggacagac agccagcatc     60
acctgctctg gagataaatt gggggataaa tatgcttgct ggtatcagca gaagccaggc    120
cagtcccctg tgctggtcat ctatcaagat accaagcggc cctcagggat ccctgagcga    180
ttctctggct ccaactctgg gaacacagcc actctgacca tcggcgggac ccagcctatg    240
gatgaggctg actattactg tcaggcgtgg gacagcagca ctgaggtggt attcggcgga    300
gggaccaagc tgaccgtcct a                                              321
```

<210> SEQ ID NO 158
<211> LENGTH: 396
<212> TYPE: DNA
<213> ORGANISM: Artificial sequence
<220> FEATURE:
<223> OTHER INFORMATION: Synthetic antibody

<400> SEQUENCE: 158

```
gatgttcaag tggtggagtc tgggggaggc ttggtgcagc cagggcggtc cctgagactc     60
tcctgtcaat gctttggatt caactttggc gattatctca tgacctggtt ccgccaggct    120
ccagggaagg ggctggagtg ggtaggtttt gttagaacca aaggttatgg cgggacatca    180
gaatacgccg cgtctgtgag aggcagattc accgtctcaa gagatgactc caggggcatc    240
```

```
gcctacctcc aaatgaacag cctgagagtc gaggacacag ccgtgtatta ctgtacaaga    300

gatagacaaa aacccactta tcaattttgg agcagttatt ttgttgatga tccttttgat    360

gtctggggcc aagggacaaa ggtcaccgtc tcttca                              396
```

<210> SEQ ID NO 159
<211> LENGTH: 324
<212> TYPE: DNA
<213> ORGANISM: Artificial sequence
<220> FEATURE:
<223> OTHER INFORMATION: Synthetic antibody

<400> SEQUENCE: 159

```
tcttctgagc tgactcagga ccctgctgtg tctgtggcct tgggacagac agtcaggatc     60

acatgccaag gagacagcct cagaagttat tctgcaagct ggtaccagca taaggcagga    120

caggcccctg tacttgtcct ctatggtaaa aacaaccggc cttcagggat ccccgaccga    180

ttctctggct ccacctcagg aaacacagct tccttgacca tcactggggc tcaggcggaa    240

gatgaggctg acttttactg taactctcga gacagcagtg gaatccgtgt ggttttcggc    300

ggagggacca agctgaccgt ccta                                           324
```

<210> SEQ ID NO 160
<211> LENGTH: 363
<212> TYPE: DNA
<213> ORGANISM: Artificial sequence
<220> FEATURE:
<223> OTHER INFORMATION: Synthetic antibody

<400> SEQUENCE: 160

```
gaagtgcagc tggtgcagtc tggagcagag gtgaaaaagc ccggggagtc tctgaggatc     60

tcctgtaagg gttctggata cagctttacc agctactgga tcagctgggt gcgccagatg    120

cccgggaaag gcctggaatg gatggggagg attgagccta gtgactctta taccaactac    180

agcccgtcct tccaaggcca cgtcaccatc tcagctgaca agtccatcag cactgcctac    240

ctgcagtgga gcagcctgaa ggcctcggac accgccatgt attattgtgc gagactaggt    300

gatagtagtg gttacgggga gattgactac tggggccagg gaaccctggt caccgtctcc    360

tca                                                                  363
```

<210> SEQ ID NO 161
<211> LENGTH: 321
<212> TYPE: DNA
<213> ORGANISM: Artificial sequence
<220> FEATURE:
<223> OTHER INFORMATION: Synthetic antibody

<400> SEQUENCE: 161

```
gacatccaga tgacccagtc tccatcctcc ctgtctgcat ctgtaggaga cagagtcacc     60

atcacttgcc gggcaagtca gagcattagc agctatttaa attggtatca gcagaaacca    120

gggaaagccc ctaagctcct gatctatgct gcatccagtt tgcaaagtgg ggtcccatca    180

aggttcagtg gcagtggatc tgggacagat ttcactctca ccatcagcag tctgcaacct    240

gaagattttg caacttacta ctgtcaacag agttacagta cccctcagac gttcggccaa    300

gggaccaagg tggaaatcaa a                                              321
```

<210> SEQ ID NO 162
<211> LENGTH: 390
<212> TYPE: DNA
<213> ORGANISM: Artificial sequence
<220> FEATURE:
<223> OTHER INFORMATION: Synthetic antibody

<400> SEQUENCE: 162
gaggtgcagc tggtgcagtc tggagcagag gtgaaaaagc ccggggagtc tctgaagatc 60
tcctgtaagg gttctggata cagctttacc agctactgga tcggctgggt gcgccagatg 120
cccgggaaag gcctggagtg gatggggatc atctatcctg gtgactctga taccagatac 180
agcccgtcct tccaaggcca ggtcaccatc tcagccgaca agtccatcag caccgcctac 240
ctgcagtgga gcagcctgaa ggcctcggac accgccatgt attactgtgc gagggctccc 300
accgtaccag ctgctatttg ggtagctct tactactact actactacat ggacgtctgg 360
ggcaaaggga ccacggtcac cgtctcctca 390

<210> SEQ ID NO 163
<211> LENGTH: 339
<212> TYPE: DNA
<213> ORGANISM: Artificial sequence
<220> FEATURE:
<223> OTHER INFORMATION: Synthetic antibody

<400> SEQUENCE: 163
gacatcgtga tgacccagtc tccagactcc ctggctgtgt ctctgggcga gagggccacc 60
atcaactgca agtccagcca gagtgtttta tacagctcca acaataagaa ctacttagct 120
tggtaccagc agaaaccagg acagcctcct aagctgctca tttactgggc atctacccgg 180
gaatccgggg tccctgaccg attcagtggc agcgggtctg ggacagattt cactctcacc 240
atcagcagcc tgcaggctga agatgtggca gtttattact gtcagcaata ttatagtact 300
tcgctcactt tcggcggagg gaccaaggtg gagatcaaa 339

<210> SEQ ID NO 164
<211> LENGTH: 357
<212> TYPE: DNA
<213> ORGANISM: Artificial sequence
<220> FEATURE:
<223> OTHER INFORMATION: Synthetic antibody

<400> SEQUENCE: 164
gaggtgcagc tggtggagtc cgggggaggc ttggtccagc cggggggggtc cctgaaactc 60 tcctgtgcag cctctgggtt caaattcagt ggctctgcta tgcattgggt ccgtcaggcc 120
tccgggagag ggctggaatg ggttggccgt atcagaagca aggccaacaa ttacgcgaca 180
acatatgctg agtccgtgaa aggcaggttc accatctcca gggatgattc acaaaacacg 240
gcgtatttgg agatgcacaa tctgagaacc gaggacacgg ccgtgtatta ttgtacgagg 300
aatgtggata cggatcacag gggctggggc cagggaaccc tggtcagtgt ctcctca 357

<210> SEQ ID NO 165
<211> LENGTH: 339
<212> TYPE: DNA
<213> ORGANISM: Artificial sequence
<220> FEATURE:
<223> OTHER INFORMATION: Synthetic antibody

<400> SEQUENCE: 165
gaaatcgtga tgacccagtc tccagacccc ctgcctgtgt ctctgggcgg gagggccacc 60
atcaactgca agtccagcca gagtctttta tacggctcca ccaataagaa ctacttagct 120
tggtaccagc agaaaccagg acagcctcct aggctgctca tttattgggc atctacccgg 180

```
gaatccgggg tccctgaccg attcagtggc agcgggtctg ggacagattt cgctctcacc    240

atcagcgacc tgcaggctga agatgtggca gtttattatt gtcagcaata ttataatgtt    300

gcgtggacgt tcggccaagg gaccaaggtg gaaatcaga                           339


<210> SEQ ID NO 166
<211> LENGTH: 116
<212> TYPE: PRT
<213> ORGANISM: Artificial sequence
<220> FEATURE:
<223> OTHER INFORMATION: Synthetic antibody

<400> SEQUENCE: 166

Gln Met Gln Leu Gln Glu Ser Gly Pro Gly Leu Val Lys Pro Ser Gly
1               5                   10                  15

Thr Leu Ser Leu Thr Cys Ala Val Ser Gly Asp Ser Ile Ser Thr Ser
            20                  25                  30

Thr Trp Trp Ser Trp Val Arg Gln Ser Pro Gly Lys Gly Leu Glu Trp
        35                  40                  45

Ile Gly Glu Ile Tyr His Ser Glu Ser Thr Asn Tyr Asn Pro Ser Leu
    50                  55                  60

Lys Ser Arg Val Ser Leu Ser Leu Asp Lys Ser Lys Asn Gln Leu Ser
65                  70                  75                  80

Leu Arg Leu Ser Ser Val Thr Ala Ala Asp Thr Gly Val Tyr Tyr Cys
                85                  90                  95

Ala Arg Gly Ser Leu Val Phe Asp Tyr Trp Gly Gln Gly Ala Gln Val
            100                 105                 110

Val Val Ser Ser
        115


<210> SEQ ID NO 167
<211> LENGTH: 107
<212> TYPE: PRT
<213> ORGANISM: Artificial sequence
<220> FEATURE:
<223> OTHER INFORMATION: Synthetic antibody

<400> SEQUENCE: 167

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Ala Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Phe Asn Asn Trp Pro Arg
                85                  90                  95

Thr Phe Gly Gln Gly Thr Lys Val Glu Ile Lys
            100                 105


<210> SEQ ID NO 168
<211> LENGTH: 122
<212> TYPE: PRT
<213> ORGANISM: Artificial sequence
<220> FEATURE:
<223> OTHER INFORMATION: Synthetic antibody
```

<400> SEQUENCE: 168

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Val Arg Asn Tyr
            20                  25                  30

Tyr Trp Ser Trp Ile Arg Gln Pro Pro Gly Glu Gly Leu Glu Trp Ile
        35                  40                  45

Gly Tyr Ile Tyr Tyr Ser Gly Ser Thr Asp Phe Asn Pro Ser Leu Lys
    50                  55                  60

Ser Arg Val Thr Met Ser Val Asp Thr Ser Lys Asn His Phe Ser Leu
65                  70                  75                  80

Lys Leu Arg Ser Val Thr Ala Ala Asp Thr Ala Met Tyr Tyr Cys Ala
                85                  90                  95

Arg Val Ala Ile Arg Thr Asp Gly Tyr Ile Arg Ala Phe Asp Ile Trp
            100                 105                 110

Gly Ala Gly Thr Met Val Thr Val Ser Ser
        115                 120
```

<210> SEQ ID NO 169
<211> LENGTH: 107
<212> TYPE: PRT
<213> ORGANISM: Artificial sequence
<220> FEATURE:
<223> OTHER INFORMATION: Synthetic antibody

<400> SEQUENCE: 169

```
Asp Ile Gln Met Thr Gln Ser Pro Ser Ser Pro Ser Ala Ser Val Gly
1               5                   10                  15

Asp Arg Val Thr Val Thr Cys Arg Ala Ser Gln Ser Ile Arg Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Thr Tyr Ser Thr Ala Trp
                85                  90                  95

Thr Phe Gly Gln Gly Thr Lys Val Glu Ile Lys
            100                 105
```

<210> SEQ ID NO 170
<211> LENGTH: 123
<212> TYPE: PRT
<213> ORGANISM: Artificial sequence
<220> FEATURE:
<223> OTHER INFORMATION: Synthetic antibody

<400> SEQUENCE: 170

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Phe Trp Ser Trp Ile Arg Gln Pro Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60
```

```
Leu Lys Ser Arg Ile Thr Ile Ser Val Asp Thr Ser Lys Asn Gln Phe
65                  70                  75                  80

Ser Leu Lys Leu Ser Ser Val Thr Ala Ala Asp Thr Ala Val Phe Tyr
                85                  90                  95

Cys Ala Arg Val Gln Thr Pro Gly Ser Asp Thr Tyr Tyr Phe Asp Tyr
            100                 105                 110

Trp Gly Gln Gly Thr Leu Val Thr Val Ser Ser
        115                 120


<210> SEQ ID NO 171
<211> LENGTH: 108
<212> TYPE: PRT
<213> ORGANISM: Artificial sequence
<220> FEATURE:
<223> OTHER INFORMATION: Synthetic antibody

<400> SEQUENCE: 171

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ser Tyr Ser Thr Pro Met
                85                  90                  95

Tyr Thr Phe Gly Gln Gly Thr Lys Leu Glu Ile Lys
            100                 105


<210> SEQ ID NO 172
<211> LENGTH: 123
<212> TYPE: PRT
<213> ORGANISM: Artificial sequence
<220> FEATURE:
<223> OTHER INFORMATION: Synthetic antibody

<400> SEQUENCE: 172

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr His Trp Gly Trp Ile Arg Gln Pro Pro Gly Lys Gly Leu Glu
        35                  40                  45

Trp Ile Gly Ser Ile Tyr Tyr Thr Gly Ser Thr Tyr Tyr Asn Pro Ser
    50                  55                  60

Leu Lys Ser Arg Val Ile Ile Ser Val Asp Ala Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Arg Ser Leu Arg Ser Gly Trp Ala Ala Ala Ile Asp Phe
            100                 105                 110

Trp Gly Gln Gly Thr Leu Val Thr Val Ser Ser
        115                 120


<210> SEQ ID NO 173
```

<211> LENGTH: 108
<212> TYPE: PRT
<213> ORGANISM: Artificial sequence
<220> FEATURE:
<223> OTHER INFORMATION: Synthetic antibody

<400> SEQUENCE: 173

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ser Tyr Ser Thr Pro Met
                85                  90                  95

Tyr Thr Phe Gly Gln Gly Thr Lys Leu Glu Ile Lys
            100                 105
```

<210> SEQ ID NO 174
<211> LENGTH: 126
<212> TYPE: PRT
<213> ORGANISM: Artificial sequence
<220> FEATURE:
<223> OTHER INFORMATION: Synthetic antibody

<400> SEQUENCE: 174

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Tyr Arg Val Thr Thr Gly Asn Tyr Tyr Tyr Tyr Gly
            100                 105                 110

Met Asp Val Trp Gly Gln Gly Thr Thr Val Thr Val Ser Ser
        115                 120                 125
```

<210> SEQ ID NO 175
<211> LENGTH: 110
<212> TYPE: PRT
<213> ORGANISM: Artificial sequence
<220> FEATURE:
<223> OTHER INFORMATION: Synthetic antibody

<400> SEQUENCE: 175

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30
```

```
Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu
            100                 105                 110


<210> SEQ ID NO 176
<211> LENGTH: 127
<212> TYPE: PRT
<213> ORGANISM: Artificial sequence
<220> FEATURE:
<223> OTHER INFORMATION: Synthetic antibody

<400> SEQUENCE: 176

Ser Thr Gln Ser Thr Trp Ala Gly Pro Gly Leu Val Lys Pro Ser Gln
1               5                   10                  15

Thr Leu Ser Leu Thr Cys Thr Val Ser Gly Gly Ser Val Ser Ser Gly
            20                  25                  30

Asp Tyr Tyr Trp Ser Trp Ile Arg Gln Pro Pro Gly Arg Gly Leu Glu
        35                  40                  45

Trp Ile Gly Tyr Ile Ser Tyr Ser Gly Ser Thr Tyr Tyr Asn Pro Ser
    50                  55                  60

Leu Glu Ser Arg Ile Thr Met Ser Gly Asp Thr Ser Lys Gln Gln Phe
65                  70                  75                  80

Ser Leu Lys Leu Ser Ser Val Thr Val Ala Asp Thr Ala Val Tyr Tyr
                85                  90                  95

Cys Ala Thr Asn Tyr Phe His Leu His Asp Phe Gly Asp Leu Tyr Trp
            100                 105                 110

Tyr Phe Asp Leu Trp Gly Arg Gly Thr Leu Val Thr Val Ser Ser
        115                 120                 125


<210> SEQ ID NO 177
<211> LENGTH: 110
<212> TYPE: PRT
<213> ORGANISM: Artificial sequence
<220> FEATURE:
<223> OTHER INFORMATION: Synthetic antibody

<400> SEQUENCE: 177

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Ala Tyr
            20                  25                  30

Asn Phe Val Ser Trp Tyr Gln Gln His Pro Gly Thr Ala Pro Lys Leu
        35                  40                  45

Leu Ile Tyr Asp Val Thr Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asn Tyr Tyr Cys Asn Ser Tyr Thr Ser Ser
                85                  90                  95

Ser His Val Val Phe Gly Gly Gly Thr Lys Leu Thr Val Leu
            100                 105                 110
```

<210> SEQ ID NO 178
<211> LENGTH: 123
<212> TYPE: PRT
<213> ORGANISM: Artificial sequence
<220> FEATURE:
<223> OTHER INFORMATION: Synthetic antibody

<400> SEQUENCE: 178

```
Gln Leu Gln Leu Gln Glu Ser Gly Pro Gly Leu Ala Arg Pro Ser Glu
1               5                   10                  15

Thr Pro Ser Leu Thr Cys Thr Val Ser Gly Gly Ser Ile Ser Ser Ser
            20                  25                  30

Val Tyr Tyr Trp Gly Trp Ile Arg Gln Pro Pro Gly Lys Gly Leu Glu
        35                  40                  45

Trp Ile Gly Ser Ile Tyr Tyr Ser Gly Tyr Thr Asn Tyr Asn Pro Ser
    50                  55                  60

Leu Lys Ser Arg Val Ser Ile Ser Val Asp Thr Ser Lys Asn Gln Phe
65                  70                  75                  80

Ser Leu Gln Leu Asn Ser Val Thr Ala Ala Asp Thr Ala Val Tyr Tyr
                85                  90                  95

Cys Ala Arg His Ser Asp Cys Gly Asn Asp Cys Tyr Tyr Phe Asp Tyr
            100                 105                 110

Trp Gly Gln Gly Thr Leu Val Thr Val Ser Ser
        115                 120
```

<210> SEQ ID NO 179
<211> LENGTH: 107
<212> TYPE: PRT
<213> ORGANISM: Artificial sequence
<220> FEATURE:
<223> OTHER INFORMATION: Synthetic antibody

<400> SEQUENCE: 179

```
Ser Tyr Glu Leu Thr Gln Pro Pro Ser Val Ser Val Ser Pro Gly Gln
1               5                   10                  15

Thr Ala Ser Ile Thr Cys Ser Gly Asp Arg Leu Gly Asp Lys Tyr Ala
            20                  25                  30

Ser Trp Tyr Gln Gln Lys Pro Gly Gln Ser Pro Val Leu Val Ile Tyr
        35                  40                  45

Gln Asp Tyr Lys Arg Pro Ser Gly Ile Pro Glu Arg Phe Ser Gly Ser
    50                  55                  60

Asn Ser Gly His Thr Ala Thr Leu Thr Ile Ser Gly Thr Gln Ala Met
65                  70                  75                  80

Asp Glu Ala Asp Tyr Phe Cys Gln Ala Trp Asp Ser Ser Asp Gly Ser
                85                  90                  95

Val Phe Gly Thr Gly Thr Lys Val Thr Val Leu
            100                 105
```

<210> SEQ ID NO 180
<211> LENGTH: 127
<212> TYPE: PRT
<213> ORGANISM: Artificial sequence
<220> FEATURE:
<223> OTHER INFORMATION: Synthetic antibody

<400> SEQUENCE: 180

```
Gln Val Gln Leu Gln Glu Ser Gly Pro Gly Leu Val Lys Pro Ser Gln
1               5                   10                  15
```

```
Thr Leu Ser Leu Thr Cys Thr Val Ser Gly Gly Ser Val Ser Ser Gly
            20                  25                  30

Asp Tyr Tyr Trp Ser Trp Ile Arg Gln Pro Pro Gly Arg Gly Leu Glu
        35                  40                  45

Trp Ile Gly Tyr Ile Ser Tyr Ser Gly Ser Thr Tyr Tyr Asn Pro Ser
    50                  55                  60

Leu Glu Ser Arg Ile Thr Met Ser Gly Asp Thr Ser Lys Gln Gln Phe
65                  70                  75                  80

Ser Leu Lys Leu Ser Ser Val Thr Val Ala Asp Thr Ala Val Tyr Tyr
                85                  90                  95

Cys Ala Thr Asn Tyr Phe His Leu His Asp Phe Gly Asp Leu Tyr Trp
            100                 105                 110

Tyr Phe Asp Leu Trp Gly Arg Gly Thr Leu Val Thr Val Ser Ser
        115                 120                 125


<210> SEQ ID NO 181
<211> LENGTH: 110
<212> TYPE: PRT
<213> ORGANISM: Artificial sequence
<220> FEATURE:
<223> OTHER INFORMATION: Synthetic antibody

<400> SEQUENCE: 181

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Ala Tyr
            20                  25                  30

Asn Phe Val Ser Trp Tyr Gln Gln His Pro Gly Thr Ala Pro Lys Leu
        35                  40                  45

Leu Ile Tyr Asp Val Thr Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asn Tyr Tyr Cys Asn Ser Tyr Thr Ser Ser
                85                  90                  95

Ser His Val Val Phe Gly Gly Gly Thr Lys Leu Thr Val Leu
            100                 105                 110


<210> SEQ ID NO 182
<211> LENGTH: 119
<212> TYPE: PRT
<213> ORGANISM: Artificial sequence
<220> FEATURE:
<223> OTHER INFORMATION: Synthetic antibody

<400> SEQUENCE: 182

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Met Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Asn Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Thr Leu Arg Ala Glu Asp Thr Ala Val Tyr Tyr Cys
                85                  90                  95
```

```
Ala Arg Gly Glu Tyr Tyr Gly Ser Gly Ser Tyr Ser Trp Gly Gln Gly
            100                 105                 110

Thr Leu Val Thr Val Ser Ser
        115


<210> SEQ ID NO 183
<211> LENGTH: 107
<212> TYPE: PRT
<213> ORGANISM: Artificial sequence
<220> FEATURE:
<223> OTHER INFORMATION: Synthetic antibody

<400> SEQUENCE: 183

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105


<210> SEQ ID NO 184
<211> LENGTH: 123
<212> TYPE: PRT
<213> ORGANISM: Artificial sequence
<220> FEATURE:
<223> OTHER INFORMATION: Synthetic antibody

<400> SEQUENCE: 184

Gln Leu Gln Leu Gln Glu Ser Gly Pro Gly Leu Ala Arg Pro Ser Glu
1               5                   10                  15

Thr Pro Ser Leu Thr Cys Thr Val Ser Gly Gly Ser Ile Ser Ser Ser
            20                  25                  30

Val Tyr Tyr Trp Gly Trp Ile Arg Gln Pro Pro Gly Lys Gly Leu Glu
        35                  40                  45

Trp Ile Gly Ser Ile Tyr Tyr Ser Gly Tyr Thr Asn Tyr Asn Pro Ser
    50                  55                  60

Leu Lys Ser Arg Val Ser Ile Ser Val Asp Thr Ser Lys Asn Gln Phe
65                  70                  75                  80

Ser Leu Gln Leu Asn Ser Val Thr Ala Ala Asp Thr Ala Val Tyr Tyr
                85                  90                  95

Cys Ala Arg His Ser Asp Cys Gly Asn Asp Cys Tyr Tyr Phe Asp Tyr
            100                 105                 110

Trp Gly Gln Gly Thr Leu Val Thr Val Ser Ser
        115                 120


<210> SEQ ID NO 185
<211> LENGTH: 107
<212> TYPE: PRT
<213> ORGANISM: Artificial sequence
<220> FEATURE:
<223> OTHER INFORMATION: Synthetic antibody
```

<400> SEQUENCE: 185

Ser Tyr Glu Leu Thr Gln Pro Pro Ser Val Ser Val Ser Pro Gly Gln
1               5                   10                  15

Thr Ala Ser Ile Thr Cys Ser Gly Asp Arg Leu Gly Asp Lys Tyr Ala
            20                  25                  30

Ser Trp Tyr Gln Gln Lys Pro Gly Gln Ser Pro Val Leu Val Ile Tyr
        35                  40                  45

Gln Asp Tyr Lys Arg Pro Ser Gly Ile Pro Glu Arg Phe Ser Gly Ser
    50                  55                  60

Asn Ser Gly His Thr Ala Thr Leu Thr Ile Ser Gly Thr Gln Ala Met
65                  70                  75                  80

Asp Glu Ala Asp Tyr Phe Cys Gln Ala Trp Asp Ser Ser Asp Gly Ser
                85                  90                  95

Val Phe Gly Thr Gly Thr Lys Val Thr Val Leu
            100                 105

<210> SEQ ID NO 186
<211> LENGTH: 121
<212> TYPE: PRT
<213> ORGANISM: Artificial sequence
<220> FEATURE:
<223> OTHER INFORMATION: Synthetic antibody

<400> SEQUENCE: 186

Gln Val His Leu Gln Glu Ser Gly Pro Gly Leu Val Lys Pro Ser Glu
1               5                   10                  15

Thr Leu Ser Leu Thr Cys Thr Val Ser Gly Gly Ser Ile Gly Thr Tyr
            20                  25                  30

Tyr Trp Ser Trp Ile Arg Gln Pro Pro Gly Lys Gly Leu Glu Trp Ile
        35                  40                  45

Gly Tyr Val Tyr His Ser Gly Ala Thr Asn Asp Asn Pro Ser Leu Met
    50                  55                  60

Ser Arg Leu Thr Met Ser Val Asp Thr Ser Lys Asn Gln Phe Ser Leu
65                  70                  75                  80

Asp Leu Arg Ser Val Thr Ala Ala Asp Thr Ala Ile Tyr Tyr Cys Ala
                85                  90                  95

Arg Glu Gly Ser Asn Gly Asp Phe Arg Gly His Phe Asp Ser Trp Gly
            100                 105                 110

Gln Gly Thr Leu Val Thr Val Ser Ser
        115                 120

<210> SEQ ID NO 187
<211> LENGTH: 110
<212> TYPE: PRT
<213> ORGANISM: Artificial sequence
<220> FEATURE:
<223> OTHER INFORMATION: Synthetic antibody

<400> SEQUENCE: 187

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Phe
            20                  25                  30

Asn Phe Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

```
Ser Gly Ser Lys Ser Gly Asn Thr Ala Ser Leu Thr Ile Ser Gly Leu
65                  70                  75                  80

Arg Thr Asp Asp Glu Gly Asp Tyr Tyr Cys Thr Ser Tyr Thr Ser Ser
                85                  90                  95

Ser Thr Val Val Phe Gly Gly Gly Thr Lys Leu Thr Val Leu
            100                 105                 110


<210> SEQ ID NO 188
<211> LENGTH: 129
<212> TYPE: PRT
<213> ORGANISM: Artificial sequence
<220> FEATURE:
<223> OTHER INFORMATION: Synthetic antibody

<400> SEQUENCE: 188

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Arg Thr Lys Tyr Asn Pro Ser Leu Ser
    50                  55                  60

Ser Gly Leu Thr Leu Ser Val Asp Lys Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Arg Gly His Val Val Val Thr Pro Ala Thr Leu Phe His Arg Val Gly
            100                 105                 110

Glu His Tyr Phe Asp Phe Trp Gly Gln Gly Thr Leu Val Ser Val Ser
        115                 120                 125

Ser


<210> SEQ ID NO 189
<211> LENGTH: 108
<212> TYPE: PRT
<213> ORGANISM: Artificial sequence
<220> FEATURE:
<223> OTHER INFORMATION: Synthetic antibody

<400> SEQUENCE: 189

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Lys Asn Tyr Tyr Ala
            20                  25                  30

Ser Trp Tyr Gln Gln Lys Pro Gly Arg Ala Pro Leu Leu Val Met Ser
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Ser Ser Arg Asp Arg Ser Asp Lys Tyr
                85                  90                  95

Trp Val Phe Gly Gly Gly Thr Lys Val Thr Val Leu
            100                 105


<210> SEQ ID NO 190
```

<211> LENGTH: 130
<212> TYPE: PRT
<213> ORGANISM: Artificial sequence
<220> FEATURE:
<223> OTHER INFORMATION: Synthetic antibody

<400> SEQUENCE: 190

```
Gln Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Thr Tyr
            20                  25                  30

Ala Ile His Trp Val Arg Gln Ala Pro Gly Gln Arg Leu Glu Trp Met
        35                  40                  45

Gly Trp Ile Asn Ala Gly Asn Gly Asp Thr Lys Tyr Ser Gln Arg Phe
    50                  55                  60

Gln Gly Arg Val Thr Val Thr Arg Asp Thr Ser Ala Asn Thr Ala Tyr
65                  70                  75                  80

Met Glu Leu Thr Ser Leu Thr Ser Glu Asp Thr Ala Val Tyr Tyr Cys
                85                  90                  95

Ala Arg Gly Trp Val Gly Cys Ile Gly Lys Arg Gly Lys Thr Cys Tyr
            100                 105                 110

Ala Asn Leu Pro Asp Asp Tyr Trp Gly Gln Gly Thr Leu Val Thr Val
        115                 120                 125

Ser Ser
    130
```

<210> SEQ ID NO 191
<211> LENGTH: 109
<212> TYPE: PRT
<213> ORGANISM: Artificial sequence
<220> FEATURE:
<223> OTHER INFORMATION: Synthetic antibody

<400> SEQUENCE: 191

```
Gln Ser Ala Leu Thr Gln Pro Ala Ser Val Ser Gly Ser Arg Gly Gln
1               5                   10                  15

Ser Ile Thr Ile Thr Cys Thr Gly Thr Ser Ser Asp Val Gly Ala Tyr
            20                  25                  30

Lys Phe Val Ser Trp Tyr Gln Gln His Pro Gly Lys Ala Pro Asn Leu
        35                  40                  45

Ile Ile Tyr Asp Val Asn Ser Arg Pro Ser Gly Val Ser Asp Arg Phe
    50                  55                  60

Ser Gly Ser Lys Ser Gly Tyr Thr Ala Ser Leu Thr Ile Ser Gly Leu
65                  70                  75                  80

Gln Ala Glu Asp Glu Ala Asp Tyr Tyr Cys Ser Ser Tyr Thr Arg Gly
                85                  90                  95

Pro Tyr Ile Phe Gly Thr Gly Thr Lys Val Thr Val Leu
            100                 105
```

<210> SEQ ID NO 192
<211> LENGTH: 125
<212> TYPE: PRT
<213> ORGANISM: Artificial sequence
<220> FEATURE:
<223> OTHER INFORMATION: Synthetic antibody

<400> SEQUENCE: 192

```
Gln Val Lys Leu Val Glu Ser Gly Gly Gly Val Val Gln Pro Gly Arg
1               5                   10                  15
```

```
Ser Leu Arg Leu Ser Cys Glu Ala Ser Arg Phe Thr Phe Asn Thr Tyr
            20                  25                  30

Gly Met His Trp Val Arg Gln Ala Pro Gly Lys Gly Leu Glu Trp Val
        35                  40                  45

Ala Val Ile Ser Tyr Asp Gly Lys Lys Lys Tyr Tyr Ala Asp Ser Ala
    50                  55                  60

Lys Gly Arg Phe Thr Ile Ser Arg Asp Asp Ser Arg Asn Thr Leu Tyr
65                  70                  75                  80

Leu Glu Met Asn Ser Leu Arg Val Glu Asp Thr Ala Val Tyr Tyr Cys
                85                  90                  95

Ala Arg Asp Leu Arg Arg Phe Tyr Ser Asn Gly Trp Phe Thr Gly Ser
            100                 105                 110

Asp Phe Trp Gly Gln Gly Thr Leu Val Thr Val Ser Ser
        115                 120                 125


<210> SEQ ID NO 193
<211> LENGTH: 108
<212> TYPE: PRT
<213> ORGANISM: Artificial sequence
<220> FEATURE:
<223> OTHER INFORMATION: Synthetic antibody

<400> SEQUENCE: 193

Glu Ile Val Leu Thr Gln Ser Pro Ala Thr Leu Ser Leu Ser Pro Gly
1               5                   10                  15

Glu Arg Ala Thr Leu Ser Cys Gly Ala Ser Gln Thr Ile Ser Ser Asn
            20                  25                  30

Asn Leu Ala Trp Tyr Gln Gln Lys Pro Gly Leu Ala Pro Arg Leu Leu
        35                  40                  45

Ile Tyr Asp Ala Ser Thr Arg Ala Ala Gly Ile Pro Arg Arg Phe Ser
    50                  55                  60

Gly Ser Gly Ser Gly Thr Asn Phe Thr Leu Thr Val Thr Arg Leu Asp
65                  70                  75                  80

Pro Glu Asp Phe Ala Leu Tyr Ser Cys Gln Gln Tyr Gly Arg Ser Pro
                85                  90                  95

Ile Thr Phe Gly Gln Gly Thr Arg Leu Glu Ile Lys
            100                 105


<210> SEQ ID NO 194
<211> LENGTH: 121
<212> TYPE: PRT
<213> ORGANISM: Artificial sequence
<220> FEATURE:
<223> OTHER INFORMATION: Synthetic antibody

<400> SEQUENCE: 194

Gln Val Glu Leu Arg Glu Ser Gly Pro Gly Leu Val Lys Pro Ser Gly
1               5                   10                  15

Thr Leu Ser Leu Thr Cys Ala Val Ser Gly Val Ser Ile Thr Ser Ser
            20                  25                  30

Asn Trp Trp Asn Trp Val Arg Gln Ser Pro Gly Lys Gly Leu Glu Trp
        35                  40                  45

Ile Gly Gln Val Tyr His Ser Gly Ser Thr Lys Tyr Asn Pro Ser Leu
    50                  55                  60

Arg Ser Arg Leu Thr Ile Ser Val Asp Lys Ser Lys Asn Gln Phe Ser
65                  70                  75                  80

Leu Lys Met Lys Tyr Val Arg Ala Ala Asp Thr Ala Val Tyr Phe Cys
                85                  90                  95
```

```
Ala Arg Asp Gly Phe Ser Gly Tyr Asp Val Ala Leu Asp Lys Trp Gly
            100                 105                 110

Gln Gly Thr Leu Val Thr Val Ser Ser
        115                 120


<210> SEQ ID NO 195
<211> LENGTH: 112
<212> TYPE: PRT
<213> ORGANISM: Artificial sequence
<220> FEATURE:
<223> OTHER INFORMATION: Synthetic antibody

<400> SEQUENCE: 195

Gln Ser Val Leu Thr Gln Pro Pro Ser Val Ser Ala Ala Pro Gly Gln
1               5                   10                  15

Arg Val Thr Ile Ser Cys Ser Gly Ser Ser Ser Asn Ile Gly Asn Ser
            20                  25                  30

Tyr Val Ser Trp Tyr Gln His Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Ala Ser Lys Ser Gly Thr Ser Ala Thr Leu Gly Ile Thr Gly Leu Arg
65                  70                  75                  80

Thr Gly Asp Glu Ala Asp Tyr Tyr Cys Ala Thr Trp Glu Ser Arg Leu
                85                  90                  95

Ser Ala Gly His Val Val Phe Gly Gly Gly Thr Lys Leu Thr Val Leu
            100                 105                 110


<210> SEQ ID NO 196
<211> LENGTH: 129
<212> TYPE: PRT
<213> ORGANISM: Artificial sequence
<220> FEATURE:
<223> OTHER INFORMATION: Synthetic antibody

<400> SEQUENCE: 196

Gln Ile Thr Leu Gln Glu Ser Gly Pro Thr Leu Val Lys Pro Thr Arg
1               5                   10                  15

Thr Leu Thr Leu Thr Cys Thr Leu Ser Gly Val Ser Leu Ser Ser Ser
            20                  25                  30

Gly Val Gly Val Gly Trp Ile Arg Gln Pro Pro Gly Arg Ala Leu Glu
        35                  40                  45

Trp Leu Ala Val Ile Tyr Trp Asp Asp Asp Lys His Tyr Arg Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg Asn Ile Val Val Val Arg Ala Asp Pro His Arg Trp
            100                 105                 110

Ala Gly Thr Phe Asp Tyr Trp Gly Gln Gly Ala Leu Val Thr Val Ser
        115                 120                 125

Ala


<210> SEQ ID NO 197
<211> LENGTH: 108
<212> TYPE: PRT
<213> ORGANISM: Artificial sequence
```

```
<220> FEATURE:
<223> OTHER INFORMATION: Synthetic antibody

<400> SEQUENCE: 197

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Ala Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Leu Gly Val Tyr Ser Cys Gln Gln Tyr Ala Gly Ser Pro
                85                  90                  95

Phe Thr Phe Gly Pro Gly Thr Lys Val Glu Ile Lys
            100                 105


<210> SEQ ID NO 198
<211> LENGTH: 127
<212> TYPE: PRT
<213> ORGANISM: Artificial sequence
<220> FEATURE:
<223> OTHER INFORMATION: Synthetic antibody

<400> SEQUENCE: 198

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gln Gly Thr Met Ile Val Val Val Thr Leu Pro Pro Gly
            100                 105                 110

Ala Phe Asp Ile Trp Gly Gln Gly Thr Met Val Thr Val Ser Ser
        115                 120                 125


<210> SEQ ID NO 199
<211> LENGTH: 119
<212> TYPE: PRT
<213> ORGANISM: Artificial sequence
<220> FEATURE:
<223> OTHER INFORMATION: Synthetic antibody

<400> SEQUENCE: 199

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Met Phe Ser Arg Tyr
            20                  25                  30

Trp Met Ser Trp Val Arg Gln Ala Pro Gly Lys Gly Leu Glu Trp Val
        35                  40                  45
```

```
Ala Asn Ile Lys Gln Asp Gly Ser Glu Lys Asn Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Thr Leu Arg Ala Glu Asp Thr Ala Val Tyr Tyr Cys
                85                  90                  95

Ala Arg Gly Glu Tyr Tyr Gly Ser Gly Ser Tyr Ser Trp Gly Gln Gly
            100                 105                 110

Thr Leu Val Thr Val Ser Ser
        115
```

<210> SEQ ID NO 200
<211> LENGTH: 112
<212> TYPE: PRT
<213> ORGANISM: Artificial sequence
<220> FEATURE:
<223> OTHER INFORMATION: Synthetic antibody

<400> SEQUENCE: 200

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Ala
                85                  90                  95

Leu Gln Ile Pro Leu Thr Phe Gly Gly Gly Thr Lys Val Glu Ile Lys
            100                 105                 110
```

<210> SEQ ID NO 201
<211> LENGTH: 123
<212> TYPE: PRT
<213> ORGANISM: Artificial sequence
<220> FEATURE:
<223> OTHER INFORMATION: Synthetic antibody

<400> SEQUENCE: 201

```
Gln Val His Leu Gln Glu Ser Gly Pro Gly Leu Val Lys Pro Ser Gln
1               5                   10                  15

Ala Leu Ser Leu Thr Cys Thr Val Ser Gly Gly Ser Ile Asn Gly Asp
            20                  25                  30

Asn Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Ile Ser Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Ala Asp Cys Gly Asn Asp Cys Tyr Tyr Phe Asp Tyr
            100                 105                 110

Trp Gly Gln Gly Ala Leu Val Thr Val Ser Ser
        115                 120
```

<210> SEQ ID NO 202
<211> LENGTH: 107
<212> TYPE: PRT
<213> ORGANISM: Artificial sequence
<220> FEATURE:
<223> OTHER INFORMATION: Synthetic antibody

<400> SEQUENCE: 202

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly His Lys Tyr Ala
            20                  25                  30

Cys Trp Tyr Gln Gln Arg Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Val
65                  70                  75                  80

Asp Glu Ala Asp Tyr Tyr Cys Gln Ala Trp Asp Ser Ser Ser Phe Tyr
                85                  90                  95

Val Phe Gly Thr Gly Thr Lys Val Thr Val Leu
            100                 105
```

<210> SEQ ID NO 203
<211> LENGTH: 121
<212> TYPE: PRT
<213> ORGANISM: Artificial sequence
<220> FEATURE:
<223> OTHER INFORMATION: Synthetic antibody

<400> SEQUENCE: 203

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly Leu Val Gly Ala Ile His Asp Ala Phe Asp Ile Trp Gly
            100                 105                 110

Gln Gly Thr Met Val Thr Val Ser Ser
        115                 120
```

<210> SEQ ID NO 204
<211> LENGTH: 107
<212> TYPE: PRT
<213> ORGANISM: Artificial sequence
<220> FEATURE:
<223> OTHER INFORMATION: Synthetic antibody

<400> SEQUENCE: 204

```
Asp Ile Gln Met Thr Gln Ser Pro Ser Thr Leu Ser Ala Ser Val Gly
1               5                   10                  15
```

```
Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105


<210> SEQ ID NO 205
<211> LENGTH: 123
<212> TYPE: PRT
<213> ORGANISM: Artificial sequence
<220> FEATURE:
<223> OTHER INFORMATION: Synthetic antibody

<400> SEQUENCE: 205

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Phe Trp Ser Trp Ile Arg Gln Pro Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Ile Thr Ile Ser Val Asp Thr Ser Lys Asn Gln Phe
65                  70                  75                  80

Ser Leu Lys Leu Ser Ser Val Thr Ala Ala Asp Thr Ala Val Phe Tyr
                85                  90                  95

Cys Ala Arg Val Gln Thr Pro Gly Ser Asp Thr Tyr Tyr Phe Asp Tyr
            100                 105                 110

Trp Gly Gln Gly Thr Leu Val Thr Val Ser Ser
        115                 120


<210> SEQ ID NO 206
<211> LENGTH: 106
<212> TYPE: PRT
<213> ORGANISM: Artificial sequence
<220> FEATURE:
<223> OTHER INFORMATION: Synthetic antibody

<400> SEQUENCE: 206

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
                85                  90                  95
```

```
Phe Gly Gly Gly Thr Glu Leu Thr Val Leu
            100                 105


<210> SEQ ID NO 207

<400> SEQUENCE: 207

000


<210> SEQ ID NO 208
<211> LENGTH: 129
<212> TYPE: PRT
<213> ORGANISM: Artificial sequence
<220> FEATURE:
<223> OTHER INFORMATION: Synthetic antibody

<400> SEQUENCE: 208

Gln Val Gln Met Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Leu
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Arg Tyr Cys Asp Ser Ala Ser Cys Tyr Val Arg Asn Tyr
            100                 105                 110

Phe Tyr Tyr Met Asp Val Trp Gly Lys Gly Thr Thr Val Thr Val Ser
        115                 120                 125

Ser


<210> SEQ ID NO 209
<211> LENGTH: 106
<212> TYPE: PRT
<213> ORGANISM: Artificial sequence
<220> FEATURE:
<223> OTHER INFORMATION: Synthetic antibody

<400> SEQUENCE: 209

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Leu Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Arg Leu Asp Ile Lys
            100                 105
```

<210> SEQ ID NO 210
<211> LENGTH: 115
<212> TYPE: PRT
<213> ORGANISM: Artificial sequence
<220> FEATURE:
<223> OTHER INFORMATION: Synthetic antibody

<400> SEQUENCE: 210

```
Gly Val Glu Leu Val Glu Ser Gly Gly Gly Ala Ala Gln Pro Gly Gly
1               5                   10                  15

Ser Leu Arg Leu Tyr Cys Ala Ala Ser Gly Phe Thr Phe Ser Asn Tyr
            20                  25                  30

Trp Met Asn Trp Val Arg Gln Gly Pro Gly Lys Gly Leu Thr Trp Ile
        35                  40                  45

Ala Arg Ile Asn Asp His Gly Asn Tyr Thr Ser Tyr Glu Asp Ser Val
    50                  55                  60

Lys Gly Arg Phe Thr Ile Ser Arg Asp Asn Thr Lys Asn Thr Val Phe
65                  70                  75                  80

Leu Gln Met Asn Ser Leu Arg Leu Asp Asp Ser Ala Val Tyr Tyr Cys
                85                  90                  95

Val Arg Ala Phe Gly Gly Gly Tyr Trp Gly Gln Gly Thr Pro Val Thr
            100                 105                 110

Val Ser Ser
        115
```

<210> SEQ ID NO 211
<211> LENGTH: 112
<212> TYPE: PRT
<213> ORGANISM: Artificial sequence
<220> FEATURE:
<223> OTHER INFORMATION: Synthetic antibody

<400> SEQUENCE: 211

```
Asp Val Val Met Thr Gln Ser Pro Leu Ser Leu Pro Val Ser Leu Gly
1               5                   10                  15

Gln Pro Ala Ser Ile Ser Cys Lys Ser Gly Gln Ser Leu Val Tyr Arg
            20                  25                  30

Asp Gly Asn Thr Tyr Leu Ser Trp Phe Phe Gln Arg Pro Gly Gln Ser
        35                  40                  45

Pro Arg Arg Leu Ile Tyr Gln Val Phe Lys Arg Asp Ser Gly Val Pro
    50                  55                  60

Asp Arg Phe Thr Gly Ser Gly Ser Gly Ser Asp Phe Thr Leu Gln Ile
65                  70                  75                  80

Ser Arg Val Gln Ser Glu Asp Val Gly Ile Tyr Tyr Cys Met Gln Ser
                85                  90                  95

Thr His Trp Pro Trp Thr Phe Gly Gln Gly Thr Lys Val Glu Ile Lys
            100                 105                 110
```

<210> SEQ ID NO 212
<211> LENGTH: 124
<212> TYPE: PRT
<213> ORGANISM: Artificial sequence
<220> FEATURE:
<223> OTHER INFORMATION: Synthetic antibody

<400> SEQUENCE: 212

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30
```

```
Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Ser Ile Ala Ala Arg Gln Asn Arg Gly Tyr Phe Asp
            100                 105                 110

Tyr Trp Gly Gln Gly Thr Leu Val Thr Val Ser Ser
        115                 120


<210> SEQ ID NO 213
<211> LENGTH: 107
<212> TYPE: PRT
<213> ORGANISM: Artificial sequence
<220> FEATURE:
<223> OTHER INFORMATION: Synthetic antibody

<400> SEQUENCE: 213

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105


<210> SEQ ID NO 214
<211> LENGTH: 116
<212> TYPE: PRT
<213> ORGANISM: Artificial sequence
<220> FEATURE:
<223> OTHER INFORMATION: Synthetic antibody

<400> SEQUENCE: 214

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Tyr Met His Trp Val Arg Gln Ala Pro Gly Lys Gly Pro Val Trp Ile
        35                  40                  45

Ser Arg Ile Asn Thr Asp Gly Ser Thr Thr Ala Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Pro Tyr Ser Gly Tyr Phe His Trp Gly Arg Gly Ala Leu Val
```

```
            100                 105                 110

Thr Val Ser Ser
        115


<210> SEQ ID NO 215
<211> LENGTH: 111
<212> TYPE: PRT
<213> ORGANISM: Artificial sequence
<220> FEATURE:
<223> OTHER INFORMATION: Synthetic antibody

<400> SEQUENCE: 215

Asp Ile Val Met Thr Gln Thr Pro Leu Ser Ser Ser Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Leu His Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr Arg Leu Tyr Thr Phe Gly Gln Gly Thr Lys Leu Glu Ile Lys
            100                 105                 110


<210> SEQ ID NO 216
<211> LENGTH: 112
<212> TYPE: PRT
<213> ORGANISM: Artificial sequence
<220> FEATURE:
<223> OTHER INFORMATION: Synthetic antibody

<400> SEQUENCE: 216

Glu Val Leu Leu Leu Glu Ser Gly Gly Gly Leu Val Gln Pro Gly Gly
1               5                   10                  15

Ser Leu Arg Leu Ser Cys Thr Val Ser Gly Phe Thr Phe Thr Asn Ser
            20                  25                  30

Trp Met His Trp Val Arg Gln Ala Pro Gly Lys Gly Leu Val Trp Val
        35                  40                  45

Ser Gly Ile Asn Pro Asp Gly Ser Lys Ile Asp His Ala Glu Ser Val
    50                  55                  60

Gln Gly Arg Phe Thr Ile Ser Arg Asp Asn Ala Lys Asn Thr Leu Tyr
65                  70                  75                  80

Leu Gln Met Asp Ser Leu Arg Asp Glu Asp Thr Ala Val Tyr Tyr Cys
                85                  90                  95

Ala Arg Trp Leu Ser Trp Gly Gln Gly Ala Leu Val Thr Val Thr Ser
            100                 105                 110


<210> SEQ ID NO 217
<211> LENGTH: 105
<212> TYPE: PRT
<213> ORGANISM: Artificial sequence
<220> FEATURE:
<223> OTHER INFORMATION: Synthetic antibody

<400> SEQUENCE: 217

Thr Ile Ser Cys Ser Gly Ser Ser Ser Asn Ile Gly Ser Asn His Val
1               5                   10                  15
```

```
Tyr Trp Tyr Gln Gln Leu Pro Gly Ser Ala Pro Gln Leu Leu Ile Ser
            20                  25                  30

Lys Asn Asn Gln Arg Pro Ser Gly Val Pro Asp Arg Phe Ser Gly Ser
        35                  40                  45

Lys Ser Gly Thr Ser Gly Ser Leu Ala Ile Ser Gly Leu Arg Ser Glu
    50                  55                  60

Asp Glu Ala Ala Tyr Tyr Cys Ala Ala Trp Asp Asp Ser Leu Arg Gly
65                  70                  75                  80

Trp Glu Phe Gly Gly Gly Thr Gln Val Thr Val Leu Gly Gln Pro Lys
                85                  90                  95

Ala Ala Pro Ser Val Thr Leu Phe Pro
            100                 105


<210> SEQ ID NO 218
<211> LENGTH: 112
<212> TYPE: PRT
<213> ORGANISM: Artificial sequence
<220> FEATURE:
<223> OTHER INFORMATION: Synthetic antibody

<400> SEQUENCE: 218

Glu Val Leu Leu Leu Glu Ser Gly Gly Gly Leu Val Gln Pro Gly Gly
1               5                   10                  15

Ser Leu Arg Leu Ser Cys Thr Val Ser Gly Phe Thr Phe Thr Asn Ser
            20                  25                  30

Trp Met His Trp Val Arg Gln Ala Pro Gly Lys Gly Leu Val Trp Val
        35                  40                  45

Ser Gly Ile Asn Pro Asp Gly Ser Lys Ile Asp His Ala Glu Ser Val
    50                  55                  60

Gln Gly Arg Phe Thr Ile Ser Arg Asp Asn Ala Lys Asn Thr Leu Tyr
65                  70                  75                  80

Leu Gln Met Asp Ser Leu Arg Asp Glu Asp Thr Ala Val Tyr Tyr Cys
                85                  90                  95

Ala Arg Trp Leu Ser Trp Gly Gln Gly Ala Leu Val Thr Val Thr Ser
            100                 105                 110


<210> SEQ ID NO 219
<211> LENGTH: 106
<212> TYPE: PRT
<213> ORGANISM: Artificial sequence
<220> FEATURE:
<223> OTHER INFORMATION: Synthetic antibody

<400> SEQUENCE: 219

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Lys
            20                  25                  30

Leu Ala Trp Phe Gln Gln Arg Leu Gly Gln Ala Pro Arg Leu Leu Ile
        35                  40                  45

Tyr Asp Ala Ser Thr Arg Ala Thr Gly Val Pro Ala Lys Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys His Gln Arg Ser Asn Trp Trp Thr
                85                  90                  95

Phe Gly Gln Gly Thr Lys Val Glu Val Lys
```

```
            100                 105


<210> SEQ ID NO 220
<211> LENGTH: 118
<212> TYPE: PRT
<213> ORGANISM: Artificial sequence
<220> FEATURE:
<223> OTHER INFORMATION: Synthetic antibody

<400> SEQUENCE: 220

Gln Val Leu Leu Val Gln Ser Glu Ala Glu Val Arg Lys Pro Gly Ala
1               5                   10                  15

Ser Val Lys Ile Ser Cys Lys Thr Ser Gly Tyr Thr Phe Thr Thr Tyr
            20                  25                  30

Phe Met His Trp Val Arg Gln Ala Pro Gly Gln Gly Leu Glu Trp Val
        35                  40                  45

Ala Ile Val Asp Pro Ser Thr Gly Asn Thr Gly Tyr Ala Gln Arg Phe
    50                  55                  60

Gln Gly Arg Val Thr Val Thr Arg Asp Thr Ser Thr Gly Thr Leu Phe
65                  70                  75                  80

Met Glu Leu Thr Ser Leu Thr Thr Glu Asp Thr Ala Met Tyr Tyr Cys
                85                  90                  95

Gly Arg Asp Arg Gly Ser Arg Ala Val Asp Ser Trp Gly Gln Gly Thr
            100                 105                 110

Leu Val Thr Val Phe Ser
        115


<210> SEQ ID NO 221
<211> LENGTH: 111
<212> TYPE: PRT
<213> ORGANISM: Artificial sequence
<220> FEATURE:
<223> OTHER INFORMATION: Synthetic antibody

<400> SEQUENCE: 221

Gln Ser Val Leu Thr Gln Pro Pro Ser Val Ser Gly Ala Pro Gly Gln
1               5                   10                  15

Arg Val Thr Ile Ser Cys Ser Gly Ser Ser Ser Asn Val Gly Pro Asn
            20                  25                  30

Thr Val Ser Trp Tyr Gln Gln Leu Pro Gly Val Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Phe Gly Thr Ser Ala Ser Leu Val Ile Gly Gly Leu Gln
65                  70                  75                  80

Ser Glu Asp Glu Ala Asp Tyr Tyr Cys Ala Ala Trp Asp Asp Ser Leu
                85                  90                  95

Asn Gly His Met Val Phe Gly Gly Gly Thr Lys Val Ala Val Leu
            100                 105                 110


<210> SEQ ID NO 222
<211> LENGTH: 115
<212> TYPE: PRT
<213> ORGANISM: Artificial sequence
<220> FEATURE:
<223> OTHER INFORMATION: Synthetic antibody

<400> SEQUENCE: 222

Gln Val Gln Leu Gln Glu Ser Gly Pro Gly Leu Ala Lys Pro Ser Glu
1               5                   10                  15
```

```
Thr Leu Ser Leu Thr Cys Thr Val Ser Gly Gly Ser Ile Ser Ser Tyr
            20                  25                  30

Phe Trp Ser Trp Ile Arg Gln Pro Ala Gly Lys Gly Leu Glu Trp Ile
        35                  40                  45

Gly Arg Ile His Thr Thr Gly Ser Thr Asn Tyr Asn Pro Ser Leu Lys
    50                  55                  60

Asn Arg Val Ile Met Ser Val Asp Thr Ser Lys Asn Gln Phe Ser Leu
65                  70                  75                  80

Asn Leu Ser Ser Val Thr Ala Ala Asp Thr Ala Val Tyr Tyr Cys Ala
                85                  90                  95

Arg Glu Gly Thr Ala Phe Asp Ile Trp Gly Gln Gly Thr Met Val Thr
            100                 105                 110

Val Ser Ser
        115


<210> SEQ ID NO 223
<211> LENGTH: 107
<212> TYPE: PRT
<213> ORGANISM: Artificial sequence
<220> FEATURE:
<223> OTHER INFORMATION: Synthetic antibody

<400> SEQUENCE: 223

Ser Tyr Glu Leu Thr Gln Ser Pro Ser Val Ser Val Ser Pro Gly Gln
1               5                   10                  15

Thr Ala Ser Ile Pro Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Glu Thr Gln Ala Met
65                  70                  75                  80

Asp Glu Ala Asp Tyr Tyr Cys Gln Ala Trp Asp Ser Ser Thr Pro Trp
                85                  90                  95

Val Phe Gly Gly Gly Thr Lys Leu Thr Val Leu
            100                 105


<210> SEQ ID NO 224
<211> LENGTH: 118
<212> TYPE: PRT
<213> ORGANISM: Artificial sequence
<220> FEATURE:
<223> OTHER INFORMATION: Synthetic antibody

<400> SEQUENCE: 224

Gln Val His Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Gly Thr Gly Ser Phe Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Ile Asn Ser Leu Arg Ala Glu Asp Thr Ala Val Tyr Tyr Cys
```

```
                85                  90                  95

Ala Arg Gly Ile Arg Ala Asp Cys Phe Asp Gln Trp Gly His Gly Thr
            100                 105                 110

Leu Val Thr Val Ser Ser
        115


<210> SEQ ID NO 225
<211> LENGTH: 108
<212> TYPE: PRT
<213> ORGANISM: Artificial sequence
<220> FEATURE:
<223> OTHER INFORMATION: Synthetic antibody

<400> SEQUENCE: 225

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Asp Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Leu Val Phe Gly Thr Gly Thr Lys Val Thr Val Leu
            100                 105


<210> SEQ ID NO 226
<211> LENGTH: 119
<212> TYPE: PRT
<213> ORGANISM: Artificial sequence
<220> FEATURE:
<223> OTHER INFORMATION: Synthetic antibody

<400> SEQUENCE: 226

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Arg Gly Gly Ser Tyr Ser Leu Asp Tyr Trp Gly Gln Gly
            100                 105                 110

Thr Leu Val Thr Val Ser Ser
        115


<210> SEQ ID NO 227
<211> LENGTH: 108
<212> TYPE: PRT
<213> ORGANISM: Artificial sequence
<220> FEATURE:
```

<223> OTHER INFORMATION: Synthetic antibody

<400> SEQUENCE: 227

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu
            100                 105
```

<210> SEQ ID NO 228
<211> LENGTH: 108
<212> TYPE: PRT
<213> ORGANISM: Artificial sequence
<220> FEATURE:
<223> OTHER INFORMATION: Synthetic antibody

<400> SEQUENCE: 228

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu
            100                 105
```

<210> SEQ ID NO 229
<211> LENGTH: 108
<212> TYPE: PRT
<213> ORGANISM: Artificial sequence
<220> FEATURE:
<223> OTHER INFORMATION: Synthetic antibody

<400> SEQUENCE: 229

```
Ser Asn Val Leu Thr Gln Pro Pro Ser Val Ser Val Ala Pro Gly Gln
1               5                   10                  15

Thr Ala Arg Ile Ser Cys Gly Gly Asn Asn Leu Glu Ser Lys Tyr Val
            20                  25                  30

His Trp Tyr Gln Gln Lys Pro Gly Gln Ala Pro Val Leu Val Val Tyr
        35                  40                  45

Glu Asp Ser Gly Arg Pro Ser Gly Ile Pro Glu Arg Phe Ser Gly Ser
    50                  55                  60

Asn Ser Gly Gly Thr Ala Thr Leu Thr Ile Ser Arg Val Glu Ala Gly
```

```
65                  70                  75                  80

Asp Glu Ala Asp Tyr Tyr Cys Gln Glu Trp Asp Thr Ser Ser Asp Tyr
                85                  90                  95

Pro Val Phe Gly Gly Gly Thr Lys Val Thr Val Leu
            100                 105


<210> SEQ ID NO 230
<211> LENGTH: 119
<212> TYPE: PRT
<213> ORGANISM: Artificial sequence
<220> FEATURE:
<223> OTHER INFORMATION: Synthetic antibody

<400> SEQUENCE: 230

Gln Val Gln Val Ala Glu Ser Gly Gly Gly Val Val Gln Pro Gly Arg
1               5                   10                  15

Ser Leu Arg Leu Ser Cys Val Ala Ser Gly Phe Thr Phe Arg Thr Lys
            20                  25                  30

Thr Met His Trp Val Arg Gln Ala Pro Gly Lys Gly Leu Glu Trp Val
        35                  40                  45

Ala Phe Ile Ser Gly Ser Gly Lys Asp Lys Ser Tyr Ala Asp Ser Val
    50                  55                  60

Lys Gly Gln Phe Thr Ile Ser Arg Asp Asn Ser Lys Asn Thr Leu Phe
65                  70                  75                  80

Leu Gln Leu Asp Ser Leu Arg Pro Glu Asp Thr Ala Val Tyr Tyr Cys
                85                  90                  95

Val Lys Asp Arg Glu Gly Thr Trp Ser Phe Asp His Trp Gly Gln Gly
            100                 105                 110

Ala Leu Val Thr Val Ser Ser
        115


<210> SEQ ID NO 231
<211> LENGTH: 110
<212> TYPE: PRT
<213> ORGANISM: Artificial sequence
<220> FEATURE:
<223> OTHER INFORMATION: Synthetic antibody

<400> SEQUENCE: 231

Gln Ser Ala Leu Thr Gln Pro Ala Ser Val Ser Gly Ser Pro Gly Gln
1               5                   10                  15

Ser Ile Thr Ile Ser Cys Thr Gly Thr Asn Asn Asp Val Gly Leu Tyr
            20                  25                  30

Asp Tyr Val Ser Trp Tyr Gln Gln His Pro Gly Arg Ala Pro Lys Leu
        35                  40                  45

Ile Ile Tyr Glu Val Thr Asn Arg Pro Ser Gly Val Ser Asp Arg Phe
    50                  55                  60

Ser Ala Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Arg Ser
                85                  90                  95

Ile Thr Trp Val Phe Gly Gly Gly Thr Lys Val Thr Val Leu
            100                 105                 110


<210> SEQ ID NO 232
<211> LENGTH: 125
<212> TYPE: PRT
<213> ORGANISM: Artificial sequence
<220> FEATURE:
```

<223> OTHER INFORMATION: Synthetic antibody

<400> SEQUENCE: 232

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Lys Tyr Tyr Asp Phe Trp Ser Gly Tyr Tyr Pro Asn Trp Phe
            100                 105                 110

Asp Pro Trp Gly Gln Gly Thr Leu Val Thr Val Ser Ser
        115                 120                 125
```

<210> SEQ ID NO 233
<211> LENGTH: 108
<212> TYPE: PRT
<213> ORGANISM: Artificial sequence
<220> FEATURE:
<223> OTHER INFORMATION: Synthetic antibody

<400> SEQUENCE: 233

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Gln
                85                  90                  95

Arg Thr Phe Gly Gln Gly Thr Lys Val Glu Ile Lys
            100                 105
```

<210> SEQ ID NO 234
<211> LENGTH: 116
<212> TYPE: PRT
<213> ORGANISM: Artificial sequence
<220> FEATURE:
<223> OTHER INFORMATION: Synthetic antibody

<400> SEQUENCE: 234

```
Gln Val Gln Leu Val Gln Ser Gly Ser Glu Leu Lys Lys Ser Gly Ala
1               5                   10                  15

Ser Val Lys Val Ser Cys Arg Ala Ser Gly Tyr Thr Phe Thr Thr Tyr
            20                  25                  30

Val Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
```

```
    50                  55                  60

Thr Gly Arg Phe Val Phe Ser Leu Asp Thr Ser Val Ser Thr Ala Tyr
65                  70                  75                  80

Leu Gln Ile Asn Ser Leu Lys Ala Glu Asp Thr Ala Val Tyr Tyr Cys
                85                  90                  95

Ala Arg Glu Tyr Asn Ser Phe Asp Tyr Trp Gly Gln Gly Thr Leu Val
            100                 105                 110

Thr Val Ser Ser
        115


<210> SEQ ID NO 235
<211> LENGTH: 111
<212> TYPE: PRT
<213> ORGANISM: Artificial sequence
<220> FEATURE:
<223> OTHER INFORMATION: Synthetic antibody

<400> SEQUENCE: 235

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Asn Asn Arg Pro Ser Gly Val Pro Asp Arg Phe
    50                  55                  60

Ser Gly Ser Arg Ser Gly Thr Ser Thr Ser Leu Ala Ile Thr Gly Leu
65                  70                  75                  80

Gln Ala Glu Asp Glu Ala Asp Tyr Tyr Cys Gln Ser Tyr Asp Phe Arg
                85                  90                  95

Leu Ser Gly Ser Val Phe Gly Gly Gly Thr Lys Val Thr Val Leu
            100                 105                 110


<210> SEQ ID NO 236
<211> LENGTH: 119
<212> TYPE: PRT
<213> ORGANISM: Artificial sequence
<220> FEATURE:
<223> OTHER INFORMATION: Synthetic antibody

<400> SEQUENCE: 236

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Ser Pro Ser Gly Gly Ser Thr Asp Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gln Val Gln Thr Asp Tyr Tyr Phe Asp Tyr Trp Gly Gln Gly
            100                 105                 110

Thr Leu Val Thr Val Ser Ser
        115
```

```
<210> SEQ ID NO 237
<211> LENGTH: 109
<212> TYPE: PRT
<213> ORGANISM: Artificial sequence
<220> FEATURE:
<223> OTHER INFORMATION: Synthetic antibody

<400> SEQUENCE: 237

Ser Tyr Val Leu Thr Gln Pro Pro Ser Val Ser Val Ala Pro Gly Gln
1               5                   10                  15

Thr Ala Arg Ile Thr Cys Gly Arg Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Ser Trp Val Phe Gly Gly Gly Thr Lys Leu Thr Val Leu
            100                 105


<210> SEQ ID NO 238
<211> LENGTH: 120
<212> TYPE: PRT
<213> ORGANISM: Artificial sequence
<220> FEATURE:
<223> OTHER INFORMATION: Synthetic antibody

<400> SEQUENCE: 238

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Ala Ile Ser Tyr Asp Gly Ser Asp Lys Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asp Ser Leu Arg Ala Glu Asp Thr Ala Val Tyr Tyr Cys
                85                  90                  95

Ala Arg Asp Arg Ser Gly Ser Tyr Tyr Trp Phe Asp Pro Trp Gly Gln
            100                 105                 110

Gly Thr Leu Val Thr Val Ser Ser
        115                 120


<210> SEQ ID NO 239
<211> LENGTH: 110
<212> TYPE: PRT
<213> ORGANISM: Artificial sequence
<220> FEATURE:
<223> OTHER INFORMATION: Synthetic antibody

<400> SEQUENCE: 239

Asn Phe Met Leu Thr Gln Pro His Ser Val Ser Glu Ser Pro Gly Arg
1               5                   10                  15

Thr Val Thr Ile Ser Cys Thr Arg Ser Ser Gly Ser Ile Ala Asn Asn
```

```
            20                  25                  30

Phe Val Gln Trp Tyr Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn Gln Val Phe Gly Gly Gly Thr Lys Leu Thr Val Leu
            100                 105                 110


<210> SEQ ID NO 240
<211> LENGTH: 122
<212> TYPE: PRT
<213> ORGANISM: Artificial sequence
<220> FEATURE:
<223> OTHER INFORMATION: Synthetic antibody

<400> SEQUENCE: 240

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Ala Ile His Trp Val Arg Gln Ala Pro Gly Gln Arg Leu Glu Trp Met
        35                  40                  45

Gly Trp Ile Asn Ala Gly Asn Gly Asp Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gly Tyr Ser Ser Ser Trp Asp Glu Gly Phe Asp Tyr Trp
            100                 105                 110

Gly Gln Gly Thr Leu Val Thr Val Ser Ser
        115                 120


<210> SEQ ID NO 241
<211> LENGTH: 106
<212> TYPE: PRT
<213> ORGANISM: Artificial sequence
<220> FEATURE:
<223> OTHER INFORMATION: Synthetic antibody

<400> SEQUENCE: 241

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Ser Gly Gln Ser Pro Val Leu Val Ile Asn
        35                  40                  45

Leu Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Gly Val
                85                  90                  95
```

```
Phe Gly Gly Gly Thr Lys Leu Thr Val Leu
            100                 105


<210> SEQ ID NO 242
<211> LENGTH: 121
<212> TYPE: PRT
<213> ORGANISM: Artificial sequence
<220> FEATURE:
<223> OTHER INFORMATION: Synthetic antibody

<400> SEQUENCE: 242

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gly Asp Ser Ser Gly Trp Tyr Met Pro Phe Asp Tyr Trp Gly
            100                 105                 110

Gln Gly Thr Leu Val Thr Val Ser Ser
        115                 120


<210> SEQ ID NO 243
<211> LENGTH: 111
<212> TYPE: PRT
<213> ORGANISM: Artificial sequence
<220> FEATURE:
<223> OTHER INFORMATION: Synthetic antibody

<400> SEQUENCE: 243

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Asn Val Val Phe Gly Gly Gly Thr Lys Leu Thr Val Leu
            100                 105                 110


<210> SEQ ID NO 244
<211> LENGTH: 123
<212> TYPE: PRT
<213> ORGANISM: Artificial sequence
<220> FEATURE:
<223> OTHER INFORMATION: Synthetic antibody

<400> SEQUENCE: 244

Gln Val Gln Leu Gln Glu Ser Gly Pro Gly Leu Val Lys Pro Ser Glu
```

```
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg His Gly Asp Ile Leu Thr Gly Phe Leu Tyr Trp Tyr Phe Asp Leu
            100                 105                 110

Trp Gly Arg Gly Thr Leu Val Thr Val Ser Ser
        115                 120


<210> SEQ ID NO 245
<211> LENGTH: 111
<212> TYPE: PRT
<213> ORGANISM: Artificial sequence
<220> FEATURE:
<223> OTHER INFORMATION: Synthetic antibody

<400> SEQUENCE: 245

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Val Val Phe Gly Gly Gly Thr Lys Leu Thr Val Leu
            100                 105                 110


<210> SEQ ID NO 246
<211> LENGTH: 121
<212> TYPE: PRT
<213> ORGANISM: Artificial sequence
<220> FEATURE:
<223> OTHER INFORMATION: Synthetic antibody

<400> SEQUENCE: 246

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Arg Ile Asp Pro Ser Asp Ser Tyr Thr Asn Tyr Ser Pro Ser Phe
    50                  55                  60

Gln Gly His Val Thr Ile Ser Ala Asp Lys Ser Ile Ser Thr Ala Tyr
65                  70                  75                  80
```

```
Leu Gln Trp Ser Ser Leu Lys Ala Ser Asp Thr Ala Met Tyr Tyr Cys
                85                  90                  95

Ala Arg His Gly Glu Gly Gly Ser Tyr Glu Glu Phe Asp Pro Trp Gly
            100                 105                 110

Gln Gly Thr Leu Val Thr Val Ser Ser
        115                 120


<210> SEQ ID NO 247
<211> LENGTH: 107
<212> TYPE: PRT
<213> ORGANISM: Artificial sequence
<220> FEATURE:
<223> OTHER INFORMATION: Synthetic antibody

<400> SEQUENCE: 247

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys
            100                 105


<210> SEQ ID NO 248
<211> LENGTH: 126
<212> TYPE: PRT
<213> ORGANISM: Artificial sequence
<220> FEATURE:
<223> OTHER INFORMATION: Synthetic antibody

<400> SEQUENCE: 248

Glu Val Gln Leu Val Gln Ser Gly Ala Glu Val Lys Lys Ala Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Gln Glu Trp Met
        35                  40                  45

Gly Ile Ile Tyr Pro Gly Asp Ser Asp Thr Thr Tyr Ser Pro Ser Phe
    50                  55                  60

Gln Gly Gln Val Thr Ile Ser Ala Asp Lys Ser Leu Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Ala Tyr Cys Gly Gly Asp Cys Phe Gly Gly Ala Glu Tyr
            100                 105                 110

Phe Gln His Trp Gly Gln Gly Thr Leu Val Thr Val Ser Ser
        115                 120                 125


<210> SEQ ID NO 249
<211> LENGTH: 113
<212> TYPE: PRT
<213> ORGANISM: Artificial sequence
```

<220> FEATURE:
<223> OTHER INFORMATION: Synthetic antibody

<400> SEQUENCE: 249

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gly Gly Thr Lys Val Glu Ile
            100                 105                 110

Lys
```

<210> SEQ ID NO 250
<211> LENGTH: 119
<212> TYPE: PRT
<213> ORGANISM: Artificial sequence
<220> FEATURE:
<223> OTHER INFORMATION: Synthetic antibody

<400> SEQUENCE: 250

```
Gln Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Val Ser Thr Met Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Ser Cys
                85                  90                  95

Ala Arg Met Asp Thr Glu Tyr Tyr Tyr Phe Asp Tyr Trp Gly Gln Gly
            100                 105                 110

Thr Leu Val Thr Val Ser Ser
        115
```

<210> SEQ ID NO 251
<211> LENGTH: 108
<212> TYPE: PRT
<213> ORGANISM: Artificial sequence
<220> FEATURE:
<223> OTHER INFORMATION: Synthetic antibody

<400> SEQUENCE: 251

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Arg Pro Gly Gln Ala Pro Val Leu Val Val Tyr
```

```
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Asn Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu
            100                 105


<210> SEQ ID NO 252
<211> LENGTH: 119
<212> TYPE: PRT
<213> ORGANISM: Artificial sequence
<220> FEATURE:
<223> OTHER INFORMATION: Synthetic antibody

<400> SEQUENCE: 252

Glu Val Gln Leu Gln Glu Ser Gly Pro Gly Leu Val Gln Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Arg Ser Tyr Tyr Tyr Tyr Tyr Met Asp Val Trp Gly Lys Gly
            100                 105                 110

Thr Thr Val Thr Val Ser Ser
        115


<210> SEQ ID NO 253
<211> LENGTH: 108
<212> TYPE: PRT
<213> ORGANISM: Artificial sequence
<220> FEATURE:
<223> OTHER INFORMATION: Synthetic antibody

<400> SEQUENCE: 253

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Tyr
                85                  90                  95

Val Val Phe Gly Gly Gly Thr Lys Leu Thr Val Leu
            100                 105
```

<210> SEQ ID NO 254
<211> LENGTH: 122
<212> TYPE: PRT
<213> ORGANISM: Artificial sequence
<220> FEATURE:
<223> OTHER INFORMATION: Synthetic antibody

<400> SEQUENCE: 254

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Leu Tyr Tyr Cys
                85                  90                  95

Ala Lys Cys Ile Asp Asn Tyr Tyr Tyr Tyr Cys Tyr Met Asp Val Trp
            100                 105                 110

Gly Lys Gly Thr Thr Val Thr Val Ser Ser
        115                 120
```

<210> SEQ ID NO 255
<211> LENGTH: 110
<212> TYPE: PRT
<213> ORGANISM: Artificial sequence
<220> FEATURE:
<223> OTHER INFORMATION: Synthetic antibody

<400> SEQUENCE: 255

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asp Tyr Val Ser Trp Tyr Gln His His Pro Gly Lys Ala Pro Lys Leu
        35                  40                  45

Met Ile Tyr Ala Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Pro Glu Asp Glu Ser Asp Tyr Tyr Cys Ser Ser Tyr Thr Ser Ser
                85                  90                  95

Ser Thr Trp Val Phe Gly Gly Gly Thr Lys Leu Thr Val Leu
            100                 105                 110
```

<210> SEQ ID NO 256
<211> LENGTH: 118
<212> TYPE: PRT
<213> ORGANISM: Artificial sequence
<220> FEATURE:
<223> OTHER INFORMATION: Synthetic antibody

<400> SEQUENCE: 256

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
```

```
            20                  25                  30

Gly Ile Thr Trp Val Arg Leu Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gly Val Gln Gly Ala Phe Asp Ile Trp Gly Gln Gly Thr
            100                 105                 110

Met Val Thr Val Ser Ser
        115


<210> SEQ ID NO 257
<211> LENGTH: 108
<212> TYPE: PRT
<213> ORGANISM: Artificial sequence
<220> FEATURE:
<223> OTHER INFORMATION: Synthetic antibody

<400> SEQUENCE: 257

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Gln
                85                  90                  95

Arg Val Phe Gly Thr Gly Thr Lys Val Thr Val Leu
            100                 105


<210> SEQ ID NO 258
<211> LENGTH: 128
<212> TYPE: PRT
<213> ORGANISM: Artificial sequence
<220> FEATURE:
<223> OTHER INFORMATION: Synthetic antibody

<400> SEQUENCE: 258

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Asn Trp Gly Asn Tyr Tyr Asp Ser Ser Gly Tyr Ser Tyr Tyr Tyr
            100                 105                 110

Tyr Tyr Met Asp Val Trp Gly Lys Gly Thr Thr Val Thr Val Ser Ser
        115                 120                 125


<210> SEQ ID NO 259
<211> LENGTH: 110
<212> TYPE: PRT
<213> ORGANISM: Artificial sequence
<220> FEATURE:
<223> OTHER INFORMATION: Synthetic antibody

<400> SEQUENCE: 259

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu
            100                 105                 110


<210> SEQ ID NO 260
<211> LENGTH: 121
<212> TYPE: PRT
<213> ORGANISM: Artificial sequence
<220> FEATURE:
<223> OTHER INFORMATION: Synthetic antibody

<400> SEQUENCE: 260

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gly Asp Ser Ser Gly Trp Tyr Met Pro Phe Asp Tyr Trp Gly
            100                 105                 110

Gln Gly Thr Leu Val Thr Val Ser Ser
        115                 120


<210> SEQ ID NO 261
<211> LENGTH: 111
<212> TYPE: PRT
<213> ORGANISM: Artificial sequence
<220> FEATURE:
<223> OTHER INFORMATION: Synthetic antibody
```

<400> SEQUENCE: 261

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Asn Val Val Phe Gly Gly Gly Thr Lys Leu Thr Val Leu
            100                 105                 110
```

<210> SEQ ID NO 262
<211> LENGTH: 121
<212> TYPE: PRT
<213> ORGANISM: Artificial sequence
<220> FEATURE:
<223> OTHER INFORMATION: Synthetic antibody

<400> SEQUENCE: 262

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gly Asp Ser Ser Gly Trp Tyr Met Pro Phe Asp Tyr Trp Gly
            100                 105                 110

Gln Gly Thr Leu Val Thr Val Ser Ser
        115                 120
```

<210> SEQ ID NO 263
<211> LENGTH: 111
<212> TYPE: PRT
<213> ORGANISM: Artificial sequence
<220> FEATURE:
<223> OTHER INFORMATION: Synthetic antibody

<400> SEQUENCE: 263

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60
```

```
Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Asn Val Val Phe Gly Gly Gly Thr Lys Leu Thr Val Leu
            100                 105                 110


<210> SEQ ID NO 264
<211> LENGTH: 121
<212> TYPE: PRT
<213> ORGANISM: Artificial sequence
<220> FEATURE:
<223> OTHER INFORMATION: Synthetic antibody

<400> SEQUENCE: 264

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Ser Arg Gln Trp Leu Val Arg Gly Phe Asp Tyr Trp Gly
            100                 105                 110

Gln Gly Thr Leu Val Thr Val Ser Ser
        115                 120


<210> SEQ ID NO 265
<211> LENGTH: 127
<212> TYPE: PRT
<213> ORGANISM: Artificial sequence
<220> FEATURE:
<223> OTHER INFORMATION: Synthetic antibody

<400> SEQUENCE: 265

Glu Ala Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Tyr Ala
            20                  25                  30

Trp Met Ser Trp Val Arg Arg Leu Pro Gly Lys Gly Leu Glu Trp Val
        35                  40                  45

Gly Arg Ile Lys Gly Lys Ala Asp Gly Glu Thr Thr Asp Tyr Ala Ala
    50                  55                  60

Pro Val Lys Gly Arg Phe Thr Ile Ser Arg Asp Asp Ser Lys Thr Thr
65                  70                  75                  80

Val Tyr Leu Gln Met Asn Thr Leu Lys Ile Glu Asp Thr Gly Val Tyr
                85                  90                  95

Tyr Cys Thr Thr Asp Ile Gly Asp Phe Tyr Asp Ser Ile Gly Tyr Ser
            100                 105                 110

Tyr Thr Asp Tyr Trp Gly Gln Gly Thr Leu Val Thr Val Ser Ser
        115                 120                 125


<210> SEQ ID NO 266
```

<211> LENGTH: 107
<212> TYPE: PRT
<213> ORGANISM: Artificial sequence
<220> FEATURE:
<223> OTHER INFORMATION: Synthetic antibody

<400> SEQUENCE: 266

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Val Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Leu Tyr Tyr Cys Gln Gln Arg Ser Asp Trp Pro Pro
                85                  90                  95

Thr Phe Gly Gln Gly Thr Lys Val Glu Ile Lys
            100                 105
```

<210> SEQ ID NO 267
<211> LENGTH: 119
<212> TYPE: PRT
<213> ORGANISM: Artificial sequence
<220> FEATURE:
<223> OTHER INFORMATION: Synthetic antibody

<400> SEQUENCE: 267

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Asn Tyr Tyr Tyr Tyr Met Asp Val Trp Gly Lys Gly
            100                 105                 110

Thr Thr Val Thr Val Ser Ser
        115
```

<210> SEQ ID NO 268
<211> LENGTH: 108
<212> TYPE: PRT
<213> ORGANISM: Artificial sequence
<220> FEATURE:
<223> OTHER INFORMATION: Synthetic antibody

<400> SEQUENCE: 268

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30
```

```
His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu
            100                 105


<210> SEQ ID NO 269
<211> LENGTH: 124
<212> TYPE: PRT
<213> ORGANISM: Artificial sequence
<220> FEATURE:
<223> OTHER INFORMATION: Synthetic antibody

<400> SEQUENCE: 269

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Val Arg Gln Ala Pro Gly Lys Gly Leu Glu Trp Val
        35                  40                  45

Gly Phe Ile Arg Ser Lys Ala Tyr Gly Gly Thr Arg Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Asn His Arg Gly Ser Ser Trp Tyr Pro Asp Ala Phe Asp
            100                 105                 110

Ile Trp Gly Gln Gly Thr Met Val Thr Val Ser Ser
        115                 120


<210> SEQ ID NO 270
<211> LENGTH: 109
<212> TYPE: PRT
<213> ORGANISM: Artificial sequence
<220> FEATURE:
<223> OTHER INFORMATION: Synthetic antibody

<400> SEQUENCE: 270

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Pro
                85                  90                  95

Asp Val Val Phe Gly Gly Gly Thr Lys Leu Thr Val Leu
            100                 105
```

<210> SEQ ID NO 271
<211> LENGTH: 117
<212> TYPE: PRT
<213> ORGANISM: Artificial sequence
<220> FEATURE:
<223> OTHER INFORMATION: Synthetic antibody

<400> SEQUENCE: 271

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Arg Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Thr Gly Arg Leu Asp Tyr Trp Gly Gln Gly Thr Leu
            100                 105                 110

Val Thr Val Ser Ser
        115
```

<210> SEQ ID NO 272
<211> LENGTH: 108
<212> TYPE: PRT
<213> ORGANISM: Artificial sequence
<220> FEATURE:
<223> OTHER INFORMATION: Synthetic antibody

<400> SEQUENCE: 272

```
Ser Tyr Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

Asn Trp Tyr Gln Gln Lys Pro Gly Gln Ala Pro Val Leu Val Val Tyr
        35                  40                  45

Asp Asp Ser Asp Arg Pro Leu Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Asn Cys Gln Val Trp Asp Ser Ser Ser Asp His
                85                  90                  95

Trp Val Phe Gly Gly Gly Thr Lys Leu Thr Val Leu
            100                 105
```

<210> SEQ ID NO 273
<211> LENGTH: 116
<212> TYPE: PRT
<213> ORGANISM: Artificial sequence
<220> FEATURE:
<223> OTHER INFORMATION: Synthetic antibody

<400> SEQUENCE: 273

```
Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Pro Gly Ser Val Lys
    50                  55                  60

Gly Arg Phe Thr Ile Ser Arg Glu Ser Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Gly Leu Gly Gly Gly Phe Asp Tyr Trp Gly Gln Gly Thr Leu Val
            100                 105                 110

Thr Val Ser Ser
        115


<210> SEQ ID NO 274
<211> LENGTH: 108
<212> TYPE: PRT
<213> ORGANISM: Artificial sequence
<220> FEATURE:
<223> OTHER INFORMATION: Synthetic antibody

<400> SEQUENCE: 274

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu
            100                 105


<210> SEQ ID NO 275
<211> LENGTH: 121
<212> TYPE: PRT
<213> ORGANISM: Artificial sequence
<220> FEATURE:
<223> OTHER INFORMATION: Synthetic antibody

<400> SEQUENCE: 275

Glu Val Gln Leu Leu Glu Ser Gly Gly Gly Leu Val Gln Pro Gly Gly
1               5                   10                  15

Ser Leu Arg Leu Ser Cys Val Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser Gly Asn Val Asp Asn Thr His Tyr Ala Asp Ser Val
    50                  55                  60

Lys Gly Arg Phe Thr Ile Ser Arg Asp Asn Ser Lys Ser Thr Leu Phe
65                  70                  75                  80

Leu Gln Met His Ser Leu Arg Ala Glu Asp Thr Ala Val Tyr Phe Cys
                85                  90                  95
```

```
Ala Lys Val Gly Gln Tyr Trp Ser Gly His Tyr Leu Asp Tyr Trp Gly
            100                 105                 110

Gln Gly Thr Leu Val Thr Val Ser Ser
        115                 120


<210> SEQ ID NO 276
<211> LENGTH: 108
<212> TYPE: PRT
<213> ORGANISM: Artificial sequence
<220> FEATURE:
<223> OTHER INFORMATION: Synthetic antibody

<400> SEQUENCE: 276

Ser Tyr Val Leu Thr Gln Pro Pro Ser Val Ser Val Ala Pro Gly Gln
1               5                   10                  15

Thr Ala Arg Met Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Asn Arg Val Glu Ala Gly
65                  70                  75                  80

Asp Glu Ala Asp Tyr Tyr Cys Gln Val Trp His Ser Asp Ser Asp Gln
                85                  90                  95

Tyr Val Phe Gly Thr Gly Thr Lys Val Thr Val Leu
            100                 105


<210> SEQ ID NO 277
<211> LENGTH: 121
<212> TYPE: PRT
<213> ORGANISM: Artificial sequence
<220> FEATURE:
<223> OTHER INFORMATION: Synthetic antibody

<400> SEQUENCE: 277

Glu Val Gln Leu Leu Glu Ser Gly Gly Gly Leu Val His Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Phe Lys Asn Thr Leu Tyr
65                  70                  75                  80

Val Gln Met Asn Ser Leu Arg Ala Glu Asp Thr Ala Val Tyr Tyr Cys
                85                  90                  95

Ala Thr Glu Asn Asp Phe Trp Ser Gly His Gln Phe Asp Tyr Trp Gly
            100                 105                 110

Gln Gly Thr Leu Val Thr Val Ser Ser
        115                 120


<210> SEQ ID NO 278
<211> LENGTH: 108
<212> TYPE: PRT
<213> ORGANISM: Artificial sequence
<220> FEATURE:
<223> OTHER INFORMATION: Synthetic antibody
```

```
<400> SEQUENCE: 278

Ser Tyr Val Leu Thr Gln Pro Pro Ser Val Ser Val Ala Pro Gly Gln
1               5                   10                  15

Thr Ala Arg Met Thr Cys Gly Gly Asn Asn Ile Gly Ser Lys Ser Val
            20                  25                  30

Gln Trp Tyr Gln Gln Lys Pro Gly Gln Ala Pro Val Leu Val Val His
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu
            100                 105


<210> SEQ ID NO 279
<211> LENGTH: 116
<212> TYPE: PRT
<213> ORGANISM: Artificial sequence
<220> FEATURE:
<223> OTHER INFORMATION: Synthetic antibody

<400> SEQUENCE: 279

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Ala Val Gly Gly Gly Phe Asp Tyr Trp Gly Gln Gly Thr Leu Val
            100                 105                 110

Thr Val Ser Ser
        115


<210> SEQ ID NO 280
<211> LENGTH: 108
<212> TYPE: PRT
<213> ORGANISM: Artificial sequence
<220> FEATURE:
<223> OTHER INFORMATION: Synthetic antibody

<400> SEQUENCE: 280

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60
```

```
Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Leu
                85                  90                  95

Tyr Val Phe Gly Thr Gly Thr Lys Val Thr Val Leu
            100                 105


<210> SEQ ID NO 281
<211> LENGTH: 123
<212> TYPE: PRT
<213> ORGANISM: Artificial sequence
<220> FEATURE:
<223> OTHER INFORMATION: Synthetic antibody

<400> SEQUENCE: 281

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Ser Arg Ala Ile Leu Thr Gly Tyr Pro Asn Trp Phe Asp Pro
            100                 105                 110

Trp Gly Gln Gly Thr Leu Val Thr Val Ser Ser
        115                 120


<210> SEQ ID NO 282
<211> LENGTH: 107
<212> TYPE: PRT
<213> ORGANISM: Artificial sequence
<220> FEATURE:
<223> OTHER INFORMATION: Synthetic antibody

<400> SEQUENCE: 282

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105


<210> SEQ ID NO 283
<211> LENGTH: 123
<212> TYPE: PRT
```

```
<213> ORGANISM: Artificial sequence
<220> FEATURE:
<223> OTHER INFORMATION: Synthetic antibody

<400> SEQUENCE: 283

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Thr Glu Asp Thr Ala Phe Tyr Tyr Cys
                85                  90                  95

Ala Lys Asp Lys Gly Asp Gly Ser Gly Ser Phe Tyr Tyr Met Asp Val
            100                 105                 110

Trp Gly Lys Gly Thr Thr Val Thr Val Ser Ser
        115                 120


<210> SEQ ID NO 284
<211> LENGTH: 107
<212> TYPE: PRT
<213> ORGANISM: Artificial sequence
<220> FEATURE:
<223> OTHER INFORMATION: Synthetic antibody

<400> SEQUENCE: 284

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Ser Cys Gln Gln Tyr Asp Asn Leu Pro Leu
                85                  90                  95

Thr Phe Gly Gly Gly Thr Lys Val Glu Ile Lys
            100                 105


<210> SEQ ID NO 285
<211> LENGTH: 116
<212> TYPE: PRT
<213> ORGANISM: Artificial sequence
<220> FEATURE:
<223> OTHER INFORMATION: Synthetic antibody

<400> SEQUENCE: 285

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45
```

```
Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Leu Gly Val Val Val Trp Pro Trp Gly Gln Gly Thr Leu Val
            100                 105                 110

Thr Val Ser Ser
        115


<210> SEQ ID NO 286
<211> LENGTH: 115
<212> TYPE: PRT
<213> ORGANISM: Artificial sequence
<220> FEATURE:
<223> OTHER INFORMATION: Synthetic antibody

<400> SEQUENCE: 286

Gln Pro Val Leu Thr Gln Pro Pro Ser Ser Ser Ala Ser Pro Gly Glu
1               5                   10                  15

Ser Ala Arg Leu Thr Cys Thr Leu Pro Ser Asp Ile Asn Val Gly Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser Asp Lys Gly Gln Gly Ser Gly Val
    50                  55                  60

Pro Ser Arg Phe Ser Gly Ser Lys Asp Ala Ser Ala Asn Thr Gly Ile
65                  70                  75                  80

Leu Leu Ile Ser Gly Leu Gln Ser Glu Asp Glu Ala Asp Tyr Tyr Cys
                85                  90                  95

Met Ile Trp Pro Ser Asn Ala Trp Val Phe Gly Gly Gly Thr Lys Leu
            100                 105                 110

Thr Val Leu
        115


<210> SEQ ID NO 287
<211> LENGTH: 117
<212> TYPE: PRT
<213> ORGANISM: Artificial sequence
<220> FEATURE:
<223> OTHER INFORMATION: Synthetic antibody

<400> SEQUENCE: 287

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Leu Ser Ser Gly Trp Tyr Glu Trp Gly Gln Gly Thr Leu
```

```
            100                 105                 110

Val Thr Val Ser Ser
        115


<210> SEQ ID NO 288
<211> LENGTH: 108
<212> TYPE: PRT
<213> ORGANISM: Artificial sequence
<220> FEATURE:
<223> OTHER INFORMATION: Synthetic antibody

<400> SEQUENCE: 288

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu
            100                 105


<210> SEQ ID NO 289
<211> LENGTH: 117
<212> TYPE: PRT
<213> ORGANISM: Artificial sequence
<220> FEATURE:
<223> OTHER INFORMATION: Synthetic antibody

<400> SEQUENCE: 289

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Leu Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Leu Arg Pro Asp Ala Phe Asp Ile Trp Gly Gln Gly Thr Met
            100                 105                 110

Val Thr Val Ser Ser
        115


<210> SEQ ID NO 290
<211> LENGTH: 108
<212> TYPE: PRT
<213> ORGANISM: Artificial sequence
<220> FEATURE:
<223> OTHER INFORMATION: Synthetic antibody

<400> SEQUENCE: 290
```

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Gly Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105


<210> SEQ ID NO 291
<211> LENGTH: 121
<212> TYPE: PRT
<213> ORGANISM: Artificial sequence
<220> FEATURE:
<223> OTHER INFORMATION: Synthetic antibody

<400> SEQUENCE: 291

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Arg Ile Glu Pro Ser Asp Ser Tyr Thr Asn Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Gly Asp Ser Ser Gly Tyr Gly Glu Ile Asp Tyr Trp Gly
            100                 105                 110

Gln Gly Thr Leu Val Thr Val Ser Ser
        115                 120


<210> SEQ ID NO 292
<211> LENGTH: 107
<212> TYPE: PRT
<213> ORGANISM: Artificial sequence
<220> FEATURE:
<223> OTHER INFORMATION: Synthetic antibody

<400> SEQUENCE: 292

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
```

```
65                  70                  75                  80

Glu Asp Phe Ala Thr Tyr Tyr Cys Gln Gln Ser Tyr Ser Thr Pro Gln
                85                  90                  95

Thr Phe Gly Gln Gly Thr Lys Val Glu Ile Lys
            100                 105


<210> SEQ ID NO 293
<211> LENGTH: 117
<212> TYPE: PRT
<213> ORGANISM: Artificial sequence
<220> FEATURE:
<223> OTHER INFORMATION: Synthetic antibody

<400> SEQUENCE: 293

Gln Val Gln Leu Met Gln Ser Gly Ala Glu Val Lys Lys Pro Gly Ala
1               5                   10                  15

Ser Val Lys Val Ser Cys Arg Ala Ser Gly Asn Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ile Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Lys Ser Glu Asp Thr Ala Val Tyr Tyr Cys
                85                  90                  95

Ala Arg Gly Glu Ser Tyr Tyr Phe Asp Tyr Trp Gly Gln Gly Thr Leu
            100                 105                 110

Val Thr Val Ser Ser
        115


<210> SEQ ID NO 294
<211> LENGTH: 108
<212> TYPE: PRT
<213> ORGANISM: Artificial sequence
<220> FEATURE:
<223> OTHER INFORMATION: Synthetic antibody

<400> SEQUENCE: 294

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Glu Ser Lys Ser Val
            20                  25                  30

His Trp Tyr Gln Gln Lys Pro Gly Gln Ala Pro Val Leu Val Val Tyr
        35                  40                  45

Asp Asp Thr Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Cys Val Phe Gly Gly Gly Thr Lys Leu Thr Val Leu
            100                 105


<210> SEQ ID NO 295
<211> LENGTH: 118
<212> TYPE: PRT
<213> ORGANISM: Artificial sequence
<220> FEATURE:
```

<223> OTHER INFORMATION: Synthetic antibody

<400> SEQUENCE: 295

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Phe Tyr Pro Ala Ala Met Asp Val Trp Gly Lys Gly Thr
            100                 105                 110

Thr Val Thr Val Ser Ser
        115
```

<210> SEQ ID NO 296
<211> LENGTH: 108
<212> TYPE: PRT
<213> ORGANISM: Artificial sequence
<220> FEATURE:
<223> OTHER INFORMATION: Synthetic antibody

<400> SEQUENCE: 296

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Arg Val Phe Gly Gly Gly Thr Lys Leu Thr Val Leu
            100                 105
```

<210> SEQ ID NO 297
<211> LENGTH: 121
<212> TYPE: PRT
<213> ORGANISM: Artificial sequence
<220> FEATURE:
<223> OTHER INFORMATION: Synthetic antibody

<400> SEQUENCE: 297

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Arg Ile Glu Pro Ser Asp Ser Tyr Thr Asn Tyr Ser Pro Ser Phe
```

```
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Gly Asp Ser Ser Gly Tyr Gly Glu Ile Asp Tyr Trp Gly
            100                 105                 110

Gln Gly Thr Leu Val Thr Val Ser Ser
        115                 120


<210> SEQ ID NO 298
<211> LENGTH: 107
<212> TYPE: PRT
<213> ORGANISM: Artificial sequence
<220> FEATURE:
<223> OTHER INFORMATION: Synthetic antibody

<400> SEQUENCE: 298

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Gln
                85                  90                  95

Thr Phe Gly Gln Gly Thr Lys Val Glu Ile Lys
            100                 105


<210> SEQ ID NO 299
<211> LENGTH: 120
<212> TYPE: PRT
<213> ORGANISM: Artificial sequence
<220> FEATURE:
<223> OTHER INFORMATION: Synthetic antibody

<400> SEQUENCE: 299

Gln Val Gln Leu Gln Glu Ser Gly Pro Gly Leu Val Lys Pro Ser Gln
1               5                   10                  15

Thr Leu Ser Leu Thr Cys Thr Val Ser Gly Asp Ser Ile Ser Gly Gly
            20                  25                  30

Asp Tyr Tyr Trp Ser Trp Ile Arg Arg Pro Ala Gly Glu Gly Leu Glu
        35                  40                  45

Trp Ile Gly Arg Val His Thr Thr Gly Ser Thr Asp Tyr Asn Pro Ser
    50                  55                  60

Leu Arg Thr Arg Val Thr Ile Ser Ile Asp Thr Ser Lys Asn His Phe
65                  70                  75                  80

Phe Leu Lys Met Thr Ser Val Thr Ala Ala Asp Thr Ala Val Tyr Tyr
                85                  90                  95

Cys Ala Arg Glu Gly Asp Tyr Ser Ala Trp Phe Asp Pro Trp Gly Gln
            100                 105                 110

Gly Ala Leu Val Thr Val Ser Ser
        115                 120
```

<210> SEQ ID NO 300
<211> LENGTH: 108
<212> TYPE: PRT
<213> ORGANISM: Artificial sequence
<220> FEATURE:
<223> OTHER INFORMATION: Synthetic antibody

<400> SEQUENCE: 300

```
Asp Ile Gln Met Thr Gln Ser Pro Ser Ser Leu Ser Ala Ser Ile Gly
1               5                   10                  15

Asp Arg Val Thr Ile Thr Cys Arg Ala Ser Gln His Ile Glu Ser Phe
            20                  25                  30

Leu Asn Trp Tyr Gln Gln Lys Pro Gly Lys Ala Pro Lys Leu Leu Ile
        35                  40                  45

Tyr Ile Ala Ser Thr Leu Gln Gly Gly Val Pro Ser Arg Phe Ser Gly
    50                  55                  60

Arg Gly Phe Gly Thr Asp Phe Thr Leu Thr Ile Asn Ser Leu Gln Pro
65                  70                  75                  80

Glu Asp Phe Ala Thr Tyr Tyr Cys Gln Gln Ser Tyr Thr Ile Ser Pro
                85                  90                  95

Ile Thr Phe Gly Gln Gly Thr Arg Leu Glu Ile Lys
            100                 105
```

<210> SEQ ID NO 301
<211> LENGTH: 124
<212> TYPE: PRT
<213> ORGANISM: Artificial sequence
<220> FEATURE:
<223> OTHER INFORMATION: Synthetic antibody

<400> SEQUENCE: 301

```
Gln Glu Gln Leu Val Glu Ser Gly Gly Gly Val Val Gln Pro Gly Arg
1               5                   10                  15

Ser Leu Arg Leu Ser Cys Ala Ala Ser Gly Phe Thr Leu Arg Gly Tyr
            20                  25                  30

Gly Ile Tyr Trp Val Arg Gln Ala Pro Gly Lys Gly Leu Glu Trp Val
        35                  40                  45

Ala Val Ile Ser His Asp Gly Lys Asn Glu Ser Tyr Thr Asp Ser Val
    50                  55                  60

Lys Gly Arg Phe Ser Ile Ser Arg Asp Lys Ser Lys Asn Thr Val Phe
65                  70                  75                  80

Leu Gln Met Asn Ser Leu Thr Thr Gln Asp Thr Ser Val Tyr Tyr Cys
                85                  90                  95

Ala Arg Trp Thr Glu Gly Ser Glu Glu Phe Tyr Tyr His Gly Leu Asp
            100                 105                 110

Val Trp Gly Gln Gly Thr Thr Val Thr Val Ser Pro
        115                 120
```

<210> SEQ ID NO 302
<211> LENGTH: 109
<212> TYPE: PRT
<213> ORGANISM: Artificial sequence
<220> FEATURE:
<223> OTHER INFORMATION: Synthetic antibody

<400> SEQUENCE: 302

```
Ser Tyr Glu Leu Thr Gln Pro Pro Ser Val Ser Val Ser Pro Gly Gln
1               5                   10                  15

Thr Ala Arg Ile Thr Cys Ser Gly His Leu Leu Pro Lys Gln Tyr Ala
```

```
            20                  25                  30

Tyr Trp Tyr Gln Gln Lys Pro Gly Gln Ala Pro Thr Leu Val Ile Tyr
        35                  40                  45

Ala Asp Tyr Asn Arg Ala Ser Gly Ile Pro Glu Arg Phe Ser Gly Ala
    50                  55                  60

Ser Ser Gly Thr Thr Val Thr Leu Thr Ile Thr Gly Val Lys Ala Glu
65                  70                  75                  80

Asp Gln Ala Asp Tyr Tyr Cys Gln Ser Ile Asp Asn Arg Phe His Tyr
                85                  90                  95

Pro Met Ile Phe Gly Gly Gly Thr Lys Leu Thr Val Leu
            100                 105


<210> SEQ ID NO 303
<211> LENGTH: 130
<212> TYPE: PRT
<213> ORGANISM: Artificial sequence
<220> FEATURE:
<223> OTHER INFORMATION: Synthetic antibody

<400> SEQUENCE: 303

Gln Ile Thr Phe Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Leu Tyr Trp Asn Asp Asp Lys Arg Tyr Thr Pro Ser
    50                  55                  60

Leu Arg Ser Arg Leu Thr Ile Thr Lys Asp Thr Ser Lys Asn Gln Val
65                  70                  75                  80

Val Leu Thr Met Thr Asp Met Asp Pro Val Asp Thr Ala Thr Tyr Tyr
                85                  90                  95

Cys Ala Arg Lys Pro Arg Asp Asp Phe Leu Arg Leu Thr Met Met Gly
            100                 105                 110

Gly Gly Asp Tyr Phe Asp Tyr Trp Gly Gln Gly Thr Leu Val Thr Val
        115                 120                 125

Ser Ser
    130


<210> SEQ ID NO 304
<211> LENGTH: 109
<212> TYPE: PRT
<213> ORGANISM: Artificial sequence
<220> FEATURE:
<223> OTHER INFORMATION: Synthetic antibody

<400> SEQUENCE: 304

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Asp Gln Tyr Ala
            20                  25                  30

Tyr Trp Tyr Gln Gln Lys Pro Gly Gln Ala Pro Val Leu Val Leu Tyr
        35                  40                  45

Lys Asp Asn Glu Arg Pro Ser Gly Ile Pro Glu Arg Phe Ser Gly Ser
    50                  55                  60

Thr Ser Gly Thr Thr Val Thr Leu Thr Ile Ser Gly Val Gln Ala Glu
65                  70                  75                  80
```

```
Asp Glu Ala Asp Tyr Tyr Cys Gln Ser Ala Asp Thr Ser Thr Ala Tyr
                85                  90                  95

His Val Ile Phe Gly Gly Gly Thr Lys Leu Thr Val Leu
            100                 105


<210> SEQ ID NO 305
<211> LENGTH: 121
<212> TYPE: PRT
<213> ORGANISM: Artificial sequence
<220> FEATURE:
<223> OTHER INFORMATION: Synthetic antibody

<400> SEQUENCE: 305

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Glu Met Asn Trp Val Arg Gln Ala Pro Gly Lys Gly Leu Glu Trp Val
        35                  40                  45

Ser Tyr Ile Ser Arg Ser Gly Thr Thr Lys His Tyr Ala Asp Ser Val
    50                  55                  60

Lys Gly Arg Phe Ala Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ala Arg Val Leu Gln Ala Pro Leu Asp Tyr Trp Gly
            100                 105                 110

Gln Gly Thr Leu Val Thr Val Ser Ser
        115                 120


<210> SEQ ID NO 306
<211> LENGTH: 108
<212> TYPE: PRT
<213> ORGANISM: Artificial sequence
<220> FEATURE:
<223> OTHER INFORMATION: Synthetic antibody

<400> SEQUENCE: 306

Ser Tyr Glu Leu Thr Gln Pro Pro Ser Val Ser Val Ala Pro Gly Glu
1               5                   10                  15

Thr Ala Arg Ile Thr Cys Gly Gly Thr Asn Ile Gly Asn Lys Ser Val
            20                  25                  30

Arg Trp Tyr Gln Gln Lys Pro Gly Gln Ala Pro Val Leu Val Ile Tyr
        35                  40                  45

Tyr Asp Asn Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Asn Ser Ser Asp His
                85                  90                  95

Ala Val Phe Gly Gly Gly Thr Lys Leu Thr Val Leu
            100                 105


<210> SEQ ID NO 307
<211> LENGTH: 121
<212> TYPE: PRT
<213> ORGANISM: Artificial sequence
<220> FEATURE:
<223> OTHER INFORMATION: Synthetic antibody
```

<400> SEQUENCE: 307

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Asn Tyr Ala Gln Asn Phe
    50                  55                  60

Gln Gly Arg Val Thr Met Thr Arg Asp Thr Ser Thr Thr Thr Val Tyr
65                  70                  75                  80

Met Glu Leu Ser Ser Leu Arg Ser Glu Asp Thr Ala Val Tyr Tyr Cys
                85                  90                  95

Ala Arg Ala Ile Tyr Trp Asn Val Pro Tyr Tyr Phe Asp Tyr Trp Gly
            100                 105                 110

Gln Gly Thr Leu Val Thr Val Ser Ser
        115                 120
```

<210> SEQ ID NO 308
<211> LENGTH: 107
<212> TYPE: PRT
<213> ORGANISM: Artificial sequence
<220> FEATURE:
<223> OTHER INFORMATION: Synthetic antibody

<400> SEQUENCE: 308

```
Glu Thr Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Trp Leu Ala Trp Tyr Gln Gln Lys Pro Gly Gln Ala Pro Arg Leu Leu
        35                  40                  45

Ile Tyr Asp Ala Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Leu Ala Val Tyr Tyr Cys Gln Gln Tyr Gly Asn Ser Pro Thr
                85                  90                  95

Thr Phe Gly Gln Gly Thr Lys Val Glu Ile Lys
            100                 105
```

<210> SEQ ID NO 309
<211> LENGTH: 123
<212> TYPE: PRT
<213> ORGANISM: Artificial sequence
<220> FEATURE:
<223> OTHER INFORMATION: Synthetic antibody

<400> SEQUENCE: 309

```
Gln Val Gln Leu Gln Glu Ser Gly Pro Gly Leu Leu Lys Pro Ser Gln
1               5                   10                  15

Thr Leu Ser Leu Thr Cys Gly Val Ser Gly Asp Ser Ile Thr Ser Thr
            20                  25                  30

Gly Asp Ser Trp Thr Trp Ile Arg Gln Pro Pro Gly Lys Gly Leu Glu
        35                  40                  45

Trp Ile Gly Tyr Ile Tyr Tyr Ser Gly Ser Ala Tyr Tyr Asn Pro Ser
    50                  55                  60
```

```
Leu Lys Ser Arg Val Thr Ile Ser Val Asp Thr Ser Lys Asn Gln Phe
65                  70                  75                  80

Ser Leu Arg Leu Arg Ser Val Thr Ala Ala Asp Thr Ala Val Tyr Tyr
                85                  90                  95

Cys Ala Arg Ala Leu Glu Tyr Gly Ala Gly Ser Trp Ala Ala Ala Phe
            100                 105                 110

Trp Gly Gln Gly Ile Leu Val Thr Val Ser Ser
        115                 120


<210> SEQ ID NO 310
<211> LENGTH: 106
<212> TYPE: PRT
<213> ORGANISM: Artificial sequence
<220> FEATURE:
<223> OTHER INFORMATION: Synthetic antibody

<400> SEQUENCE: 310

Ser Tyr Glu Val Thr Gln Pro Pro Ser Val Ser Val Ser Pro Gly Gln
1               5                   10                  15

Thr Ala Ser Ile Thr Cys Ser Gly Asp Lys Leu Val Glu Arg Tyr Val
            20                  25                  30

Ser Trp Tyr Gln Gln Lys Pro Gly Gln Ser Pro Leu Leu Val Ile Tyr
        35                  40                  45

His Asp Ile Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Pro Met
65                  70                  75                  80

Asp Glu Ala Asp Tyr Tyr Cys Gln Ala Trp Asp Ser Ser Thr Val Leu
                85                  90                  95

Phe Gly Gly Gly Thr Lys Leu Thr Val Leu
            100                 105


<210> SEQ ID NO 311
<211> LENGTH: 124
<212> TYPE: PRT
<213> ORGANISM: Artificial sequence
<220> FEATURE:
<223> OTHER INFORMATION: Synthetic antibody

<400> SEQUENCE: 311

Gln Val Gln Leu Val Gln Ser Gly Ala Glu Val Lys Lys Pro Gly Ser
1               5                   10                  15

Ser Val Lys Val Ser Cys Arg Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Gly Ile Ile Pro Ile Leu Gly Leu Thr Lys Phe Ala Gln Lys Phe
    50                  55                  60

Gln Asp Arg Val Thr Ile Thr Ala Asp Ile Ser Ala Thr Thr Thr Tyr
65                  70                  75                  80

Met Glu Leu Ser Ser Leu Thr Ser Glu Asp Thr Ala Val Tyr Tyr Cys
                85                  90                  95

Ala Arg Asn Gly Glu Gln Leu Glu Trp Ser Tyr Tyr Tyr Gly Met Asp
            100                 105                 110

Val Trp Gly Gln Gly Thr Thr Val Thr Val Ser Ser
        115                 120


<210> SEQ ID NO 312
```

```
<211> LENGTH: 113
<212> TYPE: PRT
<213> ORGANISM: Artificial sequence
<220> FEATURE:
<223> OTHER INFORMATION: Synthetic antibody

<400> SEQUENCE: 312

Asp Ile Val Met Thr Gln Ser Pro Asp Ser Leu Ala Val Ser Leu Gly
1               5                   10                  15

Glu Arg Ala Thr Ile Asn Cys Lys Pro Ser Gln Ser Ile Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Asn Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Phe Tyr Cys Gln Gln
                85                  90                  95

Tyr Tyr Thr Ile Pro Pro Thr Phe Gly Gln Gly Thr Lys Val Glu Ile
            100                 105                 110

Lys


<210> SEQ ID NO 313
<211> LENGTH: 123
<212> TYPE: PRT
<213> ORGANISM: Artificial sequence
<220> FEATURE:
<223> OTHER INFORMATION: Synthetic antibody

<400> SEQUENCE: 313

Gln Val Gln Leu Gln Gln Trp Gly Ala Gly Leu Leu Lys Pro Ser Glu
1               5                   10                  15

Thr Leu Ser Leu Thr Cys Thr Val Tyr Gly Gly Ser Phe Thr Leu Tyr
            20                  25                  30

Tyr Trp Thr Trp Ile Arg Gln Pro Pro Gly Lys Gly Leu Glu Trp Ile
        35                  40                  45

Gly Glu Ile Asn Gln Ser Gly Ser Thr Asn Tyr Asn Pro Ser Leu Arg
    50                  55                  60

Ser Arg Leu Thr Ile Ser Val Asp Thr Ser Lys Ser Gln Phe Ser Leu
65                  70                  75                  80

Lys Val Thr Ser Val Thr Ala Ala Asp Thr Ala Val Tyr Tyr Cys Ala
                85                  90                  95

Arg Gly His Asp Ser Ser Gly Tyr Tyr Ile Asp Tyr Tyr Leu Asp Val
            100                 105                 110

Trp Gly Lys Gly Thr Thr Val Thr Val Ser Ser
        115                 120


<210> SEQ ID NO 314
<211> LENGTH: 108
<212> TYPE: PRT
<213> ORGANISM: Artificial sequence
<220> FEATURE:
<223> OTHER INFORMATION: Synthetic antibody

<400> SEQUENCE: 314

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Asn Tyr Tyr Ala
```

```
            20                  25                  30

Gly Trp Tyr Gln Gln Arg Pro Gly Gln Ala Pro Val Leu Val Phe Tyr
        35                  40                  45

Gly Lys Asp Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asp Val
                85                  90                  95

Val Val Phe Gly Gly Gly Thr Lys Leu Thr Val Leu
            100                 105


<210> SEQ ID NO 315
<211> LENGTH: 122
<212> TYPE: PRT
<213> ORGANISM: Artificial sequence
<220> FEATURE:
<223> OTHER INFORMATION: Synthetic antibody

<400> SEQUENCE: 315

Gln Val Gln Leu His Glu Ser Gly Pro Gly Leu Val Lys Pro Ser Glu
1               5                   10                  15

Thr Leu Ser Leu Thr Cys Gly Val Ser Gly Tyr Thr Ile Ser Ser Asp
            20                  25                  30

Tyr Tyr Trp Gly Trp Ile Arg Gln Pro Pro Gly Lys Gly Leu Glu Trp
        35                  40                  45

Ile Gly Ser Ile Tyr Gln Asn Gly His Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Glu Leu Ser Ser Val Thr Ala Ala Asp Thr Ala Val Tyr Tyr Cys
                85                  90                  95

Ala Arg Arg Gly Asp Cys Gly Ala Asp Cys Tyr His Phe Asp Tyr Trp
            100                 105                 110

Gly Arg Gly Thr Ala Val Thr Val Ser Ser
        115                 120


<210> SEQ ID NO 316
<211> LENGTH: 108
<212> TYPE: PRT
<213> ORGANISM: Artificial sequence
<220> FEATURE:
<223> OTHER INFORMATION: Synthetic antibody

<400> SEQUENCE: 316

Ser Tyr Glu Val Thr Gln Pro Leu Ser Val Ser Val Ser Pro Gly Gln
1               5                   10                  15

Thr Ala Ser Ile Thr Cys Ser Gly Glu Lys Leu Glu Asn Lys Tyr Val
            20                  25                  30

Ser Trp Tyr Gln Gln Lys Pro Gly Gln Ser Pro Val Leu Val Met Tyr
        35                  40                  45

Gln Asp Phe Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Arg Ser Thr Phe Tyr
                85                  90                  95
```

```
Val Phe Gly Thr Gly Thr Lys Val Thr Val Val Gly
            100                 105


<210> SEQ ID NO 317
<211> LENGTH: 123
<212> TYPE: PRT
<213> ORGANISM: Artificial sequence
<220> FEATURE:
<223> OTHER INFORMATION: Synthetic antibody

<400> SEQUENCE: 317

Gln Leu Gln Leu Gln Glu Ser Gly Pro Gly Leu Val Lys Pro Ser Glu
1               5                   10                  15

Thr Leu Ser Leu Thr Cys Phe Val Pro Gly Asp Phe Leu Ser Ser Thr
            20                  25                  30

Asn Phe Tyr Trp Gly Trp Ile Arg Gln Pro Pro Gly Lys Gly Leu Glu
        35                  40                  45

Trp Ile Gly Ser Ile Tyr Asp Ser Gly Asn Thr Tyr Tyr Asn Pro Ser
    50                  55                  60

Leu Lys Ser Arg Val Thr Met Ser Ile Asp Thr Pro Lys Asn Gln Phe
65                  70                  75                  80

Ser Leu Gln Leu Ser Ser Val Thr Ala Ala Asp Thr Ala Val Tyr Tyr
                85                  90                  95

Cys Ala Arg Val Gly Asp Cys Gly Ala Asp Cys Tyr Tyr Phe Asp His
            100                 105                 110

Trp Gly Gln Gly Thr Leu Val Thr Val Ser Ser
        115                 120


<210> SEQ ID NO 318
<211> LENGTH: 107
<212> TYPE: PRT
<213> ORGANISM: Artificial sequence
<220> FEATURE:
<223> OTHER INFORMATION: Synthetic antibody

<400> SEQUENCE: 318

Ser Tyr Glu Leu Thr Gln Pro Pro Ser Val Ser Val Ser Pro Gly Gln
1               5                   10                  15

Thr Ala Ser Ile Ser Cys Ser Gly Asp Arg Leu Arg Asp Arg Tyr Val
            20                  25                  30

Ser Trp Tyr Gln Gln Lys Pro Gly Gln Ser Pro Val Val Val Ile Tyr
        35                  40                  45

Gln Asp Phe Lys Arg Pro Ser Gly Ile Pro Ala Arg Phe Ser Ala Ser
    50                  55                  60

Asn Ser Gly Asn Thr Ala Thr Leu Thr Ile Ile Gly Thr Gln Ala Met
65                  70                  75                  80

Asp Glu Ala Asp Tyr Tyr Cys Gln Ala Trp Asp Ser Phe Thr Tyr Val
                85                  90                  95

Phe Gly Ala Gly Thr Lys Val Thr Val Leu Gly
            100                 105


<210> SEQ ID NO 319
<211> LENGTH: 119
<212> TYPE: PRT
<213> ORGANISM: Artificial sequence
<220> FEATURE:
<223> OTHER INFORMATION: Synthetic antibody

<400> SEQUENCE: 319

Glu Val His Leu Val Glu Ser Gly Gly Gly Leu Val Gln Pro Gly Gly
```

```
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Ile Gly Trp Leu Ser Pro Asp Tyr Trp Gly Gln Gly
            100                 105                 110

Thr Leu Val Thr Val Ser Ser
        115


<210> SEQ ID NO 320
<211> LENGTH: 108
<212> TYPE: PRT
<213> ORGANISM: Artificial sequence
<220> FEATURE:
<223> OTHER INFORMATION: Synthetic antibody

<400> SEQUENCE: 320

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Phe Tyr Ala
            20                  25                  30

Ser Trp Tyr Gln Gln Lys Pro Gly Gln Ala Pro Ile Leu Val Phe Tyr
        35                  40                  45

Gly Gln Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Gly Gly Tyr His
                85                  90                  95

Leu Val Phe Gly Gly Gly Thr Lys Leu Thr Val Leu
            100                 105


<210> SEQ ID NO 321
<211> LENGTH: 108
<212> TYPE: PRT
<213> ORGANISM: Artificial sequence
<220> FEATURE:
<223> OTHER INFORMATION: Synthetic antibody

<400> SEQUENCE: 321

Gln Pro Val Leu Thr Gln Pro Pro Ser Ala Ser Ala Ser Leu Gly Ala
1               5                   10                  15

Ser Val Thr Leu Thr Cys Thr Leu Ser Ser Gly Tyr Ser Asn Tyr Lys
            20                  25                  30

Leu Asp Tyr His Gln Arg Pro Gly Lys Gly Pro Arg Phe Glu Met Arg
        35                  40                  45

Val Gly Thr Gly Gly Ile Val Thr Ser Thr Gly Asp Gly Ile Pro Asp
    50                  55                  60

Arg Phe Ala Val Leu Gly Ser Gly Leu Asn Arg Phe Leu Thr Ile Lys
65                  70                  75                  80
```

```
Asn Ile Gln Glu Glu Asp Glu Ser Asp Tyr His Cys Gly Pro Asp His
                85                  90                  95

Gly Arg Gly Cys Ser Ala Glu Gly Pro Arg Pro Ser
            100                 105


<210> SEQ ID NO 322
<211> LENGTH: 107
<212> TYPE: PRT
<213> ORGANISM: Artificial sequence
<220> FEATURE:
<223> OTHER INFORMATION: Synthetic antibody

<400> SEQUENCE: 322

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Gly Gly Thr Gln Pro Met
65                  70                  75                  80

Asp Glu Ala Asp Tyr Tyr Cys Gln Ala Trp Asp Ser Ser Thr Glu Val
                85                  90                  95

Val Phe Gly Gly Gly Thr Lys Leu Thr Val Leu
            100                 105


<210> SEQ ID NO 323
<211> LENGTH: 132
<212> TYPE: PRT
<213> ORGANISM: Artificial sequence
<220> FEATURE:
<223> OTHER INFORMATION: Synthetic antibody

<400> SEQUENCE: 323

Asp Val Gln Val Val Glu Ser Gly Gly Gly Leu Val Gln Pro Gly Arg
1               5                   10                  15

Ser Leu Arg Leu Ser Cys Gln Cys Phe Gly Phe Asn Phe Gly Asp Tyr
            20                  25                  30

Leu Met Thr Trp Phe Arg Gln Ala Pro Gly Lys Gly Leu Glu Trp Val
        35                  40                  45

Gly Phe Val Arg Thr Lys Gly Tyr Gly Gly Thr Ser Glu Tyr Ala Ala
    50                  55                  60

Ser Val Arg Gly Arg Phe Thr Val Ser Arg Asp Asp Ser Arg Gly Ile
65                  70                  75                  80

Ala Tyr Leu Gln Met Asn Ser Leu Arg Val Glu Asp Thr Ala Val Tyr
                85                  90                  95

Tyr Cys Thr Arg Asp Arg Gln Lys Pro Thr Tyr Gln Phe Trp Ser Ser
            100                 105                 110

Tyr Phe Val Asp Asp Pro Phe Asp Val Trp Gly Gln Gly Thr Lys Val
        115                 120                 125

Thr Val Ser Ser
    130


<210> SEQ ID NO 324
<211> LENGTH: 108
<212> TYPE: PRT
<213> ORGANISM: Artificial sequence
```

<220> FEATURE:
<223> OTHER INFORMATION: Synthetic antibody

<400> SEQUENCE: 324

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Ser Ala
            20                  25                  30

Ser Trp Tyr Gln His Lys Ala Gly Gln Ala Pro Val Leu Val Leu Tyr
        35                  40                  45

Gly Lys Asn Asn Arg Pro Ser Gly Ile Pro Asp Arg Phe Ser Gly Ser
    50                  55                  60

Thr Ser Gly Asn Thr Ala Ser Leu Thr Ile Thr Gly Ala Gln Ala Glu
65                  70                  75                  80

Asp Glu Ala Asp Phe Tyr Cys Asn Ser Arg Asp Ser Ser Gly Ile Arg
                85                  90                  95

Val Val Phe Gly Gly Gly Thr Lys Leu Thr Val Leu
            100                 105

<210> SEQ ID NO 325
<211> LENGTH: 121
<212> TYPE: PRT
<213> ORGANISM: Artificial sequence
<220> FEATURE:
<223> OTHER INFORMATION: Synthetic antibody

<400> SEQUENCE: 325

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Arg Ile Glu Pro Ser Asp Ser Tyr Thr Asn Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Gly Asp Ser Ser Gly Tyr Gly Glu Ile Asp Tyr Trp Gly
            100                 105                 110

Gln Gly Thr Leu Val Thr Val Ser Ser
        115                 120

<210> SEQ ID NO 326
<211> LENGTH: 107
<212> TYPE: PRT
<213> ORGANISM: Artificial sequence
<220> FEATURE:
<223> OTHER INFORMATION: Synthetic antibody

<400> SEQUENCE: 326

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

```
Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Gln
                85                  90                  95

Thr Phe Gly Gln Gly Thr Lys Val Glu Ile Lys
            100                 105


<210> SEQ ID NO 327
<211> LENGTH: 130
<212> TYPE: PRT
<213> ORGANISM: Artificial sequence
<220> FEATURE:
<223> OTHER INFORMATION: Synthetic antibody

<400> SEQUENCE: 327

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ala Pro Thr Val Pro Ala Ala Ile Trp Gly Ser Ser Tyr Tyr
            100                 105                 110

Tyr Tyr Tyr Tyr Met Asp Val Trp Gly Lys Gly Thr Thr Val Thr Val
        115                 120                 125

Ser Ser
    130


<210> SEQ ID NO 328
<211> LENGTH: 113
<212> TYPE: PRT
<213> ORGANISM: Artificial sequence
<220> FEATURE:
<223> OTHER INFORMATION: Synthetic antibody

<400> SEQUENCE: 328

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Ser Leu Thr Phe Gly Gly Gly Thr Lys Val Glu Ile
            100                 105                 110
```

Lys

<210> SEQ ID NO 329
<211> LENGTH: 119
<212> TYPE: PRT
<213> ORGANISM: Artificial sequence
<220> FEATURE:
<223> OTHER INFORMATION: Synthetic antibody

<400> SEQUENCE: 329

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Lys Phe Ser Gly Ser
            20                  25                  30

Ala Met His Trp Val Arg Gln Ala Ser Gly Arg Gly Leu Glu Trp Val
        35                  40                  45

Gly Arg Ile Arg Ser Lys Ala Asn Asn Tyr Ala Thr Thr Tyr Ala Glu
    50                  55                  60

Ser Val Lys Gly Arg Phe Thr Ile Ser Arg Asp Asp Ser Gln Asn Thr
65                  70                  75                  80

Ala Tyr Leu Glu Met His Asn Leu Arg Thr Glu Asp Thr Ala Val Tyr
                85                  90                  95

Tyr Cys Thr Arg Asn Val Asp Thr Asp His Arg Gly Trp Gly Gln Gly
            100                 105                 110

Thr Leu Val Ser Val Ser Ser
        115

<210> SEQ ID NO 330
<211> LENGTH: 113
<212> TYPE: PRT
<213> ORGANISM: Artificial sequence
<220> FEATURE:
<223> OTHER INFORMATION: Synthetic antibody

<400> SEQUENCE: 330

Glu Ile Val Met Thr Gln Ser Pro Asp Pro Leu Pro Val Ser Leu Gly
1               5                   10                  15

Gly Arg Ala Thr Ile Asn Cys Lys Ser Ser Gln Ser Leu Leu Tyr Gly
            20                  25                  30

Ser Thr Asn Lys Asn Tyr Leu Ala Trp Tyr Gln Gln Lys Pro Gly Gln
        35                  40                  45

Pro Pro Arg Leu Leu Ile Tyr Trp Ala Ser Thr Arg Glu Ser Gly Val
    50                  55                  60

Pro Asp Arg Phe Ser Gly Ser Gly Ser Gly Thr Asp Phe Ala Leu Thr
65                  70                  75                  80

Ile Ser Asp Leu Gln Ala Glu Asp Val Ala Val Tyr Tyr Cys Gln Gln
                85                  90                  95

Tyr Tyr Asn Val Ala Trp Thr Phe Gly Gln Gly Thr Lys Val Glu Ile
            100                 105                 110

Arg

<210> SEQ ID NO 331
<211> LENGTH: 9
<212> TYPE: PRT
<213> ORGANISM: Artificial sequence
<220> FEATURE:
<223> OTHER INFORMATION: Synthetic antibody

<400> SEQUENCE: 331

```
Gly Asp Ser Ile Ser Thr Ser Thr Trp
1               5


<210> SEQ ID NO 332
<211> LENGTH: 7
<212> TYPE: PRT
<213> ORGANISM: Artificial sequence
<220> FEATURE:
<223> OTHER INFORMATION: Synthetic antibody

<400> SEQUENCE: 332

Ile Tyr His Ser Glu Ser Thr
1               5


<210> SEQ ID NO 333
<211> LENGTH: 9
<212> TYPE: PRT
<213> ORGANISM: Artificial sequence
<220> FEATURE:
<223> OTHER INFORMATION: Synthetic antibody

<400> SEQUENCE: 333

Ala Arg Gly Ser Leu Val Phe Asp Tyr
1               5


<210> SEQ ID NO 334
<211> LENGTH: 8
<212> TYPE: PRT
<213> ORGANISM: Artificial sequence
<220> FEATURE:
<223> OTHER INFORMATION: Synthetic antibody

<400> SEQUENCE: 334

Gly Asp Ser Val Arg Asn Tyr Tyr
1               5


<210> SEQ ID NO 335
<211> LENGTH: 7
<212> TYPE: PRT
<213> ORGANISM: Artificial sequence
<220> FEATURE:
<223> OTHER INFORMATION: Synthetic antibody

<400> SEQUENCE: 335

Ile Tyr Tyr Ser Gly Ser Thr
1               5


<210> SEQ ID NO 336
<211> LENGTH: 16
<212> TYPE: PRT
<213> ORGANISM: Artificial sequence
<220> FEATURE:
<223> OTHER INFORMATION: Synthetic antibody

<400> SEQUENCE: 336

Ala Arg Val Ala Ile Arg Thr Asp Gly Tyr Ile Arg Ala Phe Asp Ile
1               5                   10                  15


<210> SEQ ID NO 337
<211> LENGTH: 10
<212> TYPE: PRT
<213> ORGANISM: Artificial sequence
<220> FEATURE:
<223> OTHER INFORMATION: Synthetic antibody

<400> SEQUENCE: 337
```

Gly Gly Ser Ile Ser Ser Gly Asp Tyr Phe
1 5 10

<210> SEQ ID NO 338
<211> LENGTH: 7
<212> TYPE: PRT
<213> ORGANISM: Artificial sequence
<220> FEATURE:
<223> OTHER INFORMATION: Synthetic antibody

<400> SEQUENCE: 338

Ile Tyr Tyr Ser Gly Ser Thr
1 5

<210> SEQ ID NO 339
<211> LENGTH: 15
<212> TYPE: PRT
<213> ORGANISM: Artificial sequence
<220> FEATURE:
<223> OTHER INFORMATION: Synthetic antibody

<400> SEQUENCE: 339

Ala Arg Val Gln Thr Pro Gly Ser Asp Thr Tyr Tyr Phe Asp Tyr
1 5 10 15

<210> SEQ ID NO 340
<211> LENGTH: 10
<212> TYPE: PRT
<213> ORGANISM: Artificial sequence
<220> FEATURE:
<223> OTHER INFORMATION: Synthetic antibody

<400> SEQUENCE: 340

Gly Gly Ser Ile Ser Ser Ser Ser Tyr His
1 5 10

<210> SEQ ID NO 341
<211> LENGTH: 7
<212> TYPE: PRT
<213> ORGANISM: Artificial sequence
<220> FEATURE:
<223> OTHER INFORMATION: Synthetic antibody

<400> SEQUENCE: 341

Ile Tyr Tyr Thr Gly Ser Thr
1 5

<210> SEQ ID NO 342
<211> LENGTH: 15
<212> TYPE: PRT
<213> ORGANISM: Artificial sequence
<220> FEATURE:
<223> OTHER INFORMATION: Synthetic antibody

<400> SEQUENCE: 342

Ala Arg Arg Ser Leu Arg Ser Gly Trp Ala Ala Ala Ile Asp Phe
1 5 10 15

<210> SEQ ID NO 343
<211> LENGTH: 10
<212> TYPE: PRT
<213> ORGANISM: Artificial sequence
<220> FEATURE:
<223> OTHER INFORMATION: Synthetic antibody

<400> SEQUENCE: 343

Gly Gly Ser Val Ser Ser Gly Ser Tyr Tyr 1 5 10

<210> SEQ ID NO 344
<211> LENGTH: 7
<212> TYPE: PRT
<213> ORGANISM: Artificial sequence
<220> FEATURE:
<223> OTHER INFORMATION: Synthetic antibody

<400> SEQUENCE: 344

Ile Tyr Tyr Ser Gly Ser Thr
1 5

<210> SEQ ID NO 345
<211> LENGTH: 18
<212> TYPE: PRT
<213> ORGANISM: Artificial sequence
<220> FEATURE:
<223> OTHER INFORMATION: Synthetic antibody

<400> SEQUENCE: 345

Ala Arg Asp Tyr Arg Val Thr Thr Gly Asn Tyr Tyr Tyr Tyr Gly Met
1 5 10 15

Asp Val

<210> SEQ ID NO 346
<211> LENGTH: 10
<212> TYPE: PRT
<213> ORGANISM: Artificial sequence
<220> FEATURE:
<223> OTHER INFORMATION: Synthetic antibody

<400> SEQUENCE: 346

Gly Gly Ser Val Ser Ser Gly Asp Tyr Tyr
1 5 10

<210> SEQ ID NO 347
<211> LENGTH: 7
<212> TYPE: PRT
<213> ORGANISM: Artificial sequence
<220> FEATURE:
<223> OTHER INFORMATION: Synthetic antibody

<400> SEQUENCE: 347

Ile Ser Tyr Ser Gly Ser Thr
1 5

<210> SEQ ID NO 348
<211> LENGTH: 19
<212> TYPE: PRT
<213> ORGANISM: Artificial sequence
<220> FEATURE:
<223> OTHER INFORMATION: Synthetic antibody

<400> SEQUENCE: 348

Ala Thr Asn Tyr Phe His Leu His Asp Phe Gly Asp Leu Tyr Trp Tyr
1 5 10 15

Phe Asp Leu

<210> SEQ ID NO 349
<211> LENGTH: 10
<212> TYPE: PRT
<213> ORGANISM: Artificial sequence
<220> FEATURE:
<223> OTHER INFORMATION: Synthetic antibody

<400> SEQUENCE: 349

Gly Gly Ser Ile Ser Ser Ser Val Tyr Tyr
1               5                   10

<210> SEQ ID NO 350
<211> LENGTH: 7
<212> TYPE: PRT
<213> ORGANISM: Artificial sequence
<220> FEATURE:
<223> OTHER INFORMATION: Synthetic antibody

<400> SEQUENCE: 350

Ile Tyr Tyr Ser Gly Tyr Thr
1               5

<210> SEQ ID NO 351
<211> LENGTH: 15
<212> TYPE: PRT
<213> ORGANISM: Artificial sequence
<220> FEATURE:
<223> OTHER INFORMATION: Synthetic antibody

<400> SEQUENCE: 351

Ala Arg His Ser Asp Cys Gly Asn Asp Cys Tyr Tyr Phe Asp Tyr
1               5                   10                  15

<210> SEQ ID NO 352
<211> LENGTH: 10
<212> TYPE: PRT
<213> ORGANISM: Artificial sequence
<220> FEATURE:
<223> OTHER INFORMATION: Synthetic antibody

<400> SEQUENCE: 352

Gly Gly Ser Val Ser Ser Gly Asp Tyr Tyr
1               5                   10

<210> SEQ ID NO 353
<211> LENGTH: 7
<212> TYPE: PRT
<213> ORGANISM: Artificial sequence
<220> FEATURE:
<223> OTHER INFORMATION: Synthetic antibody

<400> SEQUENCE: 353

Ile Ser Tyr Ser Gly Ser Thr
1               5

<210> SEQ ID NO 354
<211> LENGTH: 19
<212> TYPE: PRT
<213> ORGANISM: Artificial sequence
<220> FEATURE:
<223> OTHER INFORMATION: Synthetic antibody

<400> SEQUENCE: 354

Ala Thr Asn Tyr Phe His Leu His Asp Phe Gly Asp Leu Tyr Trp Tyr
1               5                   10                  15

Phe Asp Leu

<210> SEQ ID NO 355
<211> LENGTH: 8
<212> TYPE: PRT
<213> ORGANISM: Artificial sequence
<220> FEATURE:
<223> OTHER INFORMATION: Synthetic antibody

<400> SEQUENCE: 355

Gly Phe Met Phe Ser Arg Tyr Trp
1 5

<210> SEQ ID NO 356
<211> LENGTH: 8
<212> TYPE: PRT
<213> ORGANISM: Artificial sequence
<220> FEATURE:
<223> OTHER INFORMATION: Synthetic antibody

<400> SEQUENCE: 356

Ile Lys Gln Asp Gly Ser Glu Lys
1 5

<210> SEQ ID NO 357
<211> LENGTH: 12
<212> TYPE: PRT
<213> ORGANISM: Artificial sequence
<220> FEATURE:
<223> OTHER INFORMATION: Synthetic antibody

<400> SEQUENCE: 357

Ala Arg Gly Glu Tyr Tyr Gly Ser Gly Ser Tyr Ser
1 5 10

<210> SEQ ID NO 358
<211> LENGTH: 10
<212> TYPE: PRT
<213> ORGANISM: Artificial sequence
<220> FEATURE:
<223> OTHER INFORMATION: Synthetic antibody

<400> SEQUENCE: 358

Gly Gly Ser Ile Ser Ser Ser Val Tyr Tyr
1 5 10

<210> SEQ ID NO 359
<211> LENGTH: 7
<212> TYPE: PRT
<213> ORGANISM: Artificial sequence
<220> FEATURE:
<223> OTHER INFORMATION: Synthetic antibody

<400> SEQUENCE: 359

Ile Tyr Tyr Ser Gly Tyr Thr
1 5

<210> SEQ ID NO 360
<211> LENGTH: 15
<212> TYPE: PRT
<213> ORGANISM: Artificial sequence
<220> FEATURE:
<223> OTHER INFORMATION: Synthetic antibody

<400> SEQUENCE: 360

Ala Arg His Ser Asp Cys Gly Asn Asp Cys Tyr Tyr Phe Asp Tyr
1 5 10 15

<210> SEQ ID NO 361
<211> LENGTH: 8
<212> TYPE: PRT
<213> ORGANISM: Artificial sequence
<220> FEATURE:
<223> OTHER INFORMATION: Synthetic antibody

<400> SEQUENCE: 361

Gly Gly Ser Ile Gly Thr Tyr Tyr
1 5

<210> SEQ ID NO 362
<211> LENGTH: 7
<212> TYPE: PRT
<213> ORGANISM: Artificial sequence
<220> FEATURE:
<223> OTHER INFORMATION: Synthetic antibody

<400> SEQUENCE: 362

Val Tyr His Ser Gly Ala Thr
1 5

<210> SEQ ID NO 363
<211> LENGTH: 15
<212> TYPE: PRT
<213> ORGANISM: Artificial sequence
<220> FEATURE:
<223> OTHER INFORMATION: Synthetic antibody

<400> SEQUENCE: 363

Ala Arg Glu Gly Ser Asn Gly Asp Phe Arg Gly His Phe Asp Ser
1 5 10 15

<210> SEQ ID NO 364
<211> LENGTH: 8
<212> TYPE: PRT
<213> ORGANISM: Artificial sequence
<220> FEATURE:
<223> OTHER INFORMATION: Synthetic antibody

<400> SEQUENCE: 364

Gly Gly Ser Phe Ser Gly Tyr Tyr
1 5

<210> SEQ ID NO 365
<211> LENGTH: 7
<212> TYPE: PRT
<213> ORGANISM: Artificial sequence
<220> FEATURE:
<223> OTHER INFORMATION: Synthetic antibody

<400> SEQUENCE: 365

Ile Asn His Ser Gly Arg Thr
1 5

<210> SEQ ID NO 366
<211> LENGTH: 23
<212> TYPE: PRT
<213> ORGANISM: Artificial sequence
<220> FEATURE:
<223> OTHER INFORMATION: Synthetic antibody

<400> SEQUENCE: 366

Ala Arg Gly His Val Val Val Thr Pro Ala Thr Leu Phe His Arg Val
1 5 10 15

Gly Glu His Tyr Phe Asp Phe
20

<210> SEQ ID NO 367
<211> LENGTH: 8
<212> TYPE: PRT
<213> ORGANISM: Artificial sequence
<220> FEATURE:

<223> OTHER INFORMATION: Synthetic antibody

<400> SEQUENCE: 367

Gly Tyr Thr Phe Thr Thr Tyr Ala
1               5

<210> SEQ ID NO 368
<211> LENGTH: 8
<212> TYPE: PRT
<213> ORGANISM: Artificial sequence
<220> FEATURE:
<223> OTHER INFORMATION: Synthetic antibody

<400> SEQUENCE: 368

Ile Asn Ala Gly Asn Gly Asp Thr
1               5

<210> SEQ ID NO 369
<211> LENGTH: 23
<212> TYPE: PRT
<213> ORGANISM: Artificial sequence
<220> FEATURE:
<223> OTHER INFORMATION: Synthetic antibody

<400> SEQUENCE: 369

Ala Arg Gly Trp Val Gly Cys Ile Gly Lys Arg Gly Lys Thr Cys Tyr
1               5                   10                  15

Ala Asn Leu Pro Asp Asp Tyr
            20

<210> SEQ ID NO 370
<211> LENGTH: 8
<212> TYPE: PRT
<213> ORGANISM: Artificial sequence
<220> FEATURE:
<223> OTHER INFORMATION: Synthetic antibody

<400> SEQUENCE: 370

Arg Phe Thr Phe Asn Thr Tyr Gly
1               5

<210> SEQ ID NO 371
<211> LENGTH: 8
<212> TYPE: PRT
<213> ORGANISM: Artificial sequence
<220> FEATURE:
<223> OTHER INFORMATION: Synthetic antibody

<400> SEQUENCE: 371

Ile Ser Tyr Asp Gly Lys Lys Lys
1               5

<210> SEQ ID NO 372
<211> LENGTH: 18
<212> TYPE: PRT
<213> ORGANISM: Artificial sequence
<220> FEATURE:
<223> OTHER INFORMATION: Synthetic antibody

<400> SEQUENCE: 372

Ala Arg Asp Leu Arg Arg Phe Tyr Ser Asn Gly Trp Phe Thr Gly Ser
1               5                   10                  15

Asp Phe

<210> SEQ ID NO 373

<211> LENGTH: 9
<212> TYPE: PRT
<213> ORGANISM: Artificial sequence
<220> FEATURE:
<223> OTHER INFORMATION: Synthetic antibody

<400> SEQUENCE: 373

Gly Val Ser Ile Thr Ser Ser Asn Trp
1               5

<210> SEQ ID NO 374
<211> LENGTH: 7
<212> TYPE: PRT
<213> ORGANISM: Artificial sequence
<220> FEATURE:
<223> OTHER INFORMATION: Synthetic antibody

<400> SEQUENCE: 374

Val Tyr His Ser Gly Ser Thr
1               5

<210> SEQ ID NO 375
<211> LENGTH: 14
<212> TYPE: PRT
<213> ORGANISM: Artificial sequence
<220> FEATURE:
<223> OTHER INFORMATION: Synthetic antibody

<400> SEQUENCE: 375

Ala Arg Asp Gly Phe Ser Gly Tyr Asp Val Ala Leu Asp Lys
1               5                   10

<210> SEQ ID NO 376
<211> LENGTH: 10
<212> TYPE: PRT
<213> ORGANISM: Artificial sequence
<220> FEATURE:
<223> OTHER INFORMATION: Synthetic antibody

<400> SEQUENCE: 376

Gly Val Ser Leu Ser Ser Ser Gly Val Gly
1               5                   10

<210> SEQ ID NO 377
<211> LENGTH: 7
<212> TYPE: PRT
<213> ORGANISM: Artificial sequence
<220> FEATURE:
<223> OTHER INFORMATION: Synthetic antibody

<400> SEQUENCE: 377

Ile Tyr Trp Asp Asp Asp Lys
1               5

<210> SEQ ID NO 378
<211> LENGTH: 21
<212> TYPE: PRT
<213> ORGANISM: Artificial sequence
<220> FEATURE:
<223> OTHER INFORMATION: Synthetic antibody

<400> SEQUENCE: 378

Ala His Arg Asn Ile Val Val Val Arg Ala Asp Pro His Arg Trp Ala
1               5                   10                  15

Gly Thr Phe Asp Tyr
            20

<210> SEQ ID NO 379
<211> LENGTH: 8
<212> TYPE: PRT
<213> ORGANISM: Artificial sequence
<220> FEATURE:
<223> OTHER INFORMATION: Synthetic antibody

<400> SEQUENCE: 379

Gly Phe Thr Phe Ser Ser Tyr Ala
1               5

<210> SEQ ID NO 380
<211> LENGTH: 8
<212> TYPE: PRT
<213> ORGANISM: Artificial sequence
<220> FEATURE:
<223> OTHER INFORMATION: Synthetic antibody

<400> SEQUENCE: 380

Ile Ser Gly Ser Gly Gly Ser Thr
1               5

<210> SEQ ID NO 381
<211> LENGTH: 20
<212> TYPE: PRT
<213> ORGANISM: Artificial sequence
<220> FEATURE:
<223> OTHER INFORMATION: Synthetic antibody

<400> SEQUENCE: 381

Ala Lys Asp Gln Gly Thr Met Ile Val Val Val Thr Leu Pro Pro Gly
1               5                   10                  15

Ala Phe Asp Ile
            20

<210> SEQ ID NO 382
<211> LENGTH: 8
<212> TYPE: PRT
<213> ORGANISM: Artificial sequence
<220> FEATURE:
<223> OTHER INFORMATION: Synthetic antibody

<400> SEQUENCE: 382

Gly Phe Met Phe Ser Arg Tyr Trp
1               5

<210> SEQ ID NO 383
<211> LENGTH: 8
<212> TYPE: PRT
<213> ORGANISM: Artificial sequence
<220> FEATURE:
<223> OTHER INFORMATION: Synthetic antibody

<400> SEQUENCE: 383

Ile Lys Gln Asp Gly Ser Glu Lys
1               5

<210> SEQ ID NO 384
<211> LENGTH: 12
<212> TYPE: PRT
<213> ORGANISM: Artificial sequence
<220> FEATURE:
<223> OTHER INFORMATION: Synthetic antibody

<400> SEQUENCE: 384

Ala Arg Gly Glu Tyr Tyr Gly Ser Gly Ser Tyr Ser 1 5 10

<210> SEQ ID NO 385
<211> LENGTH: 10
<212> TYPE: PRT
<213> ORGANISM: Artificial sequence
<220> FEATURE:
<223> OTHER INFORMATION: Synthetic antibody

<400> SEQUENCE: 385

Gly Gly Ser Ile Asn Gly Asp Asn Tyr Tyr
1 5 10

<210> SEQ ID NO 386
<211> LENGTH: 7
<212> TYPE: PRT
<213> ORGANISM: Artificial sequence
<220> FEATURE:
<223> OTHER INFORMATION: Synthetic antibody

<400> SEQUENCE: 386

Ile Tyr Tyr Ser Gly Ser Thr
1 5

<210> SEQ ID NO 387
<211> LENGTH: 15
<212> TYPE: PRT
<213> ORGANISM: Artificial sequence
<220> FEATURE:
<223> OTHER INFORMATION: Synthetic antibody

<400> SEQUENCE: 387

Ala Arg Gly Ala Asp Cys Gly Asn Asp Cys Tyr Tyr Phe Asp Tyr
1 5 10 15

<210> SEQ ID NO 388
<211> LENGTH: 8
<212> TYPE: PRT
<213> ORGANISM: Artificial sequence
<220> FEATURE:
<223> OTHER INFORMATION: Synthetic antibody

<400> SEQUENCE: 388

Gly Phe Thr Phe Asp Asp Tyr Ala
1 5

<210> SEQ ID NO 389
<211> LENGTH: 8
<212> TYPE: PRT
<213> ORGANISM: Artificial sequence
<220> FEATURE:
<223> OTHER INFORMATION: Synthetic antibody

<400> SEQUENCE: 389

Ile Ser Trp Asn Ser Gly Ser Ile
1 5

<210> SEQ ID NO 390
<211> LENGTH: 14
<212> TYPE: PRT
<213> ORGANISM: Artificial sequence
<220> FEATURE:
<223> OTHER INFORMATION: Synthetic antibody

<400> SEQUENCE: 390

Ala Lys Gly Leu Val Gly Ala Ile His Asp Ala Phe Asp Ile
1 5 10

<210> SEQ ID NO 391
<211> LENGTH: 10
<212> TYPE: PRT
<213> ORGANISM: Artificial sequence
<220> FEATURE:
<223> OTHER INFORMATION: Synthetic antibody

<400> SEQUENCE: 391

Gly Gly Ser Ile Ser Ser Gly Asp Tyr Phe
1               5                   10

<210> SEQ ID NO 392
<211> LENGTH: 7
<212> TYPE: PRT
<213> ORGANISM: Artificial sequence
<220> FEATURE:
<223> OTHER INFORMATION: Synthetic antibody

<400> SEQUENCE: 392

Ile Tyr Tyr Ser Gly Ser Thr
1               5

<210> SEQ ID NO 393
<211> LENGTH: 15
<212> TYPE: PRT
<213> ORGANISM: Artificial sequence
<220> FEATURE:
<223> OTHER INFORMATION: Synthetic antibody

<400> SEQUENCE: 393

Ala Arg Val Gln Thr Pro Gly Ser Asp Thr Tyr Tyr Phe Asp Tyr
1               5                   10                  15

<210> SEQ ID NO 394
<211> LENGTH: 8
<212> TYPE: PRT
<213> ORGANISM: Artificial sequence
<220> FEATURE:
<223> OTHER INFORMATION: Synthetic antibody

<400> SEQUENCE: 394

Gly Tyr Thr Phe Thr Gly Tyr Tyr
1               5

<210> SEQ ID NO 395
<211> LENGTH: 8
<212> TYPE: PRT
<213> ORGANISM: Artificial sequence
<220> FEATURE:
<223> OTHER INFORMATION: Synthetic antibody

<400> SEQUENCE: 395

Ile Asn Pro Asn Ser Gly Gly Thr
1               5

<210> SEQ ID NO 396
<211> LENGTH: 22
<212> TYPE: PRT
<213> ORGANISM: Artificial sequence
<220> FEATURE:
<223> OTHER INFORMATION: Synthetic antibody

<400> SEQUENCE: 396

Ala Arg Gly Arg Tyr Cys Asp Ser Ala Ser Cys Tyr Val Arg Asn Tyr
1               5                   10                  15

```
Phe Tyr Tyr Met Asp Val
            20


<210> SEQ ID NO 397
<211> LENGTH: 8
<212> TYPE: PRT
<213> ORGANISM: Artificial sequence
<220> FEATURE:
<223> OTHER INFORMATION: Synthetic antibody

<400> SEQUENCE: 397

Gly Phe Thr Phe Ser Asn Tyr Trp
1               5


<210> SEQ ID NO 398
<211> LENGTH: 8
<212> TYPE: PRT
<213> ORGANISM: Artificial sequence
<220> FEATURE:
<223> OTHER INFORMATION: Synthetic antibody

<400> SEQUENCE: 398

Ile Asn Asp His Gly Asn Tyr Thr
1               5


<210> SEQ ID NO 399
<211> LENGTH: 8
<212> TYPE: PRT
<213> ORGANISM: Artificial sequence
<220> FEATURE:
<223> OTHER INFORMATION: Synthetic antibody

<400> SEQUENCE: 399

Val Arg Ala Phe Gly Gly Gly Tyr
1               5


<210> SEQ ID NO 400
<211> LENGTH: 8
<212> TYPE: PRT
<213> ORGANISM: Artificial sequence
<220> FEATURE:
<223> OTHER INFORMATION: Synthetic antibody

<400> SEQUENCE: 400

Gly Phe Thr Phe Ser Ser Tyr Gly
1               5


<210> SEQ ID NO 401
<211> LENGTH: 8
<212> TYPE: PRT
<213> ORGANISM: Artificial sequence
<220> FEATURE:
<223> OTHER INFORMATION: Synthetic antibody

<400> SEQUENCE: 401

Ile Trp Tyr Asp Gly Ser Asn Lys
1               5


<210> SEQ ID NO 402
<211> LENGTH: 17
<212> TYPE: PRT
<213> ORGANISM: Artificial sequence
<220> FEATURE:
<223> OTHER INFORMATION: Synthetic antibody

<400> SEQUENCE: 402

Ala Arg Glu Arg Ser Ile Ala Ala Arg Gln Asn Arg Gly Tyr Phe Asp
```

1               5                   10                  15

Tyr

<210> SEQ ID NO 403
<211> LENGTH: 8
<212> TYPE: PRT
<213> ORGANISM: Artificial sequence
<220> FEATURE:
<223> OTHER INFORMATION: Synthetic antibody

<400> SEQUENCE: 403

Gly Phe Thr Phe Ser Arg Tyr Tyr
1               5

<210> SEQ ID NO 404
<211> LENGTH: 8
<212> TYPE: PRT
<213> ORGANISM: Artificial sequence
<220> FEATURE:
<223> OTHER INFORMATION: Synthetic antibody

<400> SEQUENCE: 404

Ile Asn Thr Asp Gly Ser Thr Thr
1               5

<210> SEQ ID NO 405
<211> LENGTH: 9
<212> TYPE: PRT
<213> ORGANISM: Artificial sequence
<220> FEATURE:
<223> OTHER INFORMATION: Synthetic antibody

<400> SEQUENCE: 405

Ala Arg Pro Tyr Ser Gly Tyr Phe His
1               5

<210> SEQ ID NO 406
<211> LENGTH: 8
<212> TYPE: PRT
<213> ORGANISM: Artificial sequence
<220> FEATURE:
<223> OTHER INFORMATION: Synthetic antibody

<400> SEQUENCE: 406

Gly Phe Thr Phe Thr Asn Ser Trp
1               5

<210> SEQ ID NO 407
<211> LENGTH: 8
<212> TYPE: PRT
<213> ORGANISM: Artificial sequence
<220> FEATURE:
<223> OTHER INFORMATION: Synthetic antibody

<400> SEQUENCE: 407

Ile Asn Pro Asp Gly Ser Lys Ile
1               5

<210> SEQ ID NO 408
<211> LENGTH: 5
<212> TYPE: PRT
<213> ORGANISM: Artificial sequence
<220> FEATURE:
<223> OTHER INFORMATION: Synthetic antibody

<400> SEQUENCE: 408

Ala Arg Trp Leu Ser
1 5

<210> SEQ ID NO 409
<211> LENGTH: 8
<212> TYPE: PRT
<213> ORGANISM: Artificial sequence
<220> FEATURE:
<223> OTHER INFORMATION: Synthetic antibody

<400> SEQUENCE: 409

Gly Phe Thr Phe Thr Asn Ser Trp
1 5

<210> SEQ ID NO 410
<211> LENGTH: 8
<212> TYPE: PRT
<213> ORGANISM: Artificial sequence
<220> FEATURE:
<223> OTHER INFORMATION: Synthetic antibody

<400> SEQUENCE: 410

Ile Asn Pro Asp Gly Ser Lys Ile
1 5

<210> SEQ ID NO 411
<211> LENGTH: 5
<212> TYPE: PRT
<213> ORGANISM: Artificial sequence
<220> FEATURE:
<223> OTHER INFORMATION: Synthetic antibody

<400> SEQUENCE: 411

Ala Arg Trp Leu Ser
1 5

<210> SEQ ID NO 412
<211> LENGTH: 8
<212> TYPE: PRT
<213> ORGANISM: Artificial sequence
<220> FEATURE:
<223> OTHER INFORMATION: Synthetic antibody

<400> SEQUENCE: 412

Gly Tyr Thr Phe Thr Thr Tyr Phe
1 5

<210> SEQ ID NO 413
<211> LENGTH: 8
<212> TYPE: PRT
<213> ORGANISM: Artificial sequence
<220> FEATURE:
<223> OTHER INFORMATION: Synthetic antibody

<400> SEQUENCE: 413

Val Asp Pro Ser Thr Gly Asn Thr
1 5

<210> SEQ ID NO 414
<211> LENGTH: 11
<212> TYPE: PRT
<213> ORGANISM: Artificial sequence
<220> FEATURE:
<223> OTHER INFORMATION: Synthetic antibody

<400> SEQUENCE: 414

Gly Arg Asp Arg Gly Ser Arg Ala Val Asp Ser 1 5 10

<210> SEQ ID NO 415
<211> LENGTH: 8
<212> TYPE: PRT
<213> ORGANISM: Artificial sequence
<220> FEATURE:
<223> OTHER INFORMATION: Synthetic antibody

<400> SEQUENCE: 415

Gly Gly Ser Ile Ser Ser Tyr Phe
1 5

<210> SEQ ID NO 416
<211> LENGTH: 7
<212> TYPE: PRT
<213> ORGANISM: Artificial sequence
<220> FEATURE:
<223> OTHER INFORMATION: Synthetic antibody

<400> SEQUENCE: 416

Ile His Thr Thr Gly Ser Thr
1 5

<210> SEQ ID NO 417
<211> LENGTH: 9
<212> TYPE: PRT
<213> ORGANISM: Artificial sequence
<220> FEATURE:
<223> OTHER INFORMATION: Synthetic antibody

<400> SEQUENCE: 417

Ala Arg Glu Gly Thr Ala Phe Asp Ile
1 5

<210> SEQ ID NO 418
<211> LENGTH: 8
<212> TYPE: PRT
<213> ORGANISM: Artificial sequence
<220> FEATURE:
<223> OTHER INFORMATION: Synthetic antibody

<400> SEQUENCE: 418

Gly Phe Thr Phe Ser Asp Tyr Tyr
1 5

<210> SEQ ID NO 419
<211> LENGTH: 8
<212> TYPE: PRT
<213> ORGANISM: Artificial sequence
<220> FEATURE:
<223> OTHER INFORMATION: Synthetic antibody

<400> SEQUENCE: 419

Ile Ser Gly Thr Gly Ser Phe Ile
1 5

<210> SEQ ID NO 420
<211> LENGTH: 11
<212> TYPE: PRT
<213> ORGANISM: Artificial sequence
<220> FEATURE:
<223> OTHER INFORMATION: Synthetic antibody

<400> SEQUENCE: 420

Ala Arg Gly Ile Arg Ala Asp Cys Phe Asp Gln
1 5 10

<210> SEQ ID NO 421
<211> LENGTH: 8
<212> TYPE: PRT
<213> ORGANISM: Artificial sequence
<220> FEATURE:
<223> OTHER INFORMATION: Synthetic antibody

<400> SEQUENCE: 421

Gly Tyr Thr Phe Thr Ser Tyr Tyr
1               5

<210> SEQ ID NO 422
<211> LENGTH: 8
<212> TYPE: PRT
<213> ORGANISM: Artificial sequence
<220> FEATURE:
<223> OTHER INFORMATION: Synthetic antibody

<400> SEQUENCE: 422

Ile Asn Pro Ser Gly Gly Ser Thr
1               5

<210> SEQ ID NO 423
<211> LENGTH: 12
<212> TYPE: PRT
<213> ORGANISM: Artificial sequence
<220> FEATURE:
<223> OTHER INFORMATION: Synthetic antibody

<400> SEQUENCE: 423

Ala Arg Ala Arg Gly Gly Ser Tyr Ser Leu Asp Tyr
1               5                   10

<210> SEQ ID NO 424
<211> LENGTH: 8
<212> TYPE: PRT
<213> ORGANISM: Artificial sequence
<220> FEATURE:
<223> OTHER INFORMATION: Synthetic antibody

<400> SEQUENCE: 424

Gly Phe Ile Phe Asn His Phe Gly
1               5

<210> SEQ ID NO 425
<211> LENGTH: 8
<212> TYPE: PRT
<213> ORGANISM: Artificial sequence
<220> FEATURE:
<223> OTHER INFORMATION: Synthetic antibody

<400> SEQUENCE: 425

Ile Trp Tyr Asp Gly Ser Lys Lys
1               5

<210> SEQ ID NO 426
<211> LENGTH: 13
<212> TYPE: PRT
<213> ORGANISM: Artificial sequence
<220> FEATURE:
<223> OTHER INFORMATION: Synthetic antibody

<400> SEQUENCE: 426

Ala Arg Glu Arg Trp Ser Gly His Ser Tyr Leu Asp Tyr
1               5                   10

<210> SEQ ID NO 427
<211> LENGTH: 8
<212> TYPE: PRT
<213> ORGANISM: Artificial sequence
<220> FEATURE:
<223> OTHER INFORMATION: Synthetic antibody

<400> SEQUENCE: 427

Gly Phe Thr Phe Arg Thr Lys Thr
1               5

<210> SEQ ID NO 428
<211> LENGTH: 8
<212> TYPE: PRT
<213> ORGANISM: Artificial sequence
<220> FEATURE:
<223> OTHER INFORMATION: Synthetic antibody

<400> SEQUENCE: 428

Ile Ser Gly Ser Gly Lys Asp Lys
1               5

<210> SEQ ID NO 429
<211> LENGTH: 12
<212> TYPE: PRT
<213> ORGANISM: Artificial sequence
<220> FEATURE:
<223> OTHER INFORMATION: Synthetic antibody

<400> SEQUENCE: 429

Val Lys Asp Arg Glu Gly Thr Trp Ser Phe Asp His
1               5                   10

<210> SEQ ID NO 430
<211> LENGTH: 8
<212> TYPE: PRT
<213> ORGANISM: Artificial sequence
<220> FEATURE:
<223> OTHER INFORMATION: Synthetic antibody

<400> SEQUENCE: 430

Gly Phe Thr Phe Ser Ser Tyr Ala
1               5

<210> SEQ ID NO 431
<211> LENGTH: 8
<212> TYPE: PRT
<213> ORGANISM: Artificial sequence
<220> FEATURE:
<223> OTHER INFORMATION: Synthetic antibody

<400> SEQUENCE: 431

Ile Ser Gly Ser Gly Gly Ser Thr
1               5

<210> SEQ ID NO 432
<211> LENGTH: 18
<212> TYPE: PRT
<213> ORGANISM: Artificial sequence
<220> FEATURE:
<223> OTHER INFORMATION: Synthetic antibody

<400> SEQUENCE: 432

Ala Lys Lys Tyr Tyr Asp Phe Trp Ser Gly Tyr Tyr Pro Asn Trp Phe
1               5                   10                  15

Asp Pro

<210> SEQ ID NO 433
<211> LENGTH: 8
<212> TYPE: PRT
<213> ORGANISM: Artificial sequence
<220> FEATURE:
<223> OTHER INFORMATION: Synthetic antibody

<400> SEQUENCE: 433

Gly Tyr Thr Phe Thr Thr Tyr Val
1               5

<210> SEQ ID NO 434
<211> LENGTH: 8
<212> TYPE: PRT
<213> ORGANISM: Artificial sequence
<220> FEATURE:
<223> OTHER INFORMATION: Synthetic antibody

<400> SEQUENCE: 434

Ile Asn Thr Asn Thr Gly Asn Pro
1               5

<210> SEQ ID NO 435
<211> LENGTH: 9
<212> TYPE: PRT
<213> ORGANISM: Artificial sequence
<220> FEATURE:
<223> OTHER INFORMATION: Synthetic antibody

<400> SEQUENCE: 435

Ala Arg Glu Tyr Asn Ser Phe Asp Tyr
1               5

<210> SEQ ID NO 436
<211> LENGTH: 8
<212> TYPE: PRT
<213> ORGANISM: Artificial sequence
<220> FEATURE:
<223> OTHER INFORMATION: Synthetic antibody

<400> SEQUENCE: 436

Gly Tyr Thr Phe Thr Ser Tyr Tyr
1               5

<210> SEQ ID NO 437
<211> LENGTH: 8
<212> TYPE: PRT
<213> ORGANISM: Artificial sequence
<220> FEATURE:
<223> OTHER INFORMATION: Synthetic antibody

<400> SEQUENCE: 437

Ile Ser Pro Ser Gly Gly Ser Thr
1               5

<210> SEQ ID NO 438
<211> LENGTH: 12
<212> TYPE: PRT
<213> ORGANISM: Artificial sequence
<220> FEATURE:
<223> OTHER INFORMATION: Synthetic antibody

<400> SEQUENCE: 438

Ala Arg Gln Val Gln Thr Asp Tyr Tyr Phe Asp Tyr
1               5                   10

<210> SEQ ID NO 439
<211> LENGTH: 8
<212> TYPE: PRT
<213> ORGANISM: Artificial sequence
<220> FEATURE:
<223> OTHER INFORMATION: Synthetic antibody

<400> SEQUENCE: 439

Gly Phe Thr Phe Ser Ser Tyr Ala
1               5

<210> SEQ ID NO 440
<211> LENGTH: 8
<212> TYPE: PRT
<213> ORGANISM: Artificial sequence
<220> FEATURE:
<223> OTHER INFORMATION: Synthetic antibody

<400> SEQUENCE: 440

Ile Ser Tyr Asp Gly Ser Asp Lys
1               5

<210> SEQ ID NO 441
<211> LENGTH: 13
<212> TYPE: PRT
<213> ORGANISM: Artificial sequence
<220> FEATURE:
<223> OTHER INFORMATION: Synthetic antibody

<400> SEQUENCE: 441

Ala Arg Asp Arg Ser Gly Ser Tyr Tyr Trp Phe Asp Pro
1               5                   10

<210> SEQ ID NO 442
<211> LENGTH: 8
<212> TYPE: PRT
<213> ORGANISM: Artificial sequence
<220> FEATURE:
<223> OTHER INFORMATION: Synthetic antibody

<400> SEQUENCE: 442

Gly Tyr Thr Phe Thr Asn Tyr Ala
1               5

<210> SEQ ID NO 443
<211> LENGTH: 8
<212> TYPE: PRT
<213> ORGANISM: Artificial sequence
<220> FEATURE:
<223> OTHER INFORMATION: Synthetic antibody

<400> SEQUENCE: 443

Ile Asn Ala Gly Asn Gly Asp Thr
1               5

<210> SEQ ID NO 444
<211> LENGTH: 15
<212> TYPE: PRT
<213> ORGANISM: Artificial sequence
<220> FEATURE:
<223> OTHER INFORMATION: Synthetic antibody

<400> SEQUENCE: 444

Ala Arg Pro Gly Tyr Ser Ser Ser Trp Asp Glu Gly Phe Asp Tyr
1               5                   10                  15

<210> SEQ ID NO 445
<211> LENGTH: 8
<212> TYPE: PRT
<213> ORGANISM: Artificial sequence
<220> FEATURE:
<223> OTHER INFORMATION: Synthetic antibody

<400> SEQUENCE: 445

Gly Phe Thr Phe Ser Ser Tyr Trp
1               5

<210> SEQ ID NO 446
<211> LENGTH: 8
<212> TYPE: PRT
<213> ORGANISM: Artificial sequence
<220> FEATURE:
<223> OTHER INFORMATION: Synthetic antibody

<400> SEQUENCE: 446

Ile Asn Ser Asp Gly Ser Ser Thr
1               5

<210> SEQ ID NO 447
<211> LENGTH: 14
<212> TYPE: PRT
<213> ORGANISM: Artificial sequence
<220> FEATURE:
<223> OTHER INFORMATION: Synthetic antibody

<400> SEQUENCE: 447

Ala Ser Gly Asp Ser Ser Gly Trp Tyr Met Pro Phe Asp Tyr
1               5                   10

<210> SEQ ID NO 448
<211> LENGTH: 8
<212> TYPE: PRT
<213> ORGANISM: Artificial sequence
<220> FEATURE:
<223> OTHER INFORMATION: Synthetic antibody

<400> SEQUENCE: 448

Gly Gly Ser Ile Ser Ser Tyr Tyr
1               5

<210> SEQ ID NO 449
<211> LENGTH: 7
<212> TYPE: PRT
<213> ORGANISM: Artificial sequence
<220> FEATURE:
<223> OTHER INFORMATION: Synthetic antibody

<400> SEQUENCE: 449

Ile Tyr Tyr Ser Gly Ser Thr
1               5

<210> SEQ ID NO 450
<211> LENGTH: 17
<212> TYPE: PRT
<213> ORGANISM: Artificial sequence
<220> FEATURE:
<223> OTHER INFORMATION: Synthetic antibody

<400> SEQUENCE: 450

Ala Arg His Gly Asp Ile Leu Thr Gly Phe Leu Tyr Trp Tyr Phe Asp
1               5                   10                  15

Leu

<210> SEQ ID NO 451
<211> LENGTH: 8
<212> TYPE: PRT
<213> ORGANISM: Artificial sequence
<220> FEATURE:
<223> OTHER INFORMATION: Synthetic antibody

<400> SEQUENCE: 451

Gly Tyr Ser Phe Thr Ser Tyr Trp
1               5

<210> SEQ ID NO 452
<211> LENGTH: 8
<212> TYPE: PRT
<213> ORGANISM: Artificial sequence
<220> FEATURE:
<223> OTHER INFORMATION: Synthetic antibody

<400> SEQUENCE: 452

Ile Asp Pro Ser Asp Ser Tyr Thr
1               5

<210> SEQ ID NO 453
<211> LENGTH: 14
<212> TYPE: PRT
<213> ORGANISM: Artificial sequence
<220> FEATURE:
<223> OTHER INFORMATION: Synthetic antibody

<400> SEQUENCE: 453

Ala Arg His Gly Glu Gly Gly Ser Tyr Glu Glu Phe Asp Pro
1               5                   10

<210> SEQ ID NO 454
<211> LENGTH: 8
<212> TYPE: PRT
<213> ORGANISM: Artificial sequence
<220> FEATURE:
<223> OTHER INFORMATION: Synthetic antibody

<400> SEQUENCE: 454

Gly Tyr Ser Phe Thr Ser Tyr Trp
1               5

<210> SEQ ID NO 455
<211> LENGTH: 8
<212> TYPE: PRT
<213> ORGANISM: Artificial sequence
<220> FEATURE:
<223> OTHER INFORMATION: Synthetic antibody

<400> SEQUENCE: 455

Ile Tyr Pro Gly Asp Ser Asp Thr
1               5

<210> SEQ ID NO 456
<211> LENGTH: 19
<212> TYPE: PRT
<213> ORGANISM: Artificial sequence
<220> FEATURE:
<223> OTHER INFORMATION: Synthetic antibody

<400> SEQUENCE: 456

Ala Arg Gly Ala Tyr Cys Gly Gly Asp Cys Phe Gly Gly Ala Glu Tyr
1               5                   10                  15

Phe Gln His

<210> SEQ ID NO 457
<211> LENGTH: 8
<212> TYPE: PRT
<213> ORGANISM: Artificial sequence
<220> FEATURE:
<223> OTHER INFORMATION: Synthetic antibody

<400> SEQUENCE: 457

Gly Tyr Thr Phe Thr Asn Tyr Tyr
1               5

<210> SEQ ID NO 458
<211> LENGTH: 8
<212> TYPE: PRT
<213> ORGANISM: Artificial sequence
<220> FEATURE:
<223> OTHER INFORMATION: Synthetic antibody

<400> SEQUENCE: 458

Ile Asn Pro Ser Gly Val Ser Thr
1               5

<210> SEQ ID NO 459
<211> LENGTH: 12
<212> TYPE: PRT
<213> ORGANISM: Artificial sequence
<220> FEATURE:
<223> OTHER INFORMATION: Synthetic antibody

<400> SEQUENCE: 459

Ala Arg Met Asp Thr Glu Tyr Tyr Tyr Phe Asp Tyr
1               5                   10

<210> SEQ ID NO 460
<211> LENGTH: 9
<212> TYPE: PRT
<213> ORGANISM: Artificial sequence
<220> FEATURE:
<223> OTHER INFORMATION: Synthetic antibody

<400> SEQUENCE: 460

Gly Gly Ser Ile Ser Ser Ser Asn Trp
1               5

<210> SEQ ID NO 461
<211> LENGTH: 7
<212> TYPE: PRT
<213> ORGANISM: Artificial sequence
<220> FEATURE:
<223> OTHER INFORMATION: Synthetic antibody

<400> SEQUENCE: 461

Ile Tyr His Ser Gly Ser Thr
1               5

<210> SEQ ID NO 462
<211> LENGTH: 12
<212> TYPE: PRT
<213> ORGANISM: Artificial sequence
<220> FEATURE:
<223> OTHER INFORMATION: Synthetic antibody

<400> SEQUENCE: 462

Ala Arg Arg Ser Tyr Tyr Tyr Tyr Tyr Met Asp Val
1               5                   10

<210> SEQ ID NO 463
<211> LENGTH: 8
<212> TYPE: PRT
<213> ORGANISM: Artificial sequence
<220> FEATURE:
<223> OTHER INFORMATION: Synthetic antibody

<400> SEQUENCE: 463

Gly Phe Thr Phe Ser Ser Tyr Ala
1               5

<210> SEQ ID NO 464
<211> LENGTH: 8
<212> TYPE: PRT
<213> ORGANISM: Artificial sequence
<220> FEATURE:
<223> OTHER INFORMATION: Synthetic antibody

<400> SEQUENCE: 464

Ile Ser Gly Ser Gly Gly Ser Thr
1               5

<210> SEQ ID NO 465
<211> LENGTH: 15
<212> TYPE: PRT
<213> ORGANISM: Artificial sequence
<220> FEATURE:
<223> OTHER INFORMATION: Synthetic antibody

<400> SEQUENCE: 465

Ala Lys Cys Ile Asp Asn Tyr Tyr Tyr Tyr Cys Tyr Met Asp Val
1               5                   10                  15

<210> SEQ ID NO 466
<211> LENGTH: 8
<212> TYPE: PRT
<213> ORGANISM: Artificial sequence
<220> FEATURE:
<223> OTHER INFORMATION: Synthetic antibody

<400> SEQUENCE: 466

Gly Tyr Thr Phe Thr Ser Tyr Gly
1               5

<210> SEQ ID NO 467
<211> LENGTH: 8
<212> TYPE: PRT
<213> ORGANISM: Artificial sequence
<220> FEATURE:
<223> OTHER INFORMATION: Synthetic antibody

<400> SEQUENCE: 467

Ile Ser Ala Tyr Asn Gly Asn Thr
1               5

<210> SEQ ID NO 468
<211> LENGTH: 11
<212> TYPE: PRT
<213> ORGANISM: Artificial sequence
<220> FEATURE:
<223> OTHER INFORMATION: Synthetic antibody

<400> SEQUENCE: 468

Ala Arg Asp Gly Val Gln Gly Ala Phe Asp Ile
1               5                   10

<210> SEQ ID NO 469
<211> LENGTH: 8
<212> TYPE: PRT
<213> ORGANISM: Artificial sequence
<220> FEATURE:
<223> OTHER INFORMATION: Synthetic antibody

<400> SEQUENCE: 469

Gly Phe Thr Phe Ser Ser Tyr Gly
1               5

<210> SEQ ID NO 470
<211> LENGTH: 8
<212> TYPE: PRT
<213> ORGANISM: Artificial sequence
<220> FEATURE:
<223> OTHER INFORMATION: Synthetic antibody

<400> SEQUENCE: 470

Ile Ser Tyr Asp Gly Ser Asn Lys
1               5

<210> SEQ ID NO 471
<211> LENGTH: 21
<212> TYPE: PRT
<213> ORGANISM: Artificial sequence
<220> FEATURE:
<223> OTHER INFORMATION: Synthetic antibody

<400> SEQUENCE: 471

Ala Asn Trp Gly Asn Tyr Tyr Asp Ser Ser Gly Tyr Ser Tyr Tyr Tyr
1               5                   10                  15

Tyr Tyr Met Asp Val
            20

<210> SEQ ID NO 472
<211> LENGTH: 8
<212> TYPE: PRT
<213> ORGANISM: Artificial sequence
<220> FEATURE:
<223> OTHER INFORMATION: Synthetic antibody

<400> SEQUENCE: 472

Gly Phe Thr Phe Ser Ser Tyr Trp
1               5

<210> SEQ ID NO 473
<211> LENGTH: 8
<212> TYPE: PRT
<213> ORGANISM: Artificial sequence
<220> FEATURE:
<223> OTHER INFORMATION: Synthetic antibody

<400> SEQUENCE: 473

Ile Asn Ser Asp Gly Ser Ser Thr
1               5

<210> SEQ ID NO 474
<211> LENGTH: 14
<212> TYPE: PRT
<213> ORGANISM: Artificial sequence
<220> FEATURE:
<223> OTHER INFORMATION: Synthetic antibody

<400> SEQUENCE: 474

Ala Ser Gly Asp Ser Ser Gly Trp Tyr Met Pro Phe Asp Tyr
1               5                   10

<210> SEQ ID NO 475
<211> LENGTH: 8
<212> TYPE: PRT
<213> ORGANISM: Artificial sequence
<220> FEATURE:
<223> OTHER INFORMATION: Synthetic antibody

<400> SEQUENCE: 475

Gly Phe Thr Phe Ser Ser Tyr Trp
1               5

<210> SEQ ID NO 476
<211> LENGTH: 8
<212> TYPE: PRT
<213> ORGANISM: Artificial sequence
<220> FEATURE:
<223> OTHER INFORMATION: Synthetic antibody

<400> SEQUENCE: 476

Ile Asn Ser Asp Gly Ser Ser Thr
1               5

<210> SEQ ID NO 477
<211> LENGTH: 14
<212> TYPE: PRT
<213> ORGANISM: Artificial sequence
<220> FEATURE:
<223> OTHER INFORMATION: Synthetic antibody

<400> SEQUENCE: 477

Ala Ser Gly Asp Ser Ser Gly Trp Tyr Met Pro Phe Asp Tyr
1               5                   10

<210> SEQ ID NO 478
<211> LENGTH: 9
<212> TYPE: PRT
<213> ORGANISM: Artificial sequence
<220> FEATURE:
<223> OTHER INFORMATION: Synthetic antibody

<400> SEQUENCE: 478

Gly Gly Ser Ile Ser Ser Ser Asn Trp
1               5

<210> SEQ ID NO 479
<211> LENGTH: 7
<212> TYPE: PRT
<213> ORGANISM: Artificial sequence
<220> FEATURE:
<223> OTHER INFORMATION: Synthetic antibody

<400> SEQUENCE: 479

Ile Tyr His Ser Gly Ser Thr
1               5

<210> SEQ ID NO 480
<211> LENGTH: 14
<212> TYPE: PRT
<213> ORGANISM: Artificial sequence
<220> FEATURE:
<223> OTHER INFORMATION: Synthetic antibody

<400> SEQUENCE: 480

Ala Arg Asp Ser Arg Gln Trp Leu Val Arg Gly Phe Asp Tyr
1               5                   10

<210> SEQ ID NO 481
<211> LENGTH: 8
<212> TYPE: PRT
<213> ORGANISM: Artificial sequence
<220> FEATURE:
<223> OTHER INFORMATION: Synthetic antibody

<400> SEQUENCE: 481

Gly Phe Ser Phe Ser Tyr Ala Trp
1               5

<210> SEQ ID NO 482
<211> LENGTH: 10
<212> TYPE: PRT
<213> ORGANISM: Artificial sequence
<220> FEATURE:
<223> OTHER INFORMATION: Synthetic antibody

<400> SEQUENCE: 482

Ile Lys Gly Lys Ala Asp Gly Glu Thr Thr
1               5                   10

<210> SEQ ID NO 483
<211> LENGTH: 18
<212> TYPE: PRT
<213> ORGANISM: Artificial sequence
<220> FEATURE:
<223> OTHER INFORMATION: Synthetic antibody

<400> SEQUENCE: 483

Thr Thr Asp Ile Gly Asp Phe Tyr Asp Ser Ile Gly Tyr Ser Tyr Thr
1               5                   10                  15

Asp Tyr

<210> SEQ ID NO 484
<211> LENGTH: 8
<212> TYPE: PRT
<213> ORGANISM: Artificial sequence
<220> FEATURE:
<223> OTHER INFORMATION: Synthetic antibody

<400> SEQUENCE: 484

Gly Tyr Thr Phe Thr Ser Tyr Tyr
1               5

<210> SEQ ID NO 485
<211> LENGTH: 8
<212> TYPE: PRT
<213> ORGANISM: Artificial sequence
<220> FEATURE:
<223> OTHER INFORMATION: Synthetic antibody

<400> SEQUENCE: 485

Ile Asn Pro Ser Gly Gly Ser Thr
1               5

<210> SEQ ID NO 486
<211> LENGTH: 12
<212> TYPE: PRT
<213> ORGANISM: Artificial sequence
<220> FEATURE:
<223> OTHER INFORMATION: Synthetic antibody

<400> SEQUENCE: 486

Ala Arg Val Gly Asn Tyr Tyr Tyr Tyr Met Asp Val
1               5                   10

<210> SEQ ID NO 487
<211> LENGTH: 8
<212> TYPE: PRT
<213> ORGANISM: Artificial sequence
<220> FEATURE:
<223> OTHER INFORMATION: Synthetic antibody

<400> SEQUENCE: 487

Gly Phe Thr Phe Gly Asp Tyr Ala
1               5

<210> SEQ ID NO 488
<211> LENGTH: 10
<212> TYPE: PRT
<213> ORGANISM: Artificial sequence
<220> FEATURE:
<223> OTHER INFORMATION: Synthetic antibody

<400> SEQUENCE: 488

Ile Arg Ser Lys Ala Tyr Gly Gly Thr Arg
1               5                   10

<210> SEQ ID NO 489
<211> LENGTH: 15
<212> TYPE: PRT
<213> ORGANISM: Artificial sequence
<220> FEATURE:
<223> OTHER INFORMATION: Synthetic antibody

<400> SEQUENCE: 489

Thr Asn His Arg Gly Ser Ser Trp Tyr Pro Asp Ala Phe Asp Ile
1               5                   10                  15

<210> SEQ ID NO 490
<211> LENGTH: 8
<212> TYPE: PRT
<213> ORGANISM: Artificial sequence
<220> FEATURE:
<223> OTHER INFORMATION: Synthetic antibody

<400> SEQUENCE: 490

Gly Phe Thr Phe Ser Ser Tyr Ala
1               5

<210> SEQ ID NO 491
<211> LENGTH: 8
<212> TYPE: PRT
<213> ORGANISM: Artificial sequence
<220> FEATURE:
<223> OTHER INFORMATION: Synthetic antibody

<400> SEQUENCE: 491

Ile Ser Tyr Asp Gly Ser Asn Lys
1               5

<210> SEQ ID NO 492
<211> LENGTH: 10
<212> TYPE: PRT
<213> ORGANISM: Artificial sequence
<220> FEATURE:
<223> OTHER INFORMATION: Synthetic antibody

<400> SEQUENCE: 492

Ala Lys Asp Ile Thr Gly Arg Leu Asp Tyr
1               5                   10

<210> SEQ ID NO 493
<211> LENGTH: 8
<212> TYPE: PRT
<213> ORGANISM: Artificial sequence
<220> FEATURE:
<223> OTHER INFORMATION: Synthetic antibody

<400> SEQUENCE: 493

Gly Phe Thr Phe Ser Ser Tyr Asp
1 5

<210> SEQ ID NO 494
<211> LENGTH: 7
<212> TYPE: PRT
<213> ORGANISM: Artificial sequence
<220> FEATURE:
<223> OTHER INFORMATION: Synthetic antibody

<400> SEQUENCE: 494

Ile Gly Thr Ala Gly Asp Thr
1 5

<210> SEQ ID NO 495
<211> LENGTH: 10
<212> TYPE: PRT
<213> ORGANISM: Artificial sequence
<220> FEATURE:
<223> OTHER INFORMATION: Synthetic antibody

<400> SEQUENCE: 495

Ala Arg Gly Leu Gly Gly Gly Phe Asp Tyr
1 5 10

<210> SEQ ID NO 496
<211> LENGTH: 8
<212> TYPE: PRT
<213> ORGANISM: Artificial sequence
<220> FEATURE:
<223> OTHER INFORMATION: Synthetic antibody

<400> SEQUENCE: 496

Gly Phe Thr Phe Ser Asn Tyr Ala
1 5

<210> SEQ ID NO 497
<211> LENGTH: 8
<212> TYPE: PRT
<213> ORGANISM: Artificial sequence
<220> FEATURE:
<223> OTHER INFORMATION: Synthetic antibody

<400> SEQUENCE: 497

Ile Ser Gly Asn Val Asp Asn Thr
1 5

<210> SEQ ID NO 498
<211> LENGTH: 14
<212> TYPE: PRT
<213> ORGANISM: Artificial sequence
<220> FEATURE:
<223> OTHER INFORMATION: Synthetic antibody

<400> SEQUENCE: 498

Ala Lys Val Gly Gln Tyr Trp Ser Gly His Tyr Leu Asp Tyr
1 5 10

<210> SEQ ID NO 499
<211> LENGTH: 8
<212> TYPE: PRT
<213> ORGANISM: Artificial sequence
<220> FEATURE:
<223> OTHER INFORMATION: Synthetic antibody

<400> SEQUENCE: 499

Gly Phe Thr Phe Ser Ser Tyr Ala
1               5

<210> SEQ ID NO 500
<211> LENGTH: 8
<212> TYPE: PRT
<213> ORGANISM: Artificial sequence
<220> FEATURE:
<223> OTHER INFORMATION: Synthetic antibody

<400> SEQUENCE: 500

Ile Ser Gly Ser Gly Gly Ser Thr
1               5

<210> SEQ ID NO 501
<211> LENGTH: 14
<212> TYPE: PRT
<213> ORGANISM: Artificial sequence
<220> FEATURE:
<223> OTHER INFORMATION: Synthetic antibody

<400> SEQUENCE: 501

Ala Thr Glu Asn Asp Phe Trp Ser Gly His Gln Phe Asp Tyr
1               5                   10

<210> SEQ ID NO 502
<211> LENGTH: 8
<212> TYPE: PRT
<213> ORGANISM: Artificial sequence
<220> FEATURE:
<223> OTHER INFORMATION: Synthetic antibody

<400> SEQUENCE: 502

Gly Phe Thr Phe Ser Ser Tyr Asp
1               5

<210> SEQ ID NO 503
<211> LENGTH: 7
<212> TYPE: PRT
<213> ORGANISM: Artificial sequence
<220> FEATURE:
<223> OTHER INFORMATION: Synthetic antibody

<400> SEQUENCE: 503

Ile Gly Thr Ala Gly Asp Thr
1               5

<210> SEQ ID NO 504
<211> LENGTH: 10
<212> TYPE: PRT
<213> ORGANISM: Artificial sequence
<220> FEATURE:
<223> OTHER INFORMATION: Synthetic antibody

<400> SEQUENCE: 504

Ala Arg Ala Val Gly Gly Gly Phe Asp Tyr
1               5                   10

<210> SEQ ID NO 505

<211> LENGTH: 8
<212> TYPE: PRT
<213> ORGANISM: Artificial sequence
<220> FEATURE:
<223> OTHER INFORMATION: Synthetic antibody

<400> SEQUENCE: 505

Gly Gly Ser Ile Ser Ser Tyr Tyr
1 5

<210> SEQ ID NO 506
<211> LENGTH: 7
<212> TYPE: PRT
<213> ORGANISM: Artificial sequence
<220> FEATURE:
<223> OTHER INFORMATION: Synthetic antibody

<400> SEQUENCE: 506

Ile Tyr Tyr Ser Gly Ser Thr
1 5

<210> SEQ ID NO 507
<211> LENGTH: 17
<212> TYPE: PRT
<213> ORGANISM: Artificial sequence
<220> FEATURE:
<223> OTHER INFORMATION: Synthetic antibody

<400> SEQUENCE: 507

Ala Arg Gly Ser Arg Ala Ile Leu Thr Gly Tyr Pro Asn Trp Phe Asp
1 5 10 15

Pro

<210> SEQ ID NO 508
<211> LENGTH: 8
<212> TYPE: PRT
<213> ORGANISM: Artificial sequence
<220> FEATURE:
<223> OTHER INFORMATION: Synthetic antibody

<400> SEQUENCE: 508

Gly Phe Thr Phe Asp Asp Tyr Ala
1 5

<210> SEQ ID NO 509
<211> LENGTH: 8
<212> TYPE: PRT
<213> ORGANISM: Artificial sequence
<220> FEATURE:
<223> OTHER INFORMATION: Synthetic antibody

<400> SEQUENCE: 509

Ile Ser Trp Asn Ser Gly Ser Ile
1 5

<210> SEQ ID NO 510
<211> LENGTH: 16
<212> TYPE: PRT
<213> ORGANISM: Artificial sequence
<220> FEATURE:
<223> OTHER INFORMATION: Synthetic antibody

<400> SEQUENCE: 510

Ala Lys Asp Lys Gly Asp Gly Ser Gly Ser Phe Tyr Tyr Met Asp Val
1 5 10 15

<210> SEQ ID NO 511
<211> LENGTH: 8
<212> TYPE: PRT
<213> ORGANISM: Artificial sequence
<220> FEATURE:
<223> OTHER INFORMATION: Synthetic antibody

<400> SEQUENCE: 511

Gly Gly Ser Ile Ser Ser Tyr Tyr
1 5

<210> SEQ ID NO 512
<211> LENGTH: 7
<212> TYPE: PRT
<213> ORGANISM: Artificial sequence
<220> FEATURE:
<223> OTHER INFORMATION: Synthetic antibody

<400> SEQUENCE: 512

Ile Tyr Tyr Ser Gly Ser Thr
1 5

<210> SEQ ID NO 513
<211> LENGTH: 10
<212> TYPE: PRT
<213> ORGANISM: Artificial sequence
<220> FEATURE:
<223> OTHER INFORMATION: Synthetic antibody

<400> SEQUENCE: 513

Ala Arg Gly Leu Gly Val Val Val Trp Pro
1 5 10

<210> SEQ ID NO 514
<211> LENGTH: 8
<212> TYPE: PRT
<213> ORGANISM: Artificial sequence
<220> FEATURE:
<223> OTHER INFORMATION: Synthetic antibody

<400> SEQUENCE: 514

Gly Phe Thr Phe Ser Ser Tyr Gly
1 5

<210> SEQ ID NO 515
<211> LENGTH: 8
<212> TYPE: PRT
<213> ORGANISM: Artificial sequence
<220> FEATURE:
<223> OTHER INFORMATION: Synthetic antibody

<400> SEQUENCE: 515

Ile Ser Tyr Asp Gly Ser Asn Lys
1 5

<210> SEQ ID NO 516
<211> LENGTH: 10
<212> TYPE: PRT
<213> ORGANISM: Artificial sequence
<220> FEATURE:
<223> OTHER INFORMATION: Synthetic antibody

<400> SEQUENCE: 516

Ala Lys Ala Leu Ser Ser Gly Trp Tyr Glu
1 5 10

<210> SEQ ID NO 517

<211> LENGTH: 8
<212> TYPE: PRT
<213> ORGANISM: Artificial sequence
<220> FEATURE:
<223> OTHER INFORMATION: Synthetic antibody

<400> SEQUENCE: 517

Gly Gly Ser Ile Ser Ser Tyr Tyr
1               5

<210> SEQ ID NO 518
<211> LENGTH: 7
<212> TYPE: PRT
<213> ORGANISM: Artificial sequence
<220> FEATURE:
<223> OTHER INFORMATION: Synthetic antibody

<400> SEQUENCE: 518

Ile Tyr Tyr Ser Gly Ser Thr
1               5

<210> SEQ ID NO 519
<211> LENGTH: 11
<212> TYPE: PRT
<213> ORGANISM: Artificial sequence
<220> FEATURE:
<223> OTHER INFORMATION: Synthetic antibody

<400> SEQUENCE: 519

Ala Arg Gly Leu Arg Pro Asp Ala Phe Asp Ile
1               5                   10

<210> SEQ ID NO 520
<211> LENGTH: 8
<212> TYPE: PRT
<213> ORGANISM: Artificial sequence
<220> FEATURE:
<223> OTHER INFORMATION: Synthetic antibody

<400> SEQUENCE: 520

Gly Tyr Ser Phe Thr Ser Tyr Trp
1               5

<210> SEQ ID NO 521
<211> LENGTH: 8
<212> TYPE: PRT
<213> ORGANISM: Artificial sequence
<220> FEATURE:
<223> OTHER INFORMATION: Synthetic antibody

<400> SEQUENCE: 521

Ile Glu Pro Ser Asp Ser Tyr Thr
1               5

<210> SEQ ID NO 522
<211> LENGTH: 14
<212> TYPE: PRT
<213> ORGANISM: Artificial sequence
<220> FEATURE:
<223> OTHER INFORMATION: Synthetic antibody

<400> SEQUENCE: 522

Ala Arg Leu Gly Asp Ser Ser Gly Tyr Gly Glu Ile Asp Tyr
1               5                   10

<210> SEQ ID NO 523
<211> LENGTH: 8

<212> TYPE: PRT
<213> ORGANISM: Artificial sequence
<220> FEATURE:
<223> OTHER INFORMATION: Synthetic antibody

<400> SEQUENCE: 523

Gly Asn Thr Phe Thr Ser Tyr Tyr
1               5

<210> SEQ ID NO 524
<211> LENGTH: 8
<212> TYPE: PRT
<213> ORGANISM: Artificial sequence
<220> FEATURE:
<223> OTHER INFORMATION: Synthetic antibody

<400> SEQUENCE: 524

Ile Asn Pro Ser Gly Gly Ser Thr
1               5

<210> SEQ ID NO 525
<211> LENGTH: 10
<212> TYPE: PRT
<213> ORGANISM: Artificial sequence
<220> FEATURE:
<223> OTHER INFORMATION: Synthetic antibody

<400> SEQUENCE: 525

Ala Arg Gly Glu Ser Tyr Tyr Phe Asp Tyr
1               5                   10

<210> SEQ ID NO 526
<211> LENGTH: 8
<212> TYPE: PRT
<213> ORGANISM: Artificial sequence
<220> FEATURE:
<223> OTHER INFORMATION: Synthetic antibody

<400> SEQUENCE: 526

Gly Phe Thr Phe Ser Ser Tyr Ser
1               5

<210> SEQ ID NO 527
<211> LENGTH: 8
<212> TYPE: PRT
<213> ORGANISM: Artificial sequence
<220> FEATURE:
<223> OTHER INFORMATION: Synthetic antibody

<400> SEQUENCE: 527

Ile Ser Ser Ser Ser Ser Thr Ile
1               5

<210> SEQ ID NO 528
<211> LENGTH: 11
<212> TYPE: PRT
<213> ORGANISM: Artificial sequence
<220> FEATURE:
<223> OTHER INFORMATION: Synthetic antibody

<400> SEQUENCE: 528

Ala Arg Asp Phe Tyr Pro Ala Ala Met Asp Val
1               5                   10

<210> SEQ ID NO 529
<211> LENGTH: 8
<212> TYPE: PRT

<213> ORGANISM: Artificial sequence
<220> FEATURE:
<223> OTHER INFORMATION: Synthetic antibody

<400> SEQUENCE: 529

Gly Tyr Ser Phe Thr Ser Tyr Trp
1 5

<210> SEQ ID NO 530
<211> LENGTH: 8
<212> TYPE: PRT
<213> ORGANISM: Artificial sequence
<220> FEATURE:
<223> OTHER INFORMATION: Synthetic antibody

<400> SEQUENCE: 530

Ile Glu Pro Ser Asp Ser Tyr Thr
1 5

<210> SEQ ID NO 531
<211> LENGTH: 14
<212> TYPE: PRT
<213> ORGANISM: Artificial sequence
<220> FEATURE:
<223> OTHER INFORMATION: Synthetic antibody

<400> SEQUENCE: 531

Ala Arg Leu Gly Asp Ser Ser Gly Tyr Gly Glu Ile Asp Tyr
1 5 10

<210> SEQ ID NO 532
<211> LENGTH: 10
<212> TYPE: PRT
<213> ORGANISM: Artificial sequence
<220> FEATURE:
<223> OTHER INFORMATION: Synthetic antibody

<400> SEQUENCE: 532

Gly Asp Ser Ile Ser Gly Gly Asp Tyr Tyr
1 5 10

<210> SEQ ID NO 533
<211> LENGTH: 7
<212> TYPE: PRT
<213> ORGANISM: Artificial sequence
<220> FEATURE:
<223> OTHER INFORMATION: Synthetic antibody

<400> SEQUENCE: 533

Val His Thr Thr Gly Ser Thr
1 5

<210> SEQ ID NO 534
<211> LENGTH: 12
<212> TYPE: PRT
<213> ORGANISM: Artificial sequence
<220> FEATURE:
<223> OTHER INFORMATION: Synthetic antibody

<400> SEQUENCE: 534

Ala Arg Glu Gly Asp Tyr Ser Ala Trp Phe Asp Pro
1 5 10

<210> SEQ ID NO 535
<211> LENGTH: 8
<212> TYPE: PRT
<213> ORGANISM: Artificial sequence
<220> FEATURE:
<223> OTHER INFORMATION: Synthetic antibody

<400> SEQUENCE: 535

Gly Phe Thr Leu Arg Gly Tyr Gly
1 5

<210> SEQ ID NO 536
<211> LENGTH: 8
<212> TYPE: PRT
<213> ORGANISM: Artificial sequence
<220> FEATURE:
<223> OTHER INFORMATION: Synthetic antibody

<400> SEQUENCE: 536

Ile Ser His Asp Gly Lys Asn Glu
1 5

<210> SEQ ID NO 537
<211> LENGTH: 17
<212> TYPE: PRT
<213> ORGANISM: Artificial sequence
<220> FEATURE:
<223> OTHER INFORMATION: Synthetic antibody

<400> SEQUENCE: 537

Ala Arg Trp Thr Glu Gly Ser Glu Glu Phe Tyr Tyr His Gly Leu Asp
1 5 10 15

Val

<210> SEQ ID NO 538
<211> LENGTH: 10
<212> TYPE: PRT
<213> ORGANISM: Artificial sequence
<220> FEATURE:
<223> OTHER INFORMATION: Synthetic antibody

<400> SEQUENCE: 538

Gly Phe Ser Leu Ser Thr Ser Gly Val Gly
1 5 10

<210> SEQ ID NO 539
<211> LENGTH: 7
<212> TYPE: PRT
<213> ORGANISM: Artificial sequence
<220> FEATURE:
<223> OTHER INFORMATION: Synthetic antibody

<400> SEQUENCE: 539

Leu Tyr Trp Asn Asp Asp Lys
1 5

<210> SEQ ID NO 540
<211> LENGTH: 22
<212> TYPE: PRT
<213> ORGANISM: Artificial sequence
<220> FEATURE:
<223> OTHER INFORMATION: Synthetic antibody

<400> SEQUENCE: 540

Ala Arg Lys Pro Arg Asp Asp Phe Leu Arg Leu Thr Met Met Gly Gly
1 5 10 15

Gly Asp Tyr Phe Asp Tyr
20

<210> SEQ ID NO 541
<211> LENGTH: 8
<212> TYPE: PRT
<213> ORGANISM: Artificial sequence
<220> FEATURE:
<223> OTHER INFORMATION: Synthetic antibody

<400> SEQUENCE: 541

Gly Phe Thr Phe Ser Ser Phe Glu
1               5

<210> SEQ ID NO 542
<211> LENGTH: 8
<212> TYPE: PRT
<213> ORGANISM: Artificial sequence
<220> FEATURE:
<223> OTHER INFORMATION: Synthetic antibody

<400> SEQUENCE: 542

Ile Ser Arg Ser Gly Thr Thr Lys
1               5

<210> SEQ ID NO 543
<211> LENGTH: 14
<212> TYPE: PRT
<213> ORGANISM: Artificial sequence
<220> FEATURE:
<223> OTHER INFORMATION: Synthetic antibody

<400> SEQUENCE: 543

Ala Arg Gly Gly Ala Arg Val Leu Gln Ala Pro Leu Asp Tyr
1               5                   10

<210> SEQ ID NO 544
<211> LENGTH: 8
<212> TYPE: PRT
<213> ORGANISM: Artificial sequence
<220> FEATURE:
<223> OTHER INFORMATION: Synthetic antibody

<400> SEQUENCE: 544

Gly Tyr Thr Phe Thr Asp Tyr Tyr
1               5

<210> SEQ ID NO 545
<211> LENGTH: 8
<212> TYPE: PRT
<213> ORGANISM: Artificial sequence
<220> FEATURE:
<223> OTHER INFORMATION: Synthetic antibody

<400> SEQUENCE: 545

Ile Asn Pro Ser Gly Gly Ser Thr
1               5

<210> SEQ ID NO 546
<211> LENGTH: 14
<212> TYPE: PRT
<213> ORGANISM: Artificial sequence
<220> FEATURE:
<223> OTHER INFORMATION: Synthetic antibody

<400> SEQUENCE: 546

Ala Arg Ala Ile Tyr Trp Asn Val Pro Tyr Tyr Phe Asp Tyr
1               5                   10

<210> SEQ ID NO 547

<211> LENGTH: 10
<212> TYPE: PRT
<213> ORGANISM: Artificial sequence
<220> FEATURE:
<223> OTHER INFORMATION: Synthetic antibody

<400> SEQUENCE: 547

Gly Asp Ser Ile Thr Ser Thr Gly Asp Ser
1               5                   10

<210> SEQ ID NO 548
<211> LENGTH: 7
<212> TYPE: PRT
<213> ORGANISM: Artificial sequence
<220> FEATURE:
<223> OTHER INFORMATION: Synthetic antibody

<400> SEQUENCE: 548

Ile Tyr Tyr Ser Gly Ser Ala
1               5

<210> SEQ ID NO 549
<211> LENGTH: 15
<212> TYPE: PRT
<213> ORGANISM: Artificial sequence
<220> FEATURE:
<223> OTHER INFORMATION: Synthetic antibody

<400> SEQUENCE: 549

Ala Arg Ala Leu Glu Tyr Gly Ala Gly Ser Trp Ala Ala Ala Phe
1               5                   10                  15

<210> SEQ ID NO 550
<211> LENGTH: 8
<212> TYPE: PRT
<213> ORGANISM: Artificial sequence
<220> FEATURE:
<223> OTHER INFORMATION: Synthetic antibody

<400> SEQUENCE: 550

Gly Gly Thr Phe Ser Ser Tyr Thr
1               5

<210> SEQ ID NO 551
<211> LENGTH: 8
<212> TYPE: PRT
<213> ORGANISM: Artificial sequence
<220> FEATURE:
<223> OTHER INFORMATION: Synthetic antibody

<400> SEQUENCE: 551

Ile Ile Pro Ile Leu Gly Leu Thr
1               5

<210> SEQ ID NO 552
<211> LENGTH: 17
<212> TYPE: PRT
<213> ORGANISM: Artificial sequence
<220> FEATURE:
<223> OTHER INFORMATION: Synthetic antibody

<400> SEQUENCE: 552

Ala Arg Asn Gly Glu Gln Leu Glu Trp Ser Tyr Tyr Tyr Gly Met Asp
1               5                   10                  15

Val

<210> SEQ ID NO 553
<211> LENGTH: 8
<212> TYPE: PRT
<213> ORGANISM: Artificial sequence
<220> FEATURE:
<223> OTHER INFORMATION: Synthetic antibody

<400> SEQUENCE: 553

Gly Gly Ser Phe Thr Leu Tyr Tyr
1               5

<210> SEQ ID NO 554
<211> LENGTH: 7
<212> TYPE: PRT
<213> ORGANISM: Artificial sequence
<220> FEATURE:
<223> OTHER INFORMATION: Synthetic antibody

<400> SEQUENCE: 554

Ile Asn Gln Ser Gly Ser Thr
1               5

<210> SEQ ID NO 555
<211> LENGTH: 17
<212> TYPE: PRT
<213> ORGANISM: Artificial sequence
<220> FEATURE:
<223> OTHER INFORMATION: Synthetic antibody

<400> SEQUENCE: 555

Ala Arg Gly His Asp Ser Ser Gly Tyr Tyr Ile Asp Tyr Tyr Leu Asp
1               5                   10                  15

Val

<210> SEQ ID NO 556
<211> LENGTH: 9
<212> TYPE: PRT
<213> ORGANISM: Artificial sequence
<220> FEATURE:
<223> OTHER INFORMATION: Synthetic antibody

<400> SEQUENCE: 556

Gly Tyr Thr Ile Ser Ser Asp Tyr Tyr
1               5

<210> SEQ ID NO 557
<211> LENGTH: 7
<212> TYPE: PRT
<213> ORGANISM: Artificial sequence
<220> FEATURE:
<223> OTHER INFORMATION: Synthetic antibody

<400> SEQUENCE: 557

Ile Tyr Gln Asn Gly His Thr
1               5

<210> SEQ ID NO 558
<211> LENGTH: 15
<212> TYPE: PRT
<213> ORGANISM: Artificial sequence
<220> FEATURE:
<223> OTHER INFORMATION: Synthetic antibody

<400> SEQUENCE: 558

Ala Arg Arg Gly Asp Cys Gly Ala Asp Cys Tyr His Phe Asp Tyr
1               5                   10                  15

<210> SEQ ID NO 559
<211> LENGTH: 10
<212> TYPE: PRT
<213> ORGANISM: Artificial sequence
<220> FEATURE:
<223> OTHER INFORMATION: Synthetic antibody

<400> SEQUENCE: 559

Gly Asp Phe Leu Ser Ser Thr Asn Phe Tyr
1               5                   10

<210> SEQ ID NO 560
<211> LENGTH: 7
<212> TYPE: PRT
<213> ORGANISM: Artificial sequence
<220> FEATURE:
<223> OTHER INFORMATION: Synthetic antibody

<400> SEQUENCE: 560

Ile Tyr Asp Ser Gly Asn Thr
1               5

<210> SEQ ID NO 561
<211> LENGTH: 15
<212> TYPE: PRT
<213> ORGANISM: Artificial sequence
<220> FEATURE:
<223> OTHER INFORMATION: Synthetic antibody

<400> SEQUENCE: 561

Ala Arg Val Gly Asp Cys Gly Ala Asp Cys Tyr Tyr Phe Asp His
1               5                   10                  15

<210> SEQ ID NO 562
<211> LENGTH: 8
<212> TYPE: PRT
<213> ORGANISM: Artificial sequence
<220> FEATURE:
<223> OTHER INFORMATION: Synthetic antibody

<400> SEQUENCE: 562

Gly Phe Thr Phe Ser Ser Tyr Trp
1               5

<210> SEQ ID NO 563
<211> LENGTH: 8
<212> TYPE: PRT
<213> ORGANISM: Artificial sequence
<220> FEATURE:
<223> OTHER INFORMATION: Synthetic antibody

<400> SEQUENCE: 563

Ile Lys Gln Asp Gly Ser Glu Lys
1               5

<210> SEQ ID NO 564
<211> LENGTH: 12
<212> TYPE: PRT
<213> ORGANISM: Artificial sequence
<220> FEATURE:
<223> OTHER INFORMATION: Synthetic antibody

<400> SEQUENCE: 564

Ala Arg Gly Ser Ile Gly Trp Leu Ser Pro Asp Tyr
1               5                   10

<210> SEQ ID NO 565
<211> LENGTH: 8
<212> TYPE: PRT
<213> ORGANISM: Artificial sequence
<220> FEATURE:
<223> OTHER INFORMATION: Synthetic antibody

<400> SEQUENCE: 565

Gly Phe Asn Phe Gly Asp Tyr Leu
1               5

<210> SEQ ID NO 566
<211> LENGTH: 10
<212> TYPE: PRT
<213> ORGANISM: Artificial sequence
<220> FEATURE:
<223> OTHER INFORMATION: Synthetic antibody

<400> SEQUENCE: 566

Val Arg Thr Lys Gly Tyr Gly Gly Thr Ser
1               5                   10

<210> SEQ ID NO 567
<211> LENGTH: 23
<212> TYPE: PRT
<213> ORGANISM: Artificial sequence
<220> FEATURE:
<223> OTHER INFORMATION: Synthetic antibody

<400> SEQUENCE: 567

Thr Arg Asp Arg Gln Lys Pro Thr Tyr Gln Phe Trp Ser Ser Tyr Phe
1               5                   10                  15

Val Asp Asp Pro Phe Asp Val
            20

<210> SEQ ID NO 568
<211> LENGTH: 8
<212> TYPE: PRT
<213> ORGANISM: Artificial sequence
<220> FEATURE:
<223> OTHER INFORMATION: Synthetic antibody

<400> SEQUENCE: 568

Gly Tyr Ser Phe Thr Ser Tyr Trp
1               5

<210> SEQ ID NO 569
<211> LENGTH: 8
<212> TYPE: PRT
<213> ORGANISM: Artificial sequence
<220> FEATURE:
<223> OTHER INFORMATION: Synthetic antibody

<400> SEQUENCE: 569

Ile Glu Pro Ser Asp Ser Tyr Thr
1               5

<210> SEQ ID NO 570
<211> LENGTH: 14
<212> TYPE: PRT
<213> ORGANISM: Artificial sequence
<220> FEATURE:
<223> OTHER INFORMATION: Synthetic antibody

<400> SEQUENCE: 570

Ala Arg Leu Gly Asp Ser Ser Gly Tyr Gly Glu Ile Asp Tyr
1               5                   10

<210> SEQ ID NO 571
<211> LENGTH: 8
<212> TYPE: PRT
<213> ORGANISM: Artificial sequence
<220> FEATURE:
<223> OTHER INFORMATION: Synthetic antibody

<400> SEQUENCE: 571

Gly Tyr Ser Phe Thr Ser Tyr Trp
1               5

<210> SEQ ID NO 572
<211> LENGTH: 8
<212> TYPE: PRT
<213> ORGANISM: Artificial sequence
<220> FEATURE:
<223> OTHER INFORMATION: Synthetic antibody

<400> SEQUENCE: 572

Ile Tyr Pro Gly Asp Ser Asp Thr
1               5

<210> SEQ ID NO 573
<211> LENGTH: 23
<212> TYPE: PRT
<213> ORGANISM: Artificial sequence
<220> FEATURE:
<223> OTHER INFORMATION: Synthetic antibody

<400> SEQUENCE: 573

Ala Arg Ala Pro Thr Val Pro Ala Ala Ile Trp Gly Ser Ser Tyr Tyr
1               5                   10                  15

Tyr Tyr Tyr Tyr Met Asp Val
            20

<210> SEQ ID NO 574
<211> LENGTH: 8
<212> TYPE: PRT
<213> ORGANISM: Artificial sequence
<220> FEATURE:
<223> OTHER INFORMATION: Synthetic antibody

<400> SEQUENCE: 574

Gly Phe Lys Phe Ser Gly Ser Ala
1               5

<210> SEQ ID NO 575
<211> LENGTH: 10
<212> TYPE: PRT
<213> ORGANISM: Artificial sequence
<220> FEATURE:
<223> OTHER INFORMATION: Synthetic antibody

<400> SEQUENCE: 575

Ile Arg Ser Lys Ala Asn Asn Tyr Ala Thr
1               5                   10

<210> SEQ ID NO 576
<211> LENGTH: 10
<212> TYPE: PRT
<213> ORGANISM: Artificial sequence
<220> FEATURE:
<223> OTHER INFORMATION: Synthetic antibody

<400> SEQUENCE: 576

Thr Arg Asn Val Asp Thr Asp His Arg Gly
1 5 10

<210> SEQ ID NO 577
<211> LENGTH: 6
<212> TYPE: PRT
<213> ORGANISM: Artificial sequence
<220> FEATURE:
<223> OTHER INFORMATION: Synthetic antibody

<400> SEQUENCE: 577

Gln Ser Val Ser Ser Asn
1 5

<210> SEQ ID NO 578
<211> LENGTH: 3
<212> TYPE: PRT
<213> ORGANISM: Artificial sequence
<220> FEATURE:
<223> OTHER INFORMATION: Synthetic antibody

<400> SEQUENCE: 578

Ala Ala Ser
1

<210> SEQ ID NO 579
<211> LENGTH: 9
<212> TYPE: PRT
<213> ORGANISM: Artificial sequence
<220> FEATURE:
<223> OTHER INFORMATION: Synthetic antibody

<400> SEQUENCE: 579

Gln Gln Phe Asn Asn Trp Pro Arg Thr
1 5

<210> SEQ ID NO 580
<211> LENGTH: 6
<212> TYPE: PRT
<213> ORGANISM: Artificial sequence
<220> FEATURE:
<223> OTHER INFORMATION: Synthetic antibody

<400> SEQUENCE: 580

Gln Ser Ile Arg Asn Tyr
1 5

<210> SEQ ID NO 581
<211> LENGTH: 3
<212> TYPE: PRT
<213> ORGANISM: Artificial sequence
<220> FEATURE:
<223> OTHER INFORMATION: Synthetic antibody

<400> SEQUENCE: 581

Ala Ala Ser
1

<210> SEQ ID NO 582
<211> LENGTH: 9
<212> TYPE: PRT
<213> ORGANISM: Artificial sequence
<220> FEATURE:
<223> OTHER INFORMATION: Synthetic antibody

<400> SEQUENCE: 582

Gln Gln Thr Tyr Ser Thr Ala Trp Thr 1 5

<210> SEQ ID NO 583
<211> LENGTH: 6
<212> TYPE: PRT
<213> ORGANISM: Artificial sequence
<220> FEATURE:
<223> OTHER INFORMATION: Synthetic antibody

<400> SEQUENCE: 583

Gln Ser Ile Ser Ser Tyr
1 5

<210> SEQ ID NO 584
<211> LENGTH: 3
<212> TYPE: PRT
<213> ORGANISM: Artificial sequence
<220> FEATURE:
<223> OTHER INFORMATION: Synthetic antibody

<400> SEQUENCE: 584

Ala Ala Ser
1

<210> SEQ ID NO 585
<211> LENGTH: 10
<212> TYPE: PRT
<213> ORGANISM: Artificial sequence
<220> FEATURE:
<223> OTHER INFORMATION: Synthetic antibody

<400> SEQUENCE: 585

Gln Gln Ser Tyr Ser Thr Pro Met Tyr Thr
1 5 10

<210> SEQ ID NO 586
<211> LENGTH: 6
<212> TYPE: PRT
<213> ORGANISM: Artificial sequence
<220> FEATURE:
<223> OTHER INFORMATION: Synthetic antibody

<400> SEQUENCE: 586

Gln Ser Ile Ser Ser Tyr
1 5

<210> SEQ ID NO 587
<211> LENGTH: 3
<212> TYPE: PRT
<213> ORGANISM: Artificial sequence
<220> FEATURE:
<223> OTHER INFORMATION: Synthetic antibody

<400> SEQUENCE: 587

Ala Ala Ser
1

<210> SEQ ID NO 588
<211> LENGTH: 10
<212> TYPE: PRT
<213> ORGANISM: Artificial sequence
<220> FEATURE:
<223> OTHER INFORMATION: Synthetic antibody

<400> SEQUENCE: 588

Gln Gln Ser Tyr Ser Thr Pro Met Tyr Thr
1 5 10

<210> SEQ ID NO 589
<211> LENGTH: 8
<212> TYPE: PRT
<213> ORGANISM: Artificial sequence
<220> FEATURE:
<223> OTHER INFORMATION: Synthetic antibody

<400> SEQUENCE: 589

Ser Ser Asn Ile Gly Ser Asn Thr
1               5

<210> SEQ ID NO 590
<211> LENGTH: 3
<212> TYPE: PRT
<213> ORGANISM: Artificial sequence
<220> FEATURE:
<223> OTHER INFORMATION: Synthetic antibody

<400> SEQUENCE: 590

Ser Asn Asn
1

<210> SEQ ID NO 591
<211> LENGTH: 11
<212> TYPE: PRT
<213> ORGANISM: Artificial sequence
<220> FEATURE:
<223> OTHER INFORMATION: Synthetic antibody

<400> SEQUENCE: 591

Ala Ala Trp Asp Asp Ser Leu Asn Gly Trp Val
1               5                   10

<210> SEQ ID NO 592
<211> LENGTH: 9
<212> TYPE: PRT
<213> ORGANISM: Artificial sequence
<220> FEATURE:
<223> OTHER INFORMATION: Synthetic antibody

<400> SEQUENCE: 592

Ser Ser Asp Ile Gly Ala Tyr Asn Phe
1               5

<210> SEQ ID NO 593
<211> LENGTH: 3
<212> TYPE: PRT
<213> ORGANISM: Artificial sequence
<220> FEATURE:
<223> OTHER INFORMATION: Synthetic antibody

<400> SEQUENCE: 593

Asp Val Thr
1

<210> SEQ ID NO 594
<211> LENGTH: 10
<212> TYPE: PRT
<213> ORGANISM: Artificial sequence
<220> FEATURE:
<223> OTHER INFORMATION: Synthetic antibody

<400> SEQUENCE: 594

Asn Ser Tyr Thr Ser Ser Ser His Val Val
1               5                   10

<210> SEQ ID NO 595
<211> LENGTH: 6
<212> TYPE: PRT
<213> ORGANISM: Artificial sequence
<220> FEATURE:
<223> OTHER INFORMATION: Synthetic antibody

<400> SEQUENCE: 595

Arg Leu Gly Asp Lys Tyr
1 5

<210> SEQ ID NO 596
<211> LENGTH: 3
<212> TYPE: PRT
<213> ORGANISM: Artificial sequence
<220> FEATURE:
<223> OTHER INFORMATION: Synthetic antibody

<400> SEQUENCE: 596

Gln Asp Tyr
1

<210> SEQ ID NO 597
<211> LENGTH: 10
<212> TYPE: PRT
<213> ORGANISM: Artificial sequence
<220> FEATURE:
<223> OTHER INFORMATION: Synthetic antibody

<400> SEQUENCE: 597

Gln Ala Trp Asp Ser Ser Asp Gly Ser Val
1 5 10

<210> SEQ ID NO 598
<211> LENGTH: 9
<212> TYPE: PRT
<213> ORGANISM: Artificial sequence
<220> FEATURE:
<223> OTHER INFORMATION: Synthetic antibody

<400> SEQUENCE: 598

Ser Ser Asp Ile Gly Ala Tyr Asn Phe
1 5

<210> SEQ ID NO 599
<211> LENGTH: 3
<212> TYPE: PRT
<213> ORGANISM: Artificial sequence
<220> FEATURE:
<223> OTHER INFORMATION: Synthetic antibody

<400> SEQUENCE: 599

Asp Val Thr
1

<210> SEQ ID NO 600
<211> LENGTH: 10
<212> TYPE: PRT
<213> ORGANISM: Artificial sequence
<220> FEATURE:
<223> OTHER INFORMATION: Synthetic antibody

<400> SEQUENCE: 600

Asn Ser Tyr Thr Ser Ser Ser His Val Val
1 5 10

<210> SEQ ID NO 601
<211> LENGTH: 6
<212> TYPE: PRT
<213> ORGANISM: Artificial sequence
<220> FEATURE:
<223> OTHER INFORMATION: Synthetic antibody

<400> SEQUENCE: 601

Gln Ser Ile Ser Ser Trp
1 5

<210> SEQ ID NO 602
<211> LENGTH: 3
<212> TYPE: PRT
<213> ORGANISM: Artificial sequence
<220> FEATURE:
<223> OTHER INFORMATION: Synthetic antibody

<400> SEQUENCE: 602

Lys Ala Ser
1

<210> SEQ ID NO 603
<211> LENGTH: 9
<212> TYPE: PRT
<213> ORGANISM: Artificial sequence
<220> FEATURE:
<223> OTHER INFORMATION: Synthetic antibody

<400> SEQUENCE: 603

Gln Gln Tyr Asn Ser Tyr Pro Leu Thr
1 5

<210> SEQ ID NO 604
<211> LENGTH: 6
<212> TYPE: PRT
<213> ORGANISM: Artificial sequence
<220> FEATURE:
<223> OTHER INFORMATION: Synthetic antibody

<400> SEQUENCE: 604

Arg Leu Gly Asp Lys Tyr
1 5

<210> SEQ ID NO 605
<211> LENGTH: 3
<212> TYPE: PRT
<213> ORGANISM: Artificial sequence
<220> FEATURE:
<223> OTHER INFORMATION: Synthetic antibody

<400> SEQUENCE: 605

Gln Asp Tyr
1

<210> SEQ ID NO 606
<211> LENGTH: 10
<212> TYPE: PRT
<213> ORGANISM: Artificial sequence
<220> FEATURE:
<223> OTHER INFORMATION: Synthetic antibody

<400> SEQUENCE: 606

Gln Ala Trp Asp Ser Ser Asp Gly Ser Val
1 5 10

<210> SEQ ID NO 607

<211> LENGTH: 9
<212> TYPE: PRT
<213> ORGANISM: Artificial sequence
<220> FEATURE:
<223> OTHER INFORMATION: Synthetic antibody

<400> SEQUENCE: 607

Ser Ser Asp Val Gly Gly Phe Asn Phe
1 5

<210> SEQ ID NO 608
<211> LENGTH: 3
<212> TYPE: PRT
<213> ORGANISM: Artificial sequence
<220> FEATURE:
<223> OTHER INFORMATION: Synthetic antibody

<400> SEQUENCE: 608

Asp Val Ser
1

<210> SEQ ID NO 609
<211> LENGTH: 10
<212> TYPE: PRT
<213> ORGANISM: Artificial sequence
<220> FEATURE:
<223> OTHER INFORMATION: Synthetic antibody

<400> SEQUENCE: 609

Thr Ser Tyr Thr Ser Ser Ser Thr Val Val
1 5 10

<210> SEQ ID NO 610
<211> LENGTH: 6
<212> TYPE: PRT
<213> ORGANISM: Artificial sequence
<220> FEATURE:
<223> OTHER INFORMATION: Synthetic antibody

<400> SEQUENCE: 610

Ser Leu Lys Asn Tyr Tyr
1 5

<210> SEQ ID NO 611
<211> LENGTH: 3
<212> TYPE: PRT
<213> ORGANISM: Artificial sequence
<220> FEATURE:
<223> OTHER INFORMATION: Synthetic antibody

<400> SEQUENCE: 611

Gly Lys Asn
1

<210> SEQ ID NO 612
<211> LENGTH: 11
<212> TYPE: PRT
<213> ORGANISM: Artificial sequence
<220> FEATURE:
<223> OTHER INFORMATION: Synthetic antibody

<400> SEQUENCE: 612

Ser Ser Arg Asp Arg Ser Asp Lys Tyr Trp Val
1 5 10

<210> SEQ ID NO 613
<211> LENGTH: 9

<212> TYPE: PRT
<213> ORGANISM: Artificial sequence
<220> FEATURE:
<223> OTHER INFORMATION: Synthetic antibody

<400> SEQUENCE: 613

Ser Ser Asp Val Gly Ala Tyr Lys Phe
1               5

<210> SEQ ID NO 614
<211> LENGTH: 3
<212> TYPE: PRT
<213> ORGANISM: Artificial sequence
<220> FEATURE:
<223> OTHER INFORMATION: Synthetic antibody

<400> SEQUENCE: 614

Asp Val Asn
1

<210> SEQ ID NO 615
<211> LENGTH: 9
<212> TYPE: PRT
<213> ORGANISM: Artificial sequence
<220> FEATURE:
<223> OTHER INFORMATION: Synthetic antibody

<400> SEQUENCE: 615

Ser Ser Tyr Thr Arg Gly Pro Tyr Ile
1               5

<210> SEQ ID NO 616
<211> LENGTH: 7
<212> TYPE: PRT
<213> ORGANISM: Artificial sequence
<220> FEATURE:
<223> OTHER INFORMATION: Synthetic antibody

<400> SEQUENCE: 616

Gln Thr Ile Ser Ser Asn Asn
1               5

<210> SEQ ID NO 617
<211> LENGTH: 3
<212> TYPE: PRT
<213> ORGANISM: Artificial sequence
<220> FEATURE:
<223> OTHER INFORMATION: Synthetic antibody

<400> SEQUENCE: 617

Asp Ala Ser
1

<210> SEQ ID NO 618
<211> LENGTH: 9
<212> TYPE: PRT
<213> ORGANISM: Artificial sequence
<220> FEATURE:
<223> OTHER INFORMATION: Synthetic antibody

<400> SEQUENCE: 618

Gln Gln Tyr Gly Arg Ser Pro Ile Thr
1               5

<210> SEQ ID NO 619
<211> LENGTH: 8
<212> TYPE: PRT

<213> ORGANISM: Artificial sequence
<220> FEATURE:
<223> OTHER INFORMATION: Synthetic antibody

<400> SEQUENCE: 619

Ser Ser Asn Ile Gly Asn Ser Tyr
1 5

<210> SEQ ID NO 620
<211> LENGTH: 3
<212> TYPE: PRT
<213> ORGANISM: Artificial sequence
<220> FEATURE:
<223> OTHER INFORMATION: Synthetic antibody

<400> SEQUENCE: 620

Asp Asn Asn
1

<210> SEQ ID NO 621
<211> LENGTH: 13
<212> TYPE: PRT
<213> ORGANISM: Artificial sequence
<220> FEATURE:
<223> OTHER INFORMATION: Synthetic antibody

<400> SEQUENCE: 621

Ala Thr Trp Glu Ser Arg Leu Ser Ala Gly His Val Val
1 5 10

<210> SEQ ID NO 622
<211> LENGTH: 7
<212> TYPE: PRT
<213> ORGANISM: Artificial sequence
<220> FEATURE:
<223> OTHER INFORMATION: Synthetic antibody

<400> SEQUENCE: 622

Gln Ser Val Thr Ser Asn Tyr
1 5

<210> SEQ ID NO 623
<211> LENGTH: 3
<212> TYPE: PRT
<213> ORGANISM: Artificial sequence
<220> FEATURE:
<223> OTHER INFORMATION: Synthetic antibody

<400> SEQUENCE: 623

Gly Ala Ser
1

<210> SEQ ID NO 624
<211> LENGTH: 9
<212> TYPE: PRT
<213> ORGANISM: Artificial sequence
<220> FEATURE:
<223> OTHER INFORMATION: Synthetic antibody

<400> SEQUENCE: 624

Gln Gln Tyr Ala Gly Ser Pro Phe Thr
1 5

<210> SEQ ID NO 625
<211> LENGTH: 11
<212> TYPE: PRT
<213> ORGANISM: Artificial sequence
<220> FEATURE:
<223> OTHER INFORMATION: Synthetic antibody

<400> SEQUENCE: 625

Gln Ser Leu Leu His Ser Asn Gly Tyr Asn Tyr
1 5 10

<210> SEQ ID NO 626
<211> LENGTH: 3
<212> TYPE: PRT
<213> ORGANISM: Artificial sequence
<220> FEATURE:
<223> OTHER INFORMATION: Synthetic antibody

<400> SEQUENCE: 626

Leu Gly Ser
1

<210> SEQ ID NO 627
<211> LENGTH: 9
<212> TYPE: PRT
<213> ORGANISM: Artificial sequence
<220> FEATURE:
<223> OTHER INFORMATION: Synthetic antibody

<400> SEQUENCE: 627

Val Gln Ala Leu Gln Ile Pro Leu Thr
1 5

<210> SEQ ID NO 628
<211> LENGTH: 6
<212> TYPE: PRT
<213> ORGANISM: Artificial sequence
<220> FEATURE:
<223> OTHER INFORMATION: Synthetic antibody

<400> SEQUENCE: 628

Lys Leu Gly His Lys Tyr
1 5

<210> SEQ ID NO 629
<211> LENGTH: 3
<212> TYPE: PRT
<213> ORGANISM: Artificial sequence
<220> FEATURE:
<223> OTHER INFORMATION: Synthetic antibody

<400> SEQUENCE: 629

Gln Asp Ser
1

<210> SEQ ID NO 630
<211> LENGTH: 10
<212> TYPE: PRT
<213> ORGANISM: Artificial sequence
<220> FEATURE:
<223> OTHER INFORMATION: Synthetic antibody

<400> SEQUENCE: 630

Gln Ala Trp Asp Ser Ser Ser Phe Tyr Val
1 5 10

<210> SEQ ID NO 631
<211> LENGTH: 6
<212> TYPE: PRT
<213> ORGANISM: Artificial sequence
<220> FEATURE:

<223> OTHER INFORMATION: Synthetic antibody

<400> SEQUENCE: 631

Gln Ser Ile Ser Ser Trp
1               5

<210> SEQ ID NO 632
<211> LENGTH: 3
<212> TYPE: PRT
<213> ORGANISM: Artificial sequence
<220> FEATURE:
<223> OTHER INFORMATION: Synthetic antibody

<400> SEQUENCE: 632

Lys Ala Ser
1

<210> SEQ ID NO 633
<211> LENGTH: 9
<212> TYPE: PRT
<213> ORGANISM: Artificial sequence
<220> FEATURE:
<223> OTHER INFORMATION: Synthetic antibody

<400> SEQUENCE: 633

Gln Gln Tyr Asn Ser Tyr Pro Leu Thr
1               5

<210> SEQ ID NO 634
<211> LENGTH: 6
<212> TYPE: PRT
<213> ORGANISM: Artificial sequence
<220> FEATURE:
<223> OTHER INFORMATION: Synthetic antibody

<400> SEQUENCE: 634

Lys Leu Gly Asp Lys Tyr
1               5

<210> SEQ ID NO 635
<211> LENGTH: 3
<212> TYPE: PRT
<213> ORGANISM: Artificial sequence
<220> FEATURE:
<223> OTHER INFORMATION: Synthetic antibody

<400> SEQUENCE: 635

Gln Asp Thr
1

<210> SEQ ID NO 636
<211> LENGTH: 9
<212> TYPE: PRT
<213> ORGANISM: Artificial sequence
<220> FEATURE:
<223> OTHER INFORMATION: Synthetic antibody

<400> SEQUENCE: 636

Gln Ala Trp Asp Ser Ser Thr Val Val
1               5

<210> SEQ ID NO 637

<400> SEQUENCE: 637

000

<210> SEQ ID NO 638

<400> SEQUENCE: 638

000

<210> SEQ ID NO 639

<400> SEQUENCE: 639

000

<210> SEQ ID NO 640
<211> LENGTH: 6
<212> TYPE: PRT
<213> ORGANISM: Artificial sequence
<220> FEATURE:
<223> OTHER INFORMATION: Synthetic antibody

<400> SEQUENCE: 640

Gln Ser Val Ser Arg Tyr
1               5

<210> SEQ ID NO 641
<211> LENGTH: 3
<212> TYPE: PRT
<213> ORGANISM: Artificial sequence
<220> FEATURE:
<223> OTHER INFORMATION: Synthetic antibody

<400> SEQUENCE: 641

Asp Ala Ser
1

<210> SEQ ID NO 642
<211> LENGTH: 8
<212> TYPE: PRT
<213> ORGANISM: Artificial sequence
<220> FEATURE:
<223> OTHER INFORMATION: Synthetic antibody

<400> SEQUENCE: 642

Gln Gln Arg Ser Asn Trp Pro Thr
1               5

<210> SEQ ID NO 643
<211> LENGTH: 11
<212> TYPE: PRT
<213> ORGANISM: Artificial sequence
<220> FEATURE:
<223> OTHER INFORMATION: Synthetic antibody

<400> SEQUENCE: 643

Gln Ser Leu Val Tyr Arg Asp Gly Asn Thr Tyr
1               5                   10

<210> SEQ ID NO 644
<211> LENGTH: 3
<212> TYPE: PRT
<213> ORGANISM: Artificial sequence
<220> FEATURE:
<223> OTHER INFORMATION: Synthetic antibody

<400> SEQUENCE: 644

Gln Val Phe
1

<210> SEQ ID NO 645
<211> LENGTH: 9
<212> TYPE: PRT
<213> ORGANISM: Artificial sequence
<220> FEATURE:
<223> OTHER INFORMATION: Synthetic antibody

<400> SEQUENCE: 645

Met Gln Ser Thr His Trp Pro Trp Thr
1 5

<210> SEQ ID NO 646
<211> LENGTH: 6
<212> TYPE: PRT
<213> ORGANISM: Artificial sequence
<220> FEATURE:
<223> OTHER INFORMATION: Synthetic antibody

<400> SEQUENCE: 646

Gln Gly Ile Arg Asn Asp
1 5

<210> SEQ ID NO 647
<211> LENGTH: 3
<212> TYPE: PRT
<213> ORGANISM: Artificial sequence
<220> FEATURE:
<223> OTHER INFORMATION: Synthetic antibody

<400> SEQUENCE: 647

Ala Ala Ser
1

<210> SEQ ID NO 648
<211> LENGTH: 9
<212> TYPE: PRT
<213> ORGANISM: Artificial sequence
<220> FEATURE:
<223> OTHER INFORMATION: Synthetic antibody

<400> SEQUENCE: 648

Leu Gln His Asn Ser Tyr Pro Trp Thr
1 5

<210> SEQ ID NO 649
<211> LENGTH: 11
<212> TYPE: PRT
<213> ORGANISM: Artificial sequence
<220> FEATURE:
<223> OTHER INFORMATION: Synthetic antibody

<400> SEQUENCE: 649

Gln Ser Leu Val His Ser Asp Gly Asn Thr Tyr
1 5 10

<210> SEQ ID NO 650
<211> LENGTH: 3
<212> TYPE: PRT
<213> ORGANISM: Artificial sequence
<220> FEATURE:
<223> OTHER INFORMATION: Synthetic antibody

<400> SEQUENCE: 650

Lys Ile Ser
1

<210> SEQ ID NO 651
<211> LENGTH: 8
<212> TYPE: PRT
<213> ORGANISM: Artificial sequence
<220> FEATURE:
<223> OTHER INFORMATION: Synthetic antibody

<400> SEQUENCE: 651

Met Gln Gly Thr Arg Leu Tyr Thr
1               5

<210> SEQ ID NO 652
<211> LENGTH: 8
<212> TYPE: PRT
<213> ORGANISM: Artificial sequence
<220> FEATURE:
<223> OTHER INFORMATION: Synthetic antibody

<400> SEQUENCE: 652

Ser Ser Asn Ile Gly Ser Asn His
1               5

<210> SEQ ID NO 653
<211> LENGTH: 3
<212> TYPE: PRT
<213> ORGANISM: Artificial sequence
<220> FEATURE:
<223> OTHER INFORMATION: Synthetic antibody

<400> SEQUENCE: 653

Lys Asn Asn
1

<210> SEQ ID NO 654
<211> LENGTH: 11
<212> TYPE: PRT
<213> ORGANISM: Artificial sequence
<220> FEATURE:
<223> OTHER INFORMATION: Synthetic antibody

<400> SEQUENCE: 654

Ala Ala Trp Asp Asp Ser Leu Arg Gly Trp Glu
1               5                   10

<210> SEQ ID NO 655
<211> LENGTH: 6
<212> TYPE: PRT
<213> ORGANISM: Artificial sequence
<220> FEATURE:
<223> OTHER INFORMATION: Synthetic antibody

<400> SEQUENCE: 655

Gln Ser Val Ser Arg Lys
1               5

<210> SEQ ID NO 656
<211> LENGTH: 3
<212> TYPE: PRT
<213> ORGANISM: Artificial sequence
<220> FEATURE:
<223> OTHER INFORMATION: Synthetic antibody

<400> SEQUENCE: 656

Asp Ala Ser
1

<210> SEQ ID NO 657

<211> LENGTH: 8
<212> TYPE: PRT
<213> ORGANISM: Artificial sequence
<220> FEATURE:
<223> OTHER INFORMATION: Synthetic antibody

<400> SEQUENCE: 657

His Gln Arg Ser Asn Trp Trp Thr
1               5

<210> SEQ ID NO 658
<211> LENGTH: 8
<212> TYPE: PRT
<213> ORGANISM: Artificial sequence
<220> FEATURE:
<223> OTHER INFORMATION: Synthetic antibody

<400> SEQUENCE: 658

Ser Ser Asn Val Gly Pro Asn Thr
1               5

<210> SEQ ID NO 659
<211> LENGTH: 3
<212> TYPE: PRT
<213> ORGANISM: Artificial sequence
<220> FEATURE:
<223> OTHER INFORMATION: Synthetic antibody

<400> SEQUENCE: 659

Arg Asn Asn
1

<210> SEQ ID NO 660
<211> LENGTH: 12
<212> TYPE: PRT
<213> ORGANISM: Artificial sequence
<220> FEATURE:
<223> OTHER INFORMATION: Synthetic antibody

<400> SEQUENCE: 660

Ala Ala Trp Asp Asp Ser Leu Asn Gly His Met Val
1               5                   10

<210> SEQ ID NO 661
<211> LENGTH: 6
<212> TYPE: PRT
<213> ORGANISM: Artificial sequence
<220> FEATURE:
<223> OTHER INFORMATION: Synthetic antibody

<400> SEQUENCE: 661

Lys Leu Gly Asp Lys Tyr
1               5

<210> SEQ ID NO 662
<211> LENGTH: 3
<212> TYPE: PRT
<213> ORGANISM: Artificial sequence
<220> FEATURE:
<223> OTHER INFORMATION: Synthetic antibody

<400> SEQUENCE: 662

Gln Asp Thr
1

<210> SEQ ID NO 663
<211> LENGTH: 10

<212> TYPE: PRT
<213> ORGANISM: Artificial sequence
<220> FEATURE:
<223> OTHER INFORMATION: Synthetic antibody

<400> SEQUENCE: 663

Gln Ala Trp Asp Ser Ser Thr Pro Trp Val
1 5 10

<210> SEQ ID NO 664
<211> LENGTH: 6
<212> TYPE: PRT
<213> ORGANISM: Artificial sequence
<220> FEATURE:
<223> OTHER INFORMATION: Synthetic antibody

<400> SEQUENCE: 664

Asn Ile Gly Asp Lys Ser
1 5

<210> SEQ ID NO 665
<211> LENGTH: 3
<212> TYPE: PRT
<213> ORGANISM: Artificial sequence
<220> FEATURE:
<223> OTHER INFORMATION: Synthetic antibody

<400> SEQUENCE: 665

Asp Asp Ser
1

<210> SEQ ID NO 666
<211> LENGTH: 11
<212> TYPE: PRT
<213> ORGANISM: Artificial sequence
<220> FEATURE:
<223> OTHER INFORMATION: Synthetic antibody

<400> SEQUENCE: 666

Gln Val Trp Asp Ser Ser Ser Asp His Leu Val
1 5 10

<210> SEQ ID NO 667
<211> LENGTH: 6
<212> TYPE: PRT
<213> ORGANISM: Artificial sequence
<220> FEATURE:
<223> OTHER INFORMATION: Synthetic antibody

<400> SEQUENCE: 667

Asn Ile Gly Ser Lys Ser
1 5

<210> SEQ ID NO 668
<211> LENGTH: 3
<212> TYPE: PRT
<213> ORGANISM: Artificial sequence
<220> FEATURE:
<223> OTHER INFORMATION: Synthetic antibody

<400> SEQUENCE: 668

Asp Asp Ser
1

<210> SEQ ID NO 669
<211> LENGTH: 11
<212> TYPE: PRT

<213> ORGANISM: Artificial sequence
<220> FEATURE:
<223> OTHER INFORMATION: Synthetic antibody

<400> SEQUENCE: 669

Gln Val Trp Asp Ser Ser Ser Asp His Trp Val
1 5 10

<210> SEQ ID NO 670
<211> LENGTH: 6
<212> TYPE: PRT
<213> ORGANISM: Artificial sequence
<220> FEATURE:
<223> OTHER INFORMATION: Synthetic antibody

<400> SEQUENCE: 670

Asn Leu Glu Ser Lys Tyr
1 5

<210> SEQ ID NO 671
<211> LENGTH: 3
<212> TYPE: PRT
<213> ORGANISM: Artificial sequence
<220> FEATURE:
<223> OTHER INFORMATION: Synthetic antibody

<400> SEQUENCE: 671

Glu Asp Ser
1

<210> SEQ ID NO 672
<211> LENGTH: 11
<212> TYPE: PRT
<213> ORGANISM: Artificial sequence
<220> FEATURE:
<223> OTHER INFORMATION: Synthetic antibody

<400> SEQUENCE: 672

Gln Glu Trp Asp Thr Ser Ser Asp Tyr Pro Val
1 5 10

<210> SEQ ID NO 673
<211> LENGTH: 9
<212> TYPE: PRT
<213> ORGANISM: Artificial sequence
<220> FEATURE:
<223> OTHER INFORMATION: Synthetic antibody

<400> SEQUENCE: 673

Asn Asn Asp Val Gly Leu Tyr Asp Tyr
1 5

<210> SEQ ID NO 674
<211> LENGTH: 3
<212> TYPE: PRT
<213> ORGANISM: Artificial sequence
<220> FEATURE:
<223> OTHER INFORMATION: Synthetic antibody

<400> SEQUENCE: 674

Glu Val Thr
1

<210> SEQ ID NO 675
<211> LENGTH: 10
<212> TYPE: PRT
<213> ORGANISM: Artificial sequence
<220> FEATURE:
<223> OTHER INFORMATION: Synthetic antibody

<400> SEQUENCE: 675

Ser Ser Tyr Thr Arg Ser Ile Thr Trp Val
1               5                   10

<210> SEQ ID NO 676
<211> LENGTH: 6
<212> TYPE: PRT
<213> ORGANISM: Artificial sequence
<220> FEATURE:
<223> OTHER INFORMATION: Synthetic antibody

<400> SEQUENCE: 676

Gln Ser Val Ser Ser Asn
1               5

<210> SEQ ID NO 677
<211> LENGTH: 3
<212> TYPE: PRT
<213> ORGANISM: Artificial sequence
<220> FEATURE:
<223> OTHER INFORMATION: Synthetic antibody

<400> SEQUENCE: 677

Gly Ala Ser
1

<210> SEQ ID NO 678
<211> LENGTH: 10
<212> TYPE: PRT
<213> ORGANISM: Artificial sequence
<220> FEATURE:
<223> OTHER INFORMATION: Synthetic antibody

<400> SEQUENCE: 678

Gln Gln Tyr Asn Asn Trp Pro Gln Arg Thr
1               5                   10

<210> SEQ ID NO 679
<211> LENGTH: 9
<212> TYPE: PRT
<213> ORGANISM: Artificial sequence
<220> FEATURE:
<223> OTHER INFORMATION: Synthetic antibody

<400> SEQUENCE: 679

Ser Ser Asn Ile Gly Ala Gly Tyr Asp
1               5

<210> SEQ ID NO 680
<211> LENGTH: 3
<212> TYPE: PRT
<213> ORGANISM: Artificial sequence
<220> FEATURE:
<223> OTHER INFORMATION: Synthetic antibody

<400> SEQUENCE: 680

Asp Asn Asn
1

<210> SEQ ID NO 681
<211> LENGTH: 11
<212> TYPE: PRT
<213> ORGANISM: Artificial sequence
<220> FEATURE:

<223> OTHER INFORMATION: Synthetic antibody

<400> SEQUENCE: 681

Gln Ser Tyr Asp Phe Arg Leu Ser Gly Ser Val
1 5 10

<210> SEQ ID NO 682
<211> LENGTH: 6
<212> TYPE: PRT
<213> ORGANISM: Artificial sequence
<220> FEATURE:
<223> OTHER INFORMATION: Synthetic antibody

<400> SEQUENCE: 682

Asn Ile Gly Ser Lys Ser
1 5

<210> SEQ ID NO 683
<211> LENGTH: 3
<212> TYPE: PRT
<213> ORGANISM: Artificial sequence
<220> FEATURE:
<223> OTHER INFORMATION: Synthetic antibody

<400> SEQUENCE: 683

Asp Asp Ser
1

<210> SEQ ID NO 684
<211> LENGTH: 12
<212> TYPE: PRT
<213> ORGANISM: Artificial sequence
<220> FEATURE:
<223> OTHER INFORMATION: Synthetic antibody

<400> SEQUENCE: 684

Gln Val Trp Asp Ser Ser Ser Asp His Ser Trp Val
1 5 10

<210> SEQ ID NO 685
<211> LENGTH: 8
<212> TYPE: PRT
<213> ORGANISM: Artificial sequence
<220> FEATURE:
<223> OTHER INFORMATION: Synthetic antibody

<400> SEQUENCE: 685

Ser Gly Ser Ile Ala Asn Asn Phe
1 5

<210> SEQ ID NO 686
<211> LENGTH: 3
<212> TYPE: PRT
<213> ORGANISM: Artificial sequence
<220> FEATURE:
<223> OTHER INFORMATION: Synthetic antibody

<400> SEQUENCE: 686

Glu Asp Asp
1

<210> SEQ ID NO 687
<211> LENGTH: 9
<212> TYPE: PRT
<213> ORGANISM: Artificial sequence
<220> FEATURE:
<223> OTHER INFORMATION: Synthetic antibody

<400> SEQUENCE: 687

Gln Ser Tyr Asp Ser Ser Asn Gln Val
1               5

<210> SEQ ID NO 688
<211> LENGTH: 6
<212> TYPE: PRT
<213> ORGANISM: Artificial sequence
<220> FEATURE:
<223> OTHER INFORMATION: Synthetic antibody

<400> SEQUENCE: 688

Lys Leu Gly Asp Lys Tyr
1               5

<210> SEQ ID NO 689
<211> LENGTH: 3
<212> TYPE: PRT
<213> ORGANISM: Artificial sequence
<220> FEATURE:
<223> OTHER INFORMATION: Synthetic antibody

<400> SEQUENCE: 689

Leu Asp Ser
1

<210> SEQ ID NO 690
<211> LENGTH: 9
<212> TYPE: PRT
<213> ORGANISM: Artificial sequence
<220> FEATURE:
<223> OTHER INFORMATION: Synthetic antibody

<400> SEQUENCE: 690

Gln Ala Trp Asp Ser Ser Thr Gly Val
1               5

<210> SEQ ID NO 691
<211> LENGTH: 9
<212> TYPE: PRT
<213> ORGANISM: Artificial sequence
<220> FEATURE:
<223> OTHER INFORMATION: Synthetic antibody

<400> SEQUENCE: 691

Ser Ser Asp Val Gly Gly Tyr Asn Tyr
1               5

<210> SEQ ID NO 692
<211> LENGTH: 3
<212> TYPE: PRT
<213> ORGANISM: Artificial sequence
<220> FEATURE:
<223> OTHER INFORMATION: Synthetic antibody

<400> SEQUENCE: 692

Asp Val Ser
1

<210> SEQ ID NO 693
<211> LENGTH: 11
<212> TYPE: PRT
<213> ORGANISM: Artificial sequence
<220> FEATURE:
<223> OTHER INFORMATION: Synthetic antibody

<400> SEQUENCE: 693

Ser Ser Tyr Thr Ser Ser Ser Thr Asn Val Val
1 5 10

<210> SEQ ID NO 694
<211> LENGTH: 9
<212> TYPE: PRT
<213> ORGANISM: Artificial sequence
<220> FEATURE:
<223> OTHER INFORMATION: Synthetic antibody

<400> SEQUENCE: 694

Ser Ser Asp Val Gly Gly Tyr Asn Tyr
1 5

<210> SEQ ID NO 695
<211> LENGTH: 3
<212> TYPE: PRT
<213> ORGANISM: Artificial sequence
<220> FEATURE:
<223> OTHER INFORMATION: Synthetic antibody

<400> SEQUENCE: 695

Asp Val Ser
1

<210> SEQ ID NO 696
<211> LENGTH: 11
<212> TYPE: PRT
<213> ORGANISM: Artificial sequence
<220> FEATURE:
<223> OTHER INFORMATION: Synthetic antibody

<400> SEQUENCE: 696

Ser Ser Tyr Thr Ser Ser Ser Thr Leu Val Val
1 5 10

<210> SEQ ID NO 697
<211> LENGTH: 6
<212> TYPE: PRT
<213> ORGANISM: Artificial sequence
<220> FEATURE:
<223> OTHER INFORMATION: Synthetic antibody

<400> SEQUENCE: 697

Gln Ser Ile Ser Ser Tyr
1 5

<210> SEQ ID NO 698
<211> LENGTH: 3
<212> TYPE: PRT
<213> ORGANISM: Artificial sequence
<220> FEATURE:
<223> OTHER INFORMATION: Synthetic antibody

<400> SEQUENCE: 698

Ala Ala Ser
1

<210> SEQ ID NO 699
<211> LENGTH: 9
<212> TYPE: PRT
<213> ORGANISM: Artificial sequence
<220> FEATURE:
<223> OTHER INFORMATION: Synthetic antibody

<400> SEQUENCE: 699

Gln Gln Ser Tyr Ser Thr Pro Trp Thr
1 5

<210> SEQ ID NO 700
<211> LENGTH: 12
<212> TYPE: PRT
<213> ORGANISM: Artificial sequence
<220> FEATURE:
<223> OTHER INFORMATION: Synthetic antibody

<400> SEQUENCE: 700

Gln Ser Val Leu Tyr Ser Ser Asn Asn Lys Asn Tyr
1 5 10

<210> SEQ ID NO 701
<211> LENGTH: 3
<212> TYPE: PRT
<213> ORGANISM: Artificial sequence
<220> FEATURE:
<223> OTHER INFORMATION: Synthetic antibody

<400> SEQUENCE: 701

Trp Ala Ser
1

<210> SEQ ID NO 702
<211> LENGTH: 9
<212> TYPE: PRT
<213> ORGANISM: Artificial sequence
<220> FEATURE:
<223> OTHER INFORMATION: Synthetic antibody

<400> SEQUENCE: 702

Gln Gln Tyr Tyr Ser Thr Pro Leu Thr
1 5

<210> SEQ ID NO 703
<211> LENGTH: 6
<212> TYPE: PRT
<213> ORGANISM: Artificial sequence
<220> FEATURE:
<223> OTHER INFORMATION: Synthetic antibody

<400> SEQUENCE: 703

Asn Ile Gly Ser Lys Ser
1 5

<210> SEQ ID NO 704
<211> LENGTH: 3
<212> TYPE: PRT
<213> ORGANISM: Artificial sequence
<220> FEATURE:
<223> OTHER INFORMATION: Synthetic antibody

<400> SEQUENCE: 704

Asp Asp Ser
1

<210> SEQ ID NO 705
<211> LENGTH: 11
<212> TYPE: PRT
<213> ORGANISM: Artificial sequence
<220> FEATURE:
<223> OTHER INFORMATION: Synthetic antibody

<400> SEQUENCE: 705

```
Gln Val Trp Asp Ser Ser Ser Asp His Trp Val
1               5                   10


<210> SEQ ID NO 706
<211> LENGTH: 6
<212> TYPE: PRT
<213> ORGANISM: Artificial sequence
<220> FEATURE:
<223> OTHER INFORMATION: Synthetic antibody

<400> SEQUENCE: 706

Asn Ile Gly Ser Lys Ser
1               5


<210> SEQ ID NO 707
<211> LENGTH: 3
<212> TYPE: PRT
<213> ORGANISM: Artificial sequence
<220> FEATURE:
<223> OTHER INFORMATION: Synthetic antibody

<400> SEQUENCE: 707

Asp Asp Ser
1


<210> SEQ ID NO 708
<211> LENGTH: 11
<212> TYPE: PRT
<213> ORGANISM: Artificial sequence
<220> FEATURE:
<223> OTHER INFORMATION: Synthetic antibody

<400> SEQUENCE: 708

Gln Val Trp Asp Ser Ser Ser Asp Tyr Val Val
1               5                   10


<210> SEQ ID NO 709
<211> LENGTH: 9
<212> TYPE: PRT
<213> ORGANISM: Artificial sequence
<220> FEATURE:
<223> OTHER INFORMATION: Synthetic antibody

<400> SEQUENCE: 709

Ser Ser Asp Val Gly Gly Tyr Asp Tyr
1               5


<210> SEQ ID NO 710
<211> LENGTH: 3
<212> TYPE: PRT
<213> ORGANISM: Artificial sequence
<220> FEATURE:
<223> OTHER INFORMATION: Synthetic antibody

<400> SEQUENCE: 710

Ala Val Ser
1


<210> SEQ ID NO 711
<211> LENGTH: 10
<212> TYPE: PRT
<213> ORGANISM: Artificial sequence
<220> FEATURE:
<223> OTHER INFORMATION: Synthetic antibody

<400> SEQUENCE: 711

Ser Ser Tyr Thr Ser Ser Ser Thr Trp Val
```

1 5 10

<210> SEQ ID NO 712
<211> LENGTH: 6
<212> TYPE: PRT
<213> ORGANISM: Artificial sequence
<220> FEATURE:
<223> OTHER INFORMATION: Synthetic antibody

<400> SEQUENCE: 712

Asn Ile Gly Ser Lys Ser
1 5

<210> SEQ ID NO 713
<211> LENGTH: 3
<212> TYPE: PRT
<213> ORGANISM: Artificial sequence
<220> FEATURE:
<223> OTHER INFORMATION: Synthetic antibody

<400> SEQUENCE: 713

Asp Asp Ser
1

<210> SEQ ID NO 714
<211> LENGTH: 11
<212> TYPE: PRT
<213> ORGANISM: Artificial sequence
<220> FEATURE:
<223> OTHER INFORMATION: Synthetic antibody

<400> SEQUENCE: 714

Gln Val Trp Asp Ser Ser Ser Asp Gln Arg Val
1 5 10

<210> SEQ ID NO 715
<211> LENGTH: 8
<212> TYPE: PRT
<213> ORGANISM: Artificial sequence
<220> FEATURE:
<223> OTHER INFORMATION: Synthetic antibody

<400> SEQUENCE: 715

Ser Ser Asn Ile Gly Ser Asn Thr
1 5

<210> SEQ ID NO 716
<211> LENGTH: 3
<212> TYPE: PRT
<213> ORGANISM: Artificial sequence
<220> FEATURE:
<223> OTHER INFORMATION: Synthetic antibody

<400> SEQUENCE: 716

Ser Asn Asn
1

<210> SEQ ID NO 717
<211> LENGTH: 11
<212> TYPE: PRT
<213> ORGANISM: Artificial sequence
<220> FEATURE:
<223> OTHER INFORMATION: Synthetic antibody

<400> SEQUENCE: 717

Ala Ala Trp Asp Asp Ser Leu Asn Gly Trp Val
1 5 10

<210> SEQ ID NO 718
<211> LENGTH: 9
<212> TYPE: PRT
<213> ORGANISM: Artificial sequence
<220> FEATURE:
<223> OTHER INFORMATION: Synthetic antibody

<400> SEQUENCE: 718

Ser Ser Asp Val Gly Gly Tyr Asn Tyr
1 5

<210> SEQ ID NO 719
<211> LENGTH: 3
<212> TYPE: PRT
<213> ORGANISM: Artificial sequence
<220> FEATURE:
<223> OTHER INFORMATION: Synthetic antibody

<400> SEQUENCE: 719

Asp Val Ser
1

<210> SEQ ID NO 720
<211> LENGTH: 11
<212> TYPE: PRT
<213> ORGANISM: Artificial sequence
<220> FEATURE:
<223> OTHER INFORMATION: Synthetic antibody

<400> SEQUENCE: 720

Ser Ser Tyr Thr Ser Ser Ser Thr Asn Val Val
1 5 10

<210> SEQ ID NO 721
<211> LENGTH: 9
<212> TYPE: PRT
<213> ORGANISM: Artificial sequence
<220> FEATURE:
<223> OTHER INFORMATION: Synthetic antibody

<400> SEQUENCE: 721

Ser Ser Asp Val Gly Gly Tyr Asn Tyr
1 5

<210> SEQ ID NO 722
<211> LENGTH: 3
<212> TYPE: PRT
<213> ORGANISM: Artificial sequence
<220> FEATURE:
<223> OTHER INFORMATION: Synthetic antibody

<400> SEQUENCE: 722

Asp Val Ser
1

<210> SEQ ID NO 723
<211> LENGTH: 11
<212> TYPE: PRT
<213> ORGANISM: Artificial sequence
<220> FEATURE:
<223> OTHER INFORMATION: Synthetic antibody

<400> SEQUENCE: 723

Ser Ser Tyr Thr Ser Ser Ser Thr Asn Val Val
1 5 10

<210> SEQ ID NO 724
<211> LENGTH: 6
<212> TYPE: PRT
<213> ORGANISM: Artificial sequence
<220> FEATURE:
<223> OTHER INFORMATION: Synthetic antibody

<400> SEQUENCE: 724

Gln Ser Val Ser Ser Tyr
1 5

<210> SEQ ID NO 725
<211> LENGTH: 3
<212> TYPE: PRT
<213> ORGANISM: Artificial sequence
<220> FEATURE:
<223> OTHER INFORMATION: Synthetic antibody

<400> SEQUENCE: 725

Asp Ala Ser
1

<210> SEQ ID NO 726
<211> LENGTH: 9
<212> TYPE: PRT
<213> ORGANISM: Artificial sequence
<220> FEATURE:
<223> OTHER INFORMATION: Synthetic antibody

<400> SEQUENCE: 726

Gln Gln Arg Ser Asp Trp Pro Pro Thr
1 5

<210> SEQ ID NO 727
<211> LENGTH: 6
<212> TYPE: PRT
<213> ORGANISM: Artificial sequence
<220> FEATURE:
<223> OTHER INFORMATION: Synthetic antibody

<400> SEQUENCE: 727

Asn Ile Gly Ser Lys Ser
1 5

<210> SEQ ID NO 728
<211> LENGTH: 3
<212> TYPE: PRT
<213> ORGANISM: Artificial sequence
<220> FEATURE:
<223> OTHER INFORMATION: Synthetic antibody

<400> SEQUENCE: 728

Asp Asp Ser
1

<210> SEQ ID NO 729
<211> LENGTH: 11
<212> TYPE: PRT
<213> ORGANISM: Artificial sequence
<220> FEATURE:
<223> OTHER INFORMATION: Synthetic antibody

<400> SEQUENCE: 729

Gln Val Trp Asp Ser Ser Ser Asp His Trp Val
1 5 10

<210> SEQ ID NO 730
<211> LENGTH: 6
<212> TYPE: PRT
<213> ORGANISM: Artificial sequence
<220> FEATURE:
<223> OTHER INFORMATION: Synthetic antibody

<400> SEQUENCE: 730

Asn Ile Gly Ser Lys Ser
1               5

<210> SEQ ID NO 731
<211> LENGTH: 3
<212> TYPE: PRT
<213> ORGANISM: Artificial sequence
<220> FEATURE:
<223> OTHER INFORMATION: Synthetic antibody

<400> SEQUENCE: 731

Asp Asp Ser
1

<210> SEQ ID NO 732
<211> LENGTH: 12
<212> TYPE: PRT
<213> ORGANISM: Artificial sequence
<220> FEATURE:
<223> OTHER INFORMATION: Synthetic antibody

<400> SEQUENCE: 732

Gln Val Trp Asp Ser Ser Ser Asp Pro Asp Val Val
1               5                   10

<210> SEQ ID NO 733
<211> LENGTH: 6
<212> TYPE: PRT
<213> ORGANISM: Artificial sequence
<220> FEATURE:
<223> OTHER INFORMATION: Synthetic antibody

<400> SEQUENCE: 733

Asn Ile Gly Ser Lys Ser
1               5

<210> SEQ ID NO 734
<211> LENGTH: 3
<212> TYPE: PRT
<213> ORGANISM: Artificial sequence
<220> FEATURE:
<223> OTHER INFORMATION: Synthetic antibody

<400> SEQUENCE: 734

Asp Asp Ser
1

<210> SEQ ID NO 735
<211> LENGTH: 11
<212> TYPE: PRT
<213> ORGANISM: Artificial sequence
<220> FEATURE:
<223> OTHER INFORMATION: Synthetic antibody

<400> SEQUENCE: 735

Gln Val Trp Asp Ser Ser Ser Asp His Trp Val
1               5                   10

<210> SEQ ID NO 736

<211> LENGTH: 6
<212> TYPE: PRT
<213> ORGANISM: Artificial sequence
<220> FEATURE:
<223> OTHER INFORMATION: Synthetic antibody

<400> SEQUENCE: 736

Asn Ile Gly Ser Lys Ser
1               5

<210> SEQ ID NO 737
<211> LENGTH: 3
<212> TYPE: PRT
<213> ORGANISM: Artificial sequence
<220> FEATURE:
<223> OTHER INFORMATION: Synthetic antibody

<400> SEQUENCE: 737

Asp Asp Ser
1

<210> SEQ ID NO 738
<211> LENGTH: 11
<212> TYPE: PRT
<213> ORGANISM: Artificial sequence
<220> FEATURE:
<223> OTHER INFORMATION: Synthetic antibody

<400> SEQUENCE: 738

Gln Val Trp Asp Ser Ser Ser Asp His Tyr Val
1               5                   10

<210> SEQ ID NO 739
<211> LENGTH: 6
<212> TYPE: PRT
<213> ORGANISM: Artificial sequence
<220> FEATURE:
<223> OTHER INFORMATION: Synthetic antibody

<400> SEQUENCE: 739

Asn Ile Gly Ser Lys Ser
1               5

<210> SEQ ID NO 740
<211> LENGTH: 3
<212> TYPE: PRT
<213> ORGANISM: Artificial sequence
<220> FEATURE:
<223> OTHER INFORMATION: Synthetic antibody

<400> SEQUENCE: 740

Asp Asp Ser
1

<210> SEQ ID NO 741
<211> LENGTH: 11
<212> TYPE: PRT
<213> ORGANISM: Artificial sequence
<220> FEATURE:
<223> OTHER INFORMATION: Synthetic antibody

<400> SEQUENCE: 741

Gln Val Trp His Ser Asp Ser Asp Gln Tyr Val
1               5                   10

<210> SEQ ID NO 742
<211> LENGTH: 6

<212> TYPE: PRT
<213> ORGANISM: Artificial sequence
<220> FEATURE:
<223> OTHER INFORMATION: Synthetic antibody

<400> SEQUENCE: 742

Asn Ile Gly Ser Lys Ser
1               5

<210> SEQ ID NO 743
<211> LENGTH: 3
<212> TYPE: PRT
<213> ORGANISM: Artificial sequence
<220> FEATURE:
<223> OTHER INFORMATION: Synthetic antibody

<400> SEQUENCE: 743

Asp Asp Ser
1

<210> SEQ ID NO 744
<211> LENGTH: 11
<212> TYPE: PRT
<213> ORGANISM: Artificial sequence
<220> FEATURE:
<223> OTHER INFORMATION: Synthetic antibody

<400> SEQUENCE: 744

Gln Val Trp Asp Ser Ser Ser Asp His Trp Val
1               5                   10

<210> SEQ ID NO 745
<211> LENGTH: 6
<212> TYPE: PRT
<213> ORGANISM: Artificial sequence
<220> FEATURE:
<223> OTHER INFORMATION: Synthetic antibody

<400> SEQUENCE: 745

Asn Ile Gly Ser Lys Ser
1               5

<210> SEQ ID NO 746
<211> LENGTH: 3
<212> TYPE: PRT
<213> ORGANISM: Artificial sequence
<220> FEATURE:
<223> OTHER INFORMATION: Synthetic antibody

<400> SEQUENCE: 746

Asp Asp Ser
1

<210> SEQ ID NO 747
<211> LENGTH: 11
<212> TYPE: PRT
<213> ORGANISM: Artificial sequence
<220> FEATURE:
<223> OTHER INFORMATION: Synthetic antibody

<400> SEQUENCE: 747

Gln Val Trp Asp Ser Ser Ser Asp Leu Tyr Val
1               5                   10

<210> SEQ ID NO 748
<211> LENGTH: 6
<212> TYPE: PRT

<213> ORGANISM: Artificial sequence
<220> FEATURE:
<223> OTHER INFORMATION: Synthetic antibody

<400> SEQUENCE: 748

Gln Ser Ile Ser Ser Tyr
1 5

<210> SEQ ID NO 749
<211> LENGTH: 3
<212> TYPE: PRT
<213> ORGANISM: Artificial sequence
<220> FEATURE:
<223> OTHER INFORMATION: Synthetic antibody

<400> SEQUENCE: 749

Ala Ala Ser
1

<210> SEQ ID NO 750
<211> LENGTH: 9
<212> TYPE: PRT
<213> ORGANISM: Artificial sequence
<220> FEATURE:
<223> OTHER INFORMATION: Synthetic antibody

<400> SEQUENCE: 750

Gln Gln Ser Tyr Ser Thr Pro Tyr Thr
1 5

<210> SEQ ID NO 751
<211> LENGTH: 6
<212> TYPE: PRT
<213> ORGANISM: Artificial sequence
<220> FEATURE:
<223> OTHER INFORMATION: Synthetic antibody

<400> SEQUENCE: 751

Gln Asp Ile Ser Asn Tyr
1 5

<210> SEQ ID NO 752
<211> LENGTH: 3
<212> TYPE: PRT
<213> ORGANISM: Artificial sequence
<220> FEATURE:
<223> OTHER INFORMATION: Synthetic antibody

<400> SEQUENCE: 752

Asp Ala Ser
1

<210> SEQ ID NO 753
<211> LENGTH: 9
<212> TYPE: PRT
<213> ORGANISM: Artificial sequence
<220> FEATURE:
<223> OTHER INFORMATION: Synthetic antibody

<400> SEQUENCE: 753

Gln Gln Tyr Asp Asn Leu Pro Leu Thr
1 5

<210> SEQ ID NO 754
<211> LENGTH: 9
<212> TYPE: PRT
<213> ORGANISM: Artificial sequence
<220> FEATURE:
<223> OTHER INFORMATION: Synthetic antibody

<400> SEQUENCE: 754

Ser Asp Ile Asn Val Gly Ser Tyr Asn
1 5

<210> SEQ ID NO 755
<211> LENGTH: 7
<212> TYPE: PRT
<213> ORGANISM: Artificial sequence
<220> FEATURE:
<223> OTHER INFORMATION: Synthetic antibody

<400> SEQUENCE: 755

Tyr Tyr Ser Asp Ser Asp Lys
1 5

<210> SEQ ID NO 756
<211> LENGTH: 9
<212> TYPE: PRT
<213> ORGANISM: Artificial sequence
<220> FEATURE:
<223> OTHER INFORMATION: Synthetic antibody

<400> SEQUENCE: 756

Met Ile Trp Pro Ser Asn Ala Trp Val
1 5

<210> SEQ ID NO 757
<211> LENGTH: 6
<212> TYPE: PRT
<213> ORGANISM: Artificial sequence
<220> FEATURE:
<223> OTHER INFORMATION: Synthetic antibody

<400> SEQUENCE: 757

Asn Ile Gly Ser Lys Ser
1 5

<210> SEQ ID NO 758
<211> LENGTH: 3
<212> TYPE: PRT
<213> ORGANISM: Artificial sequence
<220> FEATURE:
<223> OTHER INFORMATION: Synthetic antibody

<400> SEQUENCE: 758

Asp Asp Ser
1

<210> SEQ ID NO 759
<211> LENGTH: 11
<212> TYPE: PRT
<213> ORGANISM: Artificial sequence
<220> FEATURE:
<223> OTHER INFORMATION: Synthetic antibody

<400> SEQUENCE: 759

Gln Val Trp Asp Ser Ser Ser Asp His Tyr Val
1 5 10

<210> SEQ ID NO 760
<211> LENGTH: 6
<212> TYPE: PRT
<213> ORGANISM: Artificial sequence
<220> FEATURE:

<223> OTHER INFORMATION: Synthetic antibody

<400> SEQUENCE: 760

Asn Ile Gly Ser Lys Ser
1 5

<210> SEQ ID NO 761
<211> LENGTH: 3
<212> TYPE: PRT
<213> ORGANISM: Artificial sequence
<220> FEATURE:
<223> OTHER INFORMATION: Synthetic antibody

<400> SEQUENCE: 761

Asp Asp Ser
1

<210> SEQ ID NO 762
<211> LENGTH: 11
<212> TYPE: PRT
<213> ORGANISM: Artificial sequence
<220> FEATURE:
<223> OTHER INFORMATION: Synthetic antibody

<400> SEQUENCE: 762

Gln Val Trp Asp Ser Ser Ser Asp His Val Val
1 5 10

<210> SEQ ID NO 763
<211> LENGTH: 6
<212> TYPE: PRT
<213> ORGANISM: Artificial sequence
<220> FEATURE:
<223> OTHER INFORMATION: Synthetic antibody

<400> SEQUENCE: 763

Gln Ser Ile Ser Ser Tyr
1 5

<210> SEQ ID NO 764
<211> LENGTH: 3
<212> TYPE: PRT
<213> ORGANISM: Artificial sequence
<220> FEATURE:
<223> OTHER INFORMATION: Synthetic antibody

<400> SEQUENCE: 764

Ala Ala Ser
1

<210> SEQ ID NO 765
<211> LENGTH: 9
<212> TYPE: PRT
<213> ORGANISM: Artificial sequence
<220> FEATURE:
<223> OTHER INFORMATION: Synthetic antibody

<400> SEQUENCE: 765

Gln Gln Ser Tyr Ser Thr Pro Gln Thr
1 5

<210> SEQ ID NO 766
<211> LENGTH: 6
<212> TYPE: PRT
<213> ORGANISM: Artificial sequence
<220> FEATURE:
<223> OTHER INFORMATION: Synthetic antibody

<400> SEQUENCE: 766

Asn Ile Glu Ser Lys Ser
1               5

<210> SEQ ID NO 767
<211> LENGTH: 3
<212> TYPE: PRT
<213> ORGANISM: Artificial sequence
<220> FEATURE:
<223> OTHER INFORMATION: Synthetic antibody

<400> SEQUENCE: 767

Asp Asp Thr
1

<210> SEQ ID NO 768
<211> LENGTH: 11
<212> TYPE: PRT
<213> ORGANISM: Artificial sequence
<220> FEATURE:
<223> OTHER INFORMATION: Synthetic antibody

<400> SEQUENCE: 768

Gln Val Trp Asp Ser Ser Ser Asp His Cys Val
1               5                   10

<210> SEQ ID NO 769
<211> LENGTH: 6
<212> TYPE: PRT
<213> ORGANISM: Artificial sequence
<220> FEATURE:
<223> OTHER INFORMATION: Synthetic antibody

<400> SEQUENCE: 769

Asn Ile Gly Ser Lys Ser
1               5

<210> SEQ ID NO 770
<211> LENGTH: 3
<212> TYPE: PRT
<213> ORGANISM: Artificial sequence
<220> FEATURE:
<223> OTHER INFORMATION: Synthetic antibody

<400> SEQUENCE: 770

Asp Asp Ser
1

<210> SEQ ID NO 771
<211> LENGTH: 11
<212> TYPE: PRT
<213> ORGANISM: Artificial sequence
<220> FEATURE:
<223> OTHER INFORMATION: Synthetic antibody

<400> SEQUENCE: 771

Gln Val Trp Asp Ser Ser Ser Asp His Arg Val
1               5                   10

<210> SEQ ID NO 772
<211> LENGTH: 6
<212> TYPE: PRT
<213> ORGANISM: Artificial sequence
<220> FEATURE:
<223> OTHER INFORMATION: Synthetic antibody

<400> SEQUENCE: 772

Gln Ser Ile Ser Ser Tyr
1               5

<210> SEQ ID NO 773
<211> LENGTH: 3
<212> TYPE: PRT
<213> ORGANISM: Artificial sequence
<220> FEATURE:
<223> OTHER INFORMATION: Synthetic antibody

<400> SEQUENCE: 773

Ala Ala Ser
1

<210> SEQ ID NO 774
<211> LENGTH: 9
<212> TYPE: PRT
<213> ORGANISM: Artificial sequence
<220> FEATURE:
<223> OTHER INFORMATION: Synthetic antibody

<400> SEQUENCE: 774

Gln Gln Ser Tyr Ser Thr Pro Gln Thr
1               5

<210> SEQ ID NO 775
<211> LENGTH: 6
<212> TYPE: PRT
<213> ORGANISM: Artificial sequence
<220> FEATURE:
<223> OTHER INFORMATION: Synthetic antibody

<400> SEQUENCE: 775

Gln His Ile Glu Ser Phe
1               5

<210> SEQ ID NO 776
<211> LENGTH: 3
<212> TYPE: PRT
<213> ORGANISM: Artificial sequence
<220> FEATURE:
<223> OTHER INFORMATION: Synthetic antibody

<400> SEQUENCE: 776

Ile Ala Ser
1

<210> SEQ ID NO 777
<211> LENGTH: 10
<212> TYPE: PRT
<213> ORGANISM: Artificial sequence
<220> FEATURE:
<223> OTHER INFORMATION: Synthetic antibody

<400> SEQUENCE: 777

Gln Gln Ser Tyr Thr Ile Ser Pro Ile Thr
1               5                   10

<210> SEQ ID NO 778
<211> LENGTH: 6
<212> TYPE: PRT
<213> ORGANISM: Artificial sequence
<220> FEATURE:
<223> OTHER INFORMATION: Synthetic antibody

<400> SEQUENCE: 778

Leu Leu Pro Lys Gln Tyr
1 5

<210> SEQ ID NO 779
<211> LENGTH: 3
<212> TYPE: PRT
<213> ORGANISM: Artificial sequence
<220> FEATURE:
<223> OTHER INFORMATION: Synthetic antibody

<400> SEQUENCE: 779

Ala Asp Tyr
1

<210> SEQ ID NO 780
<211> LENGTH: 12
<212> TYPE: PRT
<213> ORGANISM: Artificial sequence
<220> FEATURE:
<223> OTHER INFORMATION: Synthetic antibody

<400> SEQUENCE: 780

Gln Ser Ile Asp Asn Arg Phe His Tyr Pro Met Ile
1 5 10

<210> SEQ ID NO 781
<211> LENGTH: 6
<212> TYPE: PRT
<213> ORGANISM: Artificial sequence
<220> FEATURE:
<223> OTHER INFORMATION: Synthetic antibody

<400> SEQUENCE: 781

Ala Leu Pro Asp Gln Tyr
1 5

<210> SEQ ID NO 782
<211> LENGTH: 3
<212> TYPE: PRT
<213> ORGANISM: Artificial sequence
<220> FEATURE:
<223> OTHER INFORMATION: Synthetic antibody

<400> SEQUENCE: 782

Lys Asp Asn
1

<210> SEQ ID NO 783
<211> LENGTH: 12
<212> TYPE: PRT
<213> ORGANISM: Artificial sequence
<220> FEATURE:
<223> OTHER INFORMATION: Synthetic antibody

<400> SEQUENCE: 783

Gln Ser Ala Asp Thr Ser Thr Ala Tyr His Val Ile
1 5 10

<210> SEQ ID NO 784
<211> LENGTH: 6
<212> TYPE: PRT
<213> ORGANISM: Artificial sequence
<220> FEATURE:
<223> OTHER INFORMATION: Synthetic antibody

<400> SEQUENCE: 784

Asn Ile Gly Asn Lys Ser
1 5

<210> SEQ ID NO 785
<211> LENGTH: 3
<212> TYPE: PRT
<213> ORGANISM: Artificial sequence
<220> FEATURE:
<223> OTHER INFORMATION: Synthetic antibody

<400> SEQUENCE: 785

Tyr Asp Asn
1

<210> SEQ ID NO 786
<211> LENGTH: 11
<212> TYPE: PRT
<213> ORGANISM: Artificial sequence
<220> FEATURE:
<223> OTHER INFORMATION: Synthetic antibody

<400> SEQUENCE: 786

Gln Val Trp Asp Asn Ser Ser Asp His Ala Val
1 5 10

<210> SEQ ID NO 787
<211> LENGTH: 7
<212> TYPE: PRT
<213> ORGANISM: Artificial sequence
<220> FEATURE:
<223> OTHER INFORMATION: Synthetic antibody

<400> SEQUENCE: 787

Gln Ser Val Ser Ser Ser Trp
1 5

<210> SEQ ID NO 788
<211> LENGTH: 3
<212> TYPE: PRT
<213> ORGANISM: Artificial sequence
<220> FEATURE:
<223> OTHER INFORMATION: Synthetic antibody

<400> SEQUENCE: 788

Asp Ala Ser
1

<210> SEQ ID NO 789
<211> LENGTH: 9
<212> TYPE: PRT
<213> ORGANISM: Artificial sequence
<220> FEATURE:
<223> OTHER INFORMATION: Synthetic antibody

<400> SEQUENCE: 789

Gln Gln Tyr Gly Asn Ser Pro Thr Thr
1 5

<210> SEQ ID NO 790
<211> LENGTH: 6
<212> TYPE: PRT
<213> ORGANISM: Artificial sequence
<220> FEATURE:
<223> OTHER INFORMATION: Synthetic antibody

<400> SEQUENCE: 790

Lys Leu Val Glu Arg Tyr 1 5

<210> SEQ ID NO 791
<211> LENGTH: 3
<212> TYPE: PRT
<213> ORGANISM: Artificial sequence
<220> FEATURE:
<223> OTHER INFORMATION: Synthetic antibody

<400> SEQUENCE: 791

His Asp Ile
1

<210> SEQ ID NO 792
<211> LENGTH: 9
<212> TYPE: PRT
<213> ORGANISM: Artificial sequence
<220> FEATURE:
<223> OTHER INFORMATION: Synthetic antibody

<400> SEQUENCE: 792

Gln Ala Trp Asp Ser Ser Thr Val Leu
1 5

<210> SEQ ID NO 793
<211> LENGTH: 12
<212> TYPE: PRT
<213> ORGANISM: Artificial sequence
<220> FEATURE:
<223> OTHER INFORMATION: Synthetic antibody

<400> SEQUENCE: 793

Gln Ser Ile Leu Tyr Ser Ser Asn Asn Lys Asn Tyr
1 5 10

<210> SEQ ID NO 794
<211> LENGTH: 3
<212> TYPE: PRT
<213> ORGANISM: Artificial sequence
<220> FEATURE:
<223> OTHER INFORMATION: Synthetic antibody

<400> SEQUENCE: 794

Trp Ala Ser
1

<210> SEQ ID NO 795
<211> LENGTH: 9
<212> TYPE: PRT
<213> ORGANISM: Artificial sequence
<220> FEATURE:
<223> OTHER INFORMATION: Synthetic antibody

<400> SEQUENCE: 795

Gln Gln Tyr Tyr Thr Ile Pro Pro Thr
1 5

<210> SEQ ID NO 796
<211> LENGTH: 6
<212> TYPE: PRT
<213> ORGANISM: Artificial sequence
<220> FEATURE:
<223> OTHER INFORMATION: Synthetic antibody

<400> SEQUENCE: 796

Ser Leu Arg Asn Tyr Tyr
1 5

<210> SEQ ID NO 797
<211> LENGTH: 3
<212> TYPE: PRT
<213> ORGANISM: Artificial sequence
<220> FEATURE:
<223> OTHER INFORMATION: Synthetic antibody

<400> SEQUENCE: 797

Gly Lys Asp
1

<210> SEQ ID NO 798
<211> LENGTH: 11
<212> TYPE: PRT
<213> ORGANISM: Artificial sequence
<220> FEATURE:
<223> OTHER INFORMATION: Synthetic antibody

<400> SEQUENCE: 798

Asn Ser Arg Asp Ser Ser Gly Asp Val Val Val
1 5 10

<210> SEQ ID NO 799
<211> LENGTH: 6
<212> TYPE: PRT
<213> ORGANISM: Artificial sequence
<220> FEATURE:
<223> OTHER INFORMATION: Synthetic antibody

<400> SEQUENCE: 799

Lys Leu Glu Asn Lys Tyr
1 5

<210> SEQ ID NO 800
<211> LENGTH: 3
<212> TYPE: PRT
<213> ORGANISM: Artificial sequence
<220> FEATURE:
<223> OTHER INFORMATION: Synthetic antibody

<400> SEQUENCE: 800

Gln Asp Phe
1

<210> SEQ ID NO 801
<211> LENGTH: 10
<212> TYPE: PRT
<213> ORGANISM: Artificial sequence
<220> FEATURE:
<223> OTHER INFORMATION: Synthetic antibody

<400> SEQUENCE: 801

Gln Ala Trp Asp Arg Ser Thr Phe Tyr Val
1 5 10

<210> SEQ ID NO 802
<211> LENGTH: 6
<212> TYPE: PRT
<213> ORGANISM: Artificial sequence
<220> FEATURE:
<223> OTHER INFORMATION: Synthetic antibody

<400> SEQUENCE: 802

Arg Leu Arg Asp Arg Tyr
1 5

<210> SEQ ID NO 803
<211> LENGTH: 3
<212> TYPE: PRT
<213> ORGANISM: Artificial sequence
<220> FEATURE:
<223> OTHER INFORMATION: Synthetic antibody

<400> SEQUENCE: 803

Gln Asp Phe
1

<210> SEQ ID NO 804
<211> LENGTH: 9
<212> TYPE: PRT
<213> ORGANISM: Artificial sequence
<220> FEATURE:
<223> OTHER INFORMATION: Synthetic antibody

<400> SEQUENCE: 804

Gln Ala Trp Asp Ser Phe Thr Tyr Val
1 5

<210> SEQ ID NO 805
<211> LENGTH: 6
<212> TYPE: PRT
<213> ORGANISM: Artificial sequence
<220> FEATURE:
<223> OTHER INFORMATION: Synthetic antibody

<400> SEQUENCE: 805

Ser Leu Arg Ser Phe Tyr
1 5

<210> SEQ ID NO 806
<211> LENGTH: 3
<212> TYPE: PRT
<213> ORGANISM: Artificial sequence
<220> FEATURE:
<223> OTHER INFORMATION: Synthetic antibody

<400> SEQUENCE: 806

Gly Gln Asn
1

<210> SEQ ID NO 807
<211> LENGTH: 11
<212> TYPE: PRT
<213> ORGANISM: Artificial sequence
<220> FEATURE:
<223> OTHER INFORMATION: Synthetic antibody

<400> SEQUENCE: 807

Asn Ser Arg Asp Ser Gly Gly Tyr His Leu Val
1 5 10

<210> SEQ ID NO 808
<211> LENGTH: 7
<212> TYPE: PRT
<213> ORGANISM: Artificial sequence
<220> FEATURE:
<223> OTHER INFORMATION: Synthetic antibody

<400> SEQUENCE: 808

Ser Gly Tyr Ser Asn Tyr Lys
1 5

<210> SEQ ID NO 809
<211> LENGTH: 8
<212> TYPE: PRT
<213> ORGANISM: Artificial sequence
<220> FEATURE:
<223> OTHER INFORMATION: Synthetic antibody

<400> SEQUENCE: 809

Val Gly Thr Gly Gly Ile Val Thr
1               5

<210> SEQ ID NO 810
<211> LENGTH: 8
<212> TYPE: PRT
<213> ORGANISM: Artificial sequence
<220> FEATURE:
<223> OTHER INFORMATION: Synthetic antibody

<400> SEQUENCE: 810

Gly Pro Asp His Gly Arg Gly Cys
1               5

<210> SEQ ID NO 811
<211> LENGTH: 6
<212> TYPE: PRT
<213> ORGANISM: Artificial sequence
<220> FEATURE:
<223> OTHER INFORMATION: Synthetic antibody

<400> SEQUENCE: 811

Lys Leu Gly Asp Lys Tyr
1               5

<210> SEQ ID NO 812
<211> LENGTH: 3
<212> TYPE: PRT
<213> ORGANISM: Artificial sequence
<220> FEATURE:
<223> OTHER INFORMATION: Synthetic antibody

<400> SEQUENCE: 812

Gln Asp Thr
1

<210> SEQ ID NO 813
<211> LENGTH: 10
<212> TYPE: PRT
<213> ORGANISM: Artificial sequence
<220> FEATURE:
<223> OTHER INFORMATION: Synthetic antibody

<400> SEQUENCE: 813

Gln Ala Trp Asp Ser Ser Thr Glu Val Val
1               5                   10

<210> SEQ ID NO 814
<211> LENGTH: 6
<212> TYPE: PRT
<213> ORGANISM: Artificial sequence
<220> FEATURE:
<223> OTHER INFORMATION: Synthetic antibody

<400> SEQUENCE: 814

Ser Leu Arg Ser Tyr Ser
1               5

<210> SEQ ID NO 815

<211> LENGTH: 3
<212> TYPE: PRT
<213> ORGANISM: Artificial sequence
<220> FEATURE:
<223> OTHER INFORMATION: Synthetic antibody

<400> SEQUENCE: 815

Gly Lys Asn
1

<210> SEQ ID NO 816
<211> LENGTH: 11
<212> TYPE: PRT
<213> ORGANISM: Artificial sequence
<220> FEATURE:
<223> OTHER INFORMATION: Synthetic antibody

<400> SEQUENCE: 816

Asn Ser Arg Asp Ser Ser Gly Ile Arg Val Val
1 5 10

<210> SEQ ID NO 817
<211> LENGTH: 6
<212> TYPE: PRT
<213> ORGANISM: Artificial sequence
<220> FEATURE:
<223> OTHER INFORMATION: Synthetic antibody

<400> SEQUENCE: 817

Gln Ser Ile Ser Ser Tyr
1 5

<210> SEQ ID NO 818
<211> LENGTH: 3
<212> TYPE: PRT
<213> ORGANISM: Artificial sequence
<220> FEATURE:
<223> OTHER INFORMATION: Synthetic antibody

<400> SEQUENCE: 818

Ala Ala Ser
1

<210> SEQ ID NO 819
<211> LENGTH: 9
<212> TYPE: PRT
<213> ORGANISM: Artificial sequence
<220> FEATURE:
<223> OTHER INFORMATION: Synthetic antibody

<400> SEQUENCE: 819

Gln Gln Ser Tyr Ser Thr Pro Gln Thr
1 5

<210> SEQ ID NO 820
<211> LENGTH: 12
<212> TYPE: PRT
<213> ORGANISM: Artificial sequence
<220> FEATURE:
<223> OTHER INFORMATION: Synthetic antibody

<400> SEQUENCE: 820

Gln Ser Val Leu Tyr Ser Ser Asn Asn Lys Asn Tyr
1 5 10

<210> SEQ ID NO 821
<211> LENGTH: 3

-continued

```
<212> TYPE: PRT
<213> ORGANISM: Artificial sequence
<220> FEATURE:
<223> OTHER INFORMATION: Synthetic antibody

<400> SEQUENCE: 821

Trp Ala Ser
1


<210> SEQ ID NO 822
<211> LENGTH: 9
<212> TYPE: PRT
<213> ORGANISM: Artificial sequence
<220> FEATURE:
<223> OTHER INFORMATION: Synthetic antibody

<400> SEQUENCE: 822

Gln Gln Tyr Tyr Ser Thr Ser Leu Thr
1               5


<210> SEQ ID NO 823
<211> LENGTH: 12
<212> TYPE: PRT
<213> ORGANISM: Artificial sequence
<220> FEATURE:
<223> OTHER INFORMATION: Synthetic antibody

<400> SEQUENCE: 823

Gln Ser Leu Leu Tyr Gly Ser Thr Asn Lys Asn Tyr
1               5                   10


<210> SEQ ID NO 824
<211> LENGTH: 3
<212> TYPE: PRT
<213> ORGANISM: Artificial sequence
<220> FEATURE:
<223> OTHER INFORMATION: Synthetic antibody

<400> SEQUENCE: 824

Trp Ala Ser
1


<210> SEQ ID NO 825
<211> LENGTH: 9
<212> TYPE: PRT
<213> ORGANISM: Artificial sequence
<220> FEATURE:
<223> OTHER INFORMATION: Synthetic antibody

<400> SEQUENCE: 825

Gln Gln Tyr Tyr Asn Val Ala Trp Thr
1               5
```

HUMAN ANTIBODIES TO RIFT VALLEY FEVER VIRUS

PRIORITY CLAIM

This application is a national phase application under 35 U.S.C. § 371 of International Application No. PCT/US2021/012720, filed Jan. 8, 2021, which claims benefit of priority to U.S. Provisional Application Ser. No. 62/960,072, filed on Jan. 12, 2020, the entire contents of which are hereby incorporated by reference.

BACKGROUND

1. Field of the Disclosure

The present disclosure relates generally to the fields of medicine, infectious disease, and immunology. More particular, the disclosure relates to human antibodies binding to Rift Valley Fever Virus.

2. Background

Bunyavirales is an order of negative-sense single-stranded RNA viruses. It is the only order in the class Ellioviricetes. It was formerly known as Bunyaviridae family of viruses. The name Bunyavirales derives from Bunyamwera, where the original type species Bunyamwera orthobunyavirus was first discovered.

In 2017, the ICTV reclassified the family Bunyaviridae as Bunyavirales, a taxonomic shift from a family of viruses to an order of viruses. The body made these decisions in a 2016 convening in Budapest. Primary reasons for this alteration revolve around these observations: approximately half of viruses in the former Bunyaviridae were at the time unassigned to a genus; novel viruses discovered that were characteristic of and clustered around Bunyaviridae based on phylogenetic analyses had bi-segmented genomes (as opposed to Bunyaviridae's tri-segmentation); and plant viruses also lacking tri-segmentation were previously known to be "bunya-like" yet were not properly assigned to the family Bunyaviridae based upon the past taxonomic classifications. All five genera formerly in the family Bunyaviridae (Hantavirus, Nairovirus, Orthobunyavirus, Phlebovirus, Tospovirus) are now novel viral families, some of which have been combined. These new families include: Hantaviridae, Feraviridae, Fimoviridae, Jonviridae, Nairoviridae, Peribunyaviridae, Phasmaviridae, Phenuiviridae, and Tospoviridae.

This order of viruses belong to the fifth group of the Baltimore classification, the so-called negative-sense single stranded ribonucleic acid (−)ssRNA. They are enveloped RNA viruses. Though generally found in arthropods or rodents, certain viruses in this order occasionally infect humans Some of them also infect plants.

A majority of bunyaviruses are vector-borne. With the exception of Hantaviruses and Arenaviruses, all viruses in the Bunyavirales order are transmitted by arthropods (mosquitos, tick, or sandfly). Hantaviruses are transmitted through contact with deer mice feces. Incidence of infection is closely linked to vector activity, for example, mosquito-borne viruses are more common in the summer. Human infections with certain members of Bunyavirales, such as Rift Valley Fever Virus, are associated with significant levels of morbidity and mortality. They are also the cause of severe fever with thrombocytopenia syndrome. As such, there is a considerable need for reagents to diagnose such infections as well as treat and prevent them.

SUMMARY

Thus, in accordance with the present disclosure, a method of detecting a Rift Valley Fever Virus infection in a subject comprising (a) contacting a sample from said subject with an antibody or antibody fragment having clone-paired heavy and light chain CDR sequences from Tables 3 and 4, respectively; and (b) detecting Rift Valley Fever Virus in said sample by binding of said antibody or antibody fragment to a Rift Valley Fever Virus antigen in said sample. The sample may be is a body fluid, such as blood, sputum, tears, saliva, mucous or serum, semen, cervical or vaginal secretions, amniotic fluid, placental tissues, urine, exudate, transudate, tissue scrapings or feces. Detection may comprise ELISA, RIA, lateral flow assay or Western blot. The method may further comprise performing steps (a) and (b) a second time and determining a change in Rift Valley Fever Virus antigen levels as compared to the first assay.

The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, $F(ab')_2$ fragment, or Fv fragment.

In another embodiment, there is provided a method of treating a subject infected with Rift Valley Fever Virus or reducing the likelihood of infection of a subject at risk of contracting Rift Valley Fever Virus, comprising delivering to said subject an antibody or antibody fragment having clone-paired heavy and light chain CDR sequences from Tables 3 and 4, respectively. The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2.

The antibody may be a chimeric antibody or a bispecific antibody, or wherein the antibody fragment is a recombinant scFv (single chain fragment variable) antibody, Fab fragment, $F(ab')_2$ fragment, or Fv fragment. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, LALA PG, N297, GASD/ALIE, YTE or LS mutation or glycan modified to alter (eliminate or enhance) FcR gamma interactions such as enzymatic or chemical addition or removal of glycans or expression in a cell line engineered with a defined glycosylating pattern.

The antibody or antibody fragment may be administered prior to infection or after infection. The subject may be a pregnant female, a sexually active female, or a female undergoing fertility treatments. Delivering may comprise antibody or antibody fragment administration, or genetic delivery with an RNA or DNA sequence or vector encoding the antibody or antibody fragment.

In yet another embodiment, there is provided a monoclonal antibody, wherein the antibody or antibody fragment is characterized by clone-paired heavy and light chain CDR sequences from Tables 3 and 4, respectively. The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2.

The antibody may be a chimeric antibody or a bispecific antibody, or wherein the antibody fragment is a recombinant scFv (single chain fragment variable) antibody, Fab fragment, $F(ab')_2$ fragment, or Fv fragment. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody, or is bispecific antibody, or wherein said antibody or antibody fragment further comprises a cell penetrating peptide and/or is an intrabody.

The monoclonal antibody or antibody fragment may further comprise a domain that facilitates transfer across the blood brain barrier by binding to a transport molecule, thereby facilitating transport into the brain. The transport molecule may be transferrin receptor, heparin-binding EGF, a scavenger receptor AI or BI, EGF receptor, tumor necrosis factor, insulin or insulin-like growth factor receptor, apolipoprotein E receptor 2, leptin receptor, melanotransferrin receptor, or LDL receptor. The domain may be a peptide or an scFv (single chain fragment variable) antibody, Fab fragment, $F(ab')_2$ fragment, Fv fragment, single domain antibody (nanobody) or wherein said domain is a distinct binding specificity as part of a chimeric or bispecific antibody structure. These may further comprise a domain that facilitates transfer across a mucosal surface, such as the respiratory tract barrier, by binding to a transport molecule, thereby facilitating transport across the mucosal surface.

In still yet another embodiment, there is provided a hybridoma or engineered cell encoding an antibody or antibody fragment wherein the antibody or antibody fragment is characterized by clone-paired heavy and light chain CDR sequences from Tables 3 and 4, respectively. The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2.

The antibody may be a chimeric antibody or a bispecific antibody, or wherein the antibody fragment is a recombinant scFv (single chain fragment variable) antibody, Fab fragment, $F(ab')_2$ fragment, or Fv fragment. The antibody may be an IgG, or a recombinant IgG antibody or antibody fragment comprising an Fc portion mutated to alter (eliminate or enhance) FcR gamma interactions, such as a LALA, LALA PG, N297, GASD/ALIE, or glycan modified to alter (eliminate or enhance) FcR gamma interactions using enzymatic or chemical addition or removal of glycans or expression in a cell line engineered with a defined glycosylating pattern. The antibody may be an IgG, or a recombinant IgG antibody or antibody fragment comprising an Fc portion mutated to increase half-life such as DHS, YTE or LS mutation. The antibody may be a chimeric antibody, or is bispecific antibody, or wherein said antibody or antibody fragment further comprises a cell penetrating peptide and/or is an intrabody.

In a further embodiment, there is provided a vaccine formulation comprising one or more antibodies or antibody fragments characterized by clone-paired heavy and light chain CDR sequences from Tables 3 and 4, respectively. The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2.

The antibody may be a chimeric antibody or a bispecific antibody, or wherein the antibody fragment is a recombinant scFv (single chain fragment variable) antibody, Fab fragment, $F(ab')_2$ fragment, or Fv fragment. The antibody may be an IgG, or a recombinant IgG antibody or antibody fragment comprising an Fc portion mutated to alter (eliminate or enhance) FcR gamma interactions, such as a LALA, LALA PG, N297, GASD/ALIE, or glycan modified to alter (eliminate or enhance) FcR gamma interactions using enzymatic or chemical addition or removal of glycans or expression in a cell line engineered with a defined glycosylating pattern. The antibody may be an IgG, or a recombinant IgG antibody or antibody fragment comprising an Fc portion mutated to increase half-life such as DHS, YTE or LS mutation. The antibody may be a chimeric antibody, or is bispecific antibody, or wherein said antibody or antibody fragment further comprises a cell penetrating peptide and/or is an intrabody.

In yet a further embodiment there is provided a vaccine formulation comprising one or more expression vectors encoding a first antibody or antibody fragment as defined above. The expression vector(s) may be Sindbis virus or VEE vector(s). The vaccine may be formulated for delivery by needle injection, jet injection, or electroporation. The vaccine formulation may further comprise one or more expression vectors encoding for a second antibody or antibody fragment, such as a distinct antibody or antibody fragment as described above.

In still yet a further embodiment, there is provided a method of protecting the health of a placenta and/or fetus of a pregnant a subject infected with or at risk of infection with a Rift Valley Fever Virus comprising delivering to said subject an antibody or antibody fragment having clone-paired heavy and light chain CDR sequences from Tables 3 and 4, respectively.

The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2.

The antibody may be a chimeric antibody or a bispecific antibody, or wherein the antibody fragment is a recombinant scFv (single chain fragment variable) antibody, Fab fragment, $F(ab')_2$ fragment, or Fv fragment. The antibody may be an IgG, or a recombinant IgG antibody or antibody fragment comprising an Fc portion mutated to alter (eliminate or enhance) FcR gamma interactions, such as a LALA, LALA PG, N297, GASD/ALIE, or glycan modified to alter (eliminate or enhance) FcR gamma interactions using enzymatic or chemical addition or removal of glycans or expression in a cell line engineered with a defined glycosylating pattern. The antibody may be an IgG, or a recombinant IgG antibody or antibody fragment comprising an Fc portion mutated to increase half-life such as DHS, YTE or LS mutation. The antibody may be a chimeric antibody, or is bispecific antibody, or wherein said antibody or antibody fragment further comprises a cell penetrating peptide and/or is an intrabody.

The antibody or antibody fragment may be administered prior to infection or after infection. The subject may be a pregnant female, a sexually active female, or a female undergoing fertility treatments. Delivering may comprise antibody or antibody fragment administration, or genetic delivery with an RNA or DNA sequence or vector encoding the antibody or antibody fragment. The antibody or antibody fragment may increase the size of the placenta as compared to an untreated control. The antibody or antibody fragment may reduce viral load and/or pathology of the fetus as compared to an untreated control.

In an additional embodiment, there is provided a method of determining the antigenic integrity, correct conformation and/or correct sequence of a Rift Valley Fever Virus antigen comprising (a) contacting a sample comprising said antigen with a first antibody or antibody fragment having clone-paired heavy and light chain CDR sequences from Tables 3 and 4, respectively; and (b) determining antigenic integrity, correct conformation and/or correct sequence of said antigen by detectable binding of said first antibody or antibody fragment to said antigen. The sample may comprise recombinantly produced antigen, or a vaccine formulation or vaccine production batch. Detection may comprise ELISA, RIA, western blot, a biosensor using surface plasmon resonance or biolayer interferometry, or flow cytometric staining.

The first antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The first antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The first antibody fragment may be a recombinant scFv (single chain fragment variable) antibody, Fab fragment, $F(ab')_2$ fragment, or Fv fragment. The method may further comprise performing steps (a) and (b) a second time to determine the antigenic stability of the antigen over time.

The method may further comprise (c) contacting a sample comprising said antigen with a second antibody or antibody fragment having clone-paired heavy and light chain CDR sequences from Tables 3 and 4, respectively; and (d) determining antigenic integrity of said antigen by detectable binding of said second antibody or antibody fragment to said antigen. The second antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The second antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The second antibody fragment may be a recombinant scFv (single chain fragment variable) antibody, Fab fragment, $F(ab')_2$ fragment, or Fv fragment. The method may further comprise performing steps (c) and (d) a second time to determine the antigenic stability of the antigen over time.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A-C. Neutralization activity of mAbs from three groups. (FIG. 1A) Gn, (FIG. 1B) Gc, and (FIG. 1C) unidentified epitope binding. Error bars represent the SE of the experiment, performed in biological and technical triplicate.

FIGS. 5A-B. Effects of mAb administration. (FIG. 5A) Effect of single mAb administration on survival outcome of male/female C57BL/6 mice challenged with a lethal dose of RVFV Animals in each group (n=8/10) were treated IP with 200 μg or 10 μg of indicated mAb. *P<0.001, compared to animals treated with the DENV-2D22 negative control mAb. Mantel-Cox log-rang test was used for analysis of Kaplan-Meier survival curves. (FIG. 5**B) Effect of single mAb administration on percent weight change of C57BL/6 mice challenged with a lethal dose of RVFV. Weight data represented as the group mean and standard error of the percent change in weight of surviving animals relative to their starting weight on the day of the viral challenge.

FIGS. 6A-C. Analysis of day-3 serum and tissue RVFV titers in mice treated with a single mAb administered 2 hours prior to viral challenge. Four animals in each group were designated for sacrifice on day 3 post-infection for analysis of (FIG. 6A) serum, (FIG. 6B) liver, and (FIG. 6C) spleen virus titers. One of the control mAb-treated mice succumbed to infection prior to sacrifice, therefore titer data is only available for 3 animals. Assay limits of detection are represented by the X-axis. ***P<0.01, *P<0.05, compared to animals treated with the control mAb DENV-2D22. The order of the antibodies from left to right in the figure correlates with top to bottom in the key.

DESCRIPTION OF ILLUSTRATIVE EMBODIMENTS

Figure 1A:
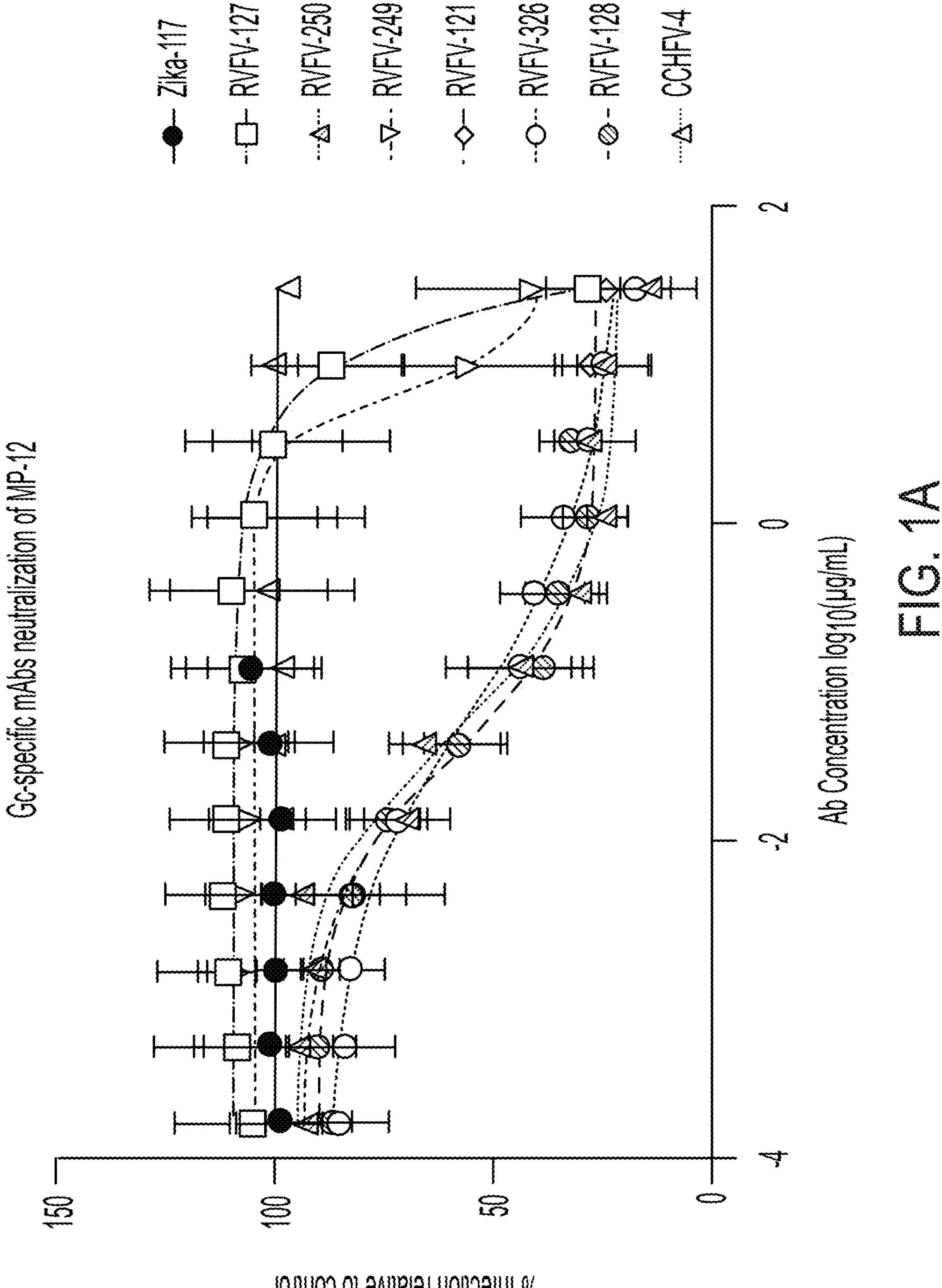
Figure 1B:
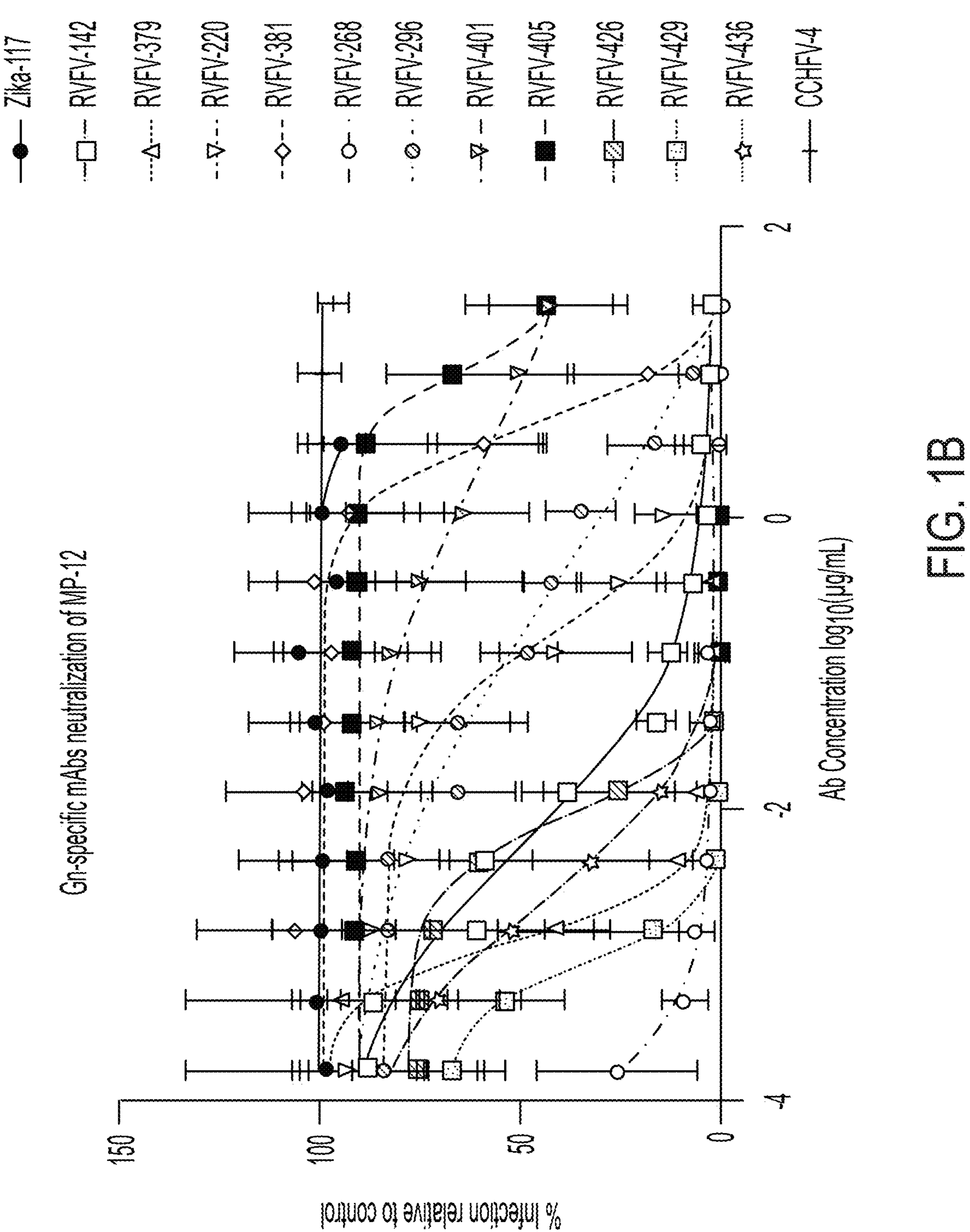
Figure 2:
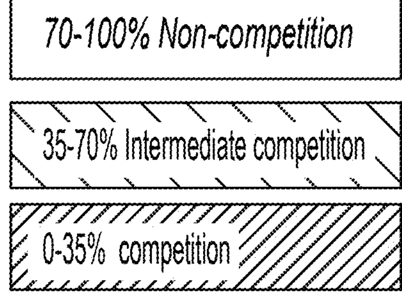
FIG. 2. Competition of Gn binding mAbs. Numbers indicate the percentage binding of second mAb labeled with Alexa Fluor 647 in the presence of the first mAb at saturating concentrations compared to binding of un-competed second mAb (representing maximal signal). MAbs were judged to compete for the same site if competed binding of the second mAbs was reduced to <35% of its maximal signal (narrow hatch marked boxes). The mAbs were considered non-competing if competed binding of the second mAb was >75% of its maximal signal (boxes with no hatch marks). The mAbs were considered mildly competing if the competed binding of the second mAb was 35-75% of its maximal binding (wide hatch marked boxes). Assay was performed in triplicate. Hatch marked boxes indicate rough estimates of competition groups.
Figure 3A:
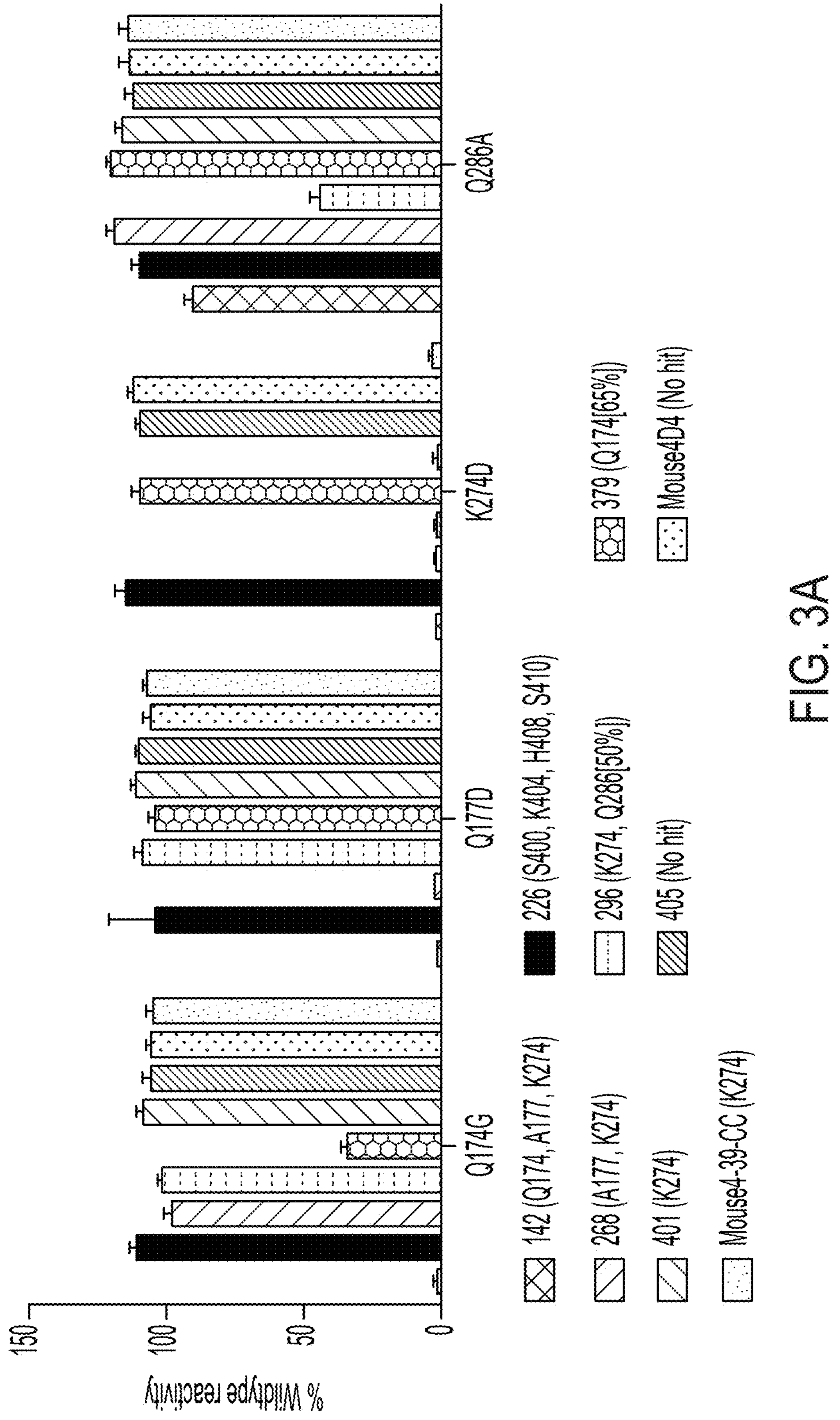
FIGS. 3A-3B. Assessment of Gn-recognizing mAbs' epitope using a Gn cell-surface displayed library designed by mutating surface exposed residues. MAbs are considered to lose binding when reactivity to mutant form compared to wild-type is <50%. The order of the antibodies from left to right in each test set are 142, 226, 268, 296, 379, 401, 405, Moust4D4 and Mouse4-39-CC (K274).
Figure 3B:
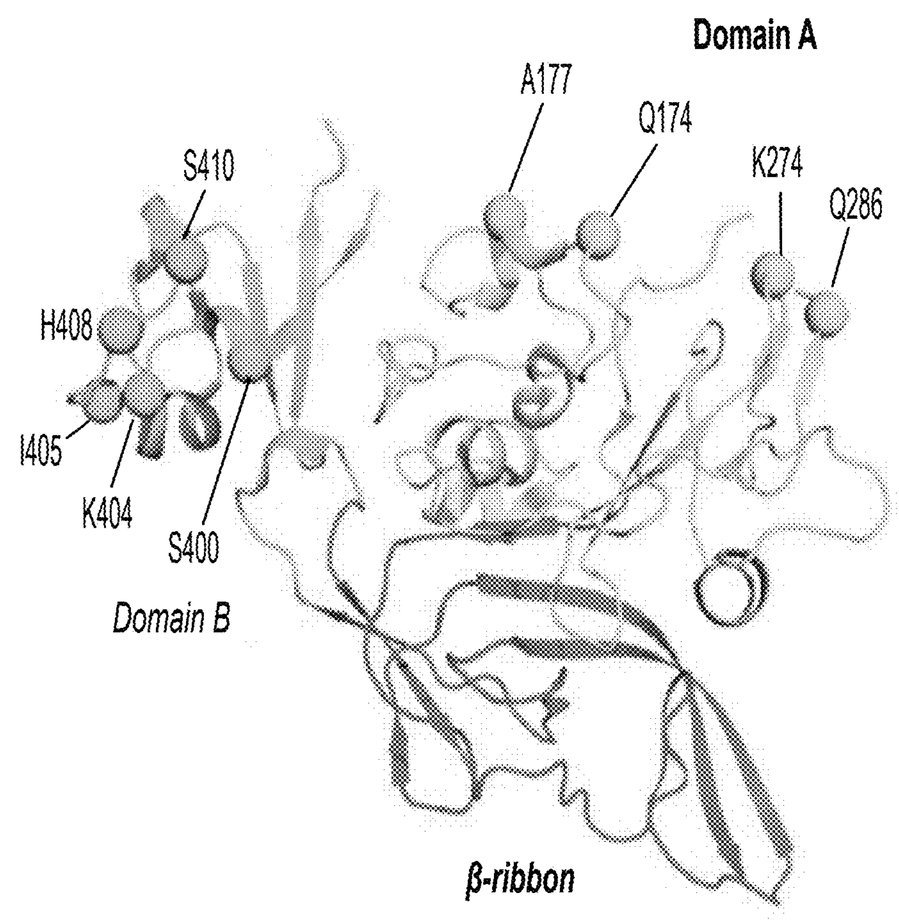
Figure 4A:
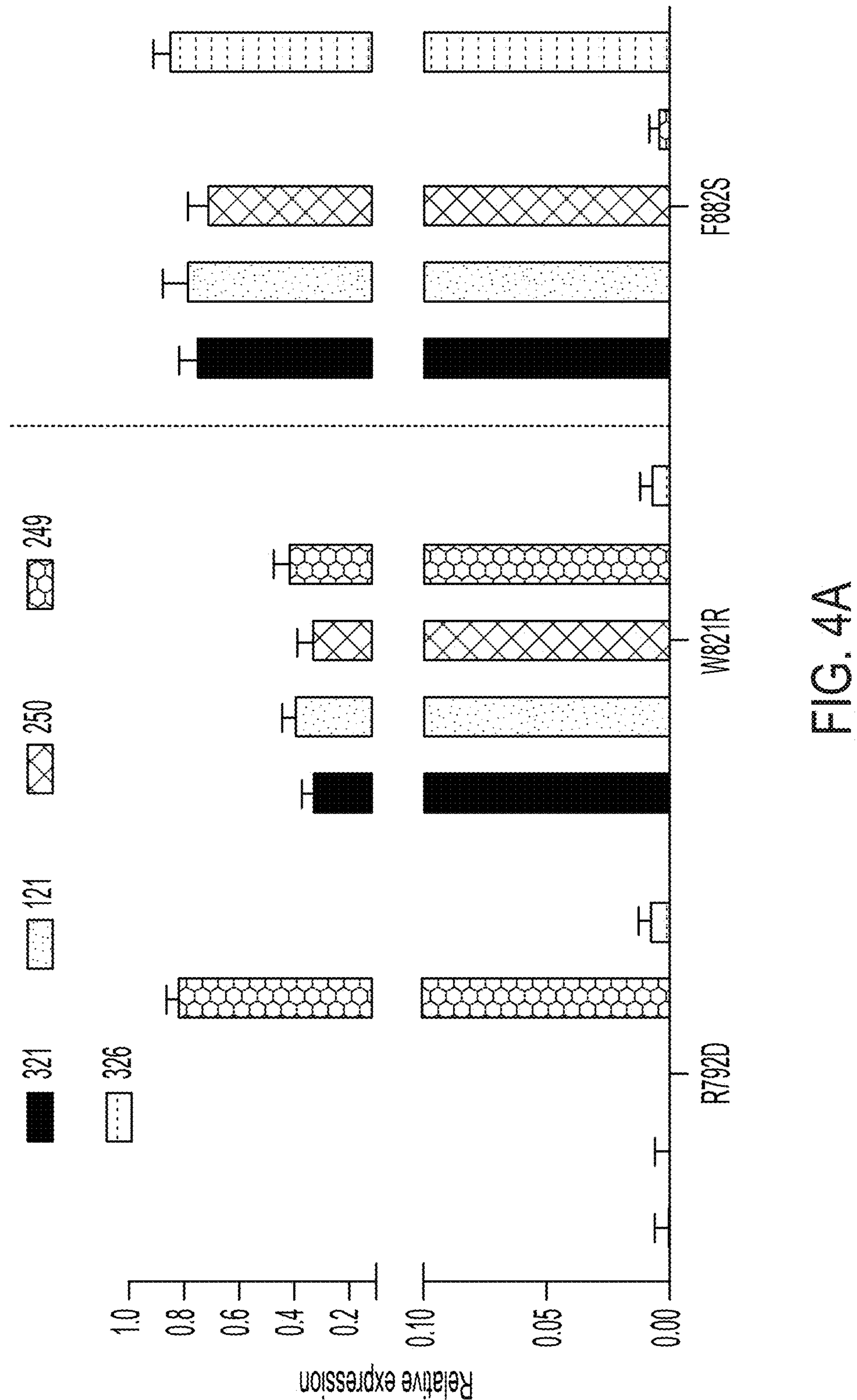
FIGS. 4A-4B. Assessment of Gc-recognizing mAbs' epitope using a Gc cell-surface displayed library designed by mutating surface exposed residues. MAbs are considered to lose binding when reactivity to mutant form compared to wild-type is <50%. The order of the antibodies from left to right in each test set are 321, 121, 250, 249 and 326.
Figure 4B:
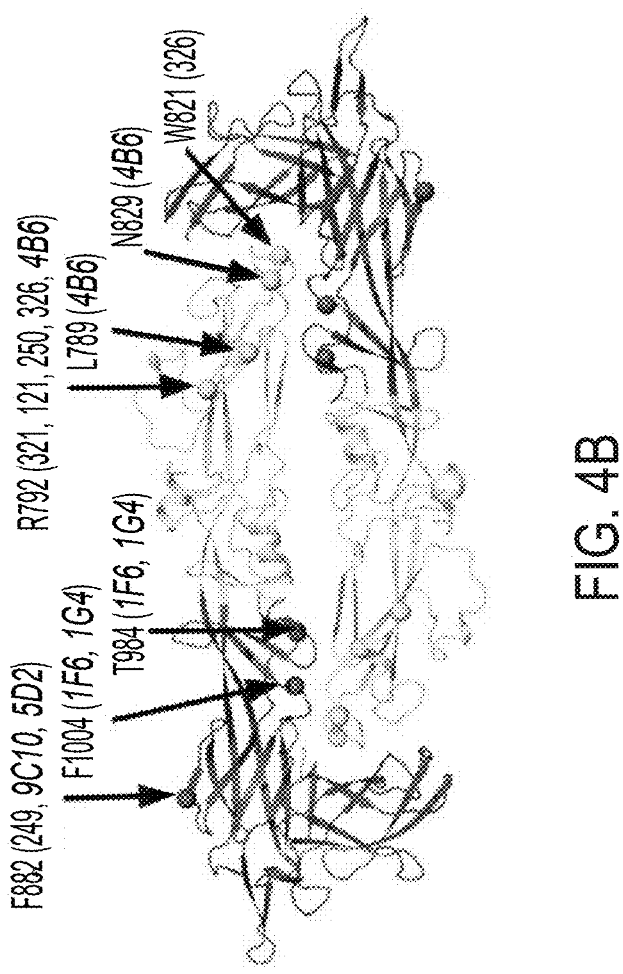
Figure 7:
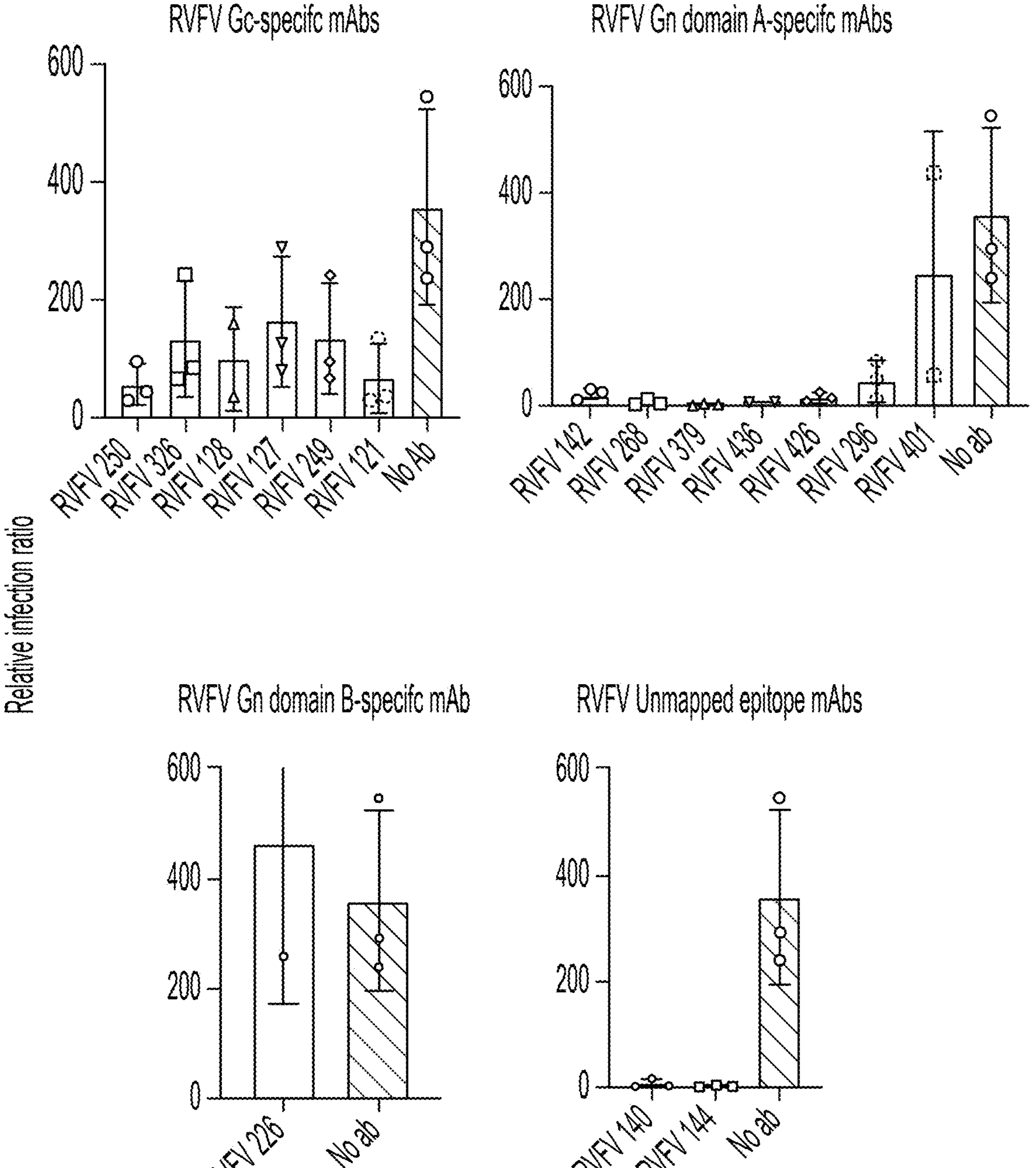
FIG. 7. Assessment of mAbs to inhibit fusion using fusion-from-without (FFWO) assay. Gn-domain A and unmapped epitope specific mAbs significantly inhibit fusion compared to no antibody control. Briefly, virus was added to cells at a MOI of 2 and allowed to attach at 4° C. for one hour, antibody was then added and washed. The pH was then altered at 37° C. to promote fusion and washed. Cells were then allowed to incubate for 24 hours at 37° C. in DMEM then subsequently fixed, stained, and assessed using a high throughput flow cytometric system (iQue). Assay was performed in triplicate. Data was analyzed using a One-Way ANOVA analyzed in Prism 8. Relative infection ratio is defined as: (permissive pH infected cell count/total cells count)/(nonpermissive pH infected cell count/total cell count).

As discussed above, there remains a need for reagents to diagnose and treat Rift Valley Fever Virus infections. Described below are human monoclonal antibodies produced from a RVFV survivors. These potently neutralizing antibodies recognize Gn and an unidentified epitope and protect against ZH501 challenge in mice. These and other aspects of the disclosure are described in detail below.

I. RIFT VALLEY FEVER VIRUS

Rift Valley Fever Virus (RVFV) virus belongs to the Bunyavirales order. This is an order of enveloped negative-sense single stranded RNA viruses. All bunyaviruses have an outer lipid envelope with two glycoproteins—G(N) and G(C)—required for cell entry. They deliver their genome into the host-cell cytoplasm by fusing their envelope with an endosomal membrane. The virus' G(C) protein has a class II membrane fusion protein architecture similar to that found in flaviviruses and alphaviruses. This structural similarity suggests that there may be a common origin for these viral families.

The 11.5 kb tripartite genome is composed of single-stranded RNA. As a Phlebovirus, it has an ambisense genome. Its L and M segments are negative-sense, but its S segment is ambisense. These three genome segments code for six major proteins: L protein (viral polymerase), the two glycoproteins G(N) and G(C), the nucleocapsid N protein, and the nonstructural NSs and NSm proteins.

The virus is transmitted through mosquito vectors, as well as through contact with the tissue of infected animals. Two species—*Culex tritaeniorhynchus* and *Aedes vexans*—are known to transmit the virus. Other potential vectors include *Aedes caspius, Aedes mcintosh, Aedes ochraceus, Culex pipiens, Culex antennatus, Culex perexiguus, Culex zombaensis* and *Culex quinquefasciatus*. Contact with infected tissue is considered to be the main source of human infections. The virus has been isolated from two bat species: the Peter's epauletted fruit bat (*Micropteropus pusillus*) and the aba roundleaf bat (*Hipposideros abae*), which are believed to be reservoirs for the virus.

Although many components of the RVFV's RNA play an important role in the virus' pathology, the nonstructural protein encoded on the S segment (NSs) is the only component that has been found to directly affect the host. NSs is hostile and combative against the hosts interferon (IFNs) antiviral response. IFNs are essential in order for the immune system to fight off viral infections in a host. This inhibitory mechanism is believed to be due to a number of reasons, the first being, competitive inhibition of the formation of the transcription factor. On this transcription factor, NSs interacts with and binds to a subunit that is needed for RNA polymerase I and II. This interaction causes competitive inhibition with another transcription factor component and prevents the assembly process of the transcription factor complex, which results in the suppression of the host antiviral response. Transcription suppression is believed to be another mechanism of this inhibitory process. This occurs when an area of NSs interacts with and binds to the host's protein, SAP30 and forms a complex. This complex causes histone acetylation to regress, which is needed for transcriptional activation of the IFN promoter. This causes IFN expression to be obstructed. Lastly, NSs has also been known to affect regular activity of double-stranded RNA-dependent protein kinase R. This protein is involved in cellular antiviral responses in the host. When RVFV is able to enter the hosts DNA, NSs forms a filamentous structure in the nucleus. This allows the virus to interact with specific areas of the hosts DNA that relates to segregation defects and induction of chromosome continuity. This increases host infectivity and decreases the host's antiviral response.

Rift Valley fever (RVF) is a viral disease caused by RVFV that can cause mild to severe symptoms. The mild symptoms may include: fever, muscle pains, and headaches which often last for up to a week. The severe symptoms may include: loss of sight beginning three weeks after the infection, infections of the brain causing severe headaches and confusion, and bleeding together with liver problems which may occur within the first few days. Those who have bleeding have a chance of death as high as 50%.

The disease is caused by the RVF virus, which is of the Phlebovirus type. It is spread by either touching infected animal blood, breathing in the air around an infected animal being butchered, drinking raw milk from an infected animal, or the bite of infected mosquitoes. Animals such as cows, sheep, goats, and camels may be affected. In these animals it is spread mostly by mosquitoes. It does not appear that one person can infect another person. The disease is diagnosed by finding antibodies against the virus or the virus itself in the blood.

Prevention of the disease in humans is accomplished by vaccinating animals against the disease. This must be done before an outbreak occurs because if it is done during an outbreak it may worsen the situation. Stopping the movement of animals during an outbreak may also be useful, as may decreasing mosquito numbers and avoiding their bites. There is a human vaccine; however, as of 2010 it is not widely available. There is no specific treatment and medical efforts are supportive.

Outbreaks of the disease have only occurred in Africa and Arabia. Outbreaks usually occur during periods of increased rain which increase the number of mosquitoes. The disease was first reported among livestock in Rift Valley of Kenya in the early 1900s, and the virus was first isolated in 1931.

In humans, the virus can cause several syndromes. Usually, sufferers have either no symptoms or only a mild illness with fever, headache, muscle pains, and liver abnormalities. In a small percentage of cases (<2%), the illness can progress to hemorrhagic fever syndrome, meningoencephalitis (inflammation of the brain and tissues lining the brain) or affect the eye. Patients who become ill usually experience fever, generalized weakness, back pain, dizziness, and weight loss at the onset of the illness. Typically, people recover within two to seven days after onset.

About 1% of people with the disease die of it. In livestock, the fatality level is significantly higher. Pregnant livestock infected with RVF abort virtually 100% of fetuses. An epizootic (animal disease epidemic) of RVF is usually first indicated by a wave of unexplained abortions. Other signs in livestock include vomiting and diarrhea, respiratory disease, fever, lethargy, anorexia and sudden death in young animals.

Diagnosis relies on viral isolation from tissues, or serological testing with an ELISA. Other methods of diagnosis include Nucleic Acid Testing (NAT), cell culture, and IgM antibody assays. As of September 2016, the Kenya Medical Research Institute (KEMRI) has developed a product called Immunoline, designed to diagnose the disease in humans much faster than in previous methods.

A person's chances of becoming infected can be reduced by taking measures to decrease contact with blood, body fluids, or tissues of infected animals and protection against mosquitoes and other bloodsucking insects. Use of mosquito repellents and bed nets are two effective methods. For persons working with animals in RVF-endemic areas, wearing protective equipment to avoid any exposure to blood or tissues of animals that may potentially be infected is an important protective measure. Potentially, establishing environmental monitoring and case surveillance systems may aid in the prediction and control of future RVF outbreaks.

No vaccines are currently available for humans. While vaccine candidates have been developed for humans, they has only been used experimentally for scientific personnel in high-risk environments. Trials of a number of vaccines, such as NDBR-103 and TSI-GSD 200, are ongoing. Different types of vaccines for veterinary use are available. The killed vaccines are not practical in routine animal field vaccination because of the need of multiple injections. Live vaccines require a single injection but are known to cause birth defects and abortions in sheep and induce only low-level protection in cattle. The live-attenuated vaccine, MP-12, has demonstrated promising results in laboratory trials in domesticated animals, but more research is needed before the vaccine can be used in the field. The live-attenuated clone 13 vaccine was recently registered and used in South Africa. Alternative vaccines using molecular recombinant constructs are in development and show promising results.

A vaccine has been conditionally approved for use in animals in the U.S. It has been shown that knockout of the NSs and NSm nonstructural proteins of this virus produces an effective vaccine in sheep as well.

RVF outbreaks occur across sub-Saharan Africa, with outbreaks occurring elsewhere infrequently. In Egypt in 1977-78, an estimated 200,000 people were infected and there were at least 594 deaths. In Kenya in 1998, the virus killed more than 400 people. In September 2000, an outbreak was confirmed in Saudi Arabia and Yemen. On 19 Oct. 2011, a case of Rift Valley fever contracted in Zimbabwe was reported in a Caucasian female traveler who returned to France after a 26-day stay in Marondera, Mashonaland East Province during July and August, 2011 but later classified as "not confirmed." Outbreaks were also reported in 2006 (Kenya), 2010 (South Africa), 2016 (Uganda), 2018 (Kenya) and 2019 (French Mayotte Islands).

Outbreaks of this disease usually correspond with the warm phases of the EI Niño/Southern Oscillation. During this time there is an increase in rainfall, flooding and greenness of vegetation index, which leads to an increase in mosquito vectors. RVFV can be transmitted vertically in mosquitos, meaning that the virus can be passed from the mother to her offspring. During dry conditions, the virus can remain viable for a number of years in the egg. Mosquitos lay their eggs in water, where they eventually hatch. As water is essential for mosquito eggs to hatch, rainfall and flooding cause an increase in the mosquito population and an increased potential for the virus.

II. MONOCLONAL ANTIBODIES AND PRODUCTION THEREOF

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In particular embodiments, the antibody is purified: (1) to greater than 95% by weight of antibody as determined by the Lowry method, and most particularly more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

The basic four-chain antibody unit is a heterotetrameric glycoprotein composed of two identical light (L) chains and two identical heavy (H) chains. An IgM antibody consists of 5 basic heterotetramer units along with an additional polypeptide called J chain, and therefore contain 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable region ($V_H$) followed by three constant domains ($C_H$) for each of the alpha and gamma chains and four $C_H$ domains for mu and isotypes. Each L chain has at the N-terminus, a variable region ($V_L$) followed by a constant domain ($C_L$) at its other end. The $V_L$ is aligned with the $V_H$ and the $C_L$ is aligned with the first constant domain of the heavy chain ($C_{H1}$). Particular amino acid residues are believed to form an interface between the light chain and heavy chain variable regions. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The L chain from any vertebrate species can be assigned to one of two clearly distinct types, called kappa and lambda based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha, delta, epsilon, gamma and mu, respectively. They gamma and alpha classes are further divided into subclasses on the basis of relatively minor differences in $C_H$ sequence and function, humans express the following subclasses: IgG1, IgG2, IgG3, IgG4, IgA1, and IgA2.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable regions. Instead, the V regions consist of relatively invariant stretches called framework regions (FRs) of 15-30 amino acids separated by shorter regions of extreme variability called "hypervariable regions" that are each 9-12 amino acids long. The variable regions of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC), antibody-dependent cellular phagocytosis (ADCP), antibody-dependent neutrophil phagocytosis (ADNP), and antibody-dependent complement deposition (ADCD).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system; Lefranc, M. P. et al. Nucl. Acids Res. 27:209-212 (1999), Ruiz, M. et al. Nucl. Acids Res. 28:219-221 (2000)). Optionally the antibody has symmetrical insertions at one or more of the following points 28, 36 (L1), 63, 74-75 (L2) and 123 (L3) in the $V_L$, and 28, 36 (H1), 63, 74-75 (H2) and 123 (H3) in the $V_{sub}$H when numbered in accordance with AHo; Honneger, A. and Plunkthun, A. J. Mol. Biol. 309:657-670 (2001)).

By "germline nucleic acid residue" is meant the nucleic acid residue that naturally occurs in a germline gene encoding a constant or variable region. "Germline gene" is the DNA found in a germ cell (i.e., a cell destined to become an egg or in the sperm). A "germline mutation" refers to a heritable change in a particular DNA that has occurred in a germ cell or the zygote at the single-cell stage, and when transmitted to offspring, such a mutation is incorporated in every cell of the body. A germline mutation is in contrast to a somatic mutation which is acquired in a single body cell. In some cases, nucleotides in a germline DNA sequence encoding for a variable region are mutated (i.e., a somatic mutation) and replaced with a different nucleotide.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present disclosure may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567) after single cell sorting of an antigen specific B cell, an antigen specific plasmablast responding to an infection or immunization, or capture of linked heavy and light chains from single cells in a bulk sorted antigen specific collection. The "monoclonal antibodies" may also be isolated from phage antibody libraries using the techniques described in Clackson et al., Nature, 352:624-628 (1991) and Marks et al., J. Mol. Biol., 222: 581-597 (1991), for example.

A. General Methods

It will be understood that monoclonal antibodies binding to bunyaviruses will have several applications. These include the production of diagnostic kits for use in detecting and diagnosing Rift Valley Fever Virus infection, as well as for treating the same. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host or identification of subjects who are immune due to prior natural infection or vaccination with a licensed or experimental vaccine. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants in animals include complete Freund's adjuvant (a non-specific stimulator of the immune response containing killed *Mycobacterium tuberculosis*), incomplete Freund's adjuvants and aluminum hydroxide adjuvant and in humans include alum, CpG, MFP59 and combinations of immunostimulatory molecules ("Adjuvant Systems", such as AS01 or AS03). Additional experimental forms of inoculation to induce Rift Valley Fever Virus-specific B cells is possible, including nanoparticle vaccines, or gene-encoded antigens delivered as DNA or RNA genes in a physical delivery system (such as lipid nanoparticle or on a gold biolistic bead), and delivered with needle, gene gun, transcutaneous electroporation device. The antigen gene also can be carried as encoded by a replication competent or defective viral vector such as adenovirus, adeno-associated virus, poxvirus, or herpesvirus, or alternatively a virus like particle.

In the case of human antibodies against natural pathogens, a suitable approach is to identify subjects that have been exposed to the pathogens, such as those who have been diagnosed as having contracted the disease, or those who have been vaccinated to generate protective immunity against the pathogen or to test the safety or efficacy of an experimental vaccine. Circulating anti-pathogen antibodies can be detected, and antibody encoding or producing B cells from the antibody-positive subject may then be obtained.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens, lymph nodes, tonsils or adenoids, bone marrow aspirates or biopsies, tissue biopsies from mucosal organs like lung or GI tract, or from circulating blood. The antibody-producing B lymphocytes from the immunized animal or immune human are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984). HMMA2.5 cells or MFP-2 cells are particularly useful examples of such cells.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. In some cases, transformation of human B cells with Epstein Barr virus (EBV) as an initial step increases the size of the B cells, enhancing fusion with the relatively large-sized myeloma cells. Transformation efficiency by EBV is enhanced by using CpG and a Chk2 inhibitor drug in the transforming medium. Alternatively, human B cells can be activated by co-culture with transfected cell lines expressing CD40 Ligand (CD154) in medium containing additional soluble factors, such as IL-21 and human B cell Activating Factor (BAFF), a Type II member of the TNF superfamily Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986) and there are processes for better efficiency (Yu et al., 2008). Fusion procedures usually produce viable hybrids at low frequencies, about $1\times10^{-6}$ to $1\times10^{-8}$, but with optimized procedures one can achieve fusion efficiencies close to 1 in 200 (Yu et al., 2008). However, relatively low efficiency of fusion does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture medium. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the medium is supplemented with hypoxanthine and thymidine as a source of nucleotides (HAT medium). Where azaserine is used, the medium is supplemented with hypoxanthine. Ouabain is added if the B cell source is an EBV-transformed human B cell line, in order to eliminate EBV-transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain may also be used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonal antibodies. Single B cells labelled with the antigen of interest can be sorted physically using paramagnetic bead selection or flow cytometric sorting, then RNA can be isolated from the single cells and antibody genes amplified by RT-PCR. Alternatively, antigen-specific bulk sorted populations of cells can be segregated into microvesicles and the matched heavy and light chain variable genes recovered from single cells using physical linkage of heavy and light chain amplicons, or common barcoding of heavy and light chain genes from a vesicle. Matched heavy and light chain genes form single cells also can be obtained from populations of antigen specific B cells by treating cells with cell-penetrating nanoparticles bearing RT-PCR primers and barcodes for marking transcripts with one barcode per cell. The antibody variable genes also can be isolated by RNA extraction of a hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

Antibodies according to the present disclosure may be defined, in the first instance, by their binding specificity.

Those of skill in the art, by assessing the binding specificity/affinity of a given antibody using techniques well known to those of skill in the art, can determine whether such antibodies fall within the scope of the instant claims. For example, the epitope to which a given antibody bind may consist of a single contiguous sequence of 3 or more (e.g., 3, 4, 5, 6, 7, 8, 9, 10, 11, 12, 13, 14, 15, 15, 17, 18, 19, 20) amino acids located within the antigen molecule (e.g., a linear epitope in a domain). Alternatively, the epitope may consist of a plurality of non-contiguous amino acids (or amino acid sequences) located within the antigen molecule (e.g., a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Hallow and Lane (Cold Spring Harbor Press, Cold Spring Harbor, N.Y.). Cross-blocking can be measured in various binding assays such as ELISA, biolayer interferometry, or surface plasmon resonance. Other methods include alanine scanning mutational analysis, peptide blot analysis (Reineke, *Methods Mol. Biol.* 248: 443-63, 2004), peptide cleavage analysis, high-resolution electron microscopy techniques using single particle reconstruction, cryoEM, or tomography, crystallographic studies and NMR analysis. In addition, methods such as epitope excision, epitope extraction and chemical modification of antigens can be employed (Tomer, *Prot. Sci.* 9: 487-496, 2000). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267: 252-259 Engen and Smith (2001) Anal. Chem. 73: 256A-265A. When the antibody neutralizes Rift Valley Fever Virus, antibody escape mutant variant organisms can be isolated by propagating Rift Valley Fever Virus in vitro or in animal models in the presence of high concentrations of the antibody. Sequence analysis of the Rift Valley Fever Virus gene encoding the antigen targeted by the antibody, reveals the mutation(s) conferring antibody escape, indicating residues in the epitope or that affect the structure of the epitope allosterically.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8.10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to Me similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the disclosure into groups of antibodies binding different epitopes.

The present disclosure includes antibodies that may bind to the same epitope, or a portion of the epitope. Likewise, the present disclosure also includes antibodies that compete for binding to a target or a fragment thereof with any of the specific exemplary antibodies described herein. One can easily determine whether an antibody binds to the same epitope as, or competes for binding with, a reference antibody by using routine methods known in the art. For example, to determine if a test antibody binds to the same epitope as a reference, the reference antibody is allowed to bind to target under saturating conditions. Next, the ability of a test antibody to bind to the target molecule is assessed. If the test antibody is able to bind to the target molecule following saturation binding with the reference antibody, it can be concluded that the test antibody binds to a different epitope than the reference antibody. On the other hand, if the test antibody is not able to bind to the target molecule following saturation binding with the reference antibody, then the test antibody may bind to the same epitope as the epitope bound by the reference antibody.

To determine if an antibody competes for binding with a reference anti-Rift Valley Fever Virus antibody, the above-described binding methodology is performed in two orientations: In a first orientation, the reference antibody is allowed to bind to the Rift Valley Fever Virus antigen under saturating conditions followed by assessment of binding of the test antibody to the Rift Valley Fever Virus antigen. In a second orientation, the test antibody is allowed to bind to the Rift Valley Fever Virus antigen under saturating conditions followed by assessment of binding of the reference antibody to the Rift Valley Fever Virus antigen. If, in both orientations, only the first (saturating) antibody is capable of binding to the Rift Valley Fever Virus, then it is concluded that the test antibody and the reference antibody compete for binding to the Rift Valley Fever Virus. As will be appreciated by a person of ordinary skill in the art, an antibody that competes for binding with a reference antibody may not necessarily bind to the identical epitope as the reference antibody but may sterically block binding, of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res.

1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this son can be performed using ELISA, RIA, surface plasmon resonance, flow cytometry or any other quantitative or qualitative antibody-binding assay available in the art. Structural studios with EM or crystallography also can demonstrate whether or not two antibodies that compete for binding recognize the same epitope.

In another aspect, there are provided monoclonal antibodies having clone-paired CDRs from the heavy and light chains as illustrated in Tables 3 and 4, respectively. Such antibodies may be produced by the clones discussed below in the Examples section using methods described herein.

In another aspect, the antibodies may be defined by their variable sequence, which include additional "framework" regions. These are provided in Tables 1 and 2 that encode or represent full variable regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (f) the amino acids may vary from those set out above by permitting conservative substitutions (discussed below). Each of the foregoing applies to the nucleic acid sequences set forth as Table 1 and the amino acid sequences of Table 2.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogeny pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor 11:105; Santou, N. Nes, M. (1987) Mol. Biol. Evol. 4:406-425; Sneath, P. H. A. and Sokal, R. R. (1973) Numerical Taxonomy—the Principles and Practice of Numerical Taxonomy, Freeman Press, San Francisco, Calif.; Wilbur, W. J. and Lipman, D. J. (1983) Proc. Natl. Acad., Sci. USA 80:726-730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One particular example of algorithms that are suitable for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403-410, respectively. BLAST and BLAST 2.0 can be used, for example with the parameters described herein, to determine percent sequence identity for the polynucleotides and polypeptides of the disclosure. Software for performing BLAST analyses is publicly available through the National Center for Biotechnology Information. The rearranged nature of an antibody sequence and the variable length of each gene requires multiple rounds of BLAST searches for a single antibody sequence. Also, manual assembly of different genes is difficult and error-prone. The sequence analysis tool IgBLAST (world-wide-web at ncbi.nlm.nih.gov/igblast/) identifies matches to the germline V, D and J genes, details at rearrangement junctions, the delineation of Ig V domain framework regions and complementarity determining regions. IgBLAST can analyze nucleotide or protein sequences and can process sequences in batches and allows searches against the germline gene databases and other sequence databases simultaneously to minimize the chance of missing possibly the best matching germline V gene.

In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) Proc. Natl. Acad. Sci.

USA 89:10915) alignments, (B) of 50, expectation (E) of 10, M=5, N=−4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

Yet another way of defining an antibody is as a "derivative" of any of the below-described antibodies and their antigen-binding fragments. The term "derivative" refers to an antibody or antigen-binding fragment thereof that immunospecifically binds to an antigen, but which comprises, one, two, three, four, five or more amino acid substitutions, additions, deletions or modifications relative to a "parental" (or wild-type) molecule. Such amino acid substitutions or additions may introduce naturally occurring (i.e., DNA-encoded) or non-naturally occurring amino acid residues. The term "derivative" encompasses, for example, as variants having altered CH1, hinge, CH2, CH3 or CH4 regions, so as to form, for example antibodies, etc., having variant Fc regions that exhibit enhanced or impaired effector or binding characteristics. The term "derivative" additionally encompasses non-amino acid modifications, for example, amino acids that may be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment, the altered carbohydrate modifications enhance antibody mediated effector function relative to the antibody lacking the carbohydrate modification. Carbohydrate modifications that lead to altered antibody mediated effector function are well known in the art (for example, see Shields, R. L. et al. (2002) "*Lack Of Fucose On Human IgG N-Linked Oligosaccharide Improves Binding To Human Fcgamma Rill And Antibody-Dependent Cellular Toxicity*," J. Biol. Chem. 277(30): 26733-26740; Davies J. et al. (2001) "*Expression Of GnTIII In A Recombinant Anti-CD*20 *CHO Production Cell Line: Expression Of Antibodies With Altered Glycoforms Leads To An Increase In ADCC Through Higher Affinity For FC Gamma RIII*," Biotechnology & Bioengineering 74(4): 288-294). Methods of altering carbohydrate contents are known to those skilled in the art, see, e.g., Wallick, S. C. et al. (1988) "*Glycosylation Of A VH Residue Of A Monoclonal Antibody Against Alpha* (1-6) *Dextran Increases Its Affinity For Antigen*," J. Exp. Med. 168(3): 1099-1109; Tao, M. H. et al. (1989) "*Studies Of Aglycosylated Chimeric Mouse-Human IgG. Role of Carbohydrate in The Structure And Effector Functions Mediated By The Human IgG Constant Region*," J. Immunol. 143(8): 2595-2601; Routledge, E. G. et al. (1995) "*The Effect of Aglycosylation on The Immunogenicity of A Humanized Therapeutic CD*3 *Monoclonal Antibody*," Transplantation 60(8):847-53; Elliott, S. et al. (2003) "*Enhancement Of Therapeutic Protein In Vivo Activities Through Glycoengineering*," Nature Biotechnol. 21:414-21; Shields, R. L. et al. (2002) "*Lack of Fucose on Human IgG N-Linked Oligosaccharide Improves Binding to Human Fcgamma RIII And Antibody-Dependent Cellular Toxicity*," J. Biol. Chem. 277(30): 26733-26740).

A derivative antibody or antibody fragment can be generated with an engineered sequence or glycosylation state to confer preferred levels of activity in antibody dependent cellular cytotoxicity (ADCC), antibody-dependent cellular phagocytosis (ADCP), antibody-dependent neutrophil phagocytosis (ADNP), or antibody-dependent complement deposition (ADCD) functions as measured by bead-based or cell-based assays or in vivo studies in animal models.

A derivative antibody or antibody fragment may be modified by chemical modifications using techniques known to those of skill in the art, including, but not limited to, specific chemical cleavage, acetylation, formulation, metabolic synthesis of tunicamycin, etc. In one embodiment, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody.

C. Engineering of Antibody Sequences

In various embodiments, one may choose to engineer sequences of the identified antibodies for a variety of reasons, such as improved expression, improved cross-reactivity or diminished off-target binding. Modified antibodies may be made by any technique known to those of skill in the art, including expression through standard molecular biological techniques, or the chemical synthesis of polypeptides. Methods for recombinant expression are addressed elsewhere in this document. The following is a general discussion of relevant goals techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full-length IgG antibodies can be generated by subcloning heavy and light chain Fv DNAs from the cloning vector into an IgG plasmid vector, transfected into 293 (e.g., Freestyle) cells or CHO cells, and antibodies can be collected and purified from the 293 or CHO cell supernatant. Other appropriate host cells systems include bacteria, such as *E. coli*, insect cells (S2, Sf9, Sf29, High Five), plant cells (e.g., tobacco, with or without engineering for human-like glycans), algae, or in a variety of non-human transgenic contexts, such as mice, rats, goats or cows.

Expression of nucleic acids encoding antibodies, both for the purpose of subsequent antibody purification, and for immunization of a host, is also contemplated. Antibody coding sequences can be RNA, such as native RNA or modified RNA. Modified RNA contemplates certain chemical modifications that confer increased stability and low immunogenicity to mRNAs, thereby facilitating expression of therapeutically important proteins. For instance, N1-methyl-pseudouridine (N1mΨ) outperforms several other nucleoside modifications and their combinations in terms of translation capacity. In addition to turning off the immune/eIF2α phosphorylation-dependent inhibition of translation, incorporated N1mΨ nucleotides dramatically alter the dynamics of the translation process by increasing ribosome pausing and density on the mRNA. Increased ribosome loading of modified mRNAs renders them more permissive for initiation by favoring either ribosome recycling on the same mRNA or de novo ribosome recruitment. Such modifications could be used to enhance antibody expression in vivo following inoculation with RNA. The RNA, whether native or modified, may be delivered as naked RNA or in a delivery vehicle, such as a lipid nanoparticle.

Alternatively, DNA encoding the antibody may be employed for the same purposes. The DNA is included in an expression cassette comprising a promoter active in the host cell for which it is designed. The expression cassette is advantageously included in a replicable vector, such as a conventional plasmid or minivector. Vectors include viral vectors, such as poxviruses, adenoviruses, herpesviruses, adeno-associated viruses, and lentiviruses are contemplated. Replicons encoding antibody genes such as Rift Valley Fever Virus replicons based on VEE virus or Sindbis virus are also contemplated. Delivery of such vectors can be performed by needle through intramuscular, subcutaneous, or intradermal routes, or by transcutaneous electroporation when in vivo expression is desired.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), $F(ab')_2$) that are produced, for example, by the proteolytic cleavage of the mAbs, or single-chain immunoglobulins producible, for example, via recombinant means. F(ab') antibody derivatives are monovalent, while F(ab')2 antibody derivatives are bivalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to $IgG_1$ can increase antibody dependent cell cytotoxicity, switching to class A can improve tissue distribution, and switching to class M can improve valency.

Alternatively or additionally, it may be useful to combine amino acid modifications with one or more further amino acid modifications that alter C1q binding and/or the complement dependent cytotoxicity (CDC) function of the Fc region of an IL-23p19 binding molecule. The binding polypeptide of particular interest may be one that binds to C1q and displays complement dependent cytotoxicity. Polypeptides with pre-existing C1q binding activity, optionally further having the ability to mediate CDC may be modified such that one or both of these activities are enhanced Amino acid modifications that alter C1q and/or modify its complement dependent cytotoxicity function are described, for example, in WO/0042072, which is hereby incorporated by reference.

One can design an Fc region of an antibody with altered effector function, e.g., by modifying C1q binding and/or FcγR binding and thereby changing CDC activity and/or ADCC activity. "Effector functions" are responsible for activating or diminishing a biological activity (e.g., in a subject). Examples of effector functions include, but are not limited to: C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions may require the Fc region to be combined with a binding domain (e.g., an antibody variable domain) and can be assessed using various assays (e.g., Fc binding assays, ADCC assays, CDC assays, etc.).

For example, one can generate a variant Fc region of an antibody with improved C1q binding and improved FcγRIII binding (e.g., having both improved ADCC activity and improved CDC activity). Alternatively, if it is desired that effector function be reduced or ablated, a variant Fc region can be engineered with reduced CDC activity and/or reduced ADCC activity. In other embodiments, only one of these activities may be increased, and, optionally, also the other activity reduced (e.g., to generate an Fc region variant with improved ADCC activity, but reduced CDC activity and vice versa).

FcRn binding. Fc mutations can also be introduced and engineered to alter their interaction with the neonatal Fc receptor (FcRn) and improve their pharmacokinetic properties. A collection of human Fc variants with improved binding to the FcRn have been described (Shields et al., (2001). High resolution mapping of the binding site on human IgG1 for FcγRI, FcγRII, FcγRIII, and FcRn and design of IgG1 variants with improved binding to the FcγR, (J. Biol. Chem. 276:6591-6604). A number of methods are known that can result in increased half-life (Kuo and Aveson, (2011)), including amino acid modifications may be generated through techniques including alanine scanning mutagenesis, random mutagenesis and screening to assess the binding to the neonatal Fc receptor (FcRn) and/or the in vivo behavior. Computational strategies followed by mutagenesis may also be used to select one of amino acid mutations to mutate.

The present disclosure therefore provides a variant of an antigen binding protein with optimized binding to FcRn. In a particular embodiment, the said variant of an antigen binding protein comprises at least one amino acid modification in the Fc region of said antigen binding protein, wherein said modification is selected from the group consisting of 226, 227, 228, 230, 231, 233, 234, 239, 241, 243, 246, 250, 252, 256, 259, 264, 265, 267, 269, 270, 276, 284, 285, 288, 289, 290, 291, 292, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 384, 385, 386, 387, 389, 390, 392, 393, 394, 395, 396, 397, 398, 399, 400, 401 403, 404, 408, 411, 412, 414, 415, 416, 418, 419, 420, 421, 422, 424, 426, 428, 433, 434, 438, 439, 440, 443, 444, 445, 446 and 447 of the Fc region as compared to said parent polypeptide, wherein the numbering of the amino acids in the Fc region is that of the EU index in Kabat. In a further aspect of the disclosure the modifications are M252Y/S254T/T256E.

Additionally, various publications describe methods for obtaining physiologically active molecules whose half-lives are modified, see for example Kontermann (2009) either by introducing an FcRn-binding polypeptide into the molecules or by fusing the molecules with antibodies whose FcRn-binding affinities are preserved but affinities for other Fc receptors have been greatly reduced or fusing with FcRn binding domains of antibodies.

Derivatized antibodies may be used to alter the half-lives (e.g., serum half-lives) of parental antibodies in a mammal, particularly a human. Such alterations may result in a half-life of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies of the present disclosure or fragments thereof in a mammal, preferably a human, results in a higher serum titer of said antibodies or antibody fragments in the mammal, and thus reduces the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor.

Beltramello et al. (2010) previously reported the modification of neutralizing mAbs, due to their tendency to enhance dengue virus infection, by generating in which leucine residues at positions 1.3 and 1.2 of CH2 domain (according to the IMGT unique numbering for C-domain) were substituted with alanine residues. This modification, also known as "LALA" mutation, abolishes antibody binding to FcγRI, FcγRII and FcγRIIIa, as described by Hessell et al. (2007). The variant and unmodified recombinant mAbs were compared for their capacity to neutralize and enhance infection by the four dengue virus serotypes. LALA variants retained the same neutralizing activity as unmodified mAb but were completely devoid of enhancing activity. LALA mutations of this nature are therefore contemplated in the context of the presently disclosed antibodies.

Altered glycosylation. A particular embodiment of the present disclosure is an isolated monoclonal antibody, or antigen binding fragment thereof, containing a substantially homogeneous glycan without sialic acid, galactose, or fucose. The monoclonal antibody comprises a heavy chain variable region and a light chain variable region, both of which may be attached to heavy chain or light chain constant regions respectively. The aforementioned substantially homogeneous glycan may be covalently attached to the heavy chain constant region.

Another embodiment of the present disclosure comprises a mAb with a novel Fc glycosylation pattern. The isolated monoclonal antibody, or antigen binding fragment thereof, is present in a substantially homogenous composition represented by the GNGN or G1/G2 glycoform. Fc glycosylation plays a significant role in anti-viral and anti-cancer properties of therapeutic mAbs. The disclosure is in line with a recent study that shows increased anti-lentivirus cell-mediated viral inhibition of a fucose free anti-HIV mAb in vitro. This embodiment of the present disclosure with homogenous glycans lacking a core fucose, showed increased protection against specific viruses by a factor greater than two-fold. Elimination of core fucose dramatically improves the ADCC activity of mAbs mediated by natural killer (NK)

cells but appears to have the opposite effect on the ADCC activity of polymorphonuclear cells (PMNs).

The isolated monoclonal antibody, or antigen binding fragment thereof, comprising a substantially homogenous composition represented by the GNGN or G1/G2 glycoform exhibits increased binding affinity for Fc gamma RI and Fc gamma RIII compared to the same antibody without the substantially homogeneous GNGN glycoform and with G0, G1F, G2F, GNF, GNGNF or GNGNFX containing glycoforms. In one embodiment of the present disclosure, the antibody dissociates from Fc gamma RI with a Kd of $1\times10^{-8}$ M or less and from Fc gamma RIII with a Kd of $1\times10^{-7}$ M or less.

Glycosylation of an Fc region is typically either N-linked or O-linked. N-linked refers to the attachment of the carbohydrate moiety to the side chain of an asparagine residue. 0-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used. The recognition sequences for enzymatic attachment of the carbohydrate moiety to the asparagine side chain peptide sequences are asparagine-X-serine and asparagine-X-threonine, where X is any amino acid except proline. Thus, the presence of either of these peptide sequences in a polypeptide creates a potential glycosylation site.

The glycosylation pattern may be altered, for example, by deleting one or more glycosylation site(s) found in the polypeptide, and/or adding one or more glycosylation site(s) that are not present in the polypeptide. Addition of glycosylation sites to the Fc region of an antibody is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites). Additionally, a change of Asn 297 to Ala can remove one of the glycosylation sites.

In certain embodiments, the antibody is expressed in cells that express beta (1,4)-N-acetylglucosaminyltransferase III (GnT III), such that GnT III adds GlcNAc to the IL-23p19 antibody. Methods for producing antibodies in such a fashion are provided in WO/9954342, WO/03011878, patent publication 20030003097A1, and Umana et al., Nature Biotechnology, 17:176-180, February 1999. Cell lines can be altered to enhance or reduce or eliminate certain post-translational modifications, such as glycosylation, using genome editing technology such as Clustered Regularly Interspaced Short Palindromic Repeats (CRISPR). For example, CRISPR technology can be used to eliminate genes encoding glycosylating enzymes in 293 or CHO cells used to express recombinant monoclonal antibodies.

Elimination of monoclonal antibody protein sequence liabilities. It is possible to engineer the antibody variable gene sequences obtained from human B cells to enhance their manufacturability and safety. Potential protein sequence liabilities can be identified by searching for sequence motifs associated with sites containing:

1) Unpaired Cys residues,
2) N-linked glycosylation,
3) Asn deamidation,
4) Asp isomerization,
5) SYE truncation,
6) Met oxidation,
7) Trp oxidation,
8) N-terminal glutamate,
9) Integrin binding,
10) CD11c/CD18 binding, or
11) Fragmentation Such motifs can be eliminated by altering the synthetic gene for the cDNA encoding recombinant antibodies.

Protein engineering efforts in the field of development of therapeutic antibodies clearly reveal that certain sequences or residues are associated with solubility differences (Fernandez-Escamilla et al., *Nature Biotech.,* 22 (10), 1302-1306, 2004; Chennamsetty et al., *PNAS,* 106 (29), 11937-11942, 2009; Voynov et al., *Biocon. Chem.,* 21(2), 385-392, 2010) Evidence from solubility-altering mutations in the literature indicate that some hydrophilic residues such as aspartic acid, glutamic acid, and serine contribute significantly more favorably to protein solubility than other hydrophilic residues, such as asparagine, glutamine, threonine, lysine, and arginine.

Stability. Antibodies can be engineered for enhanced biophysical properties. One can use elevated temperature to unfold antibodies to determine relative stability, using average apparent melting temperatures. Differential Scanning Calorimetry (DSC) measures the heat capacity, $C_p$, of a molecule (the heat required to warm it, per degree) as a function of temperature. One can use DSC to study the thermal stability of antibodies. DSC data for mAbs is particularly interesting because it sometimes resolves the unfolding of individual domains within the mAb structure, producing up to three peaks in the thermogram (from unfolding of the Fab, $C_H2$, and $C_H3$ domains). Typically unfolding of the Fab domain produces the strongest peak. The DSC profiles and relative stability of the Fc portion show characteristic differences for the human $IgG_1$, $IgG_2$, $IgG_3$, and $IgG_4$ subclasses (Garber and Demarest, *Biochem. Biophys. Res. Commun.* 355, 751-757, 2007). One also can determine average apparent melting temperature using circular dichroism (CD), performed with a CD spectrometer. Far-UV CD spectra will be measured for antibodies in the range of 200 to 260 nm at increments of 0.5 nm. The final spectra can be determined as averages of 20 accumulations. Residue ellipticity values can be calculated after background subtraction. Thermal unfolding of antibodies (0.1 mg/mL) can be monitored at 235 nm from 25-95° C. and a heating rate of 1° C./min One can use dynamic light scattering (DLS) to assess for propensity for aggregation. DLS is used to characterize size of various particles including proteins. If the system is not disperse in size, the mean effective diameter of the particles can be determined. This measurement depends on the size of the particle core, the size of surface structures, and particle concentration. Since DLS essentially measures fluctuations in scattered light intensity due to particles, the diffusion coefficient of the particles can be determined. DLS software in commercial DLA instruments displays the particle population at different diameters. Stability studies can be done conveniently using DLS. DLS measurements of a sample can show whether the particles aggregate over time or with temperature variation by determining whether the hydrodynamic radius of the particle increases. If particles aggregate, one can see a larger population of particles with a larger radius. Stability depending on temperature can be analyzed by controlling the temperature in situ. Capillary electrophoresis (CE) techniques include proven methodologies for determining features of antibody stability. One can use an iCE approach to resolve antibody protein charge variants due to deamidation, C-terminal lysines, sialylation, oxidation, glycosylation, and any other change to the protein that can result in a change in pI of the protein. Each of the expressed antibody proteins can be evaluated by high throughput, free solution isoelectric focusing (IEF) in a capillary column (cIEF), using a Protein Simple Maurice instrument. Whole-column UV absorption detection can be performed every 30 seconds for real time monitoring of molecules focusing at the isoelectric points (pIs). This approach combines the high resolution of traditional gel IEF with the advantages of quantitation and automation found in column-based separations while eliminating the need for a mobilization step. The technique yields reproducible, quantitative analysis of identity, purity, and heterogeneity profiles for the expressed antibodies. The results identify charge heterogeneity and molecular sizing on the antibodies, with both absorbance and native fluorescence detection modes and with sensitivity of detection down to 0.7 μg/mL.

Solubility. One can determine the intrinsic solubility score of antibody sequences. The intrinsic solubility scores can be calculated using CamSol Intrinsic (Sormanni et al., *J Mol Biol* 427, 478-490, 2015). The amino acid sequences for residues 95-102 (Kabat numbering) in HCDR3 of each antibody fragment such as a scFv can be evaluated via the online program to calculate the solubility scores. One also can determine solubility using laboratory techniques. Various techniques exist, including addition of lyophilized protein to a solution until the solution becomes saturated and the solubility limit is reached, or concentration by ultrafiltration in a microconcentrator with a suitable molecular weight cut-off. The most straightforward method is induction of amorphous precipitation, which measures protein solubility using a method involving protein precipitation using ammonium sulfate (Trevino et al., *J Mol Biol,* 366: 449-460, 2007). Ammonium sulfate precipitation gives quick and accurate information on relative solubility values. Ammonium sulfate precipitation produces precipitated solutions with well-defined aqueous and solid phases and requires relatively small amounts of protein. Solubility measurements performed using induction of amorphous precipitation by ammonium sulfate also can be done easily at different pH values. Protein solubility is highly pH dependent, and pH is considered the most important extrinsic factor that affects solubility.

Autoreactivity. Generally, it is thought that autoreactive clones should be eliminated during ontogeny by negative selection, however it has become clear that many human naturally occurring antibodies with autoreactive properties persist in adult mature repertoires, and the autoreactivity may enhance the antiviral function of many antibodies to pathogens. It has been noted that HCDR3 loops in antibodies during early B cell development are often rich in positive charge and exhibit autoreactive patterns (Wardemann et al., *Science* 301, 1374-1377, 2003). One can test a given antibody for autoreactivity by assessing the level of binding to human origin cells in microscopy (using adherent HeLa or HEp-2 epithelial cells) and flow cytometric cell surface staining (using suspension Jurkat T cells and 293S human embryonic kidney cells). Autoreactivity also can be surveyed using assessment of binding to tissues in tissue arrays.

Preferred residues ("Human Likeness"). B cell repertoire deep sequencing of human B cells from blood donors is being performed on a wide scale in many recent studies. Sequence information about a significant portion of the human antibody repertoire facilitates statistical assessment of antibody sequence features common in healthy humans. With knowledge about the antibody sequence features in a human recombined antibody variable gene reference database, the position specific degree of "Human Likeness" (HL) of an antibody sequence can be estimated. HL has been shown to be useful for the development of antibodies in clinical use, like therapeutic antibodies or antibodies as vaccines. The goal is to increase the human likeness of antibodies to reduce potential adverse effects and anti-antibody immune responses that will lead to significantly decreased efficacy of the antibody drug or can induce serious health implications. One can assess antibody characteristics of the combined antibody repertoire of three healthy human blood donors of about 400 million sequences in total and created a novel "relative Human Likeness" (rHL) score that focuses on the hypervariable region of the antibody. The rHL score allows one to easily distinguish between human (positive score) and non-human sequences (negative score). Antibodies can be engineered to eliminate residues that are not common in human repertoires.

Blood brain barrier. The blood brain barrier regulates the traverse of blood-circulating substances into the brain with selectivity. This barrier may reduce the entry of antibodies into the central nervous system necessary for diagnosis or therapy of central nervous system infection with Rift Valley Fever Virus. It may be possible to exploit the naturally occurring cellular trafficking systems and the receptor-mediated transfer machinery to move antibodies across the blood brain barrier safely to tissue site where the antibodies will be most effective. There have been a large number of studies of molecules that mediate active transport into the brain, including at least 20 receptors, including transferrin receptor, heparin-binding EGF, scavenger receptors AI, BI, EGF receptor, tumor necrosis factor, insulin and insulin-like growth factor receptors, apolipoprotein E receptor 2, leptin receptor, melanotransferrin receptor, or LDL receptors (Preston et al., *Adv. Pharmacol.* 71: 147-163, 2014). Here, the inventors propose to use one or more of these active transport systems to deliver a Rift Valley Fever Virus inhibiting antibody by making a chimeric or bispecific molecule that targets a transporting receptor and possesses a separate domain that targets a Rift Valley Fever Virus protein.

D. Single Chain Antibodies

A single chain variable fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma or B cell. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alanine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5\times10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Ga14 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338 describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Multispecific Antibodies

In certain embodiments, antibodies of the present disclosure are bispecific or multispecific. Bispecific antibodies are antibodies that have binding specificities for at least two different epitopes. Exemplary bispecific antibodies may bind to two different epitopes of a single antigen. Other such antibodies may combine a first antigen binding site with a binding site for a second antigen. Alternatively, an anti-pathogen arm may be combined with an arm that binds to a triggering molecule on a leukocyte, such as a T-cell receptor molecule (e.g., CD3), or Fc receptors for IgG (FcγR), such as FcγRI (CD64), FcγRII (CD32) and Fc gamma RIII (CD16), so as to focus and localize cellular defense mechanisms to the infected cell. Bispecific antibodies may also be used to localize cytotoxic agents to infected cells. These antibodies possess a pathogen-binding arm and an arm that binds the cytotoxic agent (e.g., saporin, anti-interferon-α, vinca alkaloid, ricin A chain, methotrexate or radioactive isotope hapten). Bispecific antibodies can be prepared as full-length antibodies or antibody fragments (e.g., $F(ab')_2$ bispecific antibodies). WO 96/16673 describes a bispecific anti-ErbB2/anti-Fc gamma RIII antibody and U.S. Pat. No. 5,837,234 discloses a bispecific anti-ErbB2/anti-Fc gamma RI antibody. A bispecific anti-ErbB2/Fc alpha antibody is shown in WO98/02463. U.S. Pat. No. 5,821,337 teaches a bispecific anti-ErbB2/anti-CD3 antibody.

Methods for making bispecific antibodies are known in the art. Traditional production of full-length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of ten different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

According to a different approach, antibody variable regions with the desired binding specificities (antibody-antigen combining sites) are fused to immunoglobulin constant domain sequences. Preferably, the fusion is with an Ig heavy chain constant domain, comprising at least part of the hinge, $C_{H2}$, and $C_{H3}$ regions. It is preferred to have the first heavy-chain constant region ($C_{H1}$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant effect on the yield of the desired chain combination.

In a particular embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_{H3}$ domain In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')2 fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Techniques exist that facilitate the direct recovery of Fab'-SH fragments from *E. coli*, which can be chemically coupled to form bispecific antibodies. Shalaby et al., J. Exp. Med., 175: 217-225 (1992) describe the production of a humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described (Merchant et al., *Nat. Biotechnol.* 16, 677-681 (1998). doi:10.1038/nbt0798-677pmid: 9661204). For example, bispecific antibodies have been produced using leucine zippers (Kostelny et al., J. Immunol., 148(5):1547-1553, 1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a $V_H$ connected to a $V_L$ by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

In a particular embodiment, a bispecific or multispecific antibody may be formed as a DOCK-AND-LOCK™ (DNL™) complex (see, e.g., U.S. Pat. Nos. 7,521,056; 7,527,787; 7,534,866; 7,550,143 and 7,666,400, the Examples section of each of which is incorporated herein by reference.) Generally, the technique takes advantage of the specific and high-affinity binding interactions that occur between a dimerization and docking domain (DDD) sequence of the regulatory (R) subunits of cAMP-dependent protein kinase (PKA) and an anchor domain (AD) sequence derived from any of a variety of AKAP proteins (Baillie et al., *FEBS Letters*. 2005; 579: 3264; Wong and Scott, *Nat. Rev. Mol. Cell Biol.* 2004; 5: 959). The DDD and AD peptides may be attached to any protein, peptide or other molecule. Because the DDD sequences spontaneously dimerize and bind to the AD sequence, the technique allows the formation of complexes between any selected molecules that may be attached to DDD or AD sequences.

Antibodies with more than two valencies are contemplated. For example, trispecific antibodies can be prepared (Tutt et al., J. Immunol. 147: 60, 1991; Xu et al., *Science,* 358(6359):85-90, 2017). A multivalent antibody may be internalized (and/or catabolized) faster than a bivalent antibody by a cell expressing an antigen to which the antibodies bind. The antibodies of the present disclosure can be multivalent antibodies with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable regions. For instance, the polypeptide chain(s) may comprise VD1-$(X1)_n$-VD2-$(X2)_n$-Fc, wherein VD1 is a first variable region, VD2 is a second variable region, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable region polypeptides. The multivalent antibody herein may, for instance, comprise from about two to about eight light chain variable region polypeptides. The light chain variable region polypeptides contemplated here comprise a light chain variable region and, optionally, further comprise a $C_L$ domain.

Charge modifications are particularly useful in the context of a multispecific antibody, where amino acid substitutions in Fab molecules result in reducing the mispairing of light chains with non-matching heavy chains (Bence-Jones-type side products), which can occur in the production of Fab-based bi-/multispecific antigen binding molecules with a VH/VL exchange in one (or more, in case of molecules comprising more than two antigen-binding Fab molecules) of their binding arms (see also PCT publication no. WO 2015/150447, particularly the examples therein, incorporated herein by reference in its entirety).

Accordingly, in particular embodiments, an antibody comprised in the therapeutic agent comprises (a) a first Fab molecule which specifically binds to a first antigen (b) a second Fab molecule which specifically binds to a second antigen, and wherein the variable domains VL and VH of the Fab light chain and the Fab heavy chain are replaced by each other, wherein the first antigen is an activating T cell antigen and the second antigen is a target cell antigen, or the first antigen is a target cell antigen and the second antigen is an activating T cell antigen; and wherein i) in the constant domain CL of the first Fab molecule under a) the amino acid at position 124 is substituted by a positively charged amino acid (numbering according to Kabat), and wherein in the constant domain CH1 of the first Fab molecule under a) the amino acid at position 147 or the amino acid at position 213 is substituted by a negatively charged amino acid (numbering according to Kabat EU index); or ii) in the constant domain CL of the second Fab molecule under b) the amino acid at position 124 is substituted by a positively charged amino acid (numbering according to Kabat), and wherein in the constant domain CH1 of the second Fab molecule under b) the amino acid at position 147 or the amino acid at position 213 is substituted by a negatively charged amino acid (numbering according to Kabat EU index).

The antibody may not comprise both modifications mentioned under i) and ii). The constant domains CL and CH1 of the second Fab molecule are not replaced by each other (i.e., remain unexchanged).

In another embodiment of the antibody, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 or the amino acid at position 213 is substituted independently by glutamic acid (E), or aspartic acid (D) (numbering according to Kabat EU index).

In a further embodiment, in the constant domain CL of the first Fab molecule under a) the amino acid at position 124 is substituted independently by lysine (K), arginine (R) or histidine (H) (numbering according to Kabat), and in the constant domain CH1 of the first Fab molecule under a) the amino acid at position 147 is substituted independently by glutamic acid (E), or aspartic acid (D) (numbering according to Kabat EU index).

In a particular embodiment, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)) and the amino acid at position 123 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a more particular embodiment, in the constant domain CL of the first Fab molecule under a) the amino acid at position 124 is substituted by lysine (K) (numbering according to Kabat) and the amino acid at position 123 is substituted by lysine (K) or arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

In an even more particular embodiment, in the constant domain CL of the first Fab molecule under a) the amino acid at position 124 is substituted by lysine (K) (numbering according to Kabat) and the amino acid at position 123 is substituted by arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

F. Chimeric Antigen Receptors

Artificial T cell receptors (also known as chimeric T cell receptors, chimeric immunoreceptors, chimeric antigen receptors (CARs)) are engineered receptors, which graft an arbitrary specificity onto an immune effector cell. Typically, these receptors are used to graft the specificity of a monoclonal antibody onto a T cell, with transfer of their coding sequence facilitated by retroviral vectors. In this way, a large number of target-specific T cells can be generated for adoptive cell transfer. Phase I clinical studies of this approach show efficacy.

The most common form of these molecules are fusions of single-chain variable fragments (scFv) derived from monoclonal antibodies, fused to CD3-zeta transmembrane and endodomain Such molecules result in the transmission of a zeta signal in response to recognition by the scFv of its target. An example of such a construct is 14g2a-Zeta, which is a fusion of a scFv derived from hybridoma 14g2a (which recognizes disialoganglioside GD2). When T cells express this molecule (usually achieved by oncoretroviral vector transduction), they recognize and kill target cells that express GD2 (e.g., neuroblastoma cells). To target malignant B cells, investigators have redirected the specificity of T cells using a chimeric immunoreceptor specific for the B-lineage molecule, CD19.

The variable portions of an immunoglobulin heavy and light chain are fused by a flexible linker to form a scFv. This scFv is preceded by a signal peptide to direct the nascent protein to the endoplasmic reticulum and subsequent surface expression (this is cleaved). A flexible spacer allows to the scFv to orient in different directions to enable antigen binding. The transmembrane domain is a typical hydrophobic alpha helix usually derived from the original molecule of the signaling endodomain which protrudes into the cell and transmits the desired signal.

Type I proteins are in fact two protein domains linked by a transmembrane alpha helix in between. The cell membrane lipid bilayer, through which the transmembrane domain passes, acts to isolate the inside portion (endodomain) from the external portion (ectodomain). It is not so surprising that attaching an ectodomain from one protein to an endodomain of another protein results in a molecule that combines the recognition of the former to the signal of the latter.

Ectodomain. A signal peptide directs the nascent protein into the endoplasmic reticulum. This is essential if the receptor is to be glycosylated and anchored in the cell membrane. Any eukaryotic signal peptide sequence usually works fine. Generally, the signal peptide natively attached to the amino-terminal most component is used (e.g., in a scFv with orientation light chain-linker-heavy chain, the native signal of the light-chain is used.

The antigen recognition domain is usually an scFv. There are however many alternatives. An antigen recognition domain from native T-cell receptor (TCR) alpha and beta single chains have been described, as have simple ectodomains (e.g., CD4 ectodomain to recognize HIV infected cells) and more exotic recognition components such as a linked cytokine (which leads to recognition of cells bearing the cytokine receptor). In fact, almost anything that binds a given target with high affinity can be used as an antigen recognition region.

A spacer region links the antigen binding domain to the transmembrane domain. It should be flexible enough to allow the antigen binding domain to orient in different directions to facilitate antigen recognition. The simplest form is the hinge region from IgG1. Alternatives include the $CH_2CH_3$ region of immunoglobulin and portions of CD3. For most scFv based constructs, the IgG1 hinge suffices. However, the best spacer often has to be determined empirically.

Transmembrane domain. The transmembrane domain is a hydrophobic alpha helix that spans the membrane. Generally, the transmembrane domain from the most membrane proximal component of the endodomain is used. Interestingly, using the CD3-zeta transmembrane domain may result in incorporation of the artificial TCR into the native TCR a factor that is dependent on the presence of the native CD3-zeta transmembrane charged aspartic acid residue. Different transmembrane domains result in different receptor stability. The CD28 transmembrane domain results in a brightly expressed, stable receptor.

Endodomain. This is the "business-end" of the receptor. After antigen recognition, receptors cluster and a signal is transmitted to the cell. The most commonly used endodomain component is CD3-zeta which contains 3 ITAMs. This transmits an activation signal to the T cell after antigen is bound. CD3-zeta may not provide a fully competent activation signal and additional co-stimulatory signaling is needed.

"First-generation" CARs typically had the intracellular domain from the CD3 chain, which is the primary transmitter of signals from endogenous TCRs. "Second-generation" CARs add intracellular signaling domains from various costimulatory protein receptors (e.g., CD28, 41BB, ICOS) to the cytoplasmic tail of the CAR to provide additional signals to the T cell. Preclinical studies have indicated that the second generation of CAR designs improves the antitumor activity of T cells. More recent, "third-generation" CARs combine multiple signaling domains, such as CD3z-CD28-41BB or CD3z-CD28-OX40, to further augment potency.

G. ADCs

Antibody Drug Conjugates or ADCs are a new class of highly potent biopharmaceutical drugs designed as a targeted therapy for the treatment of people with infectious disease. ADCs are complex molecules composed of an antibody (a whole mAb or an antibody fragment such as a single-chain variable fragment, or scFv) linked, via a stable chemical linker with labile bonds, to a biological active cytotoxic/anti-viral payload or drug. Antibody Drug Conjugates are examples of bioconjugates and immunoconjugates.

By combining the unique targeting capabilities of monoclonal antibodies with the cancer-killing ability of cytotoxic drugs, antibody-drug conjugates allow sensitive discrimination between healthy and diseased tissue. This means that, in contrast to traditional systemic approaches, antibody-drug conjugates target and attack the infected cell so that healthy cells are less severely affected.

In the development ADC-based anti-tumor therapies, an anticancer drug (e.g., a cell toxin or cytotoxin) is coupled to an antibody that specifically targets a certain cell marker (e.g., a protein that, ideally, is only to be found in or on infected cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cell or impairs viral replication. Due to this targeting, ideally the drug has lower side effects and gives a wider therapeutic window than other agents.

A stable link between the antibody and cytotoxic/antiviral agent is a crucial aspect of an ADC. Linkers are based on chemical motifs including disulfides, hydrazones or peptides (cleavable), or thioethers (noncleavable) and control the distribution and delivery of the cytotoxic agent to the target cell. Cleavable and noncleavable types of linkers have been proven to be safe in preclinical and clinical trials. Brentuximab vedotin includes an enzyme-sensitive cleavable linker that delivers the potent and highly toxic antimicrotubule agent Monomethyl auristatin E or MMAE, a synthetic antineoplastic agent, to human specific CD30-positive malignant cells. Because of its high toxicity MMAE, which inhibits cell division by blocking the polymerization of tubulin, cannot be used as a single-agent chemotherapeutic drug. However, the combination of MMAE linked to an anti-CD30 monoclonal antibody (cAC10, a cell membrane protein of the tumor necrosis factor or TNF receptor) proved to be stable in extracellular fluid, cleavable by cathepsin and safe for therapy. Trastuzumab emtansine, the other approved ADC, is a combination of the microtubule-formation inhibitor mertansine (DM-1), a derivative of the Maytansine, and antibody trastuzumab (Herceptin®/Genentech/Roche) attached by a stable, non-cleavable linker.

The availability of better and more stable linkers has changed the function of the chemical bond. The type of linker, cleavable or noncleavable, lends specific properties to the cytotoxic (anti-cancer) drug. For example, a non-cleavable linker keeps the drug within the cell. As a result, the entire antibody, linker and cytotoxic agent enter the targeted cancer cell where the antibody is degraded to the level of an amino acid. The resulting complex—amino acid, linker and cytotoxic agent—now becomes the active drug. In contrast, cleavable linkers are catalyzed by enzymes in the host cell where it releases the cytotoxic agent.

Another type of cleavable linker, currently in development, adds an extra molecule between the cytotoxic/antiviral drug and the cleavage site. This linker technology allows researchers to create ADCs with more flexibility without worrying about changing cleavage kinetics. Researchers are also developing a new method of peptide cleavage based on Edman degradation, a method of sequencing amino acids in a peptide. Future direction in the development of ADCs also include the development of site-specific conjugation (TDCs) to further improve stability and therapeutic index and a emitting immunoconjugates and antibody-conjugated nanoparticles.

H. BiTES

Bi-specific T-cell engagers (BiTEs) are a class of artificial bispecific monoclonal antibodies that are investigated for the use as anti-cancer drugs. They direct a host's immune system, more specifically the T cells' cytotoxic activity, against infected cells. BiTE is a registered trademark of Micromet AG.

BiTEs are fusion proteins consisting of two single-chain variable fragments (scFvs) of different antibodies, or amino acid sequences from four different genes, on a single peptide chain of about 55 kilodaltons. One of the scFvs binds to T cells via the CD3 receptor, and the other to an infected cell via a specific molecule.

Like other bispecific antibodies, and unlike ordinary monoclonal antibodies, BiTEs form a link between T cells and target cells. This causes T cells to exert cytotoxic/antiviral activity on infected cells by producing proteins like perforin and granzymes, independently of the presence of MHC I or co-stimulatory molecules. These proteins enter infected cells and initiate the cell's apoptosis. This action mimics physiological processes observed during T cell attacks against infected cells.

I. Intrabodies

In a particular embodiment, the antibody is a recombinant antibody that is suitable for action inside of a cell—such antibodies are known as "intrabodies." These antibodies may interfere with target function by a variety of mechanism, such as by altering intracellular protein trafficking, interfering with enzymatic function, and blocking protein-protein or protein-DNA interactions. In many ways, their structures mimic or parallel those of single chain and single domain antibodies, discussed above. Indeed, single-transcript/single-chain is an important feature that permits intracellular expression in a target cell, and also makes protein transit across cell membranes more feasible. However, additional features are required.

The two major issues impacting the implementation of intrabody therapeutic are delivery, including cell/tissue targeting, and stability. With respect to delivery, a variety of approaches have been employed, such as tissue-directed delivery, use of cell-type specific promoters, viral-based delivery and use of cell-permeability/membrane translocating peptides. With respect to the stability, the approach is generally to either screen by brute force, including methods that involve phage display and may include sequence maturation or development of consensus sequences, or more directed modifications such as insertion stabilizing sequences (e.g., Fc regions, chaperone protein sequences, leucine zippers) and disulfide replacement/modification.

An additional feature that intrabodies may require is a signal for intracellular targeting. Vectors that can target intrabodies (or other proteins) to subcellular regions such as the cytoplasm, nucleus, mitochondria and ER have been designed and are commercially available (Invitrogen Corp.; Persic et al., 1997).

By virtue of their ability to enter cells, intrabodies have additional uses that other types of antibodies may not achieve. In the case of the present antibodies, the ability to interact with the MUC1 cytoplasmic domain in a living cell may interfere with functions associated with the MUC1 CD, such as signaling functions (binding to other molecules) or oligomer formation. In particular, it is contemplated that such antibodies can be used to inhibit MUC1 dimer formation.

J. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies are bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

III. ACTIVE/PASSIVE IMMUNIZATION AND TREATMENT/PREVENTION OF RIFT VALLEY FEVER VIRUS INFECTION

A. Formulation and Administration

The present disclosure provides pharmaceutical compositions comprising anti-Rift Valley Fever Virus antibodies and antigens for generating the same. Such compositions comprise a prophylactically or therapeutically effective amount of an antibody or a fragment thereof, or a peptide immunogen, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, intrarectal, vaginal, topical or delivered by mechanical ventilation.

Active vaccines are also envisioned where antibodies like those disclosed are produced in vivo in a subject at risk of Rift Valley Fever Virus infection. Such vaccines can be formulated for parenteral administration, e.g., formulated for injection via the intradermal, intravenous, intramuscular, subcutaneous, or even intraperitoneal routes Administration by intradermal and intramuscular routes are contemplated. The vaccine could alternatively be administered by a topical route directly to the mucosa, for example by nasal drops, inhalation, by nebulizer, or via intrarectal or vaginal delivery. Pharmaceutically acceptable salts include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Passive transfer of antibodies, known as artificially acquired passive immunity, generally will involve the use of intravenous or intramuscular injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAb). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

B. ADCC

Antibody-dependent cell-mediated cytotoxicity (ADCC) is an immune mechanism leading to the lysis of antibody-coated target cells by immune effector cells. The target cells are cells to which antibodies or fragments thereof comprising an Fc region specifically bind, generally via the protein part that is N-terminal to the Fc region. By "antibody having increased/reduced antibody dependent cell-mediated cytotoxicity (ADCC)" is meant an antibody having increased/reduced ADCC as determined by any suitable method known to those of ordinary skill in the art.

As used herein, the term "increased/reduced ADCC" is defined as either an increase/reduction in the number of target cells that are lysed in a given time, at a given concentration of antibody in the medium surrounding the target cells, by the mechanism of ADCC defined above, and/or a reduction/increase in the concentration of antibody, in the medium surrounding the target cells, required to achieve the lysis of a given number of target cells in a given time, by the mechanism of ADCC. The increase/reduction in ADCC is relative to the ADCC mediated by the same antibody produced by the same type of host cells, using the same standard production, purification, formulation and storage methods (which are known to those skilled in the art), but that has not been engineered. For example, the increase in ADCC mediated by an antibody produced by host cells engineered to have an altered pattern of glycosylation (e.g., to express the glycosyltransferase, GnTIII, or other glycosyltransferases) by the methods described herein, is relative to the ADCC mediated by the same antibody produced by the same type of non-engineered host cells.

C. CDC

Complement-dependent cytotoxicity (CDC) is a function of the complement system. It is the processes in the immune system that kill pathogens by damaging their membranes without the involvement of antibodies or cells of the immune system. There are three main processes. All three insert one or more membrane attack complexes (MAC) into the pathogen which cause lethal colloid-osmotic swelling, i.e., CDC. It is one of the mechanisms by which antibodies or antibody fragments have an anti-viral effect.

IV. ANTIBODY CONJUGATES

Antibodies of the present disclosure may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Additional types of antibodies contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850,752, 3,939,350, 3,996,345, 4,277,437, 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. IMMUNODETECTION METHODS

In still further embodiments, the present disclosure concerns immunodetection methods for binding, purifying, removing, quantifying and otherwise generally detecting Rift Valley Fever Virus and its associated antigens. While such methods can be applied in a traditional sense, another use will be in quality control and monitoring of vaccine and other virus stocks, where antibodies according to the present disclosure can be used to assess the amount or integrity (i.e., long term stability) of antigens in viruses. Alternatively, the methods may be used to screen various antibodies for appropriate/desired reactivity profiles.

Other immunodetection methods include specific assays for determining the presence of Rift. Valley Fever Virus in a subject. A wide variety of assay formats are contemplated, but specifically those that would be used to detect Rift Valley Fever Virus in a fluid obtained from a subject, such as saliva, blood, plasma, sputum, semen or urine. In particular, semen has been demonstrated as a viable sample for detecting viruses (Purpura et al., 2016; Mansuy et al., 2016; Barzon et al., 2016; Gornet et al., 2016; Duffy et al., 2009; CDC, 2016; Halfon et al., 2010; Elder et al. 2005). The assays may be advantageously formatted for non-healthcare (home) use, including lateral flow assays (see below) analogous to home pregnancy tests. These assays may be packaged in the form of a kit with appropriate reagents and instructions to permit use by the subject of a family member.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of Rift Valley Fever Virus antibodies directed to specific parasite epitopes in samples also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing Rift Valley Fever Virus and contacting the sample with a first antibody in accordance with the present disclosure, as the case may be, under conditions effective to allow the formation of immunocomplexes.

These methods include methods for purifying Rift Valley Fever Virus or related antigens from a sample. The antibody will preferably be linked to a solid support, such as in the form of a column matrix, and the sample suspected of containing the Rift Valley Fever Virus or antigenic component will be applied to the immobilized antibody. The unwanted components will be washed from the column, leaving the Rift Valley Fever Virus antigen immunocomplexed to the immobilized antibody, which is then collected by removing the organism or antigen from the column.

The immunobinding methods also include methods for detecting and quantifying the amount of Rift Valley Fever Vitus or related components in a sample and the detection and quantification of any immune complexes formed during the binding process. Here, one would obtain a sample suspected of containing Rift. Valley Fever Virus or its antigens and contact the sample with an antibody that binds Rift Valley Fever Virus or components thereof, followed by detecting and quantifying the amount of immune complexes formed under the specific conditions. In terms of antigen detection, the biological sample analyzed may be any sample that is suspected of containing Rift Valley Fever Virus or Rift Valley Fever Virus antigen, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to Rift Valley Fever Virus or Rift Valley Fever Virus antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histo-enzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the Rift Valley Fever Virus or Rift Valley Fever Virus antigen is added to the wells. After binding and washing to remove non-specifically bound immune complexes, the bound antigen may be detected. Detection may be achieved by the addition of another anti-Rift Valley Fever Virus antibody that is linked to a detectable label. This type of ELISA is a simple "sandwich ELISA." Detection may also be achieved by the addition of a second anti-Rift Valley Fever Virus antibody, followed by the addition of a third antibody that has binding affinity for the second antibody, with the third antibody being linked to a detectable label.

In another exemplary ELISA, the samples suspected of containing the Rift Valley Fever Virus or Rift Valley Fever Virus antigen are immobilized onto the well surface and then contacted with the anti-Rift Valley Fever Virus antibodies of the disclosure. After binding and washing to remove non-specifically bound immune complexes, the bound anti-Rift Valley Fever Virus antibodies are detected. Where the initial anti-Rift Valley Fever Virus antibodies are linked to a detectable label, the immune complexes may be detected directly. Again, the immune complexes may be detected using a second antibody that has binding affinity for the first anti-Rift Valley Fever Virus antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C. or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present disclosure contemplates the use of competitive formats. This is particularly useful in the detection of Riff Valley Fever Virus antibodies in sample. In competition-based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventor proposes the use of labeled Rift Valley Fever Virus monoclonal antibodies to determine the amount of Rift Valley Fever Virus antibodies in a sample. The basic format would include contacting a known amount of Rift Valley Fever Virus monoclonal antibody (linked to a detectable label) with Rift Valley Fever Virus antigen or particle. The Rift Valley Fever Virus antigen or organism is preferably attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

B. Western Blot

The western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Lateral Flow Assays

Lateral flow assays, also known as lateral flow immunochromatographic assays, are simple devices intended to detect the presence (or absence) of a target analyte in sample (matrix) without the need for specialized and costly equipment, though many laboratory-based applications exist that are supported by reading equipment. Typically, these tests are used as low resources medical diagnostics, either for home testing, point of care testing, or laboratory use. A widely spread and well-known application is the home pregnancy test.

The technology is based on a series of capillary beds, such as pieces of porous paper or sintered polymer. Each of these elements has the capacity to transport fluid (e.g., urine) spontaneously. The first element (the sample pad) acts as a sponge and holds an excess of sample fluid. Once soaked, the fluid migrates to the second element (conjugate pad) in which the manufacturer has stored the so-called conjugate, a dried format of bio-active particles (see below) in a salt-sugar matrix that contains everything to guarantee an optimized chemical reaction between the target molecule (e.g., an antigen) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these strips, analyte has been bound on the particle and the third 'capture' molecule binds the complex. After a while, when more and more fluid has passed the stripes, particles accumulate and the stripe-area changes color. Typically, there are at least two stripes: one (the control) that captures any particle and thereby shows that reaction conditions and technology worked fine, the second contains a specific capture molecule and only captures those particles onto which an analyte molecule has been immobilized. After passing these reaction zones, the fluid enters the final porous material—the wick—that simply acts as a waste container. Lateral Flow Tests can operate as either competitive or sandwich assays. Lateral flow assays are disclosed in U.S. Pat. No. 6,485,982.

D. Immunohistochemistry

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

E. Immunodetection Kits

In still further embodiments, the present disclosure concerns immunodetection kits for use with the immunodetection methods described above. As the antibodies may be used to detect Rift Valley Fever Virus or Rift Valley Fever Virus antigens, the antibodies may be included in the kit. The immunodetection kits will thus comprise, in suitable container means, a first antibody that binds to Rift Valley Fever Virus or Rift Valley Fever Virus antigen, and optionally an immunodetection reagent.

In certain embodiments, the Rift Valley Fever Virus antibody may be pre-bound to a solid support, such as a column matrix and/or well of a microtiter plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of the Rift Valley Fever Virus or Rift Valley Fever Virus antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

F. Vaccine and Antigen Quality Control Assays

The present disclosure also contemplates the use of antibodies and antibody fragments as described herein for use in assessing the antigenic integrity of a viral antigen in a sample. Biological medicinal products like vaccines differ from chemical drugs in that they cannot normally be characterized molecularly; antibodies are large molecules of significant complexity and have the capacity to vary widely from preparation to preparation. They are also administered to healthy individuals, including children at the start of their lives, and thus a strong emphasis must be placed on their quality to ensure, to the greatest extent possible, that they are efficacious in preventing or treating life-threatening disease, without themselves causing harm.

The increasing globalization in the production and distribution of vaccines has opened new possibilities to better manage public health concerns but has also raised questions about the equivalence and interchangeability of vaccines procured across a variety of sources. International standardization of starting materials, of production and quality control testing, and the setting of high expectations for regulatory oversight on the way these products are manufactured and used, have thus been the cornerstone for continued success. But it remains a field in constant change, and continuous technical advances in the field offer a promise of developing potent new weapons against the oldest public health threats, as well as new ones—malaria, pandemic influenza, and HIV, to name a few—but also put a great pressure on manufacturers, regulatory authorities, and the wider medical community to ensure that products continue to meet the highest standards of quality attainable.

Thus, one may obtain an antigen or vaccine from any source or at any point during a manufacturing process. The quality control processes may therefore begin with preparing a sample for an immunoassay that identifies binding of an antibody or fragment disclosed herein to a viral antigen. Such immunoassays are disclosed elsewhere in this document, and any of these may be used to assess the structural/antigenic integrity of the antigen. Standards for finding the sample to contain acceptable amounts of antigenically correct and intact antigen may be established by regulatory agencies.

Another important embodiment where antigen integrity is assessed is in determining shelf-life and storage stability. Most medicines, including vaccines, can deteriorate over time. Therefore, it is critical to determine whether, over time, the degree to which an antigen, such as in a vaccine, degrades or destabilizes such that is it no longer antigenic and/or capable of generating an immune response when administered to a subject. Again, standards for finding the sample to contain acceptable amounts of antigenically intact antigen may be established by regulatory agencies.

In certain embodiments, viral antigens may contain more than one protective epitope. In these cases, it may prove useful to employ assays that look at the binding of more than one antibody, such as 2, 3, 4, 5 or even more antibodies. These antibodies bind to closely related epitopes, such that they are adjacent or even overlap each other. On the other hand, they may represent distinct epitopes from disparate parts of the antigen. By examining the integrity of multiple epitopes, a more complete picture of the antigen's overall integrity, and hence ability to generate a protective immune response, may be determined.

Antibodies and fragments thereof as described in the present disclosure may also be used in a kit for monitoring the efficacy of vaccination procedures by detecting the presence of protective Rift Valley Fever Virus antibodies. Antibodies, antibody fragment, or variants and derivatives thereof, as described in the present disclosure may also be used in a kit for monitoring vaccine manufacture with the desired immunogenicity.

VI. EXAMPLES

The following examples are included to demonstrate preferred embodiments. It should be appreciated by those of skill in the art that the techniques disclosed in the examples that follow represent techniques discovered by the inventor to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

This panel of human monoclonal antibodies was isolated from human donors that have either been given MP-12 vaccine strain of RVFV or are wild-type survivors of infection. This panel was isolated using the hybridoma process and screening by binding to cell expressing the RVFV ZH548 full length M-segment and by neutralization to MP-12. The panel has displayed extraordinary neutralization and protection capacity against wild-type virus. Unique epitope and mechanism of action are displayed by these mAbs. The most potent mAbs recognize RVFV Gn domain A, and one characterized mAbs recognize Gn domain B. Gc specific mAbs either identify fusion loop proximal region or Domain I Furthermore, a subset of potent mAbs are unable to bind to Gn or Gc head domains, indicating this is a complex uncharacterized epitope. These mAbs can be used as a prophylaxis, and therapeutic evaluation is underway.

TABLE 1

NUCLEOTIDE SEQUENCES FOR ANTIBODY VARIABLE REGIONS

| Clone | SEQ ID NO: | Chain | Variable Sequence Region |
|---|---|---|---|
| RVFV-121 | 1 | heavy | CAGATGCAGCTGCAGGAGTCGGGCCCAGGACTGGTGAAGCCTTCGGGGACCCTGTCCCTCACCTGCGCTGTCTCTGGTGACTCCATCAGCACTAGTACCTGGTGGAGTTGGGTCCGCCAGTCCCCAGGGAAGGGGCTGGAGTGGATTGGGGAAATCTATCATAGTGAGAGCACCAACTACAACCCGTCCCTCAAGAGTCGAGTCAGCTTATCACTAGACAAGTCCAAAAACCAGTTGTCCCTGAGGCTGAGCTCTGTGACCGCCGCGGACACGGGCGTGTATTACTGTGCGAGAGGAAGCTTAGTCTTTGACTACTGGGGCCAGGGAGCCCAGGTCGTCGTCTCCTCA |
| | 2 | light | GAAATAGTGATGACGCAGTCTCCAGCCACCCTGTCTGTGTCTCCAGGGGAAAGAGCCACCCTCTCCTGTAGGGCCAGTCAGAGTGTTAGCAGTAATTTAGCCTGGTACCAGCAGAAACCTGGCCAGGCTCCCAGGCTCCTCATCTATGCTGCATCCACCAGGGCCACTGGTATCCCAGCCAGGTTCAGTGGCAGTGGGTCTGGGACAGAGTTCACTCTCACCATCAGCAGCCTGCAGTCTGAAGATTTTGCAGTTTATTACTGTCAGCAGTTTAATAACTGGCCTAGGACGTTCGGCCAAGGGACCAAGGTGGAAATCAAA |
| RVFV-127 | 3 | heavy | CAGGTGCAGCTGCAGGAGTCGGGCCCAGGACTGGTGAAGCCTTCGGAGACCCTGTCCCTCACCTGCACTGTCTCTGGTGACTCCGTCAGAAATTACTACTGGAGCTGGATCCGGCAGCCCCCAGGGGAGGGACTGGAGTGGATTGGGTATATCTATTACAGTGGGAGCACCGACTTCAACCCCTCCCTCAAGAGTCGAGTCACCATGTCAGTGGACACGTCCAAGAACCACTTCTCCCTGAAGCTGAGGTCTGTGACCGCTGCGGACACGGCCATGTATTACTGTGCGAGAGTCGCTATACGTACAGATGGCTACATACGGGCTTTTGATATCTGGGGCGCAGGGACAATGGTCACCGTCTCTTCA |
| | 4 | light | GACATCCAGATGACCCAGTCTCCATCCTCCCCGTCTGCATCTGTAGGAGACAGAGTCACCGTCACTTGCCGGGCAAGTCAGAGCATTAGGAACTACTTAAATTGGTATCAGCAGAAACCAGGGAAAGCCCCTAAGCTCCTGATATATGCTGCATCCAGTTTACAAAGTGGGGTCCCATCAAGGTTCAGTGGCAGTGGATCTGGGACAGAATTCACTCTCACCATCAGCAGTCTGCAACCTGAAGATTTTGCAACGTACTACTGTCAACAGACGTACAGTACCGCGTGGACGTTCGGCCAAGGGACCAAGGTGGAAATCAAA |
| RVFV-128A | 5 | heavy | CAGGTGCAGCTGCAGGAGTCGGGCCCAGGACTGGTGAAGCCTTCACAGACCCTGTCCCTCACCTGCACTGTCTCTGGTGGCTCCATCAGCAGTGGTGATTACTTCTGGAGTTGGATCCGCCAGCCCCCAGGGAAGGGCCTGGAGTGGATTGGGTACATCTATTACAGTGGGAGCACCTACTACAACCCGTCCCTCAAGAGTCGAATTACCATATCAGTAGACACGTCCAAGAACCAGTTTTCCCTGAAGCTGAGCTCTGTGACTGCCGCAGACACGGCCGTGTTTTACTGTGCCAGAGTCCAGACTCCGGGGAGTGATACTTACTACTTTGACTACTGGGGCCAGGGAACCCTGGTCACCGTCTCCTCA |
| | 6 | light | GACATCCAGATGACCCAGTCTCCATCCTCCCTGTCTGCTTCTGTAGGAGACAGAGTCACCATCACTTGCCGGGCAAGTCAGAGCATTAGCAGCTATTTAAATTGGTATCAGCAGAAACCAGGGAAAGCCCCTAAGCTCCTGATCTATGCTGCATCCAGTTTGCAAAGTGGGGTCCCATCAAGGTTCAGTGGCAGTGGATCTGGGACAGATTTCACTCTCACCATCAGCAGTCTGCAACCTGAAGATTTTGCAACTTACTTCTGTCAACAGAGTTACAGTACCCCTATGTACACTTTTGGCCAGGGGACCAAGCTGGAGATCAAA |
| RVFV-128B | 7 | heavy | CAGCTGCAGCTGCAGGAGTCGGGCCCAGGACTGGTGAAGCCATCGGAGACCCTGTCCCTCACCTGCACTGTCTCTGGTGGCTCCATCAGCAGTAGTAGTTACCACTGGGGCTGGATCCGCCAGCCCCCAGGGAAGGGGCTGGAGTGGATTGGCAGTATTTATTATACTGGGAGCACCTACTACAACCCGTCCCTCAAGAGTCGAGTCATCATATCCGTAGACGCGTCCAAGAACCAGTTCTCCCTGAAGCTGAGCTCTGTGACCGCCGCAGACACGGCTGTCTATTACTGTGCGAGACGGTCGCTTAGGAGTGGCTGGGCCGCCGCTATTGACTTCTGGGGCCAGGGAACCCTGGTCACCGTCTCCTCA |
| | 8 | light | GACATCCAGATGACCCAGTCTCCATCCTCCCTGTCTGCTTCTGTAGGAGACAGAGTCACCATCACTTGCCGGGCAAGTCAGAGCATTAGCAGCTATTTAAATTGGTATCAGCAGAAACCAGGGAAAGCCCCTAAGCTCCTGATCTATGCTGCATCCAGTTTGCAAAGTGGGGTCCCATCAAGGTTCAGTGGCAGTGGATCTGGGACAGATTTCACTCTCACCATCAGCAGTCTGCAACCTGAAGATTTTGCAACTTACTTCTGTCAACAGAGTTACAGTACCCCTATGTACACTTTTGGCCAGGGGACCAAGCTGGAGATCAAA |
| RVFV-132 | 9 | heavy | CAGGTGCAGCTGCAGGAGTCGGGCCCAGGACTGGTGAAGCCTTCGGAGACCCTGTCCCTCACCTGCACTGTCTCTGGTGGCTCCGTCAGCAGTGGTAGTTACTACTGGAGCTGGATCCGGCAGCCCCCAGGGAAGGGACTGGAGTGGATTGGGTATATCTATTACAGTGGGAGCACCAACTACAACCCCTCCCTCAAGAGTCGAGTCACCATATCAGTAGACACGTCCAAGAACCAGTTCTCCCTGAAGCTGAGCTCTGTGACCGCTGCGGACACGGCCGTGTATTACTGTGCGAGAGATTATCGCGTGACTACGGGGAACTACTACTACTACGGTATGGACGTCTGGGGCCAAGGGACCACGGTCACCGTCTCCTCA |
| | 10 | light | CAGTCTGTGCTGACTCAGCCACCCTCAGCGTCTGGGACCCCCGGGCAGAGGGTCACCATCTCTTGTTCTGGAAGCAGCTCCAACATCGGAAGTAATACTGTAAACTGGTACCAGCAGCTCCCAGGAACGGCCCCCAAACTCCTCATCTATAGTAATAATCAGCGGCCCTCAGGGGTCCCTGACCGATTCTCTGGCTCCAAGTCTGGCACCTCAGCCTCCCTGGCCATCAGTGGGCTCCAGTCTGAGGATGAGGCTGATTATTACTGTGCAGCATGGGATGACAGCCTGAATGGTTGGGTGTTCGGCGGAGGGACCAAGCTGACCGTCCTA |
| RVFV-140A | 11 | heavy | TCAACGCAGAGTACATGGGCGGGCCCAGGACTGGTGAAGCCTTCACAGACCCTGTCCCTCACCTGCACTGTCTCTGGTGGCTCCGTCAGCAGTGGTGATTACTACTGGAGTTGGATCCGCCAGCCCCCAGGGAGGGGCCTGGAGTGGATTGGGTACATCTCTTACAGTGGGAGCACCTATTACAACCCGTCCCTCGAGAGTCGAATTACCATGTCAGGCGACACGTCCAAGCAGCAGTTCTCCCTGAAGCTGAGCTCTGTGACTGTCGCGGACACGGCCGTCTATTACTGTGCCACCAATTACTTCCATTTACATGACTTCGGTGACCTCTACTGGTACTTCGATCTCTGGGGCCGTGGCACCCTGGTCACTGTCTCCTCA |
| | 12 | light | CAGTCTGCCCTGACTCAGCCTGCCTCCGTGTCTGGGTCTCCTGGACAGTCGATCACCATCTCCTGCACTGGAACCAGCAGTGACATTGGTGCTTATAACTTTGTCTCCTGGTACCAACAACACCCAGGCACAGCCCCCAAACTCCTGATTTATGATGTCACTAATCGGCCCTCAGGGGTTTCTAATCGCTTCTCTGGCTCCAAGTCTGGCAACACGGCCTCCCTGACCATCTCTGGGCTCCAGGCTGAGGACGAGGCTAATTATTACTGCAACTCATATACAAGCAGCAGTCATGTGGTCTTCGGCGGCGGGACCAAGCTGACCGTCCTA |
| RVFV-140B | 13 | heavy | CAGTTGCAGCTGCAGGAGTCGGGCCCAGGACTGGCGAGGCCTTCGGAGACCCCGTCCCTCACCTGCACTGTCTCTGGTGGCTCCATCAGTAGTAGTGTTTACTATTGGGGCTGGATCCGCCAGCCCCCAGGGAAGGGGCTGGAGTGGATTGGGAGTATCTATTATAGTGGGTACACCAACTACAACCCGTCCCTCAAGAGTCGAGTCTCCATATCTGTAGACACGTCCAAGAACCAGTTCTCCCTGCAACTGAACTCTGTGACCGCCGCAGACACGGCTGTTTATTACTGTGCGAGACATTCGGATTGTGGTAATGATTGCTATTACTTTGACTACTGGGGCCAGGGAACCCTGGTCACCGTCTCCTCA |

TABLE 1-continued

| NUCLEOTIDE SEQUENCES FOR ANTIBODY VARIABLE REGIONS | | | |
|---|---|---|---|
| Clone | SEQ ID NO: | Chain | Variable Sequence Region |
| | 14 | light | TCCTATGAGCTGACTCAGCCACCCTCAGTGTCCGTGTCCCCAGGACAGACAGCCAGCATCACCTGCTCTGGAGATAGATTGGGGGATAAATATGCTTCCTGGTATCAGCAGAAGCCAGGCCAGTCCCCTGTGCTGGTCATCTATCAAGATTACAAGCGGCCCTCAGGGATCCCTGAGCGATTCTCTGGCTCCAACTCTGGGCACACAGCCACTCTGACCATCAGCGGGACCCAGGCTATGGATGAGGCTGACTATTTCTGTCAGGCGTGGGACAGCAGTGATGGTTCTGTCTTCGGAACTGGGACCAAGGTCACCGTCCTG |
| RVFV-140C | 15 | heavy | CAGGTGCAGCTGCAGGAGTCGGGCCCAGGACTGGTGAAGCCTTCACAGACCCTGTCCCTCACCTGCACTGTCTCTGGTGGCTCCGTCAGCAGTGGTGATTACTACTGGAGTTGGATCCGCCAGCCCCCAGGGAGGGGCCTGGAGTGGATTGGGTACATCTCTTACAGTGGGAGCACCTATTACAACCCGTCCCTCGAGAGTCGAATTACCATGTCAGGCGACACGTCCAAGCAGCAGTTCTCCCTGAAGCTGAGCTCTGTGACTGTCGCGGACACGGCCGTCTATTACTGTGCCACCAATTACTTCCATTTACATGACTTCGGTGACCTCTACTGGTACTTCGATCTCTGGGGCCGTGGCACCCTGGTCACTGTCTCCTCA |
| | 16 | light | CAGTCTGCCCTGACTCAGCCTGCCTCCGTGTCTGGGTCTCCTGGACAGTCGATCACCATCTCCTGCACTGGAACCAGCAGTGACATTGGTGCTTATAACTTTGTCTCCTGGTACCAACAACACCCAGGCACAGCCCCCAAACTCCTGATTTATGATGTCACTAATCGGCCCTCAGGGGTTTCTAATCGCTTCTCTGGCTCCAAGTCTGGCAACACGGCCTCCCTGACCATCTCTGGGCTCCAGGCTGAGGACGAGGCTAATTATTACTGCAACTCATATACAAGCAGCAGTCATGTGGTCTTCGGCGGCGGGACCAAGCTGACCGTCCTA |
| RVFV-142A | 17 | heavy | GAGGTGCAGCTGGTGGAGTCTGGGGGAGGCTTGGTCCAGCCTGGGGGGTCCCTGAGACTCTCCTGTGCAGCCTCTGGATTCATGTTTAGTCGGTATTGGATGAGCTGGGTCCGCCAGGCTCCAGGGAAGGGGCTGGAGTGGGTGGCCAACATAAAGCAAGATGGAAGTGAGAAAAACTATGTGGACTCTGTGAAGGGCCGATTCACCATCTCCAGAGACAACGCCAAGAACTCACTGTATCTGCAAATGAACACCCTGAGAGCCGAGGACACGGCTGTGTATTACTGTGCGAGAGGAGAATACTATGGTTCAGGGAGTTATTCCTGGGGCCAGGGGACCCTGGTCACCGTCTCCTCA |
| | 18 | light | GACATCCAGATGACCCAGTCTCCTTCCACCCTGTCTGCATCTGTAGGAGACAGAGTCACCATCACTTGCCGGGCCAGTCAGAGTATTAGTAGCTGGTTGGCCTGGTATCAGCAGAAACCAGGGAAAGCCCCTAAGCTCCTGATCTATAAGGCGTCTAGTTTAGAAAGTGGGGTCCCATCAAGGTTCAGCGGCAGTGGATCTGGGACAGAATTCACTCTCACCATCAGCAGCCTGCAGCCTGATGATTTTGCAACTTATTACTGCCAACAGTATAATAGTTACCCGCTCACTTTCGGCGGAGGGACCAAGGTGGAGATCAAA |
| RVFV-142B | 19 | heavy | CAGTTGCAGCTGCAGGAGTCGGGCCCAGGACTGGCGAGGCCTTCGGAGACCCCGTCCCTCACCTGCACTGTCTCTGGTGGCTCCATCAGTAGTAGTGTTTACTATTGGGGCTGGATCCGCCAGCCCCCAGGGAAGGGGCTGGAGTGGATTGGGAGTATCTATTATAGTGGGTACACCAACTACAACCCGTCCCTCAAGAGTCGAGTCTCCATATCTGTAGACACGTCCAAGAACCAGTTCTCCCTGCAACTGAACTCTGTGACCGCCGCAGACACGGCTGTTTATTACTGTGCGAGACATTCGGATTGTGGTAATGATTGCTATTACTTTGACTACTGGGGCCAGGGAACCCTGGTCACCGTCTCCTCA |
| | 20 | light | TCCTATGAGCTGACTCAGCCACCCTCAGTGTCCGTGTCCCCAGGACAGACAGCCAGCATCACCTGCTCTGGAGATAGATTGGGGGATAAATATGCTTCCTGGTATCAGCAGAAGCCAGGCCAGTCCCCTGTGCTGGTCATCTATCAAGATTACAAGCGGCCCTCAGGGATCCCTGAGCGATTCTCTGGCTCCAACTCTGGGCACACAGCCACTCTGACCATCAGCGGGACCCAGGCTATGGATGAGGCTGACTATTTCTGTCAGGCGTGGGACAGCAGTGATGGTTCTGTCTTCGGAACTGGGACCAAGGTCACCGTCCTG |
| RVFV-144 | 21 | heavy | CAGGTGCACCTGCAGGAGTCGGGCCCAGGACTGGTGAAGCCTTCGGAGACCCTGTCCCTCACCTGCACTGTCTCTGGTGGCTCCATCGGCACTTACTACTGGAGCTGGATCCGGCAGCCCCCAGGGAAGGGACTGGAGTGGATTGGGTATGTCTATCACAGTGGGGCCACCAACGACAACCCCTCCCTCATGAGTCGACTCACCATGTCAGTAGACACGTCCAAGAACCAGTTCTCCCTGGACCTGAGGTCTGTGACCGCTGCGGACACGGCCATATATTACTGTGCGAGAGAAGGCTCCAATGGTGACTTCCGAGGGCATTTTGACTCCTGGGGCCAGGGAACCCTGGTCACCGTCTCCTCA |
| | 22 | light | CAGTCTGCCCTGACTCAGCCTGCCTCCGTGTCTGGGTCTCCTGGACAGTCGATCACCATCTCCTGCACTGGAACCAGCAGTGACGTTGGTGGCTTTAACTTTGTCTCCTGGTACCAACAACACCCAGGCAAAGCCCCCAAACTCATGATTTATGATGTCAGTAACCGGCCCTCAGGGGTTTCTAATCGCTTCTCTGGCTCCAAGTCTGGCAACACGGCCTCCCTGACCATCTCTGGGCTCCGGACTGACGACGAGGGTGATTATTACTGCACTTCATACACAAGCAGCAGCACTGTTGTGTTCGGCGGAGGGACCAAGCTGACCGTCCTA |
| RVFV-151 | 23 | heavy | CAGGTGCAGCTACAACAGTGGGGCGCAGGACTGTTGAAGCCTTCGGAGACCCTGTCCCTCACCTGCGCTGTCTATGGTGGGTCCTTCAGTGGTTACTACTGGAGTTGGATCCGCCAGCCCCCAGGGAAGGGGCTGGAGTGGATTGGGGAAATCAATCATAGTGGAAGAACCAAGTACAATCCGTCCCTCTCGAGTGGGCTCACCTTGTCGGTGGACAAGTCCAAGAACCAGTTCTCCCTGAAACTGAGGTCTGTGACCGCCGCGGACACGGCTGTGTATTACTGTGCGAGAGGACATGTCGTTGTGACACCTGCTACTCTCTTTCACCGGGTCGGCGAACACTACTTTGACTTCTGGGGCCAGGGAACCCTGGTCTCCGTCTCCTCA |
| | 24 | light | TCTTCTGAGCTGACTCAGGACCCTGCTGTGTCTGTGGCCTTGGGACAGACAGTCAGGATCACATGCCAAGGAGACAGCCTCAAAAACTATTATGCAAGCTGGTACCAGCAGAAGCCAGGTCGGGCCCCTTTACTTGTCATGTCTGGTAAAAACAACCGGCCCTCAGGGATCCCAGATCGATTCTCTGGCTCCAGCTCAGGAAACACAGCTTCCTTGACCATCACTGGGGCTCAGGCGGAGGATGAGGCTGACTATTACTGTAGCTCCCGGGACAGAAGTGATAAGTATTGGGTTTTCGGCGGAGGGACCAAGGTGACCGTCCTA |
| RVFV-154 | 25 | heavy | CAGGTCCAACTTGTGCAGTCTGGGGCTGAGGTGAAGAGGCCTGGGGCCTCAGTGAAGGTTTCCTGCAAGGCTTCTGGATACACCTTCACTACCTATGCAATACACTGGGTGCGCCAGGCCCCCGGACAAAGGCTTGAGTGGATGGGATGGATCAACGCTGGCAACGGAGACACAAAATACTCACAGAGGTTCCAGGGCAGAGTCACCGTCACCAGGGACACATCCGCGAACACAGCCTACATGGAACTGACCAGCCTGACATCCGAAGACACGGCTGTGTATTACTGTGCGAGAGGTTGGGTGGGTTGTATTGGTAAAAGGGGTAAAACCTGTTACGCGAATTTACCAGATGACTACTGGGGCCAGGGAACCCTGGTCACCGTCTCCTCA |
| | 26 | light | CAGTCTGCCCTGACTCAGCCTGCCTCCGTGTCTGGGTCTCGTGGACAGTCGATCACCATCACCTGCACTGGAACCAGCAGTGACGTTGGTGCTTACAAGTTTGTCTCCTGGTACCAACAACACCCAGGCAAAGCCCCCAATCTCATTATTTATGATGTCAATAGTCGGCCCTCAGGGGTTTCTGATCGCTTCTCTGGCTCCAAGTCTGGCTACACGGCCTCCCTGACCATCTCTGGGCTCCAGGCTGAGGACGAGGCTGATTATTACTGCAGCTCATATACAAGGGGCCCTTATATCTTCGGAACTGGGACCAAGGTCACCGTCCTA |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| RVFV-158 | 27 | heavy | CAGGTGAAGCTGGTGGAGTCTGGGGGAGGCGTGGTCCAGCCTGGGAGGTCCCTGAGACTCTCCTGTGAAGCCTCTAGATTCACCTTCAATACCTACGGCATGCACTGGGTCCGCCAGGCTCCAGGCAAGGGGCTGGAGTGGGTGGCAGTTATATCATATGATGGAAAGAAGAAATACTATGCAGACTCCGCGAAGGGCCGATTCACCATCTCCAGAGACGACTCCAGGAACACACTGTATCTGGAGATGAACAGCCTGCGAGTTGAGGACACGGCTGTGTATTATTGTGCGAGAGATTTAAGGAGATTTTATAGCAATGGCTGGTTCACGGGGTCGGACTTTTGGGGCCAGGGAACCCTGGTCACCGTCTCCTCA |
| | 28 | light | GAAATTGTGTTGACGCAGTCTCCAGCCACCCTGTCTTTGTCTCCAGGGGAGAGAGCCACCCTCTCCTGCGGGGCCAGTCAAACTATTAGCAGCAACAACTTAGCCTGGTATCAGCAGAAACCTGGCCTGGCGCCCAGGCTCCTCATCTATGATGCTTCCACCAGGGCCGCTGGCATCCCACGCAGATTCAGTGGCAGTGGGTCTGGGACAAACTTCACTCTCACCGTCACCAGACTGGACCCTGAAGATTTTGCACTGTATTCCTGTCAGCAGTATGGTCGCTCACCGATCACCTTCGGCCAAGGGACACGACTGGAGATTAAA |
| RVFV-164 | 29 | heavy | CAGGTGGAGCTGCGGGAGTCGGGCCCAGGACTGGTGAAGCCTTCGGGGACCCTGTCCCTCACCTGCGCTGTCTCTGGTGTGTCCATCACCAGTAGTAACTGGTGGAATTGGGTCCGCCAGTCCCCAGGGAAGGGGCTGGAGTGGATTGGGCAAGTCTATCATAGTGGGAGCACCAAGTACAACCCATCCCTCAGGAGTCGACTCACCATATCAGTGGACAAGTCCAAGAACCAGTTCTCCCTGAAGATGAAATATGTGCGCGCCGCGGACACGGCCGTATACTTCTGTGCGAGAGACGGATTTAGTGGTTACGATGTTGCACTTGACAAGTGGGGCCAGGGAACCCTGGTCACCGTCTCTTCA |
| | 30 | light | CAGTCTGTGTTGACGCAGCCGCCCTCAGTGTCTGCGGCCCCAGGACAGAGGGTCACCATCTCCTGCTCTGGAAGCAGCTCCAACATTGGGAATAGTTATGTATCCTGGTACCAGCACCTCCCGGGAACAGCCCCCAAACTCCTCATTTATGACAATAATAAGCGACCCTCAGGGATTCCTGACCGATTCTCTGCCTCCAAGTCTGGCACGTCAGCCACCCTGGGCATCACCGGACTCCGGACTGGGGACGAGGCCGATTATTACTGCGCAACATGGGAGAGCCGCCTGAGTGCTGGCCATGTGGTCTTCGGCGGAGGGACCAAGCTGACCGTCCTC |
| RVFV-166 | 31 | heavy | CAGATCACCTTGCAGGAGTCTGGTCCTACGCTGGTGAAACCCACACGGACCCTCACGCTGACCTGCACCCTCTCTGGGGTCTCACTCAGTAGTAGTGGAGTGGGTGTGGGCTGGATCCGCCAGCCCCCCGGAAGGGCCCTGGAGTGGCTTGCAGTCATCTATTGGGATGATGATAAGCACTACAGGCCATCTCTGAAGAGCAGGCTCACCATCACCAAGGACACCTCCAAAAACCAGGTGGTCCTTACAATGACCAACATGGACCCTGTGGACACAGCCACATATTACTGTGCACACCGAAATATTGTGGTAGTACGAGCTGATCCGCACCGTTGGGCGGGGACCTTTGACTACTGGGGCCAGGGAGCCCTGGTCACCGTCTCGGCA |
| | 32 | light | GAAATTGTGTTGACGCAGTCTCCAGGCACCCTGTCTTTGTCTCCAGGGGAAAGAGCCACCCTCTCCTGCAGGGCCAGTCAGAGTGTTACCAGCAACTACTTAGCCTGGTACCAGCAGAAGCCTGGCCAGGCTCCCAGACTCCTCATCTATGGTGCATCCAGCAGGGCCGCTGGCATCCCAGACAGGTTCAGTGGCAGTGGGTCTGGGACAGACTTCACTCTCACCATCAGCAGGCTGGAGCCTGAAGATCTTGGAGTGTATTCCTGTCAGCAGTACGCTGGTTCACCGTTCACTTTCGGCCCTGGGACCAAAGTGGAAATCAAA |
| RVFV-206 | 33 | heavy | GAGGTGCAGCTGTTGGAGTCTGGGGGAGGCTTGGTACAGCCTGGGGGGTCCCTGAGACTCTCCTGTGCAGCCTCTGGATTCACCTTTAGCAGCTATGCCATGAGCTGGGTCCGCCAGGCTCCAGGGAAGGGGCTGGAGTGGGTCTCAGCTATTAGTGGTAGTGGTGGTAGCACATACTACGCAGACTCCGTGAAGGGCCGGTTCACCATCTCCAGAGACAATTCCAAGAACACGCTGTATCTGCAAATGAACAGCCTGAGAGCCGAGGACACGGCCGTATATTACTGTGCGAAAGATCAAGGAACTATGATAGTAGTGGTTACACTCCCCCCTGGTGCTTTTGATATCTGGGGCCAAGGGACAATGGTCACCGTCTCTTCA |
| RVFV-211 | 34 | heavy | GAGGTGCAGCTGGTGGAGTCTGGGGGAGGCTTGGTCCAGCCTGGGGGGTCCCTGAGACTCTCCTGTGCAGCCTCTGGATTCATGTTTAGTCGGTATTGGATGAGCTGGGTCCGCCAGGCTCCAGGGAAGGGGCTGGAGTGGGTGGCCAACATAAAGCAAGATGGAAGTGAGAAAAACTATGTGGACTCTGTGAAGGGCCGATTCACCATCTCCAGAGACAACGCCAAGAACTCACTGTATCTGCAAATGAACACCCTGAGAGCCGAGGACACGGCTGTGTATTACTGTGCGAGAGGAGAATACTATGGTTCAGGGAGTTATTCCTGGGGCCAGGGGACCCTGGTCACCGTCTCCTCA |
| | 35 | light | GATATTGTGATGACTCAGTCTCCACTCTCCCTGCCCGTCACCCCTGGAGAGCCGGCCTCCATCTCCTGCAGGTCTAGTCAGAGCCTCCTGCATAGTAATGGATACAACTATTTGGATTGGTACCTGCAGAAGCCAGGGCAGTCTCCACAGCTCCTGATCTATTTGGGTTCTAATCGGGCCTCCGGGGTCCCTGACAGGTTCAGTGGCAGTGGATCAGGCACAGATTTTACACTGAAAATCAGCAGAGTGGAGGCTGAGGATGTTGGAGTTTATTACTGCGTGCAAGCTCTACAAATTCCTCTCACTTTCGGCGGAGGGACCAAGGTGGAGATCAAG |
| RVFV-220 | 36 | heavy | CAGGTGCATCTGCAGGAGTCGGGCCCAGGACTGGTGAAGCCTTCACAGGCCCTGTCCCTCACCTGCACTGTCTCTGGTGGCTCCATCAACGGTGATAATTACTACTGGAGTTGGATCCGCCAGCCCCCAGGGAAGGGCCTGGAGTGGATTGGGTACATCTATTACAGTGGGAGCACCTACTACAACCCGTCCCTCAAGAGTCGAATTAGCATATCAGTAGACACGTCCAAGAACCAGTTCTCCCTGAAACTGAGCTCTGTGACTGCCGCAGACACGGCCGTGTATTACTGTGCCAGAGGTGCGGATTGCGGTAATGATTGCTATTACTTTGACTACTGGGGCCAGGGAGCCCTGGTCACCGTCTCCTCA |
| | 37 | light | TCCTATGAGCTGACTCAGCCACCCTCAGTGTCCGTGTCCCCAGGACAGACAGCCAGCATCACCTGCTCTGGAGATAAATTGGGACATAAATATGCTTGCTGGTATCAGCAGAGGCCAGGCCAGTCCCCTGTGCTGGTCATCTATCAAGATAGTAAGCGGCCCTCAGGGATCCCTGAGCGATTCTCTGGCTCCAATTCTGGGAACACAGCCACTCTGACCATCAGCGGGACCCAGGCTGTGGATGAGGCTGACTATTACTGTCAGGCGTGGGACAGCAGCTCCTTCTATGTCTTCGGAACTGGGACCAAGGTCACCGTCCTA |
| RVFV-226 | 38 | heavy | GAAGTGCAGCTGGTGGAGTCTGGGGGAGGCTTGGTACAGCCTGGCAGGTCCCTGAGACTCTCCTGTGCAGCCTCTGGATTCACCTTTGATGATTATGCCATGCACTGGGTCCGGCAAGCTCCAGGGAAGGGCCTGGAGTGGGTCTCAGGTATTAGTTGGAATAGTGGTAGCATAGGCTATGTGGACTCTGTGAAGGGCCGATTCACCATCTCCAGAGACAACGCCAAGAACTCCCTGTATCTGCAAATGAACAGTCTGAGAGCTGAGGACACGGCCTTGTATTACTGTGCAAAAGGTCTAGTGGGAGCTATTCACGATGCTTTTGATATCTGGGGCCAAGGGACAATGGTCACCGTCTCTTCA |
| | 39 | light | GACATCCAGATGACCCAGTCTCCTTCCACCCTGTCTGCATCTGTAGGAGACAGAGTCACCATCACTTGCCGGGCCAGTCAGAGTATTAGTAGCTGGTTGGCCTGGTATCAGCAGAAACCAGGGAAAGCCCCTAAGCTCCTGATCTATAAGGCGTCTAGTTTAGAAAGTGGGGTCCCATCAAGGTTCAGCGGCAGTGGATCTGGGACAGAATTCACTCTCACCATCAGCAGCCTGCAGCCTGATGATTTTGCAACTTATTACTGCCAACAGTATAATAGTTACCCGCTCACTTTCGGCGGAGGGACCAAGGTGGAGATCAAA |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| RVFV-229 | 40 | heavy | CAGGTGCAGCTGCAGGAGTCGGGCCCAGGACTGGTGAAGCCTTCACAGACCCTGTCCCTCACCTGCACTGTCTCTGGTGGCTCCATCAGCAGTGGTGATTACTTCTGGAGTTGGATCCGCCAGCCCCCAGGGAAGGGCCTGGAGTGGATTGGGTACATCTATTACAGTGGGAGCACCTACTACAACCCGTCCCTCAAGAGTCGAATTACCATATCAGTAGACACGTCCAAGAACCAGTTTTCCCTGAAGCTGAGCTCTGTGACTGCCGCAGACACGGCCGTGTTTTACTGTGCCAGAGTCCAGACTCCGGGGAGTGATACTTACTACTTTGACTACTGGGGCCAGGGAACCCTGGTCACCGTCTCCTCA |
| | 41 | light | TCCTATGAGCTGACTCAGCCACCCTCAGTGTCCGTGTCCCCAGGGCAGACAGCCAGCATCACCTGCTCTGGAGATAAATTGGGGGATAAATATGCTTGCTGGTATCAGCAGAAGCCAGGCCAGTCCCCTGTGCTGGTCATCTATCAAGATACCAAGCGGCCCTCAGGGATCCCTGAGCGATTCTCTGGCTCCAACTCTGGGAACACAGCCACTCTGACCATCAGCGGGACCCAGGCTATGGATGAGGCTGACTATTACTGTCAGGCGTGGGACAGCAGCACTGTGGTATTCGGCGGAGGGACCGAGCTGACCGTCCTA |
| RVFV-235B | 43 | heavy | CAGGTGCAGATGGTGCAGTCTGGGGCTGAGGTGAAGAAGCCTGGGGCCTCAGTGAAGGTCTCCTGCAAGGCTTCTGGATACACCTTCACCGGCTACTATATGCACTGGGTGCGACAGGCCCCTGGACAAGGCCTTGAGTGGATGGGATGGATCAACCCTAACAGTGGTGGAACAAACTATGCACAGAAACTTCAGGGCAGGGTCACCATGACCAGGGACACGTCCATCAGCACAGCCTACATGGAGCTGAGCAGGCTGAGATCTGACGACACAGCCGTGTATTACTGTGCGAGAGGCCGTTATTGTGATAGTGCCAGTTGCTATGTCCGTAACTACTTCTACTACATGGACGTCTGGGGCAAAGGGACCACGGTCACCGTCTCCTCA |
| | 44 | light | GAAATTGTGTTGACACAGTCTCCAGCCACCCTGTCTTTGTCTCCAGGGGAAAGAGCCACCCTCTCCTGCAGGGCCAGTCAGAGTGTTAGCAGGTACTTAGCCTGGTACCAACAGAAACTTGGCCAGGCTCCCAGGCTCCTCATCTATGATGCATCCAACAGGGCCACTGGCATCCCAGCCAGGTTCAGTGGCAGTGGGTCTGGGACAGACTTCACTCTCACCATCAGCAGCCTAGAGCCTGAAGATTTTGCAGTTTATTACTGTCAGCAACGTAGCAACTGGCCCACCTTCGGCCAAGGGACACGACTGGACATTAAA |
| RVFV-239 | 45 | heavy | GGAGTGGAGTTGGTGGAGTCCGGGGGAGGGGCAGCTCAGCCGGGGGGGTCCCTGAGACTCTACTGTGCAGCCTCTGGATTCACCTTCAGTAACTACTGGATGAACTGGGTTCGCCAAGGTCCAGGAAAGGGTCTGACCTGGATCGCACGTATTAATGATCATGGGAATTATACAAGTTATGAGGACTCCGTGAAGGGCCGATTCACCATCTCCAGAGACAACACCAAGAATACAGTGTTTTTGCAAATGAACAGTCTGAGACTCGACGACTCGGCTGTCTATTACTGTGTACGAGCCTTCGGGGGGGGCTACTGGGGCCAGGGAACCCCGGTCACCGTCTCCTCA |
| | 46 | light | GATGTTGTGATGACTCAGTCTCCACTCTCCCTGCCCGTCTCCCTTGGACAGCCGGCCTCCATCTCCTGCAAGTCTGGTCAGAGTCTCGTATATAGAGATGGAAACACCTACTTGAGTTGGTTTTTCCAGAGGCCAGGCCAATCTCCAAGGCGCCTAATTTATCAGGTTTTTAAGCGGGACTCTGGGGTCCCAGACAGATTCACCGGCAGTGGGTCAGGCTCCGATTTCACACTGCAAATCAGCAGGGTGCAGTCTGAGGATGTTGGAATTTATTACTGCATGCAATCTACACACTGGCCGTGGACGTTCGGCCAAGGGACCAAGGTGGAAATCAAA |
| RVFV-243 | 47 | heavy | CAGGTGCAGCTGGTGGAGTCTGGGGGAGGCGTGGTCCAGCCTGGGAGGTCCCTGAGACTCTCCTGTGCAGCGTCTGGATTCACCTTCAGTAGCTATGGCATGCACTGGGTCCGCCAGGCTCCAGGCAAGGGGCTGGAGTGGGTGGCAGTTATATGGTATGATGGAAGTAATAAATACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGAACGGAGTATAGCAGCTCGTCAGAACCGGGGGTACTTTGACTACTGGGGCCAGGGAACCCTGGTCACCGTCTCCTCA |
| | 48 | light | GACATCCAGATGACCCAGTCTCCATCCTCCCTGTCTGCATCTGTAGGAGACAGAGTCACCATCACTTGCCGGGCAAGTCAGGGCATTAGAAATGATTTAGGCTGGTATCAGCAGAAACCAGGGAAAGCCCCTAAGCGCCTGATCTATGCTGCATCCAGTTTGCAAAGTGGGGTCCCATCAAGGTTCAGCGGCAGTGGATCTGGGACAGAATTCACTCTCACAATCAGCAGCCTGCAGCCTGAAGATTTTGCAACTTATTACTGTCTACAGCATAATAGTTACCCGTGGACGTTCGGCCAAGGGACCAAGGTGGAAATCAAA |
| RVFV-247 | 49 | heavy | GAGGTGCAGCTGGTGGAGTCCGGGGGAGGCTTAGTTCAGCCGGGGGGGTCCCTGAGACTCTCCTGTGCAGCCTCCGGATTCACCTTCAGCAGGTACTATATGCACTGGGTCCGCCAAGCTCCAGGGAAGGGGCCGGTGTGGATCTCACGTATTAACACTGATGGGAGCACCACAGCGTATGCCGACTCCGTGAAGGGCCGATTCACCATCTCCAGAGACAACGCCAAGAACACATTGTATTTGCAAATGAACAGTCTGAGAGTCGAAGATACGGCTGTGTATTATTGTGCAAGGCCCTATAGTGGGTACTTCCACTGGGGCCGGGGAGCCCTGGTCACCGTCTCCTCA |
| | 50 | light | GATATCGTGATGACCCAGACTCCACTCTCCTCATCTGTAACCCTTGGACAGCCGGCCTCCATCTCCTGCAGGTCTAGTCAAAGCCTCGTACACAGTGATGGAAACACCTACTTGAATTGGCTTCACCAGAGGCCAGGCCAGCCTCCAAGACTCCTAATTTATAAGATTTCTAATCGGTTCTCTGGGGTCCCAGATAGATTCAGTGGCAGTGGGGCAGGGACAGATTTCACACTGAAAATCAGCAGGGTGGAAGCTGAGGATGTCGGGGTTTATTACTGCATGCAAGGTACACGATTGTACACTTTTGGCCAGGGGACCAAGCTGGAGATCAAA |
| RVFV-248A | 51 | heavy | GAGGTGCTGCTGCTGGAGTCTGGGGGAGGCTTAGTCCAGCCTGGGGGGTCCCTGAGACTCTCCTGTACAGTCTCTGGATTCACCTTCACTAACTCCTGGATGCACTGGGTCCGCCAAGCTCCAGGGAAGGGGCTGGTGTGGGTCTCAGGTATTAATCCTGATGGGAGCAAAATAGACCACGCGGAGTCCGTGCAGGGCCGATTCACCATCTCCAGAGACAACGCCAAGAACACGCTTTATCTGCAAATGGACAGTCTGAGAGACGAGGACACGGCTGTTTATTACTGCGCAAGGTGGCTATCCTGGGGCCAGGGAGCCCTGGTCACCGTCACCTCA |
| | 52 | light | ACCATCTCTTGTTCTGGAAGCAGCTCCAACATCGGAAGTAATCATGTTTATTGGTACCAACAACTCCCAGGATCGGCCCCCAACTCCTCATTTCTAAGAATAATCAGCGGCCCTCAGGGGTCCCTGACCGATTCTCTGGCTCCAAGTCTGGCACCTCAGGTTCCCTGGCCATCAGTGGGCTCCGGTCCGAGGATGAGGCTGCTTATTATTGTGCAGCATGGGATGACAGCCTGCGTGGTTGGGAATTCGGCGGAGGGACCCAGGTGACCGTCCTAGGTCAGCCCAAGGCTGCCCCCTCGGTCACTCTGTTCCCA |
| RVFV-248B | 53 | heavy | GAGGTGCTGCTGCTGGAGTCTGGGGGAGGCTTAGTCCAGCCTGGGGGGTCCCTGAGACTCTCCTGTACAGTCTCTGGATTCACCTTCACTAACTCCTGGATGCACTGGGTCCGCCAAGCTCCAGGGAAGGGGCTGGTGTGGGTCTCAGGTATTAATCCTGATGGGAGCAAAATAGACCACGCGGAGTCCGTGCAGGGCCGATTCACCATCTCCAGAGACAACGCCAAGAACACGCTTTATCTGCAAATGGACAGTCTGAGAGACGAGGACACGGCTGTTTATTACTGCGCAAGGTGGCTATCCTGGGGCCAGGGAGCCCTGGTCACCGTCACCTCA |

TABLE 1-continued

| NUCLEOTIDE SEQUENCES FOR ANTIBODY VARIABLE REGIONS | | | |
|---|---|---|---|
| Clone | SEQ ID NO: | Chain | Variable Sequence Region |
| | 54 | light | GAAATTGTGTTGACACAGTCTCCAGCCACCCTGTCTTTGTCTCCAGGGGAAAGAGCCACCCTCTCCTGCAGGGCCAGTC AGAGTGTTAGCAGGAAATTAGCCTGGTTCCAGCAGAGACTTGGCCAGGCTCCCAGACTCCTCATCTATGATGCATCCA CCAGGGCCACTGGTGTCCCAGCCAAGTTCAGTGGCAGTGGGTCTGGGACAGACTTCACTCTCACCATCAGCAGCCTAG AGCCTGAAGATTTTGCAGTTTATTACTGTCACCAGCGTAGCAACTGGTGGACGTTCGGCCAAGGGACCAAGGTGGAA GTCAAG |
| RVFV-249 | 55 | heavy | CAGGTGCTTCTGGTACAGTCTGAGGCTGAGGTGCGGAAGCCTGGGGCCTCAGTTAAAATTTCCTGCAAGACATCTGGA TACACCTTCACCACCTACTTTATGCACTGGGTGCGACAGGCCCCTGGACAAGGGCTTGAGTGGGTGGCAATTGTCGAC CCTAGTACTGGAAACACAGGCTACGCACAGAGGTTCCAGGGCAGAGTCACCGTGACCAGGGACACGTCCACGGGAAC ACTCTTCATGGAACTGACCAGCCTGACAACAGAGGACACGGCCATGTACTACTGTGGTAGAGATCGTGGCTCCCGGGC GGTTGACTCCTGGGGCCAAGGAACCCTGGTCACCGTCTTTTCA |
| | 56 | light | CAGTCTGTGCTGACTCAGCCACCCTCAGTGTCTGGGGCCCCCGGGCAGAGGGTCACTATCTCTTGTTCTGGAAGCAGC TCCAACGTCGGACCTAATACTGTAAGCTGGTACCAACAACTCCCAGGAGTGGCCCCCAAACTCCTCATCTATCGTAATA ATCAGCGCCCCTCAGGGGTCCCTGACCGATTTTCTGGCTCCAAATTTGGCACCTCAGCCTCCCTGGTCATCGGTGGGCT CCAGTCTGAGGATGAGGCTGACTATTATTGTGCAGCATGGGATGACAGCCTGAATGGCCATATGGTGTTCGGCGGAG GGACCAAAGTGGCCGTCCTA |
| RVFV-250 | 57 | heavy | CAGGTGCAGCTGCAGGAGTCGGGCCCAGGACTGGCGAAGCCTTCGGAGACCCTGTCCCTCACCTGCACTGTCTCTGGT GGCTCCATCAGTAGTTACTTTTGGAGCTGGATCCGGCAGCCCGCCGGGAAGGGACTGGAGTGGATTGGGCGTATCCA TACCACTGGGAGCACCAACTACAACCCCTCCCTCAAGAATCGAGTCATCATGTCAGTAGACACGTCCAAGAACCAGTTC TCCCTGAACCTGAGCTCTGTGACCGCCGCGGACACGGCCGTGTATTACTGTGCGAGAGAAGGGACGGCTTTTGATATC TGGGGCCAAGGGACAATGGTCACCGTCTCTTCA |
| | 58 | light | TCCTATGAGCTGACTCAGTCACCCTCAGTGTCCGTGTCCCCAGGACAGACAGCCAGCATCCCCTGCTCTGGAGATAAAT TGGGGGATAAATATGCTTGCTGGTATCAGCAGAAGCCAGGCCAGTCCCCTGTGCTGGTCATCTATCAAGATACCAAGC GGCCCTCAGGGATCCCTGAGCGATTCTCTGGCTCCAACTCTGGGAACACAGCCACTCTGACCATCAGCGAGACCCAGG CTATGGATGAGGCTGACTATTACTGTCAGGCGTGGGACAGCAGCACTCCATGGGTGTTCGGCGGAGGGACCAAGCTG ACCGTCCTA |
| RVFV-263 | 59 | heavy | CAGGTGCACCTGGTGGAGTCTGGGGGAGGCTTGGTCAAGCCTGGAGGGTCCCTGAGACTCTCCTGTGCAGCCTCTGG ATTCACCTTCAGTGACTACTACATGAGCTGGATCCGCCAGGCTCCAGGGAAGGGGCTGGAGTGGGTTTCATACATTAG TGGTACTGGTAGTTTCATATACTACGCAGACTCTGTGAAGGGCCGATTCACCATCTCCAGGGACAACGCCAAGAACTC ACTGTATCTGCAGATCAACAGCCTGAGAGCCGAGGACACGGCCGTGTATTACTGTGCGAGAGGAATCAGGGCTGACT GCTTTGACCAGTGGGGCCACGGAACCCTGGTCACCGTCTCCTCA |
| | 60 | light | TCCTATGTGCTGACTCAGCCACCCTCGGTGTCAGTGGCCCCAGGACAGACGGCCAGGATTACCTGTGGGGGAAACAAC ATTGGAGATAAAAGTGTGCACTGGTACCAGCAGAAGCCAGGCCAGGCCCCTGTGCTGGTCGTCTATGATGATAGCGA CCGGCCCTCAGGGATCCCTGAGCGATTCTCTGGCTCCAACTCTGGGAACACGGCCACCCTGACCATCAGCAGGGTCGA AGCCGGGGATGAGGCCGACTATTACTGTCAGGTGTGGGATAGTAGTAGTGATCATCTTGTCTTCGGAACTGGGACCA AGGTCACCGTCCTA |
| RVFV-266 | 61 | heavy | CAGGTGCAGCTGGTGCAGTCTGGGGCTGAGGTGAAGAAGCCTGGGGCCTCAGTGAAGGTTTCCTGCAAGGCATCTGG ATACACCTTCACCAGCTACTATATGCACTGGGTGCGACAGGCCCCTGGACAAGGGCTTGAGTGGATGGGAATAATCAA CCCTAGTGGTGGTAGCACAAGCTACGCACAGAAGTTCCAGGGCAGAGTCACCATGACCAGGGACACGTCCACGAGCA CAGTCTACATGGAGCTGAGCAGCCTGAGATCTGAGGACACGGCCGTGTATTACTGTGCGAGAGCCCGTGGGGGGAGC TACTCCCTTGACTACTGGGGCCAGGGAACCCTGGTCACCGTCTCCTCA |
| | 62 | light | TCCTATGTGCTGACTCAGCCACCCTCGGTGTCAGTGGCCCCAGGACAGACGGCCAGGATTACCTGTGGGGGAAACAAC ATTGGAAGTAAAAGTGTGCACTGGTACCAGCAGAAGCCAGGCCAGGCCCCTGTGCTGGTCGTCTATGATGATAGCGA CCGGCCCTCAGGGATCCCTGAGCGATTCTCTGGCTCCAACTCTGGGAACACGGCCACCCTGACCATCAGCAGGGTCGA AGCCGGGGATGAGGCCGACTATTACTGTCAGGTGTGGGATAGTAGTAGTGATCATTGGGTGTTCGGCGGAGGGACCA AGCTGACCGTCCTA |
| RVFV-268 | 63 | heavy | CAGGTTCACCTGGTGGAGTCGGGGGGAGGCGTGGTCCAGCCTGGGAAGTCCCTGAGACTCTCCTGTGCAGCGTCTGG ATTCATCTTCAATCATTTTGGCATCCACTGGGTCCGCCAGTCTCCAGGCAAGGGGCTGGAGTGGGTGGCAGTCATATG GTATGATGGAAGTAAAAAATACTTTGCAGACTCCGTGAAGGGCCGATTCAGCATCTCCAGAGACAATTCCCAGAACAC TGTGTATCTACAAATGAACAGCCTGAGAACCGAGGACACGGCTGTGTATTACTGTGCGAGAGAGAGATGGAGTGGTC ATTCGTACCTTGACTACTGGGGCCATGGAGCCCTGGTCACCGTCTCCTCA |
| | 64 | light | TCCAATGTGCTGACTCAGCCACCCTCGGTGTCTGTGGCCCCAGGACAGACGGCCAGGATTTCCTGTGGGGGAAACAAC CTTGAAAGTAAATATGTGCACTGGTACCAGCAGAAGCCAGGCCAGGCCCCTGTGCTAGTCGTCTATGAAGATAGCGGC CGGCCCTCGGGGATCCCTGAGCGATTCTCTGGCTCCAACTCTGGGGGTACGGCCACCCTGACCATCAGCAGGGTCGAA GCCGGGGATGAGGCCGACTATTACTGTCAGGAGTGGGATACTAGTAGTGATTATCCGGTGTTCGGCGGAGGGACCAA GGTGACCGTCCTA |
| RVFV-278 | 65 | heavy | CAGGTGCAGGTGGCGGAGTCTGGGGGAGGCGTGGTCCAGCCTGGGAGGTCTCTGAGACTCTCCTGTGTAGCCTCTGG ATTCACCTTTAGGACTAAAACCATGCATTGGGTCCGCCAGGCTCCAGGCAAGGGGCTGGAGTGGGTGGCGTTTATTTC GGGTAGTGGAAAAGATAAATCCTACGCAGACTCCGTGAAGGGCCAATTCACCATCTCCAGAGACAACTCCAAGAACAC GCTGTTTCTGCAATTGGATAGCCTGAGACCTGAGGACACGGCTGTCTATTACTGTGTGAAAGATAGAGAGGGGACTTG GTCCTTTGACCACTGGGGCCAGGGAGCCCTGGTCACCGTCTCCTCA |
| | 66 | light | CAGTCTGCCCTGACTCAGCCTGCCTCCGTGTCTGGGTCTCCTGGACAGTCGATCACCATCTCCTGCACTGGAACCAACA ATGACGTTGGTCTTTATGACTATGTCTCCTGGTACCAACAACACCCAGGCAGAGCCCCCAAACTCATCATTTATGAGGT CACTAATCGGCCCTCAGGGGTTTCTGATCGCTTCTCTGCTTCCAAGTCTGGCAACACGGCCTCCCTGACCATCTCTGGGC TCCAGGCTGAGGACGAGGCTGATTATTACTGCAGCTCATATACAAGAAGCATCACTTGGGTGTTCGGCGGGGGGACC AAGGTGACCGTCCTG |

TABLE 1-continued

NUCLEOTIDE SEQUENCES FOR ANTIBODY VARIABLE REGIONS

| Clone | SEQ ID NO: | Chain | Variable Sequence Region |
| --- | --- | --- | --- |
| RVFV-284 | 67 | heavy | GAGGTGCAGCTGTTGGAGTCTGGGGGAGGCTTGGTACAGCCTGGGGGGTCCCTGAGACTCTCCTGTGCAGCCTCTGG ATTCACCTTTAGCAGCTATGCCATGAGCTGGGTCCGCCAGGCTCCAGGGAAGGGGCTGGAGTGGGTCTCAGCTATTAG TGGTAGTGGTGGTAGCACATACTACGCAGACTCCGTGAAGGGCCGGTTCACCATCTCCAGAGACAATTCCAAGAACAC GCTGTATCTGCAAATGAACAGCCTGAGAGCCGAGGACACGGCCGTATATTACTGTGCGAAAAAGTATTACGATTTTTG GAGTGGTTATTACCCGAACTGGTTCGACCCCTGGGGCCAGGGAACCCTGGTCACCGTCTCCTCA |
| | 68 | light | GAAATAGTGATGACGCAGTCTCCAGCCACCCTGTCTGTGTCTCCAGGGGAAAGAGCCACCCTCTCCTGCAGGGCCAGT CAGAGTGTTAGCAGCAACTTAGCCTGGTACCAGCAGAAACCTGGCCAGGCTCCCAGGCTCCTCATCTATGGTGCATCC ACCAGGGCCACTGGTATCCCAGCCAGGTTCAGTGGCAGTGGGTCTGGGACAGAGTTCACTCTCACCATCAGCAGCCTG CAGTCTGAAGATTTTGCAGTTTATTACTGTCAGCAGTATAATAACTGGCCTCAGCGGACGTTCGGCCAAGGGACCAAG GTGGAAATCAAA |
| RVFV-296A | 69 | heavy | CAGGTGCAGCTGGTGCAATCTGGGTCTGAGTTGAAGAAGTCTGGGGCCTCCGTGAAGGTTTCCTGTAGGGCTTCTGG ATACACCTTCACTACCTATGTTATGAATTGGGTGCGACAGGCCCCTGGACAAGGGCTTGAGTGGATGGGATGGATCAA CACCAACACTGGGAACCCAACGTATGCCCAGGGCTTCACAGGACGCTTTGTCTTCTCCTTAGACACCTCTGTCAGCACG GCATATCTACAGATCAACAGCCTAAAGGCTGAGGACACTGCCGTGTATTATTGTGCGAGGGAGTACAATAGCTTTGAC TATTGGGGCCAGGGAACCCTGGTCACCGTCTCCTCA |
| | 70 | light | CAGTCTGTGCTGACGCAGCCGCCCTCAGTGTCTGGGGCCCCAGGGCAGAGGGTCACCATCTCCTGCACTGGGAGCAG CTCCAACATCGGGGCAGGTTATGATGTACACTGGTACCAGCAGCTTCCAGGAACAGCCCCCAAACTCCTCATCTATGAT AACAACAATCGGCCCTCAGGGGTCCCTGACCGATTCTCTGGCTCCAGGTCTGGCACCTCAACCTCCCTGGCCATCACTG GGCTCCAGGCTGAAGATGAGGCTGATTATTACTGCCAGTCCTATGATTTCAGGCTGAGTGGTTCGGTATTCGGCGGAG GGACCAAAGTCACCGTCCTA |
| RVFV-299 | 71 | heavy | CAGGTGCAGCTGGTGCAGTCTGGGGCTGAGGTGAAGAAGCCTGGGGCCTCAGTGAAGGTTTCCTGCAAGGCATCTGG ATACACCTTCACCAGCTACTATATGCACTGGGTGCGACAGGCCCCTGGACAAGGGCTTGAGTGGATGGGAATAATCAG CCCTAGTGGTGGTAGCACAGACTACGCACAGAAGTTCCAGGGCAGAGTCACCATGACCAGGGACACGTCCACGAGCA CAGTCTACATGGAACTGAGCAGCCTGAGATCTGAGGACACGGCCGTGTATTACTGTGCGAGACAAGTGCAGACTGAT TACTACTTTGACTACTGGGGCCAGGGAACCCTGGTCACCGTCTCCTCA |
| | 72 | light | TCCTATGTGCTGACTCAGCCACCCTCGGTGTCAGTGGCCCCAGGACAGACGGCCAGGATTACCTGTGGGAGAAACAAC ATTGGAAGTAAAAGTGTGCACTGGTACCAGCAGAAGCCAGGCCAGGCCCCTGTGCTGGTCGTCTATGATGATAGCGA CCGGCCCTCAGGGATCCCTGAGCGATTCTCTGGCTCCAACTCTGGGAACACGGCCACCCTGACCATCAGCAGGGTCGA AGCCGGGGATGAGGCCGACTATTACTGTCAGGTGTGGGATAGTAGTAGTGATCACTCTTGGGTGTTCGGCGGAGGGA CCAAGCTGACCGTCCTG |
| RVFV-300 | 73 | heavy | CAGGTGCAGCTGGTGGAGTCTGGGGGAGGCGTGGTCCAGCCTGGGAGGTCCCTGAGACTCTCCTGTGCAGCCTCTGG ATTCACCTTCAGTAGCTATGCTATGCACTGGGTCCGCCAGGCTCCAGGCAAGGGGCTGGAGTGGGTAGCAGCTATATC ATATGATGGAAGTGATAAATACTACGCAGACTCCGTGAAGGGCCGATTCACCATCTCCAGAGACAATTCCAAGAACAC GGTGTATCTGCAAATGGACAGCCTGAGAGCTGAGGACACGGCTGTGTATTACTGTGCGAGAGATCGGAGTGGGAGCT ACTACTGGTTCGACCCCTGGGGCCAGGGAACCCTGGTCACCGTCTCCTCA |
| | 74 | light | AATTTTATGCTGACTCAGCCCCACTCTGTGTCGGAGTCTCCGGGGAGGACGGTAACCATCTCCTGCACCCGCAGCAGT GGCAGCATTGCCAACAACTTTGTGCAGTGGTACCAGCAGCGCCCGGGCAGTTCCCCCACCACTGTGATCTATGAGGAT GACCAAAGACCCTCTGGGGTCCCTGATCGGTTCTCTGGCTCCATCGACAGCTCCTCCAACTCTGCCTCCCTCACCATCTC TGGACTGAAGACTGAGGACGAGGCTGACTACTACTGTCAGTCTTATGATAGCAGCAATCAGGTGTTCGGCGGAGGGA CCAAGCTGACCGTCCTA |
| RVFV-302A | 75 | heavy | CAGGTCCAGCTTGTGCAGTCTGGGGCTGAGGTGAAGAAGCCTGGGGCCTCAGTGAAGGTTTCCTGCAAGGCTTCTGG ATACACCTTCACTAACTATGCTATACATTGGGTGCGCCAGGCCCCCGGACAAAGGCTTGAGTGGATGGGATGGATCAA CGCTGGCAATGGTGACACAAAATATTCACAGAAGTTCCAGGGCAGAGTCACCATTACCAGGGACACATCCGCGAGCA CAGCCTACATGGAGCTGAGCAGCCTGAGATCTGAAGACACGGCTGTGTATTACTGTGCGAGACCCGGGTATAGCAGC AGCTGGGATGAGGGCTTTGACTACTGGGGCCAGGGAACCCTGGTCACCGTCTCCTCA |
| | 76 | light | TCGTATGAGCTGACTCAGCCACCCTCAGTGTCCGTGTCCCCAGGACAGACAGCCAGCATCACCTGCTCTGGAGATAAA TTGGGGGATAAATATGCTTGCTGGTATCAGCAGAAGTCAGGCCAGTCCCCTGTGCTGGTCATCAATCTAGATAGCAAG CGGCCCTCAGGGATCCCTGAGCGATTCTCTGGCTCCAACTCTGGGAACACAGCCACTCTGACCATCAGCGGGACCCAG GCTATGGATGAGGCTGACTATTACTGTCAGGCGTGGGACAGCAGCACTGGGGTTTTCGGCGGAGGGACCAAGCTGAC CGTCCTA |
| RVFV-302B | 77 | heavy | GAGGTGCAGCTGGTGGAGTCCGGGGGAGGCTTAGTTCAGCCTGGGGGGTCCCTGAGACTCTCCTGTGCAGCCTCTGG ATTCACCTTCAGTAGCTACTGGATGCACTGGGTCCGCCAAGCTCCAGGGAAGGGGCTGGTGTGGGTCTCACGTATTAA TAGTGATGGGAGTAGCACAAGCTACGCGGACTCCGTGAAGGGCCGATTCACCATCTCCAGAGACAACGCCAAGAACA CGCTGTATCTGCAAATGAACAGTCTGAGAGCCGAGGACACGGCTGTGTATTACTGTGCAAGTGGGGATAGCAGTGGC TGGTACATGCCATTTGACTACTGGGGCCAGGGAACCCTGGTCACCGTCTCCTCA |
| | 78 | light | CAGTCTGCCCTGACTCAGCCTGCCTCCGTGTCTGGGTCTCCTGGACAGTCGATCACCATCTCCTGCACTGGAACCAGCA GTGACGTTGGTGGTTATAACTATGTCTCCTGGTACCAACAGCACCCAGGCAAAGCCCCCAAACTCATGATTTATGATGT CAGTAATCGGCCCTCAGGGGTTTCTAATCGCTTCTCTGGCTCCAAGTCTGGCAACACGGCCTCCCTGACCATCTCTGGG CTCCAGGCTGAGGACGAGGCTGATTATTACTGCAGCTCATATACAAGCAGCAGCACTAATGTGGTATTCGGCGGAGG GACCAAGCTGACCGTCCTA |
| RVFV-304B | 79 | heavy | CAGGTGCAGCTGCAGGAGTCGGGCCCAGGACTGGTGAAGCCTTCGGAGACCCTGTCCCTCACCTGCACTGTCTCTGGT GGCTCCATCAGTAGTTACTACTGGAGCTGGATCCGGCAGCCCCCAGGGAAGGGACTGGAGTGGATTGGGTATATCTA TTACAGTGGGAGCACCAACTACAACCCCTCCCTCAAGAGTCGAGTCACCATATCAGTAGACACGTCCAAGAACCAGTTC TCCCTGAAGCTGAGCTCTGTGACCGCCGCAGACACGGCCGTGTATTACTGTGCGAGACATGGGGATATTTTGACTGGT TTCTTGTACTGGTACTTCGATCTCTGGGGCCGTGGCACCCTGGTCACTGTCTCCTCA |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| | 80 | light | CAGTCTGCCCTGACTCAGCCTGCCTCCGTGTCTGGGTCTCCTGGACAGTCGATCACCATCTCCTGCACTGGAACCAGCAGTGACGTTGGTGGTTATAACTATGTCTCCTGGTACCAACAGCACCCAGGCAAAGCCCCCAAACTCATGATTTATGATGTCAGTAATCGGCCCTCAGGGGTTTCTAATCGCTTCTCTGGCTCCAAGTCTGGCAACACGGCCTCCCTGACCATCTCTGGGCTCCAGGCTGAGGACGAGGCTGATTATTACTGCAGCTCATATACAAGCAGCAGCACTCTAGTGGTATTCGGCGGAGGGACCAAGCTGACCGTCCTA |
| RVFV-307 | 81 | heavy | GAAGTGCAGCTGGTGCAGTCTGGAGCAGAGGTGAAAAAGCCCGGGGAGTCTCTGAGGATCTCCTGTAAGGGTTCTGGATACAGCTTTACCAGCTACTGGATCAGCTGGGTGCGCCAGATGCCCGGGAAAGGCCTGGAGTGGATGGGGAGGATTGATCCTAGTGACTCTTATACCAACTACAGCCCGTCCTTCCAAGGCCACGTCACCATCTCAGCTGACAAGTCCATCAGCACTGCCTACCTGCAGTGGAGCAGCCTGAAGGCCTCGGACACCGCCATGTATTACTGTGCGAGACATGGAGAGGGTGGGAGCTACGAGGAGTTCGACCCCTGGGGCCAGGGAACCCTGGTCACCGTCTCCTCA |
| | 82 | light | GACATCCAGATGACCCAGTCTCCATCCTCCCTGTCTGCATCTGTAGGAGACAGAGTCACCATCACTTGCCGGGCAAGTCAGAGCATTAGCAGCTATTTAAATTGGTATCAGCAGAAACCAGGGAAAGCCCCTAAGCTCCTGATCTATGCTGCATCCAGTTTGCAAAGTGGGGTCCCATCAAGGTTCAGTGGCAGTGGATCTGGGACAGATTTCACTCTCACCATCAGCAGTCTGCAACCTGAAGATTTTGCAACTTACTACTGTCAACAGAGTTACAGTACCCCGTGGACGTTCGGCCAAGGGACCAAGGTGGAAATCAAA |
| RVFV-308 | 83 | heavy | GAGGTGCAGCTGGTGCAGTCTGGAGCAGAGGTGAAAAAGGCCGGGGAGTCTCTGAAGATCTCCTGTAAGGGTTCTGGATACAGCTTTACCAGCTACTGGATCGGCTGGGTGCGCCAGATGCCCGGGAAAGGCCAGGAGTGGATGGGAATCATCTATCCTGGTGACTCTGATACCACATACAGCCCGTCCTTCCAAGGCCAGGTCACCATCTCAGCCGACAAGTCCCTCAGCACCGCCTACCTGCAGTGGAGCAGCCTGAAGGCCTCGGACACCGCCATGTATTACTGTGCGAGAGGGGCATATTGTGGTGGTGATTGCTTTGGGGGCGCTGAATACTTCCAGCACTGGGGCCAGGGCACCCTGGTCACCGTCTCCTCA |
| | 84 | light | GACATCGTGATGACCCAGTCTCCAGACTCCCTGGCTGTGTCTCTGGGCGAGAGGGCCACCATCAACTGCAAGTCCAGCCAGAGTGTTTTATACAGCTCCAACAATAAGAACTACTTAGCTTGGTACCAGCAGAAACCAGGACAGCCTCCTAAGCTGCTCATTTACTGGGCATCTACCCGGGAATCCGGGGTCCCTGACCGATTCAGTGGCAGCGGGTCTGGGACAGATTTCACTCTCACCATCAGCAGCCTGCAGGCTGAAGATGTGGCAGTTTATTACTGTCAGCAGTATTATAGTACTCCGCTCACTTTCGGCGGAGGGACCAAGGTGGAGATCAAA |
| RVFV-309 | 85 | heavy | CAGGTGCAGCTGGTGCAGTCTGGGGCTGAGGTGAAGAGGCCTGGGGCCTCAGTGAAGGTTTCCTGCAAGGCATCTGGATATACCTTCACCAACTACTATATGCACTGGGTGCGACAGGCCCCTGGACAAGGGCTTGAGTGGATGGGAATAATCAACCCTAGTGGTGTTAGCACAATGTACGCACAGAAGTTCCAGGGCAGAGTCACCATGACCAGGGACACGTCCACGAGCACAGTCTACATGGAGCTGAGCAGCCTGAGATCTGAGGACACGGCCGTGTATTCCTGTGCGAGAATGGATACTGAATACTACTACTTTGACTACTGGGGCCAGGGAACCCTGGTCACCGTCTCCTCA |
| | 86 | light | TCCTATGTGCTGACTCAGCCACCCTCGGTGTCAGTGGCCCCAGGACAGACGGCCAGGATTACCTGTGGGGGAAACAACATTGGAAGTAAAAGTGTGCACTGGTACCAGCAGAGGCCAGGCCAGGCCCCTGTGCTGGTCGTCTATGATGATAGCGACCGGCCCTCAGGGATCCCTGAGCGATTCTCTGGCTCCAACTCTGGGAACACGGCCACCCTGACCATCAACAGGGTCGAAGCCGGGGATGAGGCCGACTATTACTGTCAGGTGTGGGATAGTAGTAGTGATCATTGGGTGTTCGGCGGAGGGACCAAGCTGACCGTCCTA |
| RVFV-311 | 87 | heavy | GAGGTGCAGCTGCAGGAGTCGGGCCCAGGACTGGTGCAGCCTTCGGGGACCCTGTCCCTCACCTGCGCTGTCTCTGGTGGCTCCATCAGCAGTAGTAACTGGTGGAGTTGGGTCCGCCAGCCCCCAGGGAAGGGGCTGGAGTGGATTGGGGAAATCTATCATAGTGGGAGCACCAACTACAACCCGTCCCTCAAGAGTCGAGTCACCATATCAGTAGACAAGTCCAAGAACCAGTTCTCCCTGAAGCTGAGCTCTGTGACCGCCGCGGACACGGCCGTGTACTACTGTGCGAGACGCTCCTACTACTACTACTACATGGACGTCTGGGGCAAAGGGACCACGGTCACCGTCTCCTCA |
| | 88 | light | TCCTATGTGCTGACTCAGCCACCCTCGGTGTCAGTGGCCCCAGGACAGACGGCCAGGATTACCTGTGGGGGAAACAACATTGGAAGTAAAAGTGTGCACTGGTACCAGCAGAAGCCAGGCCAGGCCCCTGTGCTGGTCGTCTATGATGATAGCGACCGGCCCTCAGGGATCCCTGAGCGATTCTCTGGCTCCAACTCTGGGAACACGGCCACCCTGACCATCAGCAGGGTCGAAGCCGGGGATGAGGCCGACTATTACTGTCAGGTGTGGGATAGTAGTAGTGATTATGTGGTATTCGGCGGAGGGACCAAGCTGACCGTCCTA |
| RVFV-313 | 89 | heavy | GAGGTGCAGCTGTTGGAGTCTGGGGGAGGCTTGGTACAGCCGGGGGGGTCCCTGAGACTCTCCTGTGCAGCCTCTGGATTCACCTTTAGTAGTTATGCCATGAGCTGGGTCCGCCAGGCTCCAGGGAAGGGGCTGGAGTGGGTCTCAGTTATTAGTGGTAGTGGTGGTAGCACATACTACGCAGACTCCGTGAAGGGCCGGTTCACCATCTCCAGAGACAATTCCAAGAACACACTGTATCTGCAAATGAGTAGCCTGAGAGCCGAGGACACGGCCCTTTATTACTGTGCGAAATGTATCGATAACTACTACTACTACTGCTACATGGACGTCTGGGGCAAAGGGACCACGGTCACCGTCTCCTCA |
| | 90 | light | CAGTCTGCCCTGACTCAGCCTGCCTCCGTGTCTGGGTCTCCTGGACAGTCGATCACCATCTCCTGCACTGGAACCAGCAGTGACGTTGGTGGTTATGACTATGTCTCCTGGTACCAACACCACCCAGGCAAAGCCCCCAAACTCATGATTTATGCTGTCAGTAATCGGCCCTCAGGGGTTTCTAATCGCTTCTCTGGCTCCAAGTCTGGCAACACGGCCTCCCTGACCATCTCTGGGCTCCAGCCTGAGGACGAATCTGATTATTACTGCAGCTCATATACAAGCAGCAGCACTTGGGTGTTCGGCGGAGGGACCAAGCTGACCGTCCTA |
| RVFV-314 | 91 | heavy | CAGGTTCAGCTGGTGCAGTCTGGAGCTGAGGTGAAGAAGCCTGGGGCCTCAGTGAAGGTCTCCTGCAAGGCTTCTGGTTACACCTTTACTAGCTATGGTATCACCTGGGTGCGACTGGCCCCTGGACAAGGGCTTGAGTGGATGGGATGGATCAGCGCTTACAATGGTAACACAAACTATGCACAGAAGCTCCAGGGCAGAGTCACCATGACCACAGACACATCCACGAGCACAGCCTACATGGAGCTGAGGAGCCTGAGATCTGACGACACGGCCGTGTATTACTGTGCGAGAGATGGGGTTCAGGGTGCTTTTGATATCTGGGGCCAAGGGACAATGGTCACCGTCTCTTCA |
| | 92 | light | TCCTATGTGCTGACTCAGCCACCCTCGGTGTCAGTGGCCCCAGGACAGACGGCCAGGATTACCTGTGGGGGAAACAACATTGGAAGTAAAAGTGTGCACTGGTACCAGCAGAAGCCAGGCCAGGCCCCTGTGCTGGTCGTCTATGATGATAGCGACCGGCCCTCAGGGATCCCTGAGCGATTCTCTGGCTCCAACTCTGGGAACACGGCCACCCTGACCATCAGCAGGGTCGAAGCCGGGGATGAGGCCGACTATTACTGTCAGGTGTGGGATAGTAGTAGTGATCAAAGGGTCTTCGGAACTGGGACCAAGGTCACCGTCCTA |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| RVFV-315 | 93 | heavy | CAGGTGCAGCTGGTGGAGTCTGGGGGAGGCGTGGTCCAGCCTGGGAGGTCCCTGAGACTCTCCTGTGCAGCCTCTGGATTCACCTTCAGTAGCTATGGCATGCACTGGGTCCGCCAGGCTCCAGGCAAGGGGCTGGAGTGGGTGGCAGTTATATCATATGATGGAAGTAATAAATACTATGCAGACTCCGTGAAGGGCCGATTCACCATCTCCAGAGACAATTCCAAGAACACGCTGTATCTGCAAATGAACAGCCTGAGAGCTGAGGACACGGCTGTGTATTACTGTGCGAATTGGGGCAATTACTATGATAGTAGTGGTTACAGCTACTACTACTACTACATGGACGTCTGGGGCAAAGGGACCACGGTCACCGTCTCCTCA |
| | 94 | light | CAGTCTGTGCTGACTCAGCCACCCTCAGCGTCTGGGACCCCCGGGCAGAGGGTCACCATCTCTTGTTCTGGAAGCAGCTCCAACATCGGAAGTAATACTGTAAACTGGTACCAGCAGCTCCCAGGAACGGCCCCCAAACTCCTCATCTATAGTAATAATCAGCGGCCCTCAGGGGTCCCTGACCGATTCTCTGGCTCCAAGTCTGGCACCTCAGCCTCCCTGGCCATCAGTGGGCTCCAGTCTGAGGATGAGGCTGATTATTACTGTGCAGCATGGGATGACAGCCTGAATGGTTGGGTGTTCGGCGGAGGGACCAAGCTGACCGTCCTA |
| RVFV-320 | 95 | heavy | GAGGTGCAGCTGGTGGAGTCCGGGGGAGGCTTAGTTCAGCCTGGGGGGTCCCTGAGACTCTCCTGTGCAGCCTCTGGATTCACCTTCAGTAGCTACTGGATGCACTGGGTCCGCCAAGCTCCAGGGAAGGGGCTGGTGTGGGTCTCACGTATTAATAGTGATGGGAGTAGCACAAGCTACGCGGACTCCGTGAAGGGCCGATTCACCATCTCCAGAGACAACGCCAAGAACACGCTGTATCTGCAAATGAACAGTCTGAGAGCCGAGGACACGGCTGTGTATTACTGTGCAAGTGGGGATAGCAGTGGCTGGTACATGCCATTTGACTACTGGGGCCAGGGAACCCTGGTCACCGTCTCCTCA |
| | 96 | light | CAGTCTGCCCTGACTCAGCCTGCCTCCGTGTCTGGGTCTCCTGGACAGTCGATCACCATCTCCTGCACTGGAACCAGCAGTGACGTTGGTGGTTATAACTATGTCTCCTGGTACCAACAGCACCCAGGCAAAGCCCCCAAACTCATGATTTATGATGTCAGTAATCGGCCCTCAGGGGTTTCTAATCGCTTCTCTGGCTCCAAGTCTGGCAACACGGCCTCCCTGACCATCTCTGGGCTCCAGGCTGAGGACGAGGCTGATTATTACTGCAGCTCATATACAAGCAGCAGCACTAATGTGGTATTCGGCGGAGGGACCAAGCTGACCGTCCTA |
| RVFV-321 | 97 | heavy | GAGGTGCAGCTGGTGGAGTCCGGGGGAGGCTTAGTTCAGCCTGGGGGGTCCCTGAGACTCTCCTGTGCAGCCTCTGGATTCACCTTCAGTAGCTACTGGATGCACTGGGTCCGCCAAGCTCCAGGGAAGGGGCTGGTGTGGGTCTCACGTATTAATAGTGATGGGAGTAGCACAAGCTACGCGGACTCCGTGAAGGGCCGATTCACCATCTCCAGAGACAACGCCAAGAACACGCTGTATCTGCAAATGAACAGTCTGAGAGCCGAGGACACGGCTGTGTATTACTGTGCAAGTGGGGATAGCAGTGGCTGGTACATGCCATTTGACTACTGGGGCCAGGGAACCCTGGTCACCGTCTCCTCA |
| | 98 | light | CAGTCTGCCCTGACTCAGCCTGCCTCCGTGTCTGGGTCTCCTGGACAGTCGATCACCATCTCCTGCACTGGAACCAGCAGTGACGTTGGTGGTTATAACTATGTCTCCTGGTACCAACAGCACCCAGGCAAAGCCCCCAAACTCATGATTTATGATGTCAGTAATCGGCCCTCAGGGGTTTCTAATCGCTTCTCTGGCTCCAAGTCTGGCAACACGGCCTCCCTGACCATCTCTGGGCTCCAGGCTGAGGACGAGGCTGATTATTACTGCAGCTCATATACAAGCAGCAGCACTAATGTGGTATTCGGCGGAGGGACCAAGCTGACCGTCCTA |
| RVFV-322 | 99 | heavy | CAGGTGCAGCTGCAGGAGTCGGGCCCAGGACTGGTGAAGCCTTCGGGGACCCTGTCCCTCACCTGCGCTGTCTCTGGTGGCTCCATCAGCAGTAGTAACTGGTGGAGTTGGGTCCGCCAGCCCCCAGGGAAGGGGCTGGAGTGGATTGGGGAAATCTATCATAGTGGGAGCACCAACTACAACCCGTCCCTCAAGAGTCGAGTCACCATATCAGTAGACAAGTCCAAGAACCAGTTCTCCCTGAAGCTGAGCTCTGTGACCGCCGCGGACACGGCCGTGTATTACTGTGCGAGAGATTCGCGGCAGTGGCTGGTACGGGGTTTTGACTACTGGGGCCAGGGAACCCTGGTCACCGTCTCCTCA |
| RVFV-326 | 100 | Heavy | GAGGCACAGCTGGTGGAGTCTGGGGGAGGCTTGGTAAAGCCGGGGGGGTCCCTTAGACTCTCCTGTGCAGCCTCTGGGTTCAGTTTCAGTTACGCCTGGATGAGTTGGGTCCGCCGACTTCCAGGGAAGGGGCTGGAGTGGGTTGGCCGTATTAAAGGCAAGGCTGATGGTGAGACAACTGACTACGCTGCACCCGTGAAAGGCAGATTCACCATCTCGAGAGATGATTCAAAGACCACGGTGTATCTGCAAATGAACACCCTGAAAATCGAGGACACAGGCGTCTATTACTGTACCACAGATATTGGCGATTTCTATGACAGTATTGGATACTCTTATACTGACTACTGGGGCCAGGGAACCCTGGTCACCGTCTCCTCA |
| | 101 | Light | GAAATTGTGTTGACACAGTCTCCAGCCACCCTGTCTTTGTCTCCGGGGGAAAGAGCCACCCTCTCCTGCAGGGCCAGTCAGAGTGTTTCCAGTTACTTAGCCTGGTACCAACAGAAACCTGGCCAGGCTCCCAGGCTCCTCATCTATGATGCATCCAACAGGGCCACTGGCATCCCAGTCAGGTTCAGTGGCAGTGGGTCTGGGACAGACTTCACTCTCACCATCAGCAGCCTAGAGCCTGAAGATTTTGCCCTTTATTACTGTCAGCAGCGTAGCGACTGGCCTCCGACGTTCGGCCAAGGGACCAAGGTGGAAATCAAA |
| RVFV-330 | 102 | Heavy | CAGGTGCAGCTGGTGCAGTCTGGGGCTGAGGTGAAGAAGCCTGGGGCCTCAGTGAAGGTTTCCTGCAAGGCATCTGGATACACCTTCACCAGCTACTATATGCACTGGGTGCGACAGGCCCCTGGACAAGGGCTTGAGTGGATGGGAATAATCAACCCTAGTGGTGGTAGCACAAGCTACGCACAGAAGTTCCAGGGCAGAGTCACCATGACCAGGGACACGTCCACGAGCACAGTCTACATGGAGCTGAGCAGCCTGAGATCTGAGGACACGGCCGTGTATTACTGTGCGAGAGTTGGGAACTACTACTACTACATGGACGTCTGGGGCAAAGGGACCACGGTCACCGTCTCCTCA |
| | 103 | Light | TCCTATGTGCTGACTCAGCCACCCTCGGTGTCAGTGGCCCCAGGACAGACGGCCAGGATTACCTGTGGGGGAAACAACATTGGAAGTAAAAGTGTGCACTGGTACCAGCAGAAGCCAGGCCAGGCCCCTGTGCTGGTCGTCTATGATGATAGCGACCGGCCCTCAGGGATCCCTGAGCGATTCTCTGGCTCCAACTCTGGGAACACGGCCACCCTGACCATCAGCAGGGTCGAAGCCGGGGATGAGGCCGACTATTACTGTCAGGTGTGGGATAGTAGTAGTGATCATTGGGTGTTCGGCGGAGGGACCAAGCTGACCGTCCTA |
| RVFV-331 | 104 | Heavy | GAGGTGCAGCTGGTGGAGTCTGGGGGAGGCTTGGTACAGCCAGGGCGGTCCCTGAGACTCTCCTGTACAGCTTCTGGATTCACCTTTGGTGATTATGCTATGAGCTGGGTCCGCCAGGCTCCAGGGAAGGGGCTGGAGTGGGTAGGTTTCATTAGAAGCAAAGCTTATGGTGGGACAAGAGAATACGCCGCGTCTGTGAAAGGCAGATTCACCATCTCAAGAGATGATTCCAAAAGCATCGCCTATCTGCAAATGAACAGCCTGAAAACCGAGGACACAGCCGTGTATTATTGTACTAACCATCGTGGCAGCAGCTGGTACCCGGATGCTTTTGATATCTGGGGCCAAGGGACAATGGTCACCGTCTCTTCA |
| | 105 | Light | TCCTATGTGCTGACTCAGCCACCCTCGGTGTCAGTGGCCCCAGGAAAGACGGCCAGGATTACCTGTGGGGGAAACAACATTGGAAGTAAAAGTGTGCACTGGTACCAGCAGAAGCCAGGCCAGGCCCCTGTGCTGGTCGTCTATGATGATAGCGACCGGCCCTCAGGGATCCCTGAGCGATTCTCTGGCTCCAACTCTGGGAACACGGCCACCCTGACCATCAGCAGGGTCGAAGCCGGGGATGAGGCCGACTATTACTGTCAGGTGTGGGATAGTAGTAGTGATCCCGATGTGGTATTCGGCGGAGGGACCAAGCTGACCGTCCTA |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| RVFV-332 | 106 | Heavy | CAGGTGCAGCTGGTGGAGTCTGGGGGAGGCGTGGTCCAGCCTGGGAGGTCCCTGAGACTCTCCTGTGCAGCCTCTGG ATTCACCTTCAGTAGTTATGCTATGCACTGGGTCCGCCAGGCTCCAGGCAGGGGGCTGGAGTGGGTGGCAGTTATATC ATATGATGGAAGTAATAAATACTACGCAGACTCCGTGAAGGGCCGATTCACCATCTCCAGAGACAATTCCAAGAACAC GCTGTATCTGCAAATGAACAGCCTGAGAGCTGAGGACACGGCTGTGTATTACTGTGCTAAAGATATAACTGGGAGACT TGACTACTGGGGCCAGGGAACCCTGGTCACCGTCTCCTCA |
| | 107 | Light | TCCTATGGGCTGACTCAGCCACCCTCGGTGTCAGTGGCCCCAGGACAGACGGCCAGGATTACCTGTGGGGGAAACAA CATTGGAAGTAAAAGTGTGAACTGGTACCAGCAGAAGCCAGGCCAGGCCCCTGTGCTGGTCGTCTATGATGATAGCG ACCGGCCCTTAGGGATCCCTGAGCGATTCTCTGGCTCCAACTCTGGGAACACGGCCACCCTGACCATCAGCAGGGTCG AAGCCGGGGATGAGGCCGACTATAACTGTCAGGTGTGGGATAGTAGTAGTGATCATTGGGTGTTCGGCGGAGGGAC CAAGCTGACCGTCCTA |
| RVFV-335 | 108 | Heavy | GAGGTGCAGCTGGTGGAGTCTGGGGGAGGCTTGGTACAGCCTGGGGGGTCCCTGAGACTCTCCTGTGCAGCCTCTGG ATTCACCTTCAGTAGCTACGACATGCACTGGGTCCGCCAAGCTACAGGAAAAGGTCTGGAATGGGTCTCAGCTATTGG TACTGCTGGTGACACATACTATCCAGGCTCCGTGAAGGGCCGATTCACCATCTCCAGAGAAAGTGCCAAGAACTCCTT GTATCTTCAAATGAACAGCCTGAGAGCCGGGGACACGGCTGTGTATTACTGTGCAAGAGGTCTTGGAGGGGGGGTTTG ACTACTGGGGCCAGGGAACCCTGGTCACCGTCTCCTCA |
| | 109 | Light | TCCTATGTGCTGACTCAGCCACCCTCGGTGTCAGTGGCCCCAGGAAAGACGGCCAGGATTACCTGTGGGGGAAACAA CATTGGAAGTAAAAGTGTGCACTGGTACCAGCAGAAGCCAGGCCAGGCCCCTGTGCTGGTCGTCTATGATGATAGCG ACCGGCCCTCAGGGATCCCTGAGCGATTCTCTGGCTCCAACTCTGGGAACACGGCCACCCTGACCATCAGCAGGGTCG AAGCCGGGGATGAGGCCGACTATTACTGTCAGGTGTGGGATAGTAGTAGCGATCATTATGTCTTCGGAACTGGGACC AAGGTCACCGTCCTA |
| RVFV-337 | 110 | Heavy | GAGGTGCAGCTGTTGGAGTCTGGGGGAGGCTTGGTACAGCCGGGGGGGTCCCTGAGACTCTCCTGCGTAGCCTCTGG ATTCACCTTTAGCAACTATGCCATGAGCTGGGTCCGCCAGGCTCCAGGGAAGGGGCTGGAGTGGGTCTCCGCGATTA GCGGTAATGTTGATAACACACACTACGCAGACTCCGTGAAGGGCCGGTTCACCATCTCCAGAGACAATTCCAAGAGCA CACTGTTTCTGCAAATGCACAGCCTGAGAGCCGAGGACACGGCCGTATATTTCTGTGCGAAAGTGGGCCAATATTGGA GTGGTCATTATCTGGACTACTGGGGCCAGGGAACCCTGGTCACCGTCTCCTCA |
| | 111 | Light | TCCTATGTGCTGACTCAGCCACCCTCGGTGTCAGTGGCCCCAGGACAGACGGCCAGGATGACCTGTGGGGGAAACAA TATTGGAAGTAAAAGTGTGCACTGGTATCAGCAGAAGCCAGGCCAGGCCCCTGTACTGGTCGTCTATGATGATAGCGA CCGGCCCTCGGGGATCCCTGAGCGATTCTCTGGCTCCAACTCTGGGAACACGGCCACCCTGACCATCAACAGGGTCGA AGCCGGGGATGAGGCCGACTATTACTGTCAGGTGTGGCATAGTGATAGTGATCAATATGTCTTCGGAACTGGGACGA AGGTCACCGTCCTA |
| RVFV-338 | 112 | Heavy | GAGGTGCAGCTGTTGGAGTCTGGGGGAGGCTTGGTACACCCTGGGGGGTCCCTGAGACTCTCCTGTGCAGCCTCTGG ATTCACCTTTAGCAGCTATGCCATGAGCTGGGTCCGCCAGGCTCCAGGGAAGGGGCTGGAGTGGGTCTCAGCTATTAG TGGTAGTGGTGGCAGCACATACTACGCAGACTCCGTGAAGGGCCGGTTCACCATCTCCAGAGACAATTTCAAGAACAC ACTGTATGTGCAAATGAACAGCCTGAGAGCCGAGGACACGGCCGTATATTACTGTGCGACAGAGAACGACTTTTGGA GTGGTCACCAGTTTGACTACTGGGGCCAGGGAACCCTGGTCACTGTCTCCTCA |
| | 113 | Light | TCCTATGTGCTGACTCAGCCACCCTCGGTGTCAGTGGCCCCAGGACAGACGGCCAGGATGACCTGTGGGGGAAACAA TATTGGAAGTAAAAGTGTGCAGTGGTACCAGCAGAAGCCAGGCCAGGCCCCTGTGCTGGTCGTCCATGATGATAGCG ACCGGCCCTCAGGGATCCCTGAGCGATTCTCTGGCTCCAACTCTGGGAACACGGCCACCCTGACCATCAGCAGGGTCG AAGCCGGGGATGAGGCCGACTATTACTGTCAGGTGTGGGATAGTAGTAGTGATCATTGGGTGTTCGGCGGAGGGACC AAGCTGACCGTCCTA |
| RVFV-347 | 114 | Heavy | GAGGTGCAGCTGGTGGAGTCTGGGGGAGGCTTGGTACAGCCTGGGGGGTCCCTGAGACTCTCCTGTGCAGCCTCTGG ATTCACCTTCAGTAGCTACGACATGCACTGGGTCCGCCAAGCTACAGGAAAAGGTCTGGAGTGGGTCTCAGCTATTGG TACTGCTGGTGACACATACTATCCAGGCTCCGTGAAGGGCCGATTCACCATCTCCAGAGAAAATGCCAAGAACTCCTT GTATCTTCAAATGAACAGCCTGAGAGCCGGGGACACGGCTGTGTATTACTGTGCAAGAGCGGTGGGGGGGGGGTTT GACTACTGGGGCCAGGGAACCCTGGTCACCGTCTCCTCA |
| | 115 | Light | TCCTATGTGCTGACTCAGCCACCCTCGGTGTCAGTGGCCCCAGGAAAGACGGCCAGGATTACCTGTGGGGGAAACAA CATTGGAAGTAAAAGTGTGCACTGGTACCAGCAGAAGCCAGGCCAGGCCCCTGTGCTGGTCGTCTATGATGATAGCG ACCGGCCCTCAGGGATCCCTGAGCGATTCTCTGGCTCCAACTCTGGGAACACGGCCACCCTGACCATCAGCAGGGTCG AAGCCGGGGATGAGGCCGACTATTACTGTCAGGTGTGGGATAGTAGTAGTGATCTTTATGTCTTCGGAACTGGGACCA AGGTCACCGTCCTA |
| RVFV-349A | 116 | Heavy | CAGGTGCAGCTGCAGGAGTCGGGCCCAGGACTGGTGAAGCCTTCGGAGACCCTGTCCCTCACCTGCACTGTCTCTGGT GGCTCCATCAGTAGTTACTACTGGAGCTGGATCCGGCAGCCCCCAGGGAAGGGACTGGAGTGGATTGGGTATATCTA TTACAGTGGGAGCACCAACTACAACCCCTCCCTCAAGAGTCGAGTCACCATATCAGTAGACACGTCCAAGAACCAGTTC TCCCTGAAGCTGAGCTCTGTGACCGCTGCGGACACGGCCGTGTATTACTGTGCGAGAGGGTCAAGGGCAATTTTGACT GGTTACCCCAACTGGTTCGACCCCTGGGGCCAGGGAACCCTGGTCACCGTCTCCTCA |
| | 117 | Light | GACATCCAGATGACCCAGTCTCCATCCTCCCTGTCTGCATCTGTAGGAGACAGAGTCACCATCACTTGCCGGGCAAGTC AGAGCATTAGCAGCTATTTAAATTGGTATCAGCAGAAACCAGGGAAAGCCCCTAAGCTCCTGATCTATGCTGCATCCA GTTTGCAAAGTGGGGTCCCATCAAGGTTCAGTGGCAGTGGATCTGGGACAGATTTCACTCTCACCATCAGCAGTCTGC AACCTGAAGATTTTGCAACTTACTACTGTCAACAGAGTTACAGTACTCCGTACACTTTTGGCCAGGGGACCAAGCTGGA GATCAAA |
| RVFV-349B | 118 | Heavy | GAAGTGCAGCTGGTGGAGTCTGGGGGAGGCTTGGTACAGCCTGGCAGGTCCCTGAGACTCTCCTGTGCAGCCTCTGG ATTCACCTTTGATGACTATGCCATGCACTGGGTCCGGCAAGCTCCAGGGAAGGGCCTGGAGTGGGTCTCAGGTATTAG TTGGAATAGTGGTAGCATAGGCTATGCGGACTCTGTGAAGGGCCGATTCACCATCTCCAGAGACAACGCCAAGAACTC CCTGTATCTGCAAATGAACAGTCTGAGAACTGAGGACACGGCCTTCTATTACTGTGCAAAAGATAAAGGAGATGGTTC GGGGAGTTTCTACTACATGGACGTCTGGGGCAAAGGGACCACGGTCACCGTCTCCTCA |

TABLE 1-continued

| NUCLEOTIDE SEQUENCES FOR ANTIBODY VARIABLE REGIONS | | | |
|---|---|---|---|
| Clone | SEQ ID NO: | Chain | Variable Sequence Region |
| | 119 | Light | GACATCCAGATGACCCAGTCTCCATCCTCCCTGTCTGCATCTGTAGGAGACAGAGTCACCATCACTTGCCAGGCGAGTCAGGACATTAGCAACTATTTAAATTGGTATCAGCAGAAACCAGGGAAAGCCCCTAAGCTCCTGATCTACGATGCATCCAATTTGGAAACAGGGGTCCCATCAAGGTTCAGTGGAAGTGGATCTGGGACAGATTTTACTTTCACCATCAGCAGCCTGCAGCCTGAAGATATTGCAACATATTCCTGTCAACAGTATGATAATCTCCCGCTCACTTTCGGCGGAGGGACCAAGGTGGAGATCAAA |
| RVFV-352 | 120 | Heavy | CAGGTGCAGCTGCAGGAGTCGGGCCCAGGACTGGTGAAGCCTTCGGAGACCCTGTCCCTCACCTGCACTGTCTCTGGTGGCTCCATCAGTAGTTACTACTGGAGCTGGATCCGGCAGCCCCCAGGGAAGGGACTGGAGTGGATTGGGTATATCTATTACAGTGGGAGCACCAACTACAACCCCTCCCTCAAGAGTCGAGTCACCATATCAGTAGACACGTCCAAGAACCAGTTCTCCCTGAAGCTGAGCTCTGTGACCGCTGCGGACACGGCCGTGTATTACTGTGCGAGAGGGTTGGGGGTAGTAGTCTGGCCCTGGGGCCAGGGAACCCTGGTCACCGTCTCCTCA |
| | 121 | Light | CAGCCTGTGCTGACTCAGCCACCTTCCTCCTCCGCATCTCCTGGAGAATCCGCCAGACTCACCTGCACCTTGCCCAGTGACATCAATGTTGGTAGCTACAACATATACTGGTACCAGCAGAAGCCAGGGAGCCCTCCCAGGTATCTCCTGTACTACTACTCAGACTCAGATAAGGGCCAGGGCTCTGGAGTCCCCAGCCGCTTCTCTGGATCCAAAGATGCTTCAGCCAATACAGGGATTTTACTCATCTCCGGGCTCCAGTCTGAGGATGAGGCTGACTATTACTGTATGATTTGGCCAAGCAATGCCTGGGTGTTCGGCGGAGGGACCAAGCTGACCGTCCTA |
| RVFV-354 | 122 | Heavy | CAGGTGCAGCTGGTGGAGTCTGGGGGAGGCGTGGTCCAGCCTGGGAGGTCCCTGAGACTCTCCTGTGCAGCCTCTGGATTCACCTTCAGTAGCTATGGCATGCACTGGGTCCGCCAGGCTCCAGGCAAGGGGCTGGAGTGGGTGGCAGTTATATCATATGATGGAAGTAATAAATACTATGCAGACTCCGTGAAGGGCCGATTCACCATCTCCAGAGACAATTCCAAGAACACGCTGTATCTGCAAATGAACAGCCTGAGAGCTGAGGACACGGCTGTGTATTACTGTGCGAAAGCTTTGAGCAGTGGCTGGTACGAATGGGGCCAGGGAACCCTGGTCACCGTCTCCTCA |
| | 123 | Light | TCCTATGTGCTGACTCAGCCACCCTCGGTGTCAGTGGCCCCAGGACAGACGGCCAGGATTACCTGTGGGGGAAACAACATTGGAAGTAAAAGTGTGCACTGGTACCAGCAGAAGCCAGGCCAGGCCCCTGTGCTGGTCGTCTATGATGATAGCGACCGGCCCTCAGGGATCCCTGAGCGATTCTCTGGCTCCAACTCTGGGAACACGGCCACCCTGACCATCAGCAGGGTCGAAGCCGGGGATGAGGCCGACTATTACTGTCAGGTGTGGGATAGTAGTAGTGATCATTATGTCTTCGGAACTGGGACCAAGGTCACCGTCCTA |
| RVFV-356 | 124 | Heavy | CAGGTGCAGCTGCAGGAGTCGGGCCCAGGACTGGTGAAGCCTTCGGAGACCCTGTCCCTCACCTGCACTGTCTCTGGTGGCTCCATCAGTAGTTACTACTGGAGCTGGATCCGGCAGCCCCCAGGGAAGGGACTGGAGTGGATCGGGTATATCTATTACAGTGGGAGCACCAACTACAACCCCTCCCTCAAGAGTCGAGTCACCATATCATTAGACACGTCCAAGAACCAGTTCTCCCTGAAGCTGAGCTCTGTGACCGCTGCGGACACGGCCGTGTATTACTGTGCGAGGGGACTCCGGCCGGATGCTTTTGATATCTGGGGCCAAGGGACAATGGTCACCGTCTCTTCA |
| | 125 | Light | TCCTATGTGCTGACTCAGCCACCCTCGGTGTCAGTGGCCCCAGGACAGACGGCCAGGATTACCTGTGGGGGAAACAACATTGGAAGTAAAAGTGTGCACTGGTACCAGCAGAAGCCAGGCCAGGCCCCTGGGCTGGTCGTCTATGATGATAGCGACCGGCCCTCAGGGATCCCTGAGCGATTCTCTGGCTCCAACTCTGGGAACACGGCCACCCTGACCATCAGCAGGGTCGAAGCCGGGGATGAGGCCGACTATTACTGTCAGGTGTGGGATAGTAGTAGTGATCATGTGGTATTCGGCGGAGGGACCAAGCTGACCGTCCTA |
| RVFV-362 | 126 | Heavy | GAAGTGCAGCTGGTGCAGTCTGGAGCAGAGGTGAAAAAGCCCGGGGAGTCTCTGAGGATCTCCTGTAAGGGTTCTGGATACAGCTTTACCAGCTACTGGATCAGCTGGGTGCGCCAGATGCCCGGGAAAGGCCTGGAATGGATGGGGAGGATTGAGCCTAGTGACTCTTATACCAACTACAGCCCGTCCTTCCAAGGCCACGTCACCATCTCAGCTGACAAGTCCATCAGCACTGCCTACCTGCAGTGGAGCAGCCTGAAGGCCTCGGACACCGCCATGTATTATTGTGCGAGACTAGGTGATAGTAGTGGTTACGGGGAGATTGACTACTGGGGCCAGGGAACCCTGGTCACCGTCTCCTCA |
| | 127 | Light | GACATCCAGATGACCCAGTCTCCATCCTCCCTGTCTGCATCTGTAGGAGACAGAGTCACCATCACTTGCCGGGCAAGTCAGAGCATTAGCAGCTATTTAAATTGGTATCAGCAGAAACCAGGGAAAGCCCCTAAGCTCCTGATCTATGCTGCATCCAGTTTGCAAAGTGGGGTCCCATCAAGGTTCAGTGGCAGTGGATCTGGGACAGATTTCACTCTCACCATCAGCAGTCTGCAACCTGAAGATTTTGCAACTTACTACTGTCAACAGAGTTACAGTACCCCTCAGACGTTCGGCCAAGGGACCAAGGTGGAAATCAAA |
| RVFV-363 | 128 | Heavy | CAGGTGCAGCTGATGCAGTCTGGGGCTGAGGTGAAGAAGCCTGGGGCCTCAGTGAAGGTTTCCTGCAGGGCATCTGGAAACACCTTCACCAGCTACTATATGCACTGGGTGCGACAGGCCCCTGGACAAGGGCTTGAGTGGATGGGAATAATCAACCCTAGTGGTGGTAGCACAATCTACGCACAGAAGTTCCAGGGCAGAGTCACCATGACCAGGGACACGTCCACGAGCACAGTATACATGGAGTTGAGCAGCCTGAAATCTGAGGACACGGCCGTGTATTACTGTGCGAGAGGCGAATCGTACTACTTTGACTACTGGGGCCAGGGAACCCTGGTCACCGTCTCCTCA |
| | 129 | Light | TCCTATGTGCTGACTCAGCCACCCTCGGTGTCAGTGGCCCCAGGAAAGACGGCCAGGATTACCTGTGGGGGAAACAACATTGAAAGTAAAAGTGTGCACTGGTACCAGCAGAAGCCAGGCCAGGCCCCTGTGCTGGTCGTCTATGATGATACCGACCGGCCCTCAGGGATCCCTGAGCGATTCTCTGGCTCCAACTCTGGGAACACGGCCACCCTGACCATCAGCAGGGTCGAAGCCGGGGATGAGGCCGACTATTACTGTCAGGTGTGGGATAGTAGTAGTGATCATTGCGTGTTCGGCGGAGGGACCAAGCTGACCGTCCTA |
| RVFV-370 | 130 | Heavy | GAGGTGCAGCTGGTGGAGTCTGGGGGAGGCTTGGTACAGCCTGGGGGGTCCCTGAGACTCTCCTGTGCAGCCTCTGGATTCACCTTCAGTAGCTATAGCATGAACTGGGTCCGCCAGGCTCCAGGGAAGGGGCTGGAGTGGGTTTCATACATTAGTAGTAGTAGTAGTACCATATACTACGCAGACTCTGTGAAGGGCCGATTCACCATCTCCAGAGACAATGCCAAGAACTCACTGTATCTGCAAATGAACAGCCTGAGAGACGAGGACACGGCTGTGTATTACTGTGCGAGAGATTTTTACCCAGCTGCTATGGACGTCTGGGGCAAAGGGACCACGGTCACCGTCTCCTCA |
| | 131 | Light | TCCTATGTGCTGACTCAGCCACCCTCGGTGTCAGTGGCCCCAGGACAGACGGCCAGGATTACCTGTGGGGGAAACAACATTGGAAGTAAAAGTGTGCACTGGTACCAGCAGAAGCCAGGCCAGGCCCCTGTGCTGGTCGTCTATGATGATAGCGACCGGCCCTCAGGGATCCCTGAGCGATTCTCTGGCTCCAACTCTGGGAACACGGCCACCCTGACCATCAGCAGGGTCGAAGCCGGGGATGAGGCCGACTATTACTGTCAGGTGTGGGATAGTAGTAGTGATCATCGGGTGTTCGGCGGAGGGACCAAGCTGACCGTCCTA |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| RVFV-378 | 132 | Heavy | GAGGTGCAGCTGGTGCAGTCTGGAGCAGAGGTGAAAAAGCCCGGGGAGTCTCTGAGGATCTCCTGTAAGGGTTCTG GATACAGCTTTACCAGCTACTGGATCAGCTGGGTGCGCCAGATGCCCGGGAAAGGCCTGGAATGGATGGGGAGGATT GAGCCTAGTGACTCTTATACCAACTACAGCCCGTCCTTCCAAGGCCACGTCACCATCTCAGCTGACAAGTCCATCAGCA CTGCCTACCTGCAGTGGAGCAGCCTGAAGGCCTCGGACACCGCCATGTATTATTGTGCGAGACTAGGTGATAGTAGTG GTTACGGGGAGATTGACTACTGGGGCCAGGGAACCCTGGTCACCGTCTCCTCA |
| | 133 | Light | GACATCCAGATGACCCAGTCTCCATCCTCCCTGTCTGCATCTGTAGGAGACAGAGTCACCATCACTTGCCGGGCAAGTC AGAGCATTAGCAGCTATTTAAATTGGTATCAGCAGAAACCAGGGAAAGCCCCTAAGCTCCTGATCTATGCTGCATCCA GTTTGCAAAGTGGGGTCCCATCAAGGTTCAGTGGCAGTGGATCTGGGACAGATTTCACTCTCACCATCAGCAGTCTGC AACCTGAAGATTTTGCAACTTACTACTGTCAACAGAGTTACAGTACCCCTCAGACGTTCGGCCAAGGGACCAAGGTGG AAATCAAA |
| RVFV-379 | 134 | Heavy | CAGGTGCAGCTGCAGGAGTCGGGCCCAGGACTGGTGAAGCCTTCACAGACCCTGTCCCTCACCTGCACTGTCTCTGGT GACTCCATCAGCGGTGGTGATTATTACTGGAGTTGGATCCGGCGGCCCGCCGGGGAGGGCCTGGAGTGGATTGGGC GTGTTCATACTACTGGGAGTACCGACTACAACCCCTCCCTCAGGACTCGAGTCACCATATCAATAGACACGTCCAAGAA CCACTTCTTTCTGAAGATGACCTCTGTGACCGCCGCAGACACGGCCGTGTATTACTGTGCGAGAGAGGGGGATTATAG TGCCTGGTTCGACCCCTGGGGCCAGGGAGCCCTGGTCACCGTCTCCTCA |
| | 135 | Light | GACATCCAGATGACCCAGTCTCCTTCCTCCCTGTCTGCATCTATAGGAGACAGAGTCACCATCACTTGCCGGGCAAGTC AGCACATTGAGAGTTTTTTAAATTGGTATCAGCAGAAACCAGGGAAAGCCCCTAAACTCCTAATCTATATTGCATCCAC TTTGCAAGGTGGGGTCCCATCAAGGTTCAGTGGCCGTGGATTTGGGACAGATTTCACTCTCACCATCAACAGTCTGCA ACCTGAAGATTTTGCAACTTACTACTGTCAGCAGAGTTACACTATCTCTCCGATCACCTTCGGCCAGGGGACACGACTG GAAATTAAA |
| RVFV-381 | 136 | Heavy | CAGGAGCAGTTGGTTGAGTCTGGGGGAGGCGTGGTCCAGCCTGGGAGGTCCCTGAGACTCTCCTGTGCAGCCTCTGG ATTCACCCTCAGGGGCTATGGAATTTACTGGGTCCGCCAGGCTCCAGGCAAGGGGCTGGAGTGGGTGGCAGTTATAT CACATGATGGCAAAAATGAATCTTACACAGACTCCGTGAAGGGCCGATTCTCCATCTCCAGAGACAAAAGTAAGAATA CGGTCTTTCTGCAAATGAACAGCCTGACAACTCAAGACACTTCTGTCTATTACTGTGCGAGATGGACTGAGGGATCAG AGGAATTCTACTACCATGGTCTGGACGTCTGGGGCCAAGGGACCACGGTCACCGTCTCCCCA |
| | 137 | Light | TCCTATGAGCTGACACAGCCACCGTCGGTGTCAGTGTCCCCAGGACAGACGGCCAGGATCACCTGCTCTGGACATCTA CTGCCAAAACAATATGCTTATTGGTACCAGCAGAAGCCAGGCCAGGCCCCGACACTGGTGATATATGCAGACTATAAC AGGGCCTCAGGGATCCCTGAGCGATTCTCTGGCGCCAGCTCAGGGACCACAGTCACCTTGACCATCACTGGGGTCAAG GCAGAAGACCAGGCTGACTATTATTGTCAATCAATAGACAATCGTTTTCATTATCCTATGATATTCGGCGGCGGGACCA AACTGACCGTCCTA |
| RVFV-401A | 138 | Heavy | CAGATCACCTTCAAGGAGTCTGGTCCTACGCTGGTGAAACCCACACAGACCCTCACGCTGACCTGCACCTTCTCTGGGT TCTCACTCAGCACTAGTGGAGTGGGTGTGGGCTGGATCCGTCAGCCCCCAGGAAAGGCCCTGGAGTGGCTTGCCCTCC TTTATTGGAATGATGATAAGCGCTACACCCCATCTCTGAGGAGCAGGCTCACCATCACCAAGGACACCTCCAAAAACCA GGTGGTCCTCACAATGACCGACATGGACCCTGTTGACACAGCCACATATTATTGTGCACGCAAGCCTAGGGACGACTT CTTACGTCTTACTATGATGGGGGGGGGGGATTACTTTGACTACTGGGGCCAGGGAACCCTGGTCACCGTCTCCTCA |
| RVFV-401B | 139 | Light | TCCTATGAGCTGACACAGCCACCCTCGGTGTCAGTGTCCCCAGGACAGACGGCCAGGATCACCTGCTCTGGAGATGCA TTGCCAGACCAATATGCTTATTGGTACCAGCAGAAGCCAGGCCAGGCCCCTGTCCTGGTGTTATATAAAGACAATGAG AGGCCCTCAGGGATCCCTGAGCGATTCTCTGGCTCCACCTCAGGGACAACAGTCACGTTGACCATCAGTGGAGTCCAG GCAGAAGACGAGGCTGACTATTACTGTCAATCAGCAGACACCAGTACTGCTTACCATGTTATATTCGGCGGAGGGACC AAGCTGACCGTCCTA |
| RVFV-405 | 140 | Heavy | GAGGTGCAGCTGGTGGAGTCTGGGGGAGGGTTGGTGCAGCCTGGAGGGTCCCTGAGACTCTCCTGTGCAGCCTCTG GATTCACCTTCAGTAGTTTTGAAATGAACTGGGTCCGCCAGGCTCCAGGGAAGGGCCTGGAGTGGGTTTCATACATTA GTAGGAGTGGTACTACCAAACACTACGCAGACTCTGTGAAGGGCCGATTCGCCATCTCCAGAGACGACGCCAAGAACT CACTTTATCTGCAAATGAACAGTCTGAGAGCCGAGGACACGGCTGTTTATTACTGTGCGAGAGGGGGAGCCCGGGTG CTACAGGCCCCTCTTGACTACTGGGGCCAGGGAACCCTGGTCACCGTCTCCTCA |
| | 141 | Light | TCCTATGAGCTGACTCAGCCACCCTCAGTGTCAGTGGCCCCAGGAGAGACGGCCAGGATTACCTGTGGTGGAACCAAC ATTGGAAATAAAAGTGTGCGCTGGTACCAGCAGAAGCCAGGCCAGGCCCCTGTGTTGGTCATCTATTATGATAACGAC CGGCCGTCAGGGATCCCTGAGCGATTCTCTGGCTCCAACTCTGGGAACACGGCCACCCTGACCATCAGCAGGGTCGAA GCCGGGGATGAGGCCGACTACTACTGTCAGGTGTGGGATAATAGTAGTGATCACGCGGTATTCGGCGGAGGGACCA AGCTGACCGTCCTA |
| RVFV-419A | 142 | Heavy | CAGGTGCAGCTGGTGCAGTCTGGGGCTGAGGTGAAGAAGCCTGGGGCCTCAGTGAAGGTTTCCTGCAAGGCATCTGG ATACACCTTCACCGACTATTATATGCACTGGGTGCGACAGGCCCCTGGACAAGGGCTTGAGTGGATGGGAATAATCAA CCCTAGTGGTGGCAGCACAAACTACGCACAGAATTTCCAGGGCAGAGTCACCATGACCAGGGACACGTCCACGACCA CAGTCTACATGGAGCTGAGCAGCCTGAGATCTGAGGACACGGCCGTGTATTACTGTGCGAGAGCAATTTACTGGAAC GTCCCGTACTATTTTGACTACTGGGGCCAGGGAACCCTGGTCACCGTCTCCTCA |
| | 143 | Light | GAAACTGTGTTGACGCAGTCTCCAGGCACTCTGTCTTTGTCTCCAGGGGAAAGAGCCACCCTCTCCTGCAGGGCCAGT CAGAGTGTTAGCAGCAGCTGGTTAGCCTGGTACCAGCAGAAACCTGGCCAGGCTCCCAGGCTCCTCATCTATGATGCA TCCAGGGCCACTGGCATCCCAGACAGGTTCAGTGGCAGTGGGTCTGGGACAGACTTCACTCTCACCATCAGCAGATTG GAGCCTGAAGATTTAGCAGTGTATTACTGTCAGCAGTATGGTAACTCACCTACAACGTTCGGCCAAGGGACCAAGGTG GAAATCAAA |
| RVFV-426A | 144 | Heavy | CAGGTGCAGCTGCAGGAGTCGGGCCCAGGACTGCTGAAGCCTTCACAGACCCTGTCCCTCACCTGCGGTGTCTCTGGT GACTCCATCACCAGTACTGGTGACTCCTGGACCTGGATCCGGCAGCCACCAGGGAAGGGGCTGGAGTGGATTGGGTA TATCTATTACAGTGGGAGCGCCTACTATAACCCGTCCCTCAAGAGTCGAGTCACCATTTCAGTAGACACGTCCAAGAAC CAGTTCTCCCTGAGGCTGAGGTCTGTGACCGCCGCGGACACGGCCGTCTATTATTGTGCCAGAGCCTTGGAGTATGGT GCAGGGAGTTGGGCGGCGGCCTTCTGGGGCCAGGGAATACTAGTCACCGTCTCCTCA |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| | 145 | Light | TCCTATGAGGTGACTCAACCACCCTCAGTGTCCGTGTCCCCAGGACAGACAGCCAGCATCACCTGTTCTGGAGATAAATTGGTGGAGAGATATGTTTCCTGGTATCAGCAGAAGCCTGGCCAGTCCCCTCTACTAGTCATCTATCATGATATCAAACGGCCCTCAGGGATCCCTGAGCGATTCTCTGGCTCCAACTCTGGGAACACAGCCACTCTGACCATCAGCGGGACCCAGCCTATGGATGAGGCCGACTATTACTGTCAGGCGTGGGACAGCAGCACTGTGCTCTTCGGCGGAGGGACCAAGCTGACCGTCCTA |
| RVFV-429A | 146 | Heavy | CAGGTCCAGCTGGTGCAGTCTGGGGCTGAGGTGAAGAAGCCTGGGTCCTCGGTGAAGGTCTCCTGCAGGGCTTCTGGAGGCACATTCAGCAGCTATACTATCAGCTGGGTGCGACAGGCCCCTGGCCAAGGACTTGAGTGGATGGGGGGGATCATCCCTATCCTTGGTCTAACAAAGTTCGCACAGAAGTTCCAGGACAGAGTCACCATTACCGCGGACATATCCGCGACCACAACCTACATGGAACTGAGTAGCCTGACATCTGAGGACACGGCCGTCTATTACTGTGCGAGAAATGGGGAGCAGCTCGAGTGGAGCTACTACTACGGTATGGACGTCTGGGGCCAAGGGACCACGGTCACCGTCTCCTCA |
| | 147 | Light | GACATCGTGATGACCCAGTCTCCAGACTCCCTGGCTGTGTCTCTGGGCGAGAGGGCCACCATCAACTGCAAGCCCAGCCAGAGTATTTTATACAGCTCCAACAATAAGAACTACTTAGCTTGGTACCAGCAGAAACCAGGACAGCCTCCTAAACTGCTCATTAACTGGGCATCTACCCGGGAATCCGGGGTCCCTGACCGATTCAGTGGCAGCGGGTCTGGGACAGACTTCACTCTCACCATCAGCAGCCTGCAGGCTGAAGATGTGGCAGTTTTTTACTGTCAACAATATTATACTATTCCCCCGACGTTCGGCCAAGGGACCAAGGTGGAAATCAAA |
| RVFV-431A | 148 | Heavy | CAGGTGCAGCTACAGCAGTGGGGCGCAGGACTATTGAAGCCTTCGGAGACCCTGTCCCTCACCTGCACTGTCTATGGTGGGTCCTTCACTCTTTACTACTGGACCTGGATCCGCCAGCCCCCAGGGAAGGGGCTGGAGTGGATTGGGGAAATCAATCAGAGTGGAAGCACCAACTACAACCCGTCCCTCAGGAGTCGACTCACCATATCAGTAGACACGTCCAAGAGCCAGTTCTCCCTGAAGGTGACCTCTGTGACCGCCGCGGACACGGCTGTGTATTACTGTGCGAGAGGCCATGATAGTAGTGGTTATTATATCGACTACTACTTGGACGTCTGGGGCAAAGGGACCACGGTCACCGTCTCCTCA |
| | 149 | Light | TCTTCTGAGCTGACTCAGGACCCTGCTGTGTCTGTGGCCTTGGGACAGACAGTCAGGATCACATGCCAAGGAGACAGCCTCAGAAACTATTATGCAGGCTGGTACCAGCAGAGGCCAGGACAGGCCCCTGTTCTTGTCTTCTATGGTAAAGACAACCGGCCCTCAGGGATCCCAGACCGATTCTCTGGCTCCAGCTCAGGAAACACAGCTTCCTTGACCATCACTGGGGCTCAGGCGGAAGATGAGGCTGACTATTACTGTAACTCCCGGGACAGCAGTGGTGACGTTGTGGTATTCGGCGGAGGGACCAAGCTGACCGTCCTA |
| RVFV-436A | 150 | Heavy | CAGGTGCAGCTGCACGAGTCGGGCCCAGGACTGGTGAAGCCTTCGGAGACCCTGTCCCTCACCTGCGGTGTCTCTGGTTACACCATAAGCAGTGATTACTACTGGGGCTGGATCCGGCAGCCCCCAGGGAAGGGGCTGGAGTGGATTGGGAGTATCTATCAAAATGGGCACACCTACTACAACCCGTCCCTCAAGAGTCGAGTCACCATTTCGGTAGACACGTCCAAGAACCAATTCTCCCTAGAGCTGAGCTCTGTGACCGCCGCAGACACGGCCGTATATTACTGTGCGAGAAGGGGGGATTGTGGTGCTGATTGCTACCACTTTGACTATTGGGGCCGGGGAACGGCGGTCACCGTCTCCTCA |
| | 151 | Light | TCCTATGAGGTGACTCAGCCACTCTCAGTGTCCGTGTCCCCAGGACAGACAGCCAGCATCACCTGCTCTGGAGAAAAATTGGAAAATAAATATGTTTCCTGGTATCAGCAGAAGCCAGGCCAGTCCCCTGTACTGGTTATGTATCAAGATTTCAAGCGGCCCTCAGGGATCCCTGAGCGATTCTCTGGCTCCAACTCTGGGAACACAGCCACTCTGACCATCAGCGGGACCCAGGCTATGGATGAGGCTGACTATTACTGTCAGGCGTGGGACAGGAGCACCTTTTATGTCTTCGGAACTGGGACCAAGGTCACCGTCGTAGGT |
| RVFV-443B | 152 | Heavy | CAGTTGCAGCTGCAGGAGTCGGGCCCAGGACTGGTGAAGCCTTCGGAGACCCTGTCCCTCACTTGCTTTGTCCCTGGTGACTTCCTCAGCAGTACTAATTTCTACTGGGGCTGGATCCGCCAGCCCCCAGGAAAGGGACTGGAGTGGATTGGGAGTATTTATGACAGTGGGAACACTTACTACAACCCGTCCCTCAAGAGTCGAGTCACCATGTCAATAGACACGCCCAAGAACCAGTTCTCCCTGCAGCTGAGTTCTGTGACCGCCGCGGACACGGCCGTATATTACTGCGCGCGAGTCGGGGATTGTGGTGCAGACTGCTACTACTTTGACCACTGGGGCCAGGGAACCCTGGTCACCGTCTCCTCA |
| | 153 | Light | TCCTATGAACTGACTCAGCCACCCTCAGTGTCCGTGTCCCCAGGACAGACAGCCAGCATCTCTTGTTCTGGAGATAGGTTGCGGGATAGATATGTTTCCTGGTATCAGCAGAAGCCAGGCCAGTCCCCTGTGGTAGTCATCTATCAAGACTTCAAGCGGCCCTCAGGGATCCCTGCGCGATTCTCTGCCTCCAACTCTGGCAACACAGCCACTCTGACCATCATCGGGACCCAGGCTATGGATGAGGCTGACTATTACTGTCAGGCGTGGGACAGCTTCACTTATGTCTTCGGAGCTGGGACCAAGGTCACCGTCCTTGGT |
| RVFV-451B | 154 | Heavy | GAGGTGCATCTGGTGGAGTCTGGGGGAGGCTTGGTCCAGCCTGGGGGGTCCCTGAGACTCTCCTGTGCAGCCTCTGGATTCACCTTTAGTAGTTATTGGATGAGCTGGGTCCGCCAGGCTCCAGGGAAGGGGCTGGAGTGGGTGGCCAACATAAAGCAAGATGGAAGTGAGAAATATTATGTGGACTCTGTGAAGGGCCGATTCACCATCTCCAGAGACAACGCCAAGAACTCACTGTATCTGCAAATGAACAGCCTGAGAGCCGAGGACACGGCTGTGTATTACTGTGCGAGGGGGTCGATCGGGTGGTTATCCCCTGACTACTGGGGCCAGGGAACGCTGGTCACCGTCTCCTCA |
| RVFV-451B-a | 155 | Light | TCTTCTGAGCTGACTCAGGACCCTGCTGTGTCTGTGGCCTTGGGACAGACAGTCAGGATCACATGCCAAGGAGACAGCCTCAGAAGCTTTTATGCAAGCTGGTACCAGCAGAAGCCAGGACAGGCCCCTATACTTGTCTTCTATGGTCAAAACAACCGGCCCTCAGGGATCCCAGACCGATTCTCTGGCTCCAGTTCAGGAAACACAGCTTCCTTGACCATCACTGGGGCTCAGGCGGAAGATGAGGCTGACTATTACTGTAACTCCCGGGACAGCGGTGGTTACCATCTGGTGTTCGGCGGAGGGACCAAGCTGACCGTCCTA |
| RVFV-451B-b | 156 | Light | CAGCCTGTGCTGACTCAGCCACCCTCTGCATCAGCCTCCCTGGGAGCCTCGGTCACACTCACCTGCACCCTGAGCAGCGGCTACAGTAATTATAAACTGGACTGATACCACCAGAGACCAGGGAAGGGCCCCCGATTTGAGATGCGAGTGGGCACTGGTGGGATTGTGACATCCACGGGGGATGGCATCCCTGATCGCTTCGCAGTCTTGGGCTCAGGCCTGAATCGGTTCCTGACCATCAAGAACATCCAGGAAGAGGATGAGAGTGACTACCACTGTGGGCCAGACCATGGGCGTGGGTGTTCGGCGGAGGGACCAAGGTGACCGTCC |
| RVFV-459A | 157 | Light | TCCTATGAGTTGACTCAGCCACCCTCAGTGTCCGTGTCCCCAGGACAGACAGCCAGCATCACCTGCTCTGGAGATAAATTGGGGGATAAATATGCTTGCTGGTATCAGCAGAAGCCAGGCCAGTCCCCTGTGCTGGTCATCTATCAAGATACCAAGCGGCCCTCAGGGATCCCTGAGCGATTCTCTGGCTCCAACTCTGGGAACACAGCCACTCTGACCATCGGCGGGACCCAGCCTATGGATGAGGCTGACTATTACTGTCAGGCGTGGGACAGCAGCACTGAGGTGGTATTCGGCGGAGGGACCAAGCTGACCGTCCTA |

TABLE 1-continued

| NUCLEOTIDE SEQUENCES FOR ANTIBODY VARIABLE REGIONS | | | |
|---|---|---|---|
| Clone | SEQ ID NO: | Chain | Variable Sequence Region |
| RVFV-76 | 158 | Heavy | GATGTTCAAGTGGTGGAGTCTGGGGGAGGCTTGGTGCAGCCAGGGCGGTCCCTGAGACTCTCCTGTCAATGCTTTGGATTCAACTTTGGCGATTATCTCATGACCTGGTTCCGCCAGGCTCCAGGGAAGGGGCTGGAGTGGGTAGGTTTTGTTAGAACCAAAGGTTATGGCGGGACATCAGAATACGCCGCGTCTGTGAGAGGCAGATTCACCGTCTCAAGAGATGACTCCAGGGGCATCGCCTACCTCCAAATGAACAGCCTGAGAGTCGAGGACACAGCCGTGTATTACTGTACAAGAGATAGACAAAAACCCACTTATCAATTTTGGAGCAGTTATTTTGTTGATGATCCTTTTGATGTCTGGGGCCAAGGGACAAAGGTCACCGTCTCTTCA |
| | 159 | Light | TCTTCTGAGCTGACTCAGGACCCTGCTGTGTCTGTGGCCTTGGGACAGACAGTCAGGATCACATGCCAAGGAGACAGCCTCAGAAGTTATTCTGCAAGCTGGTACCAGCATAAGGCAGGACAGGCCCCTGTACTTGTCCTCTATGGTAAAAACAACCGGCCTTCAGGGATCCCCGACCGATTCTCTGGCTCCACCTCAGGAAACACAGCTTCCTTGACCATCACTGGGGCTCAGGCGGAAGATGAGGCTGACTTTTACTGTAACTCTCGAGACAGCAGTGGAATCCGTGTGGTTTTCGGCGGAGGGACCAAGCTGACCGTCCTA |
| RVFV-778 | 160 | Heavy | GAAGTGCAGCTGGTGCAGTCTGGAGCAGAGGTGAAAAAGCCCGGGGAGTCTCTGAGGATCTCCTGTAAGGGTTCTGGATACAGCTTTACCAGCTACTGGATCAGCTGGGTGCGCCAGATGCCCGGGAAAGGCCTGGAATGGATGGGGAGGATTGAGCCTAGTGACTCTTATACCAACTACAGCCCGTCCTTCCAAGGCCACGTCACCATCTCAGCTGACAAGTCCATCAGCACTGCCTACCTGCAGTGGAGCAGCCTGAAGGCCTCGGACACCGCCATGTATTATTGTGCGAGACTAGGTGATAGTAGTGGTTACGGGGAGATTGACTACTGGGGCCAGGGAACCCTGGTCACCGTCTCCTCA |
| | 161 | Light | GACATCCAGATGACCCAGTCTCCATCCTCCCTGTCTGCATCTGTAGGAGACAGAGTCACCATCACTTGCCGGGCAAGTCAGAGCATTAGCAGCTATTTAAATTGGTATCAGCAGAAACCAGGGAAAGCCCCTAAGCTCCTGATCTATGCTGCATCCAGTTTGCAAAGTGGGGTCCCATCAAGGTTCAGTGGCAGTGGATCTGGGACAGATTTCACTCTCACCATCAGCAGTCTGCAACCTGAAGATTTTGCAACTTACTACTGTCAACAGAGTTACAGTACCCCTCAGACGTTCGGCCAAGGGACCAAGGTGGAAATCAAA |
| RVFV-86 | 162 | Heavy | GAGGTGCAGCTGGTGCAGTCTGGAGCAGAGGTGAAAAAGCCCGGGGAGTCTCTGAAGATCTCCTGTAAGGGTTCTGGATACAGCTTTACCAGCTACTGGATCGGCTGGGTGCGCCAGATGCCCGGGAAAGGCCTGGAGTGGATGGGGATCATCTATCCTGGTGACTCTGATACCAGATACAGCCCGTCCTTCCAAGGCCAGGTCACCATCTCAGCCGACAAGTCCATCAGCACCGCCTACCTGCAGTGGAGCAGCCTGAAGGCCTCGGACACCGCCATGTATTACTGTGCGAGGGCTCCCACCGTACCAGCTGCTATTTGGGGTAGCTCTTACTACTACTACTACTACATGGACGTCTGGGGCAAAGGGACCACGGTCACCGTCTCCTCA |
| | 163 | Light | GACATCGTGATGACCCAGTCTCCAGACTCCCTGGCTGTGTCTCTGGGCGAGAGGGCCACCATCAACTGCAAGTCCAGCCAGAGTGTTTTATACAGCTCCAACAATAAGAACTACTTAGCTTGGTACCAGCAGAAACCAGGACAGCCTCCTAAGCTGCTCATTTACTGGGCATCTACCCGGGAATCCGGGGTCCCTGACCGATTCAGTGGCAGCGGGTCTGGGACAGATTTCACTCTCACCATCAGCAGCCTGCAGGCTGAAGATGTGGCAGTTTATTACTGTCAGCAATATTATAGTACTTCGCTCACTTTCGGCGGAGGGACCAAGGTGGAGATCAAA |
| RVFV-95 | 164 | Heavy | GAGGTGCAGCTGGTGGAGTCCGGGGGAGGCTTGGTCCAGCCGGGGGGGTCCCTGAAACTCTCCTGTGCAGCCTCTGGGTTCAAATTCAGTGGCTCTGCTATGCATTGGGTCCGTCAGGCCTCCGGGAGAGGGCTGGAATGGGTTGGCCGTATCAGAAGCAAGGCCAACAATTACGCGACAACATATGCTGAGTCCGTGAAAGGCAGGTTCACCATCTCCAGGGATGATTCACAAAACACGGCGTATTTGGAGATGCACAATCTGAGAACCGAGGACACGGCCGTGTATTATTGTACGAGGAATGTGGATACGGATCACAGGGGCTGGGGCCAGGGAACCCTGGTCAGTGTCTCCTCA |
| | 165 | Light | GAAATCGTGATGACCCAGTCTCCAGACCCCCTGCCTGTGTCTCTGGGCGGGAGGGCCACCATCAACTGCAAGTCCAGCCAGAGTCTTTTATACGGCTCCACCAATAAGAACTACTTAGCTTGGTACCAGCAGAAACCAGGACAGCCTCCTAGGCTGCTCATTTATTGGGCATCTACCCGGGAATCCGGGGTCCCTGACCGATTCAGTGGCAGCGGGTCTGGGACAGATTTCGCTCTCACCATCAGCGACCTGCAGGCTGAAGATGTGGCAGTTTATTATTGTCAGCAATATTATAATGTTGCGTGGACGTTCGGCCAAGGGACCAAGGTGGAAATCAGA |

TABLE 2

| PROTEIN SEQUENCES FOR ANTIBODY VARIABLE REGIONS | | | |
|---|---|---|---|
| Clone | SEQ ID NO: | Chain | Variable Sequence |
| RVFV-121 | 166 | Heavy | QMQLQESGPGLVKPSGTLSLTCAVSGDSISTSTWWSWVRQSPGKGLEWIGEIYHSESTNYNPSLKSRVSLSLDKSKNQLSLRLSSVTAADTGVYYCARGSLVFDYWGQGAQVVVSS |
| | 167 | Light | EIVMTQSPATLSVSPGERATLSCRASQSVSSNLAWYQQKPGQAPRLLIYAASTRATGIPARFSGSGSGTEFTLTISSLQSEDFAVYYCQQFNNWPRTFGQGTKVEIK |
| RVFV-127 | 168 | Heavy | QVQLQESGPGLVKPSETLSLTCTVSGDSVRNYYWSWIRQPPGEGLEWIGYIYYSGSTDFNPSLKSRVTMSVDTSKNHFSLKLRSVTAADTAMYYCARVAIRTDGYIRAFDIWGAGTMVTVSS |
| | 169 | Light | DIQMTQSPSSPSASVGDRVTVTCRASQSIRNYLNWYQQKPGKAPKLLIYAASSLQSGVPSRFSGSGSGTEFTLTISSLQPEDFATYYCQQTYSTAWTFGQGTKVEIK |
| RVFV-128A | 170 | Heavy | QVQLQESGPGLVKPSQTLSLTCTVSGGSISSGDYFWSWIRQPPGKGLEWIGYIYYSGSTYYNPSLKSRITISVDTSKNQFSLKLSSVTAADTAVFYCARVQTPGSDTYYFDYWGQGTLVTVSS |

TABLE 2-continued

PROTEIN SEQUENCES FOR ANTIBODY VARIABLE REGIONS

| Clone | SEQ ID NO: | Chain | Variable Sequence |
|---|---|---|---|
| | 171 | Light | DIQMTQSPSSLSASVGDRVTITCRASQSISSYLNWYQQKPGKAPKLLIYAAS SLQSGVPSRFSGSGSGTDFTLTISSLQPEDFATYFCQQSYSTPMYTFGQGT KLEIK |
| RVFV-128B | 172 | Heavy | QLQLQESGPGLVKPSETLSLTCTVSGGSISSSSYHWGWIRQPPGKGLEWIG SIYYTGSTYYNPSLKSRVIISVDASKNQFSLKLSSVTAADTAVYYCARRSLRS GWAAAIDFWGQGTLVTVSS |
| | 173 | Light | DIQMTQSPSSLSASVGDRVTITCRASQSISSYLNWYQQKPGKAPKLLIYAAS SLQSGVPSRFSGSGSGTDFTLTISSLQPEDFATYFCQQSYSTPMYTFGQGT KLEIK |
| RVFV-132 | 174 | Heavy | QVQLQESGPGLVKPSETLSLTCTVSGGSVSSGSYYWSWIRQPPGKGLEWI GYIYYSGSTNYNPSLKSRVTISVDTSKNQFSLKLSSVTAADTAVYYCARDYR VTTGNYYYYGMDVWGQGTTVTVSS |
| | 175 | Light | QSVLTQPPSASGTPGQRVTISCSGSSSNIGSNTVNWYQQLPGTAPKLLIYS NNQRPSGVPDRFSGSKSGTSASLAISGLQSEDEADYYCAAWDDSLNGWV FGGGTKLTVL |
| RVFV-140A | 176 | Heavy | STQSTWAGPGLVKPSQTLSLTCTVSGGSVSSGDYYWSWIRQPPGRGLEW IGYISYSGSTYYNPSLESRITMSGDTSKQQFSLKLSSVTVADTAVYYCATNYF HLHDFGDLYWYFDLWGRGTLVTVSS |
| | 177 | Light | QSALTQPASVSGSPGQSITISCTGTSSDIGAYNFVSWYQQHPGTAPKLLIY DVTNRPSGVSNRFSGSKSGNTASLTISGLQAEDEANYYCNSYTSSSHVVFG GGTKLTVL |
| RVFV-140B | 178 | Heavy | QLQLQESGPGLARPSETPSLTCTVSGGSISSSVYYWGWIRQPPGKGLEWI GSIYYSGYTNYNPSLKSRVSISVDTSKNQFSLQLNSVTAADTAVYYCARHSD CGNDCYYFDYWGQGTLVTVSS |
| | 179 | Light | SYELTQPPSVSVSPGQTASITCSGDRLGDKYASWYQQKPGQSPVLVIYQD YKRPSGIPERFSGSNSGHTATLTISGTQAMDEADYFCQAWDSSDGSVFGT GTKVTVL |
| RVFV-140C | 180 | Heavy | QVQLQESGPGLVKPSQTLSLTCTVSGGSVSSGDYYWSWIRQPPGRGLEW IGYISYSGSTYYNPSLESRITMSGDTSKQQFSLKLSSVTVADTAVYYCATNYF HLHDFGDLYWYFDLWGRGTLVTVSS |
| | 181 | Light | QSALTQPASVSGSPGQSITISCTGTSSDIGAYNFVSWYQQHPGTAPKLLIY DVTNRPSGVSNRFSGSKSGNTASLTISGLQAEDEANYYCNSYTSSSHVVFG GGTKLTVL |
| RVFV-142A | 182 | Heavy | EVQLVESGGGLVQPGGSLRLSCAASGFMFSRYWMSWVRQAPGKGLEW VANIKQDGSEKNYVDSVKGRFTISRDNAKNSLYLQMNTLRAEDTAVYYCA RGEYYGSGSYSWGQGTLVTVSS |
| | 183 | Light | DIQMTQSPSTLSASVGDRVTITCRASQSISSWLAWYQQKPGKAPKLLIYKA SSLESGVPSRFSGSGSGTEFTLTISSLQPDDFATYYCQQYNSYPLTFGGGTK VEIK |
| RVFV-142B | 184 | Heavy | QLQLQESGPGLARPSETPSLTCTVSGGSISSSVYYWGWIRQPPGKGLEWI GSIYYSGYTNYNPSLKSRVSISVDTSKNQFSLQLNSVTAADTAVYYCARHSD CGNDCYYFDYWGQGTLVTVSS |
| | 185 | Light | SYELTQPPSVSVSPGQTASITCSGDRLGDKYASWYQQKPGQSPVLVIYQD YKRPSGIPERFSGSNSGHTATLTISGTQAMDEADYFCQAWDSSDGSVFGT GTKVTVL |
| RVFV-144 | 186 | Heavy | QVHLQESGPGLVKPSETLSLTCTVSGGSIGTYYWSWIRQPPGKGLEWIGY VYHSGATNDNPSLMSRLTMSVDTSKNQFSLDLRSVTAADTAIYYCAREGS NGDFRGHFDSWGQGTLVTVSS |
| | 187 | Light | QSALTQPASVSGSPGQSITISCTGTSSDVGGFNFVSWYQQHPGKAPKLMI YDVSNRPSGVSNRFSGSKSGNTASLTISGLRTDDEGDYYCTSYTSSSTVVFG GGTKLTVL |
| RVFV-151 | 188 | Heavy | QVQLQQWGAGLLKPSETLSLTCAVYGGSFSGYYWSWIRQPPGKGLEWIG EINHSGRTKYNPSLSSGLTLSVDKSKNQFSLKLRSVTAADTAVYYCARGHV VVTPATLFHRVGEHYFDFWGQGTLVSVSS |
| | 189 | Light | SSELTQDPAVSVALGQTVRITCQGDSLKNYYASWYQQKPGRAPLLVMSG KNNRPSGIPDRFSGSSSGNTASLTITGAQAEDEADYYCSSRDRSDKYWVF GGGTKVTVL |
| RVFV-154 | 190 | Heavy | QVQLVQSGAEVKRPGASVKVSCKASGYTFTTYAIHWVRQAPGQRLEWM GWINAGNGDTKYSQRFQGRVTVTRDTSANTAYMELTSLTSEDTAVYYCA RGWVGCIGKRGKTCYANLPDDYWGQGTLVTVSS |
| | 191 | Light | QSALTQPASVSGSRGQSITITCTGTSSDVGAYKFVSWYQQHPGKAPNLIIY DVNSRPSGVSDRFSGSKSGYTASLTISGLQAEDEADYYCSSYTRGPYIFGTG TKVTVL |

TABLE 2-continued

PROTEIN SEQUENCES FOR ANTIBODY VARIABLE REGIONS

| Clone | SEQ ID NO: | Chain | Variable Sequence |
|---|---|---|---|
| RVFV-158 | 192 | Heavy | QVKLVESGGGVVQPGRSLRLSCEASRFTFNTYGMHWVRQAPGKGLEWVAVISYDGKKKYYADSAKGRFTISRDDSRNTLYLEMNSLRVEDTAVYYCARDLRRFYSNGWFTGSDFWGQGTLVTVSS |
| | 193 | Light | EIVLTQSPATLSLSPGERATLSCGASQTISSNNLAWYQQKPGLAPRLLIYDASTRAAGIPRRFSGSGSGTNFTLTVTRLDPEDFALYSCQQYGRSPITFGQGTRLEIK |
| RVFV-164 | 194 | Heavy | QVELRESGPGLVKPSGTLSLTCAVSGVSITSSNWWNWVRQSPGKGLEWIGQVYHSGSTKYNPSLRSRLTISVDKSKNQFSLKMKYVRAADTAVYFCARDGFSGYDVALDKWGQGTLVTVSS |
| | 195 | Light | QSVLTQPPSVSAAPGQRVTISCSGSSSNIGNSYVSWYQHLPGTAPKLLIYDNNKRPSGIPDRFSASKSGTSATLGITGLRTGDEADYYCATWESRLSAGHVVFGGGTKLTVL |
| RVFV-166 | 196 | Heavy | QITLQESGPTLVKPTRTLTLTCTLSGVSLSSSGVGVGWIRQPPGRALEWLAVIYWDDDKHYRPSLKSRLTITKDTSKNQVVLTMTNMDPVDTATYYCAHRNIVVVRADPHRWAGTFDYWGQGALVTVSA |
| | 197 | Light | EIVLTQSPGTLSLSPGERATLSCRASQSVTSNYLAWYQQKPGQAPRLLIYGASSRAAGIPDRFSGSGSGTDFTLTISRLEPEDLGVYSCQQYAGSPFTFGPGTKVEIK |
| RVFV-206 | 198 | Heavy | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKDQGTMIVVVTLPPGAFDIWGQGTMVTVSS |
| RVFV-211 | 199 | Heavy | EVQLVESGGGLVQPGGSLRLSCAASGFMFSRYWMSWVRQAPGKGLEWVANIKQDGSEKNYVDSVKGRFTISRDNAKNSLYLQMNTLRAEDTAVYYCARGEYYGSGSYSWGQGTLVTVSS |
| | 200 | Light | DIVMTQSPLSLPVTPGEPASISCRSSQSLLHSNGYNYLDWYLOKPGQSPQLLIYLGSNRASGVPDRFSGSGSGTDFTLKISRVEAEDVGVYYCVQALQIPLTFGGGTKVEIK |
| RVFV-220 | 201 | Heavy | QVHLQESGPGLVKPSQALSLTCTVSGGSINGDNYYWSWIRQPPGKGLEWIGYIYYSGSTYYNPSLKSRISISVDTSKNQFSLKLSSVTAADTAVYYCARGADCGNDCYYFDYWGQGALVTVSS |
| | 202 | Light | SYELTQPPSVSVSPGQTASITCSGDKLGHKYACWYQQRPGQSPVLVIYQDSKRPSGIPERFSGSNSGNTATLTISGTQAVDEADYYCQAWDSSSFYVFGTGTKVTVL |
| RVFV-226 | 203 | Heavy | EVQLVESGGGLVQPGRSLRLSCAASGFTFDDYAMHWVRQAPGKGLEWVSGISWNSGSIGYVDSVKGRFTISRDNAKNSLYLQMNSLRAEDTALYYCAKGLVGAIHDAFDIWGQGTMVTVSS |
| | 204 | Light | DIQMTQSPSTLSASVGDRVTITCRASQSISSWLAWYQQKPGKAPKLLIYKASSLESGVPSRFSGSGSGTEFTLTISSLQPDDFATYYCQQYNSYPLTFGGGTKVEIK |
| RVFV-229 | 205 | Heavy | QVQLQESGPGLVKPSQTLSLTCTVSGGSISSGDYFWSWIRQPPGKGLEWIGYIYYSGSTYYNPSLKSRITISVDTSKNQFSLKLSSVTAADTAVFYCARVQTPGSDTYYFDYWGQGTLVTVSS |
| | 206 | Light | SYELTQPPSVSVSPGQTASITCSGDKLGDKYACWYQQKPGQSPVLVIYQDTKRPSGIPERFSGSNSGNTATLTISGTQAMDEADYYCQAWDSSTVVFGGGTELTVL |
| RVFV-235B | 208 | Heavy | QVQMVQSGAEVKKPGASVKVSCKASGYTFTGYYMHWVRQAPGQGLEWMGWINPNSGGTNYAQKLQGRVTMTRDTSISTAYMELSRLRSDDTAVYYCARGRYCDSASCYVRNYFYYMDVWGKGTTVTVSS |
| | 209 | Light | EIVLTQSPATLSLSPGERATLSCRASQSVSRYLAWYQQKLGQAPRLLIYDASNRATGIPARFSGSGSGTDFTLTISSLEPEDFAVYYCQQRSNWPTFGQGTRLDIK |
| RVFV-239 | 210 | Heavy | GVELVESGGGAAQPGGSLRLYCAASGFTFSNYWMNWVRQGPGKGLTWIARINDHGNYTSYEDSVKGRFTISRDNTKNTVFLQMNSLRLDDSAVYYCVRAFGGGYWGQGTPVTVSS |
| | 211 | Light | DVVMTQSPLSLPVSLGQPASISCKSGQSLVYRDGNTYLSWFFQRPGQSPRRLIYQVFKRDSGVPDRFTGSGSGSDFTLQISRVQSEDVGIYYCMQSTHWPWTFGQGTKVEIK |
| RVFV-243 | 212 | Heavy | QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARERSIAARQNRGYFDYWGQGTLVTVSS |
| | 213 | Light | DIQMTQSPSSLSASVGDRVTITCRASQGIRNDLGWYQQKPGKAPKRLIYAASSLQSGVPSRFSGSGSGTEFTLTISSLQPEDFATYYCLQHNSYPWTFGQGTKVEIK |

TABLE 2-continued

PROTEIN SEQUENCES FOR ANTIBODY VARIABLE REGIONS

| Clone | SEQ ID NO: | Chain | Variable Sequence |
|---|---|---|---|
| RVFV-247 | 214 | Heavy | EVQLVESGGGLVQPGGSLRLSCAASGFTFSRYYMHWVRQAPGKGPVWISRINTDGSTTAYADSVKGRFTISRDNAKNTLYLQMNSLRVEDTAVYYCARPYSGYFHWGRGALVTVSS |
| | 215 | Light | DIVMTQTPLSSSVTLGQPASISCRSSQSLVHSDGNTYLNWLHQRPGQPPRLLIYKISNRFSGVPDRFSGSGAGTDFTLKISRVEAEDVGVYYCMQGTRLYTFGQGTKLEIK |
| RVFV-248A | 216 | Heavy | EVLLLESGGGLVQPGGSLRLSCTVSGFTFTNSWMHWVRQAPGKGLVWVSGINPDGSKIDHAESVQGRFTISRDNAKNTLYLQMDSLRDEDTAVYYCARWLSWGQGALVTVTS |
| | 217 | Light | TISCSGSSSNIGSNHVYWYQQLPGSAPQLLISKNNQRPSGVPDRFSGSKSGTSGSLAISGLRSEDEAAYYCAAWDDSLRGWEFGGGTQVTVLGQPKAAPSVTLFP |
| RVFV-248B | 218 | Heavy | EVLLLESGGGLVQPGGSLRLSCTVSGFTFTNSWMHWVRQAPGKGLVWVSGINPDGSKIDHAESVQGRFTISRDNAKNTLYLQMDSLRDEDTAVYYCARWLSWGQGALVTVTS |
| | 219 | Light | EIVLTQSPATLSLSPGERATLSCRASQSVSRKLAWFQQRLGQAPRLLIYDASTRATGVPAKFSGSGSGTDFTLTISSLEPEDFAVYYCHQRSNWWTFGQGTKVEVK |
| RVFV-249 | 220 | Heavy | QVLLVQSEAEVRKPGASVKISCKTSGYTFTTYFMHWVRQAPGQGLEWVAIVDPSTGNTGYAQRFQGRVTVTRDTSTGTLFMELTSLTTEDTAMYYCGRDRGSRAVDSWGQGTLVTVFS |
| | 221 | Light | QSVLTQPPSVSGAPGQRVTISCSGSSSNVGPNTVSWYQQLPGVAPKLLIYRNNQRPSGVPDRFSGSKFGTSASLVIGGLQSEDEADYYCAAWDDSLNGHMVFGGGTKVAVL |
| RVFV-250 | 222 | Heavy | QVQLQESGPGLAKPSETLSLTCTVSGGSISSYFWSWIRQPAGKGLEWIGRIHTTGSTNYNPSLKNRVIMSVDTSKNQFSLNLSSVTAADTAVYYCAREGTAFDIWGQGTMVTVSS |
| | 223 | Light | SYELTQSPSVSVSPGQTASIPCSGDKLGDKYACWYQQKPGQSPVLVIYQDTKRPSGIPERFSGSNSGNTATLTISETQAMDEADYYCQAWDSSTPWVFGGGTKLTVL |
| RVFV-263 | 224 | Heavy | QVHLVESGGGLVKPGGSLRLSCAASGFTFSDYYMSWIRQAPGKGLEWVSYISGTGSFIYYADSVKGRFTISRDNAKNSLYLQINSLRAEDTAVYYCARGIRADCFDQWGHGTLVTVSS |
| | 225 | Light | SYVLTQPPSVSVAPGQTARITCGGNNIGDKSVHWYQQKPGQAPVLVVYDDSDRPSGIPERFSGSNSGNTATLTISRVEAGDEADYYCQVWDSSSDHLVFGTGTKVTVL |
| RVFV-266 | 226 | Heavy | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARARGGSYSLDYWGQGTLVTVSS |
| | 227 | Light | SYVLTQPPSVSVAPGQTARITCGGNNIGSKSVHWYQQKPGQAPVLVVYDDSDRPSGIPERFSGSNSGNTATLTISRVEAGDEADYYCQVWDSSSDHWVFGGGTKLTVL |
| RVFV-268 | 228 | Heavy | QVHLVESGGGVVQPGKSLRLSCAASGFIFNHFGIHWVRQSPGKGLEWVAVIWYDGSKKYFADSVKGRFSISRDNSQNTVYLQMNSLRTEDTAVYYCARERWSGHSYLDYWGHGALVTVSS |
| | 229 | Light | SNVLTQPPSVSVAPGQTARISCGGNNLESKYVHWYQQKPGQAPVLVVYEDSGRPSGIPERFSGSNSGGTATLTISRVEAGDEADYYCQEWDTSSDYPVFGGGTKVTVL |
| RVFV-278 | 230 | Heavy | QVQVAESGGGVVQPGRSLRLSCVASGFTFRTKTMHWVRQAPGKGLEWVAFISGSGKDKSYADSVKGQFTISRDNSKNTLFLQLDSLRPEDTAVYYCVKDREGTWSFDHWGQGALVTVSS |
| | 231 | Light | QSALTQPASVSGSPGQSITISCTGTNNDVGLYDYVSWYQQHPGRAPKLIIYEVTNRPSGVSDRFSASKSGNTASLTISGLQAEDEADYYCSSYTRSITWVFGGGTKVTVL |
| RVFV-284 | 232 | Heavy | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKKYYDFWSGYYPNWFDPWGQGTLVTVSS |
| | 233 | Light | EIVMTQSPATLSVSPGERATLSCRASQSVSSNLAWYQQKPGQAPRLLIYGASTRATGIPARFSGSGSGTEFTLTISSLQSEDFAVYYCQQYNNWPQRTFGQGTKVEIK |
| RVFV-296A | 234 | Heavy | QVQLVQSGSELKKSGASVKVSCRASGYTFTTYVMNWVRQAPGQGLEWMGW1NTNTGNPTYAQGFTGRFVFSLDTSVSTAYLQINSLKAEDTAVYYCAREYNSFDYWGQGTLVTVSS |

TABLE 2-continued

PROTEIN SEQUENCES FOR ANTIBODY VARIABLE REGIONS

| Clone | SEQ ID NO: | Chain | Variable Sequence |
|---|---|---|---|
| | 235 | Light | QSVLTQPPSVSGAPGQRVTISCTGSSSNIGAGYDVHWYQQLPGTAPKLLIY DNNNRPSGVPDRFSGSRSGTSTSLAITGLQAEDEADYYCQSYDFRLSGSVF GGGTKVTVL |
| RVFV-299 | 236 | Heavy | QVQLVQSGAEVKKPGASVKVSCKASGYTFTSYYMHWVRQAPGQGLEW MGIISPSGGSTDYAQKFQGRVTMTRDTSTSTVYMELSSLRSEDTAVYYCA RQVQTDYYFDYWGQGTLVTVSS |
| | 237 | Light | SYVLTQPPSVSVAPGQTARITCGRNNIGSKSVHWYQQKPGQAPVLVVYD DSDRPSGIPERFSGSNSGNTATLTISRVEAGDEADYYCQVWDSSSDHSWV FGGGTKLTVL |
| RVFV-300 | 238 | Heavy | QVQLVESGGGVVQPGRSLRLSCAASGFTFSSYAMHWVRQAPGKGLEWV AAISYDGSDKYYADSVKGRFTISRDNSKNTVYLQMDSLRAEDTAVYYCAR DRSGSYYWFDPWGQGTLVTVSS |
| | 239 | Light | NFMLTQPHSVSESPGRTVTISCTRSSGSIANNFVQWYQQRPGSSPTTVIYE DDQRPSGVPDRFSGSIDSSSNSASLTISGLKTEDEADYYCQSYDSSNQVFG GGTKLTVL |
| RVFV-302A | 240 | Heavy | QVQLVQSGAEVKKPGASVKVSCKASGYTFTNYAIHWVRQAPGQRLEWM GWINAGNGDTKYSQKFQGRVTITRDTSASTAYMELSSLRSEDTAVYYCAR PGYSSSWDEGFDYWGQGTLVTVSS |
| | 241 | Light | SYELTQPPSVSVSPGQTASITCSGDKLGDKYACWYQQKSGQSPVLVINLDS KRPSGIPERFSGSNSGNTATLTISGTQAMDEADYYCQAWDSSTGVFGGG TKLTVL |
| RVFV-302B | 242 | Heavy | EVQLVESGGGLVQPGGSLRLSCAASGFTFSSYWMHWVRQAPGKGLVW VSRINSDGSSTSYADSVKGRFTISRDNAKNTLYLQMNSLRAEDTAVYYCAS GDSSGWYMPFDYWGQGTLVTVSS |
| | 243 | Light | QSALTQPASVSGSPGQSITISCTGTSSDVGGYNYVSWYQQHPGKAPKLMI YDVSNRPSGVSNRFSGSKSGNTASLTISGLQAEDEADYYCSSYTSSSTNVVF GGGTKLTVL |
| RVFV-304B | 244 | Heavy | QVQLQESGPGLVKPSETLSLTCTVSGGSISSYYWSWIRQPPGKGLEWIGYI YYSGSTNYNPSLKSRVTISVDTSKNQFSLKLSSVTAADTAVYYCARHGDILT GFLYWYFDLWGRGTLVTVSS |
| | 245 | Light | QSALTQPASVSGSPGQSITISCTGTSSDVGGYNYVSWYQQHPGKAPKLMI YDVSNRPSGVSNRFSGSKSGNTASLTISGLQAEDEADYYCSSYTSSSTLVVF GGGTKLTVL |
| RVFV-307 | 246 | Heavy | EVQLVQSGAEVKKPGESLRISCKGSGYSFTSYWISWVRQMPGKGLEWM GRIDPSDSYTNYSPSFQGHVTISADKSISTAYLQWSSLKASDTAMYYCARH GEGGSYEEFDPWGQGTLVTVSS |
| | 247 | Light | DIQMTQSPSSLSASVGDRVTITCRASQSISSYLNWYQQKPGKAPKLLIYAAS SLQSGVPSRFSGSGSGTDFTLTISSLQPEDFATYYCQQSYSTPWTFGQGTK VEIK |
| RVFV-308 | 248 | Heavy | EVQLVQSGAEVKKAGESLKISCKGSGYSFTSYWIGWVRQMPGKGQEWM GHYPGDSDTTYSPSFQGQVTISADKSLSTAYLQWSSLKASDTAMYYCARG AYCGGDCFGGAEYFQHWGQGTLVTVSS |
| | 249 | Light | DIVMTQSPDSLAVSLGERATINCKSSQSVLYSSNNKNYLAWYQQKPGQPP KLLIYWASTRESGVPDRFSGSGSGTDFTLTISSLQAEDVAVYYCQQYYSTPL TFGGGTKVEIK |
| RVFV-309 | 250 | Heavy | QVQLVQSGAEVKRPGASVKVSCKASGYTFTNYYMHWVRQAPGQGLEW MGIINPSGVSTMYAQKFQGRVTMTRDTSTSTVYMELSSLRSEDTAVYSCA RMDTEYYYFDYWGQGTLVTVSS |
| | 251 | Light | SYVLTQPPSVSVAPGQTARITCGGNNIGSKSVHWYQQRPGQAPVLVVYD DSDRPSGIPERFSGSNSGNTATLTINRVEAGDEADYYCQVWDSSSDHWV FGGGTKLTVL |
| RVFV-311 | 252 | Heavy | EVQLQESGPGLVQPSGTLSLTCAVSGGSISSSNWWSWVRQPPGKGLEWI GEIYHSGSTNYNPSLKSRVTISVDKSKNQFSLKLSSVTAADTAVYYCARRSY YYYYMDVWGKGTTVTVSS |
| | 253 | Light | SYVLTQPPSVSVAPGQTARITCGGNNIGSKSVHWYQQKPGQAPVLVVYD DSDRPSGIPERFSGSNSGNTATLTISRVEAGDEADYYCQVWDSSSDYVVF GGGTKLTVL |
| RVFV-313 | 254 | Heavy | EVQLLESGGGLVQPGGSLRLSCAASGFTFSSYAMSWVRQAPGKGLEWVS VISGSGGSTYYADSVKGRFTISRDNSKNTLYLQMSSLRAEDTALYYCAKCID NYYYYCYMDVWGKGTTVTVSS |
| | 255 | Light | QSALTQPASVSGSPGQSITISCTGTSSDVGGYDYVSWYQHHPGKAPKLMI YAVSNRPSGVSNRFSGSKSGNTASLTISGLQPEDESDYYCSSYTSSSTWVF GGGTKLTVL |

TABLE 2-continued

PROTEIN SEQUENCES FOR ANTIBODY VARIABLE REGIONS

| Clone | SEQ ID NO: | Chain | Variable Sequence |
|---|---|---|---|
| RVFV-314 | 256 | Heavy | QVQLVQSGAEVKKPGASVKVSCKASGYTFTSYGITWVRLAPGQGLEWMGWISAYNGNTNYAQKLQGRVTMTTDTSTSTAYMELRSLRSDDTAVYYCARDGVQGAFDIWGQGTMVTVSS |
| | 257 | Light | SYVLTQPPSVSVAPGQTARITCGGNNIGSKSVHWYQQKPGQAPVLVVYDDSDRPSGIPERFSGSNSGNTATLTISRVEAGDEADYYCQVWDSSSDQRVFGTGTKVTVL |
| RVFV-315 | 258 | Heavy | QVQLVESGGGVVQPGRSLRLSCAASGFTFSSYGMHWVRQAPGKGLEWVAVISYDGSNKYYADSVKGRFTISRDNSKNTLYLQMNSLRAEDTAVYYCANWGNYYDSSGYSYYYYYMDVWGKGTTVTVSS |
| | 259 | Light | QSVLTQPPSASGTPGQRVTISCSGSSSNIGSNTVNWYQQLPGTAPKLLIYSNNQRPSGVPDRFSGSKSGTSASLAISGLQSEDEADYYCAAWDDSLNGWVFGGGTKLTVL |
| RVFV-320 | 260 | Heavy | EVQLVESGGGLVQPGGSLRLSCAASGFTFSSYWMHWVRQAPGKGLVWVSRINSDGSSTSYADSVKGRFTISRDNAKNTLYLQMNSLRAEDTAVYYCASGDSSGWYMPFDYWGQGTLVTVSS |
| | 261 | Light | QSALTQPASVSGSPGQSITISCTGTSSDVGGYNYVSWYQQHPGKAPKLMIYDVSNRPSGVSNRFSGSKSGNTASLTISGLQAEDEADYYCSSYTSSSTNVVFGGGTKLTVL |
| RVFV-321 | 262 | Heavy | EVQLVESGGGLVQPGGSLRLSCAASGFTFSSYWMHWVRQAPGKGLVWVSRINSDGSSTSYADSVKGRFTISRDNAKNTLYLQMNSLRAEDTAVYYCASGDSSGWYMPFDYWGQGTLVTVSS |
| | 263 | Light | QSALTQPASVSGSPGQSITISCTGTSSDVGGYNYVSWYQQHPGKAPKLMIYDVSNRPSGVSNRFSGSKSGNTASLTISGLQAEDEADYYCSSYTSSSTNVVFGGGTKLTVL |
| RVFV-322 | 264 | Heavy | QVQLQESGPGLVKPSGTLSLTCAVSGGSISSSNWWSWVRQPPGKGLEWIGEIYHSGSTNYNPSLKSRVTISVDKSKNQFSLKLSSVTAADTAVYYCARDSRQWLVRGFDYWGQGTLVTVSS |
| RVFV-326 | 265 | Heavy | EAQLVESGGGLVKPGGSLRLSCAASGFSFSYAWMSWVRRLPGKGLEWVGRIKGKADGETTDYAAPVKGRFTISRDDSKTTVYLQMNTLKIEDTGVYYCTTDIGDFYDSIGYSYTDYWGQGTLVTVSS |
| | 266 | Light | EIVLTQSPATLSLSPGERATLSCRASQSVSSYLAWYQQKPGQAPRLLIYDASNRATGIPVRFSGSGSGTDFTLTISSLEPEDFALYYCQQRSDWPPTFGQGTKVEIK |
| RVFV-330 | 267 | Heavy | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARVGNYYYYMDVWGKGTTVTVSS |
| | 268 | Light | SYVLTQPPSVSVAPGQTARITCGGNNIGSKSVHWYQQKPGQAPVLVVYDDSDRPSGIPERFSGSNSGNTATLTISRVEAGDEADYYCQVWDSSSDHWVFGGGTKLTVL |
| RVFV-331 | 269 | Heavy | EVQLVESGGGLVQPGRSLRLSCTASGFTFGDYAMSWVRQAPGKGLEWVGFIRSKAYGGTREYAASVKGRFTISRDDSKSIAYLQMNSLKTEDTAVYYCTNHRGSSWYPDAFDIWGQGTMVTVSS |
| | 270 | Light | SYVLTQPPSVSVAPGKTARITCGGNNIGSKSVHWYQQKPGQAPVLVVYDDSDRPSGIPERFSGSNSGNTATLTISRVEAGDEADYYCQVWDSSSDPDVVFGGGTKLTVL |
| RVFV-332 | 271 | Heavy | QVQLVESGGGVVQPGRSLRLSCAASGFTFSSYAMHWVRQAPGRGLEWVAVISYDGSNKYYADSVKGRFTISRDNSKNTLYLQMNSLRAEDTAVYYCAKDITGRLDYWGQGTLVTVSS |
| | 272 | Light | SYGLTQPPSVSVAPGQTARITCGGNNIGSKSVNWYQQKPGQAPVLWYDDSDRPLGIPERFSGSNSGNTATLTISRVEAGDEADYNCQVWDSSSDHWVFGGGTKLTVL |
| RVFV-335 | 273 | Heavy | EVQLVESGGGLVQPGGSLRLSCAASGFTFSSYDMHWVRQATGKGLEWVSAIGTAGDTYYPGSVKGRFTISRESAKNSLYLQMNSLRAGDTAVYYCARGLGGGFDYWGQGTLVTVSS |
| | 274 | Light | SYVLTQPPSVSVAPGKTARITCGGNNIGSKSVHWYQQKPGQAPVLVVYDDSDRPSGIPERFSGSNSGNTATLTISRVEAGDEADYYCQVWDSSSDHYVFGTGTKVTVL |
| RVFV-337 | 275 | Heavy | EVQLLESGGGLVQPGGSLRLSCVASGFTFSNYAMSWVRQAPGKGLEWVSAISGNVDNTHYADSVKGRFTISRDNSKSTLFLQMHSLRAEDTAVYFCAKVGQYWSGHYLDYWGQGTLVTVSS |
| | 276 | Light | SYVLTQPPSVSVAPGQTARMTCGGNNIGSKSVHWYQQKPGQAPVLVVYDDSDRPSGIPERFSGSNSGNTATLTINRVEAGDEADYYCQVWHSDSDQYVFGTGTKVTVL |

TABLE 2-continued

PROTEIN SEQUENCES FOR ANTIBODY VARIABLE REGIONS

| Clone | SEQ ID NO: | Chain | Variable Sequence |
|---|---|---|---|
| RVFV-338 | 277 | Heavy | EVQLLESGGGLVHPGGSLRLSCAASGFTFSSYAMSWVRQAPGKGLEWVSAISGSGGSTYYADSVKGRFTISRDNFKNTLYVQMNSLRAEDTAVYYCATENDFWSGHQFDYWGQGTLVTVSS |
| | 278 | Light | SYVLTQPPSVSVAPGQTARMTCGGNNIGSKSVQWYQQKPGQAPVLVVHDDSDRPSGIPERFSGSNSGNTATLTISRVEAGDEADYYCQVWDSSSDHWVFGGGTKLTVL |
| RVFV-347 | 279 | Heavy | EVQLVESGGGLVQPGGSLRLSCAASGFTFSSYDMHWVRQATGKGLEWVSAIGTAGDTYYPGSVKGRFTISRENAKNSLYLQMNSLRAGDTAVYYCARAVGGGFDYWGQGTLVTVSS |
| | 280 | Light | SYVLTQPPSVSVAPGKTARITCGGNNIGSKSVHWYQQKPGQAPVLVVYDDSDRPSGIPERFSGSNSGNTATLTISRVEAGDEADYYCQVWDSSSDLYVFGTGTKVTVL |
| RVFV-349A | 281 | Heavy | QVQLQESGPGLVKPSETLSLTCTVSGGSISSYYWSWIRQPPGKGLEWIGYIYYSGSTNYNPSLKSRVTISVDTSKNQFSLKLSSVTAADTAVYYCARGSRAILTGYPNWFDPWGQGTLVTVSS |
| | 282 | Light | DIQMTQSPSSLSASVGDRVTITCRASQSISSYLNWYQQKPGKAPKLLIYAASSLQSGVPSRFSGSGSGTDFTLTISSLQPEDFATYYCQQSYSTPYTFGQGTKLEIK |
| RVFV-349B | 283 | Heavy | EVQLVESGGGLVQPGRSLRLSCAASGFTFDDYAMHWVRQAPGKGLEWVSGISWNSGSIGYADSVKGRFTISRDNAKNSLYLQMNSLRTEDTAFYYCAKDKGDGSGSFYYMDVWGKGTTVTVSS |
| | 284 | Light | DIQMTQSPSSLSASVGDRVTITCQASQDISNYLNWYQQKPGKAPKLLIYDASNLETGVPSRFSGSGSGTDFTFTISSLQPEDIATYSCQQYDNLPLTFGGGTKVEIK |
| RVFV-352 | 285 | Heavy | QVQLQESGPGLVKPSETLSLTCTVSGGSISSYYWSWIRQPPGKGLEWIGYIYYSGSTNYNPSLKSRVTISVDTSKNQFSLKLSSVTAADTAVYYCARGLGVVVWPWGQGTLVTVSS |
| | 286 | Light | QPVLTQPPSSSASPGESARLTCTLPSDINVGSYNIYWYQQKPGSPPRYLLYYYSDSDKGQGSGVPSRFSGSKDASANTGILLISGLQSEDEADYYCMIWPSNAWVFGGGTKLTVL |
| RVFV-354 | 287 | Heavy | QVQLVESGGGVVQPGRSLRLSCAASGFTFSSYGMHWVRQAPGKGLEWVAVISYDGSNKYYADSVKGRFTISRDNSKNTLYLQMNSLRAEDTAVYYCAKALSSGWYEWGQGTLVTVSS |
| | 288 | Light | SYVLTQPPSVSVAPGQTARITCGGNNIGSKSVHWYQQKPGQAPVLVVYDDSDRPSGIPERFSGSNSGNTATLTISRVEAGDEADYYCQVWDSSSDHYVFGTGTKVTVL |
| RVFV-356 | 289 | Heavy | QVQLQESGPGLVKPSETLSLTCTVSGGSISSYYWSWIRQPPGKGLEWIGYIYYSGSTNYNPSLKSRVTISLDTSKNQFSLKLSSVTAADTAVYYCARGLRPDAFDIWGQGTMVTVSS |
| | 290 | Light | SYVLTQPPSVSVAPGQTARITCGGNNIGSKSVHWYQQKPGQAPGLVVYDDSDRPSGIPERFSGSNSGNTATLTISRVEAGDEADYYCQVWDSSSDHVVFGGGTKLTVL |
| RVFV-362 | 291 | Heavy | EVQLVQSGAEVKKPGESLRISCKGSGYSFTSYWISWVRQMPGKGLEWMGRIEPSDSYTNYSPSFQGHVTISADKSISTAYLQWSSLKASDTAMYYCARLGDSSGYGEIDYWGQGTLVTVSS |
| | 292 | Light | DIQMTQSPSSLSASVGDRVTITCRASQSISSYLNWYQQKPGKAPKLLIYAASSLQSGVPSRFSGSGSGTDFTLTISSLQPEDFATYYCQQSYSTPQTFGQGTKVEIK |
| RVFV-363 | 293 | Heavy | QVQLMQSGAEVKKPGASVKVSCRASGNTFTSYYMHWVRQAPGQGLEWMGIINPSGGSTIYAQKFQGRVTMTRDTSTSTVYMELSSLKSEDTAVYYCARGESYYFDYWGQGTLVTVSS |
| | 294 | Light | SYVLTQPPSVSVAPGKTARITCGGNNIESKSVHWYQQKPGQAPVLVVYDDTDRPSGIPERFSGSNSGNTATLTISRVEAGDEADYYCQVWDSSSDHCVFGGGTKLTVL |
| RVFV-370 | 295 | Heavy | EVQLVESGGGLVQPGGSLRLSCAASGFTFSSYSMNWVRQAPGKGLEWVSYISSSSSTIYYADSVKGRFTISRDNAKNSLYLQMNSLRDEDTAVYYCARDFYPAAMDVWGKGTTVTVSS |
| | 296 | Light | SYVLTQPPSVSVAPGQTARITCGGNNIGSKSVHWYQQKPGQAPVLVVYDDSDRPSGIPERFSGSNSGNTATLTISRVEAGDEADYYCQVWDSSSDHRVFGGGTKLTVL |
| RVFV-378 | 297 | Heavy | EVQLVQSGAEVKKPGESLRISCKGSGYSFTSYWISWVRQMPGKGLEWMGRIEPSDSYTNYSPSFQGHVTISADKSISTAYLQWSSLKASDTAMYYCARLGDSSGYGEIDYWGQGTLVTVSS |

TABLE 2-continued

PROTEIN SEQUENCES FOR ANTIBODY VARIABLE REGIONS

| Clone | SEQ ID NO: | Chain | Variable Sequence |
|---|---|---|---|
| | 298 | Light | DIQMTQSPSSLSASVGDRVTITCRASQSISSYLNWYQQKPGKAPKLLIYAAS SLQSGVPSRFSGSGSGTDFTLTISSLQPEDFATYYCQQSYSTPQTFGQGTKV EIK |
| RVFV-379 | 299 | Heavy | QVQLQESGPGLVKPSQTLSLTCTVSGDSISGGDYYWSWIRRPAGEGLEWI GRVHTTGSTDYNPSLRTRVTISIDTSKNHFFLKMTSVTAADTAVYYCAREG DYSAWFDPWGQGALVTVSS |
| | 300 | Light | DIQMTQSPSSLSASIGDRVTITCRASQHIESFLNWYQQKPGKAPKLLIYIAST LQGGVPSRFSGRGFGTDFTLTINSLQPEDFATYYCQQSYTISPITFGQGTRL EIK |
| RVFV-381 | 301 | Heavy | QEQLVESGGGVVQPGRSLRLSCAASGFTLRGYGIYWVRQAPGKGLEWVA VISHDGKNESYTDSVKGRFSISRDKSKNTVFLQMNSLTTQDTSVYYCARW TEGSEEFYYHGLDVWGQGTTVTVSP |
| | 302 | Light | SYELTQPPSVSVSPGQTARITCSGHLLPKQYAYWYQQKPGQAPTLVIYADY NRASGIPERFSGASSGTTVTLTITGVKAEDQADYYCQSIDNRFHYPMIFGG GTKLTVL |
| RVFV-401A | 303 | Heavy | QITFKESGPTLVKPTQTLTLTCTFSGFSLSTSGVGVGWIRQPPGKALEWLAL LYWNDDKRYTPSLRSRLTITKDTSKNQVVLTMTDMDPVDTATYYCARKPR DDFLRLTMMGGGDYFDYWGQGTLVTVSS |
| RVFV-401B | 304 | Light | SYELTQPPSVSVSPGQTARITCSGDALPDQYAYWYQQKPGQAPVLVLYKD NERPSGIPERFSGSTSGTTVTLTISGVQAEDEADYYCQSADTSTAYHVIFGG GTKLTVL |
| RVFV-405 | 305 | Heavy | EVQLVESGGGLVQPGGSLRLSCAASGFTFSSFEMNWVRQAPGKGLEWV SYISRSGTTKHYADSVKGRFAISRDDAKNSLYLQMNSLRAEDTAVYYCARG GARVLQAPLDYWGQGTLVTVSS |
| | 306 | Light | SYELTQPPSVSVAPGETARITCGGTNIGNKSVRWYQQKPGQAPVLVIYYD NDRPSGIPERFSGSNSGNTATLTISRVEAGDEADYYCQVWDNSSDHAVFG GGTKLTVL |
| RVFV-419A | 307 | Heavy | QVQLVQSGAEVKKPGASVKVSCKASGYTFTDYYMHWVRQAPGQGLEW MGIINPSGGSTNYAQNFQGRVTMTRDTSTTTVYMELSSLRSEDTAVYYCA RAIYWNVPYYFDYWGQGTLVTVSS |
| | 308 | Light | ETVLTQSPGTLSLSPGERATLSCRASQSVSSSWLAWYQQKPGQAPRLLIYD ASRATGIPDRFSGSGSGTDFTLTISRLEPEDLAVYYCQQYGNSPTTFGQGTK VEIK |
| RVFV-426A | 309 | Heavy | QVQLQESGPGLLKPSQTLSLTCGVSGDSITSTGDSWTWIRQPPGKGLEWI GYIYYSGSAYYNPSLKSRVTISVDTSKNQFSLRLRSVTAADTAVYYCARALEY GAGSWAAAFWGQGILVTVSS |
| | 310 | Light | SYEVTQPPSVSVSPGQTASITCSGDKLVERYVSWYQQKPGQSPLLVIYHDI KRPSGIPERFSGSNSGNTATLTISGTQPMDEADYYCQAWDSSTVLFGGGT KLTVL |
| RVFV-429A | 311 | Heavy | QVQLVQSGAEVKKPGSSVKVSCRASGGTFSSYTISWVRQAPGQGLEWM GGIIPILGLTKFAQKFQDRVTITADISATTTYMELSSLTSEDTAVYYCARNGE QLEWSYYYGMDVWGQGTTVTVSS |
| | 312 | Light | DIVMTQSPDSLAVSLGERATINCKPSQSILYSSNNKNYLAWYQQKPGQPP KLLINWASTRESGVPDRFSGSGSGTDFTLTISSLQAEDVAVFYCQQYYTIPP TFGQGTKVEIK |
| RVFV-431A | 313 | Heavy | QVQLQQWGAGLLKPSETLSLTCTVYGGSFTLYYWTWIRQPPGKGLEWIG EINQSGSTNYNPSLRSRLTISVDTSKSQFSLKVTSVTAADTAVYYCARGHDS SGYYIDYYLDVWGKGTTVTVSS |
| | 314 | Light | SSELTQDPAVSVALGQTVRITCQGDSLRNYYAGWYQQRPGQAPVLVFYG KDNRPSGIPDRFSGSSSGNTASLTITGAQAEDEADYYCNSRDSSGDVVVFG GGTKLTVL |
| RVFV-436A | 315 | Heavy | QVQLHESGPGLVKPSETLSLTCGVSGYTISSDYYWGWIRQPPGKGLEWIG SIYQNGHTYYNPSLKSRVTISVDTSKNQFSLELSSVTAADTAVYYCARRGDC GADCYHFDYWGRGTAVTVSS |
| | 316 | Light | SYEVTQPLSVSVSPGQTASITCSGEKLENKYVSWYQQKPGQSPVLVMYQD FKRPSGIPERFSGSNSGNTATLTISGTQAMDEADYYCQAWDRSTFYVFGT GTKVTVVG |
| RVFV-443B | 317 | Heavy | QLQLQESGPGLVKPSETLSLTCFVPGDFLSSTNFYWGWIRQPPGKGLEWI GSIYDSGNTYYNPSLKSRVTMSIDTPKNQFSLQLSSVTAADTAVYYCARVG DCGADCYYFDHWGQGTLVTVSS |
| | 318 | Light | SYELTQPPSVSVSPGQTASISCSGDRLRDRYVSWYQQKPGQSPVVVIYQD FKRPSGIPARFSASNSGNTATLTIIGTQAMDEADYYCQAWDSFTYVFGAG TKVTVLG |

TABLE 2-continued

| PROTEIN SEQUENCES FOR ANTIBODY VARIABLE REGIONS | | | |
|---|---|---|---|
| Clone | SEQ ID NO: | Chain | Variable Sequence |
| RVFV-451B | 319 | Heavy | EVHLVESGGGLVQPGGSLRLSCAASGFTFSSYWMSWVRQAPGKGLEWVANIKQDGSEKYYVDSVKGRFTISRDNAKNSLYLQMNSLRAEDTAVYYCARGSIGWLSPDYWGQGTLVTVSS |
| RVFV-451B-a | 320 | Light | SSELTQDPAVSVALGQTVRITCQGDSLRSFYASWYQQKPGQAPILVFYGQNNRPSGIPDRFSGSSSGNTASLTITGAQAEDEADYYCNSRDSGGYHLVFGGGTKLTVL |
| RVFV-451B-b | 321 | Light | QPVLTQPPSASASLGASVTLTCTLSSGYSNYKLD*YHQRPGKGPRFEMRVGTGGIVTSTGDGIPDRFAVLGSGLNRFLTIKNIQEEDESDYHCGPDHGRGCSAEGPR*PS |
| RVFV-459A | 322 | Light | SYELTQPPSVSVSPGQTASITCSGDKLGDKYACWYQQKPGQSPVLVIYQDTKRPSGIPERFSGSNSGNTATLTIGGTQPMDEADYYCQAWDSSTEVVFGGGTKLTVL |
| RVFV-76 | 323 | Heavy | DVQVVESGGGLVQPGRSLRLSCQCFGFNFGDYLMTWFRQAPGKGLEWVGFVRTKGYGGTSEYAASVRGRFTVSRDDSRGIAYLQMNSLRVEDTAVYYCTRDRQKPTYQFWSSYFVDDPFDVWGQGTKVTVSS |
| | 324 | Light | SSELTQDPAVSVALGQTVRITCQGDSLRSYSASWYQHKAGQAPVLVLYGKNNRPSGIPDRFSGSTSGNTASLTITGAQAEDEADFYCNSRDSSGIRVVFGGGTKLTVL |
| RVFV-778 | 325 | Heavy | EVQLVQSGAEVKKPGESLRISCKGSGYSFTSYWISWVRQMPGKGLEWMGRIEPSDSYTNYSPSFQGHVTISADKSISTAYLQWSSLKASDTAMYYCARLGDSSGYGEIDYWGQGTLVTVSS |
| | 326 | Light | DIQMTQSPSSLSASVGDRVTITCRASQSISSYLNWYQQKPGKAPKLLIYAASSLQSGVPSRFSGSGSGTDFTLTISSLQPEDFATYYCQQSYSTPQTFGQGTKVEIK |
| RVFV-86 | 327 | Heavy | EVQLVQSGAEVKKPGESLKISCKGSGYSFTSYWIGWVRQMPGKGLEWMGHYPGDSDTRYSPSFQGQVTISADKSISTAYLQWSSLKASDTAMYYCARAPTVPAAIWGSSYYYYYMDVWGKGTTVTVSS |
| | 328 | Light | DIVMTQSPDSLAVSLGERATINCKSSQSVLYSSNNKNYLAWYQQKPGQPPKLLIYWASTRESGVPDRFSGSGSGTDFTLTISSLQAEDVAVYYCQQYYSTSLTFGGGTKVEIK |
| RVFV-95 | 329 | Heavy | EVQLVESGGGLVQPGGSLKLSCAASGFKFSGSAMHWVRQASGRGLEWVGRIRSKANNYATTYAESVKGRFTISRDDSQNTAYLEMHNLRTEDTAVYYCTRNVDTDHRGWGQGTLVSVSS |
| | 330 | Light | EIVMTQSPDPLPVSLGGRATINCKSSQSLLYGSTNKNYLAWYQQKPGQPPRLLIYWASTRESGVPDRFSGSGSGTDFALTISDLQAEDVAVYYCQQYYNVAWTFGQGTKVEIR |

TABLE 3

| CDR HEAVY CHAIN SEQUENCES | | | |
|---|---|---|---|
| Clone | CDRH1 (SEQ ID NO:) | CDRH2 (SEQ ID NO:) | CDRH3 (SEQ ID NO:) |
| RVFV-121 | GDSISTSTW 331 | IYHSEST 332 | ARGSLVFDY 333 |
| RVFV-127 | GDSVRNYY 334 | IYYSGST 335 | ARVAIRTDGYIRAFDI 336 |
| RVFV-128A | GGSISSGDYF 337 | IYYSGST 338 | ARVQTPGSDTYYFDY 339 |
| RVFV-128B | GGSISSSSYH 340 | IYYTGST 341 | ARRSLRSGWAAAIDF 342 |
| RVFV-132 | GGSVSSGSYY 343 | IYYSGST 344 | ARDYRVTTGNYYYYGMDV 345 |
| RVFV-140A | GGSVSSGDYY 346 | ISYSGST 347 | ATNYFHLHDFGDLYWYFDL 348 |
| RVFV-140B | GGSISSSVYY 349 | IYYSGYT 350 | ARHSDCGNDCYYFDY 351 |

TABLE 3-continued

CDR HEAVY CHAIN SEQUENCES

| Clone | CDRH1 (SEQ ID NO:) | CDRH2 (SEQ ID NO:) | CDRH3 (SEQ ID NO:) |
|---|---|---|---|
| RVFV-140C | GGSVSSGDYY 352 | ISYSGST 353 | ATNYFHLHDFGDLYWYFDL 354 |
| RVFV-142A | GFMFSRYW 355 | IKQDGSEK 356 | ARGEYYGSGSYS 357 |
| RVFV-142B | GGSISSSVYY 358 | IYYSGYT 359 | ARHSDCGNDCYYFDY 360 |
| RVFV-144 | GGSIGTYY 361 | VYHSGAT 362 | AREGSNGDFRGHFDS 363 |
| RVFV-151 | GGSFSGYY 364 | INHSGRT 365 | ARGHVVVTPATLFHRVGEHYFDF 366 |
| RVFV-154 | GYTFTTYA 367 | INAGNGDT 368 | ARGWVGCIGKRGKTCYANLPDDY 369 |
| RVFV-158 | RFTFNTYG 370 | ISYDGKKK 371 | ARDLRRFYSNGWFTGSDF 372 |
| RVFV-164 | GVSITSSNW 373 | VYHSGST 374 | ARDGFSGYDVALDK 375 |
| RVFV-166 | GVSLSSSGVG 376 | IYWDDDK 377 | AHRNIVVVRADPHRWAGTFDY 378 |
| RVFV-206 | GFTFSSYA 379 | ISGSGGST 380 | AKDQGTMIVVVTLPPGAFDI 381 |
| RVFV-211 | GFMFSRYW 382 | IKQDGSEK 383 | ARGEYYGSGSYS 384 |
| RVFV-220 | GGSINGDNYY 385 | IYYSGST 386 | ARGADCGNDCYYFDY 387 |
| RVFV-226 | GFTFDDYA 388 | ISWNSGSI 389 | AKGLVGAIHDAFDI 390 |
| RVFV-229 | GGSISSGDYF 391 | IYYSGST 392 | ARVQTPGSDTYYFDY 393 |
| RVFV-235B | GYTFTGYY 394 | INPNSGGT 395 | ARGRYCDSASCYVRNYFYYMDV 396 |
| RVFV-239 | GFTFSNYW 397 | INDHGNYT 398 | VRAFGGGY 399 |
| RVFV-243 | GFTFSSYG 400 | IWYDGSNK 401 | ARERSIAARQNRGYFDY 402 |
| RVFV-247 | GFTFSRYY 403 | INTDGSTT 404 | ARPYSGYFH 405 |
| RVFV-248A | GFTFTNSW 406 | INPDGSKI 407 | ARWLS 408 |
| RVFV-248B | GFTFTNSW 409 | INPDGSKI 410 | ARWLS 411 |
| RVFV-249 | GYTFTTYF 412 | VDPSTGNT 413 | GRDRGSRAVDS 414 |
| RVFV-250 | GGSISSYF 415 | IHTTGST 416 | AREGTAFDI 417 |
| RVFV-263 | GFTFSDYY 418 | ISGTGSFI 419 | ARGIRADCFDQ 420 |
| RVFV-266 | GYTFTSYY 421 | INPSGGST 422 | ARARGGSYSLDY 423 |
| RVFV-268 | GFIFNHFG 424 | IWYDGSKK 425 | ARERWSGHSYLDY 426 |

TABLE 3-continued

| CDR HEAVY CHAIN SEQUENCES | | | |
|---|---|---|---|
| Clone | CDRH1 (SEQ ID NO:) | CDRH2 (SEQ ID NO:) | CDRH3 (SEQ ID NO:) |
| RVFV-278 | GFTFRTKT 427 | ISGSGKDK 428 | VKDREGTWSFDH 429 |
| RVFV-284 | GFTFSSYA 430 | ISGSGGST 431 | AKKYYDFWSGYYPNWFDP 432 |
| RVFV-296A | GYTFTTYV 433 | INTNTGNP 434 | AREYNSFDY 435 |
| RVFV-299 | GYTFTSYY 436 | ISPSGGST 437 | ARQVQTDYYFDY 438 |
| RVFV-300 | GFTFSSYA 439 | ISYDGSDK 440 | ARDRSGSYYWFDP 441 |
| RVFV-302A | GYTFTNYA 442 | INAGNGDT 443 | ARPGYSSSWDEGFDY 444 |
| RVFV-302B | GFTFSSYW 445 | INSDGSST 446 | ASGDSSGWYMPFDY 447 |
| RVFV-304B | GGSISSYY 448 | IYYSGST 449 | ARHGDILTGFLYWYFDL 450 |
| RVFV-307 | GYSFTSYW 451 | IDPSDSYT 452 | ARHGEGGSYEEFDP 453 |
| RVFV-308 | GYSFTSYW 454 | IYPGDSDT 455 | ARGAYCGGDCFGGAEYFQH 456 |
| RVFV-309 | GYTFTNYY 457 | INPSGVST 458 | ARMDTEYYYFDY 459 |
| RVFV-311 | GGSISSSNW 460 | IYHSGST 461 | ARRSYYYYYMDV 462 |
| RVFV-313 | GFTFSSYA 463 | ISGSGGST 464 | AKCIDNYYYYCYMDV 465 |
| RVFV-314 | GYTFTSYG 466 | ISAYNGNT 467 | ARDGVQGAFDI 468 |
| RVFV-315 | GFTFSSYG 469 | ISYDGSNK 470 | ANWGNYYDSSGYSYYYYYMDV 471 |
| RVFV-320 | GFTFSSYW 472 | INSDGSST 473 | ASGDSSGWYMPFDY 474 |
| RVFV-321 | GFTFSSYW 475 | INSDGSST 476 | ASGDSSGWYMPFDY 477 |
| RVFV-322 | GGSISSSNW 478 | IYHSGST 479 | ARDSRQWLVRGFDY 480 |
| RVFV-326 | GFSFSYAW 481 | IKGKADGETT 482 | TTDIGDFYDSIGYSYTDY 483 |
| RVFV-330 | GYTFTSYY 484 | INPSGGST 485 | ARVGNYYYYMDV 486 |
| RVFV-331 | GFTFGDYA 487 | IRSKAYGGTR 488 | TNHRGSSWYPDAFDI 489 |
| RVFV-332 | GFTFSSYA 490 | ISYDGSNK 491 | AKDITGRLDY 492 |
| RVFV-335 | GFTFSSYD 493 | IGTAGDT 494 | ARGLGGGFDY 495 |
| RVFV-337 | GFTFSNYA 496 | ISGNVDNT 497 | AKVGQYWSGHYLDY 498 |
| RVFV-338 | GFTFSSYA 499 | ISGSGGST 500 | ATENDFWSGHQFDY 501 |

TABLE 3-continued

| CDR HEAVY CHAIN SEQUENCES | | | |
|---|---|---|---|
| Clone | CDRH1 (SEQ ID NO:) | CDRH2 (SEQ ID NO:) | CDRH3 (SEQ ID NO:) |
| RVFV-347 | GFTFSSYD 502 | IGTAGDT 503 | ARAVGGGFDY 504 |
| RVFV-349A | GGSISSYY 505 | IYYSGST 506 | ARGSRAILTGYPNWFDP 507 |
| RVFV-349B | GFTFDDYA 508 | ISWNSGSI 509 | AKDKGDGSGSFYYMDV 510 |
| RVFV-352 | GGSISSYY 511 | IYYSGST 512 | ARGLGVVVWP 513 |
| RVFV-354 | GFTFSSYG 514 | ISYDGSNK 515 | AKALSSGWYE 516 |
| RVFV-356 | GGSISSYY 517 | IYYSGST 518 | ARGLRPDAFDI 519 |
| RVFV-362 | GYSFTSYW 520 | IEPSDSYT 521 | ARLGDSSGYGEIDY 522 |
| RVFV-363 | GNTFTSYY 523 | INPSGGST 524 | ARGESYYFDY 525 |
| RVFV-370 | GFTFSSYS 526 | ISSSSSTI 527 | ARDFYPAAMDV 528 |
| RVFV-378 | GYSFTSYW 529 | IEPSDSYT 530 | ARLGDSSGYGEIDY 531 |
| RVFV-379 | GDSISGGDYY 532 | VHTTGST 533 | AREGDYSAWFDP 534 |
| RVFV-381 | GFTLRGYG 535 | ISHDGKNE 536 | ARWTEGSEEFYYHGLDV 537 |
| RVFV-401A | GFSLSTSGVG 538 | LYWNDDK 539 | ARKPRDDFLRLTMMGGGDYFDY 540 |
| RVFV-405 | GFTFSSFE 541 | ISRSGTTK 542 | ARGGARVLQAPLDY 543 |
| RVFV-419A | GYTFTDYY 544 | INPSGGST 545 | ARAIYWNVPYYFDY 546 |
| RVFV-426A | GDSITSTGDS 547 | IYYSGSA 548 | ARALEYGAGSWAAAF 549 |
| RVFV-429A | GGTFSSYT 550 | IIPILGLT 551 | ARNGEQLEWSYYYGMDV 552 |
| RVFV-431A | GGSFTLYY 553 | INQSGST 554 | ARGHDSSGYYIDYYLDV 555 |
| RVFV-436A | GYTISSDYY 556 | IYQNGHT 557 | ARRGDCGADCYHFDY 558 |
| RVFV-443B | GDFLSSTNFY 559 | IYDSGNT 560 | ARVGDCGADCYYFDH 561 |
| RVFV-451B | GFTFSSYW 562 | IKQDGSEK 563 | ARGSIGWLSPDY 564 |
| RVFV-76 | GFNFGDYL 565 | VRTKGYGGTS 566 | TRDRQKPTYQFWSSYFVDDPFDV 567 |
| RVFV-778 | GYSFTSYW 568 | IEPSDSYT 569 | ARLGDSSGYGEIDY 570 |
| RVFV-86 | GYSFTSYW 571 | IYPGDSDT 572 | ARAPTVPAAIWGSSYYYYYYMDV 573 |
| RVFV-95 | GFKFSGSA 574 | IRSKANNYAT 575 | TRNVDTDHRG 576 |

TABLE 4

| CDR LIGHT CHAIN SEQUENCES | | | |
|---|---|---|---|
| Clone | CDRL1 (SEQ ID NO:) | CDRL2 (SEQ ID NO:) | CDRL3 (SEQ ID NO:) |
| RVFV-121 | QSVSSN 577 | AAS 578 | QQFNNWPRT 579 |
| RVFV-127 | QSIRNY 580 | AAS 581 | QQTYSTAWT 582 |
| RVFV-128A | QSISSY 583 | AAS 584 | QQSYSTPMYT 585 |
| RVFV-128B | QSISSY 586 | AAS 587 | QQSYSTPMYT 588 |
| RVFV-132 | SSNIGSNT 589 | SNN 590 | AAWDDSLNGWV 591 |
| RVFV-140A | SSDIGAYNF 592 | DVT 593 | NSYTSSSHVV 594 |
| RVFV-140B | RLGDKY 595 | QDY 596 | QAWDSSDGSV 597 |
| RVFV-140C | SSDIGAYNF 598 | DVT 599 | NSYTSSSHVV 600 |
| RVFV-142A | QSISSW 601 | KAS 602 | QQYNSYPLT 603 |
| RVFV-142B | RLGDKY 604 | QDY 605 | QAWDSSDGSV 606 |
| RVFV-144 | SSDVGGFNF 607 | DVS 608 | TSYTSSSTVV 609 |
| RVFV-151 | SLKNYY 610 | GKN 611 | SSRDRSDKYWV 612 |
| RVFV-154 | SSDVGAYKF 613 | DVN 614 | SSYTRGPYI 615 |
| RVFV-158 | QTISSNN 616 | DAS 617 | QQYGRSPIT 618 |
| RVFV-164 | SSNIGNSY 619 | DNN 620 | ATWESRLSAGHVV 621 |
| RVFV-166 | QSVTSNY 622 | GAS 623 | QQYAGSPFT 624 |
| RVFV-211 | QSLLHSNGYNY 625 | LGS 626 | VQALQIPLT 627 |
| RVFV-220 | KLGHKY 628 | QDS 629 | QAWDSSSFYV 630 |
| RVFV-226 | QSISSW 631 | KAS 632 | QQYNSYPLT 633 |
| RVFV-229 | KLGDKY 634 | QDT 635 | QAWDSSTVV 636 |
| RVFV-235B | QSVSRY 640 | DAS 641 | QQRSNWPT 642 |
| RVFV-239 | QSLVYRDGNTY 643 | QVF 644 | MQSTHWPWT 645 |
| RVFV-243 | QGIRND 646 | AAS 647 | LQHNSYPWT 648 |
| RVFV-247 | QSLVHSDGNTY 649 | KIS 650 | MQGTRLYT 651 |
| RVFV-248A | SSNIGSNH 652 | KNN 653 | AAWDDSLRGWE 654 |

TABLE 4-continued

CDR LIGHT CHAIN SEQUENCES

| Clone | CDRL1 (SEQ ID NO:) | CDRL2 (SEQ ID NO:) | CDRL3 (SEQ ID NO:) |
|---|---|---|---|
| RVFV-248B | QSVSRK 655 | DAS 656 | HQRSNWWT 657 |
| RVFV-249 | SSNVGPNT 658 | RNN 659 | AAWDDSLNGHMV 660 |
| RVFV-250 | KLGDKY 661 | QDT 662 | QAWDSSTPWV 663 |
| RVFV-263 | NIGDKS 664 | DDS 665 | QVWDSSSDHLV 666 |
| RVFV-266 | NIGSKS 667 | DDS 668 | QVWDSSSDHWV 669 |
| RVFV-268 | NLESKY 670 | EDS 671 | QEWDTSSDYPV 672 |
| RVFV-278 | NNDVGLYDY 673 | EVT 674 | SSYTRSITWV 675 |
| RVFV-284 | QSVSSN 676 | GAS 677 | QQYNNWPQRT 678 |
| RVFV-296A | SSNIGAGYD 679 | DNN 680 | QSYDFRLSGSV 681 |
| RVFV-299 | NIGSKS 682 | DDS 683 | QVWDSSSDHSWV 684 |
| RVFV-300 | SGSIANNF 685 | EDD 686 | QSYDSSNQV 687 |
| RVFV-302A | KLGDKY 688 | LDS 689 | QAWDSSTGV 690 |
| RVFV-302B | SSDVGGYNY 691 | DVS 692 | SSYTSSSTNVV 693 |
| RVFV-304B | SSDVGGYNY 694 | DVS 695 | SSYTSSSTLVV 696 |
| RVFV-307 | QSISSY 697 | AAS 698 | QQSYSTPWT 699 |
| RVFV-308 | QSVLYSSNNKNY 700 | WAS 701 | QQYYSTPLT 702 |
| RVFV-309 | NIGSKS 703 | DDS 704 | QVWDSSSDHWV 705 |
| RVFV-311 | NIGSKS 706 | DDS 707 | QVWDSSSDYVV 708 |
| RVFV-313 | SSDVGGYDY 709 | AVS 710 | SSYTSSSTWV 711 |
| RVFV-314 | NIGSKS 712 | DDS 713 | QVWDSSSDQRV 714 |
| RVFV-315 | SSNIGSNT 715 | SNN 716 | AAWDDSLNGWV 717 |
| RVFV-320 | SSDVGGYNY 718 | DVS 719 | SSYTSSSTNVV 720 |
| RVFV-321 | SSDVGGYNY 721 | DVS 722 | SSYTSSSTNVV 723 |
| RVFV-326 | QSVSSY 724 | DAS 725 | QQRSDWPPT 726 |
| RVFV-330 | NIGSKS 727 | DDS 728 | QVWDSSSDHWV 729 |

TABLE 4-continued

| CDR LIGHT CHAIN SEQUENCES | | | |
|---|---|---|---|
| Clone | CDRL1 (SEQ ID NO:) | CDRL2 (SEQ ID NO:) | CDRL3 (SEQ ID NO:) |
| RVFV-331 | NIGSKS 730 | DDS 731 | QVWDSSSDPDVV 732 |
| RVFV-332 | NIGSKS 733 | DDS 734 | QVWDSSSDHWV 735 |
| RVFV-335 | NIGSKS 736 | DDS 737 | QVWDSSSDHYV 738 |
| RVFV-337 | NIGSKS 739 | DDS 740 | QVWHSDSDQYV 741 |
| RVFV-338 | NIGSKS 742 | DDS 743 | QVWDSSSDHWV 744 |
| RVFV-347 | NIGSKS 745 | DDS 746 | QVWDSSSDLYV 747 |
| RVFV-349A | QSISSY 748 | AAS 749 | QQSYSTPYT 750 |
| RVFV-349B | QDISNY 751 | DAS 752 | QQYDNLPLT 753 |
| RVFV-352 | SDINVGSYN 754 | YYSDSDK 755 | MIWPSNAWV 756 |
| RVFV-354 | NIGSKS 757 | DDS 758 | QVWDSSSDHYV 759 |
| RVFV-356 | NIGSKS 760 | DDS 761 | QVWDSSSDHVV 762 |
| RVFV-362 | QSISSY 763 | AAS 764 | QQSYSTPQT 765 |
| RVFV-363 | NIESKS 766 | DDT 767 | QVWDSSSDHCV 768 |
| RVFV-370 | NIGSKS 769 | DDS 770 | QVWDSSSDHRV 771 |
| RVFV-378 | QSISSY 772 | AAS 773 | QQSYSTPQT 774 |
| RVFV-379 | QHIESF 775 | IAS 776 | QQSYTISPIT 777 |
| RVFV-381 | LLPKQY 778 | ADY 779 | QSIDNRFHYPMI 780 |
| RVFV-401B | ALPDQY 781 | KDN 782 | QSADTSTAYHVI 783 |
| RVFV-405 | NIGNKS 784 | YDN 785 | QVWDNSSDHAV 786 |
| RVFV-419A | QSVSSSW 787 | DAS 788 | QQYGNSPTT 789 |
| RVFV-426A | KLVERY 790 | HDI 791 | QAWDSSTVL 792 |
| RVFV-429A | QSILYSSNNKNY 793 | WAS 794 | QQYYTIPPT 795 |
| RVFV-431A | SLRNYY 796 | GKD 797 | NSRDSSGDVVV 798 |
| RVFV-436A | KLENKY 799 | QDF 800 | QAWDRSTFYV 801 |
| RVFV-443B | RLRDRY 802 | QDF 803 | QAWDSFTYV 804 |

TABLE 4-continued

| CDR LIGHT CHAIN SEQUENCES | | | |
|---|---|---|---|
| Clone | CDRL1 (SEQ ID NO:) | CDRL2 (SEQ ID NO:) | CDRL3 (SEQ ID NO:) |
| RVFV-451B-a | SLRSFY 805 | GQN 806 | NSRDSGGYHLV 807 |
| RVFV-451B-b | SGYSNYK 808 | VGTGGIVT 809 | GPDHGRGC 810 |
| RVFV-459A | KLGDKY 811 | QDT 812 | QAWDSSTEW 813 |
| RVFV-76 | SLRSYS 814 | GKN 815 | NSRDSSGIRVV 816 |
| RVFV-778 | QSISSY 817 | AAS 818 | QQSYSTPQT 819 |
| RVFV-86 | QSVLYSSNNKNY 820 | WAS 821 | QQYYSTSLT 822 |
| RVFV-95 | QSLLYGSTNKNY 823 | WAS 824 | QQYYNVAWT 825 |

TABLE 5

| Summary of human IgG panel against Rift Valley Fever virus | | | | | |
|---|---|---|---|---|---|
| Name | IC50 (ng/ml) | Isotype | Target | Mechanism | Competition |
| RVFV-142 | 5.3 | IgG1 | Gn domain A | Fusion X | 379, 268, 296 |
| RVFV-379 | 1.4 | IgG1 | Gn domain A | Not tested | 268296 |
| RVFV-268 | <0.17 | IgG1 | Gn domain A | Not tested | 379296 |
| RVFV-296 | 345 | IgG1 | Gn domain A | Not tested | |
| RVFV-405 | Non-neut | IgG1 | Gn | Not tested | Untested |
| RVFV-226 | 15,340 | IgG1 | Gn domain B | Fusion X | 296 |
| RVFV-401 | Non-neut | IgG1 | Gn domain A | Not tested | Untested |
| RVFV-381 | 5340 | IgG1 | Gn | Not tested | 296 |
| RVFV-426 | 42 | IgG1 | Gn | | |
| RVFV-429 | 0.4 | IgG1 | Gn | | |
| RVFV-436 | 1.5 | IgG1 | Gn | | |
| RVFV-250 | 123 | IgG1 | Gc | Unknown | Domain2 |
| RVFV-326 | 374 | IgG1 | Gc | Not tested | Unknown |
| RVFV-128 | 372 | IgG1 | Gc | Not tested | Unknown |
| RVFV-249 | Non-neut | IgG1 | Gc | Not tested | Domain1 |
| RVFV-121 | 103 | IgG1 | Gc | Unknown | Domain2 |
| RVFV-239 | Non-neut | IgG1 | Gc | | |
| RVFV-127 | 23,403 | IgG1 | GC | | |
| RVFV-166 | Non-neut | IgG1 | Unknown | Fusion X | |
| RVFV-144 | 1.5 | IgG1 | Unknown | Fusion X/Receptor blockade | |
| RVFV-220 | 146 | IgG1 | Unknown | Unknown | |
| RVFV-140 | 0.3 | IgG1 | Unknown | Fusion X/Receptor blockade | |
| RVFV-229 | 3869 | IgG1 | Unknown | Not tested | |

Observed IC50 value, isotype, target, mechanism, and competing monoclonal antibody (mAb) are indicated for each respective mAb.

TABLE 6

| $IC_{50}$ values for each mAbs against RVFV-ZH501, RVFV-SA51, and RVFV-MP-12 performed in BSL-4 conditions | | | | |
|---|---|---|---|---|
| Antibody | IC50 (ng/ml) ZH501 | SA51 | MP-12 | Fold-Change ZH501/MP-12 |
| RVFV IgG 268 | 0.17 | 0.51 | 0.1 | 1.7 |
| RVFV IgG 142 | 1.52 | 1.52 | 5.9 | 0.3 |

TABLE 6-continued

| $IC_{50}$ values for each mAbs against RVFV-ZH501, RVFV-SA51, and RVFV-MP-12 performed in BSL-4 conditions | | | | |
|---|---|---|---|---|
| Antibody | IC50 (ng/ml) ZH501 | SA51 | MP-12 | Fold-Change ZH501/MP-12 |
| RVFV IgG 436A | 4.57 | 4.57 | 2.5 | 1.8 |
| RVFV IgG 429 | 4.57 | 4.57 | 0.9 | 5.1 |
| RVFV IgG 379 | 4.57 | 13 | 1.3 | 3.5 |
| RVFV IgG 140 | 13 | 4.57 | 1.1 | 11.8 |
| RVFV IgG 426A | 41 | 120 | 9.1 | 4.5 |
| RVFV IgG 296 | 120 | 120 | 638 | 0.2 |

TABLE 6-continued

IC$_{50}$ values for each mAbs against RVFV-ZH501, RVFV-SA51, and RVFV-MP-12 performed in BSL-4 conditions

| Antibody | IC50 (ng/ml) ZH501 | SA51 | MP-12 | Fold-Change ZH501/MP-12 |
|---|---|---|---|---|
| RVFV IgG 220 | 120 | 120 | 157 | 0.8 |
| RVFV IgG 250 | 120 | 120 | 51 | 2.4 |
| RVFV IgG 401 | 370 | 1110 | 2120 | 0.2 |
| RVFV IgG 128 | 370 | 370 | 38 | 9.7 |
| RVFV IgG 121 | 1110 | 1110 | 35 | 31.7 |
| RVFV IgG 326 | 1110 | 370 | 70 | 15.9 |
| RVFV IgG 144 | 3330 | 3330 | 1.9 | 1752.6 |
| RVFV IgG 381 | 10000 | 10000 | 4435 | 2.3 |
| RVFV IgG 226 | 10000 | 3330 | 7692 | 1.3 |
| RVFV IgG 229 | 10000 | 10000 | 3040 | 3.3 |
| RVFV IgG 405 | 30000 | 30000 | 30000 | 1 |
| RVFV IgG 249 | 30000 | 30000 | 6787 | 4.4 |

Fold-change reported as a ratio of ZH501 over MP-12. MP-12 neutralization assays were performed in triplicate, while most ZH501-related data are in triplicate, and the SA51-related data is in experimental duplicates.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567
U.S. Pat. No. 4,867,973
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,565,332
U.S. Pat. No. 5,856,456
U.S. Pat. No. 5,880,270
U.S. Pat. No. 6,485,982
"Antibodies: A Laboratory Manual," Cold Spring Harbor Press, Cold Spring Harbor, NY, 1988.
Abbondanzo et al., *Am. J. Pediatr. Hematol. Oncol.,* 12(4), 480-489, 1990.
Allred et al., *Arch. Surg.,* 125(1), 107-113, 1990.
Atherton et al., *Biol. of Reproduction,* 32, 155-171, 1985.
Barzon et al., *Euro Surveill.* 2016 Aug. 11; 21(32).
Beltramello et al., *Cell Host Microbe* 8, 271-283, 2010.
Brown et al., *J. Immunol. Meth.,* 12; 130(1):111-121, 1990.
Campbell, In: *Monoclonal Antibody Technology, Laboratory Techniques in Biochemistry and Molecular Biology*, Vol. 13, Burden and Von Knippenberg, Eds. pp. 75-83, Amsterdam, Elsevier, 1984.
Capaldi et al., *Biochem. Biophys. Res. Comm.,* 74(2):425-433, 1977.
De Jager et al., *Semin. Nucl. Med.* 23(2), 165-179, 1993.
Dholakia et al., *J. Biol. Chem.,* 264, 20638-20642, 1989.
Diamond et al., *J Virol* 77, 2578-2586, 2003.
Doolittle and Ben-Zeev, *Methods Mol. Biol.,* 109:215-237, 1999.
Duffy et al., *N. Engl. J. Med.* 360, 2536-2543, 2009.
Elder et al. Infections, infertility and assisted reproduction. Part II: Infections in reproductive medicine & Part III: Infections and the assisted reproductive laboratory. *Cambridge UK: Cambridge University Press;* 2005.
Gefter et al., *Somatic Cell Genet.,* 3:231-236, 1977.
Gornet et al., *Semin Reprod Med.* 2016 September; 34(5): 285-292. Epub 2016 Sep. 14.
Gulbis and Galand, *Hum. Pathol.* 24(12), 1271-1285, 1993.
Halfon et al., *PLoS ONE* 2010; 5 (5) e10569
Hessell et al., *Nature* 449, 101-4, 2007.
Khatoon et al., *Ann. of Neurology,* 26, 210-219, 1989.
King et al., *J. Biol. Chem.,* 269, 10210-10218, 1989.
Kohler and Milstein, *Eur. J. Immunol.,* 6, 511-519, 1976.
Kohler and Milstein, *Nature,* 256, 495-497, 1975.
Kyte and Doolittle, *J. Mol. Biol.,* 157(1):105-132, 1982.
Mansuy et al., *Lancet Infect Dis.* 2016 October; 16(10): 1106-7.
Nakamura et al., In: *Enzyme Immunoassays: Heterogeneous and Homogeneous Systems*, Chapter 27, 1987.
O'Shannessy et al., *J. Immun. Meth.,* 99, 153-161, 1987.
Persic et al., *Gene* 187:1, 1997
Potter and Haley, *Meth. Enzymol.,* 91, 613-633, 1983.
Purpura et al., *Lancet Infect Dis.* 2016 October; 16(10): 1107-8. Epub 2016 Sep. 19.
Remington's Pharmaceutical Sciences, 15th Ed., 3:624-652, 1990.
Tang et al., *J. Biol. Chem.,* 271:28324-28330, 1996.
Wawrzynczak & Thorpe, In: *Immunoconjugates, Antibody Conjugates In Radioimaging And Therapy Of Cancer*, Vogel (Ed.), NY, Oxford University Press, 28, 1987.
Yu et al., *J Immunol Methods* 336, 142-151, doi: 10.1016/j.jim.2008.04.008, 2008.
Sidwell R W, and Smee D F. 2003. Viruses of the Bunya- and Togavridiae families: potential as bioterrorism agents and means of control. *Antiviral Res.* 57: 101-111.
Zhang, W. et al., 2002. Placement of the structural proteins in Sindbis virus. *J. Virol.* 76, 11645-58(2002).
Klasse P J. 2014. Neutralization of virus infectivity by antibodies: old problems in new perspectives. *Advances in Biology.* 2014: 157895.
Burton D R. 2002. Antibodies, viruses and vaccines. Nature Reviews Immunology. 2: 706-713. Jin et al., 2015. *Cell Rep.* 13(11):2553-2564.
Smith S A, and Crowe J E. 2015. Use of human hybridoma technology to isolate human monoclonal antibodies. *Microbiology Spectrum.* 3: 1-12.
Yu et al., 2008. An optimized electrofusion-based protocol for generating virus-specific human monoclonal antibodies. *J Immunol Methods.* 336(2): 142-151.

What is claimed is:

1. A method of treating a subject infected with Rift Valley Fever Virus or reducing the likelihood of infection of a subject at risk of contracting Rift Valley Fever Virus, comprising delivering to said subject an antibody or antibody fragment comprising (i) heavy chain CDR1-3 comprising SEQ ID NO: 346, SEQ ID NO: 347 and SEQ ID NO: 348, respectively, and light chain CDR1-3 comprising SEQ ID NO: 592, SEQ ID NO: 593 and SEQ ID NO: 594, respectively; (ii) heavy chain CDR1-3 comprising SEQ ID NO: 424, SEQ ID NO: 425 and SEQ ID NO: 426, respectively, and light chain CDR1-3 comprising SEQ ID NO: 670, SEQ ID NO: 671 and SEQ ID NO: 672, respectively; or (iii) heavy chain CDR1-3 comprising SEQ ID NO: 532, SEQ ID NO: 533 and SEQ ID NO: 534, respectively, and light chain CDR1-3 comprising SEQ ID NO: 775, SEQ ID NO: 776 and SEQ ID NO: 777, respectively.

2. The method of claim 1, wherein said antibody or antibody fragment comprises heavy and light chain variable sequences comprising (i) SEQ ID NO: 176 and SEQ ID NO: 177, respectively; (ii) SEQ ID NO: 228 and SEQ ID NO: 229, respectively; or (iii) SEQ ID NO: 299 and SEQ ID NO: 300, respectively.

3. The method of claim 1, wherein said antibody or antibody fragment comprises heavy and light chain variable sequences having 70%, 80% or 90% identity to (i) SEQ ID NO: 176 and SEQ ID NO: 177, respectively; (ii) SEQ ID NO: 228 and SEQ ID NO: 229, respectively; or (iii) SEQ ID NO: 299 and SEQ ID NO: 300, respectively.

4. The method of claim 1, wherein said antibody or antibody fragment comprises heavy and light chain variable sequences having 95% identity to (i) SEQ ID NO: 176 and SEQ ID NO: 177, respectively; (ii) SEQ ID NO: 228 and SEQ ID NO: 229, respectively; or (iii) SEQ ID NO: 299 and SEQ ID NO: 300, respectively.

5. The method of claim 1, wherein said antibody is an IgG, or a recombinant IgG antibody or antibody fragment comprising an Fc portion mutated to eliminate or enhance FcR interactions, to increase half-life and/or increase therapeutic efficacy, or glycan modified to alter eliminate or enhance FcR interactions.

6. The method of claim 1, wherein said antibody or antibody fragment is administered after infection.

7. The method of claim 1, wherein said subject is a pregnant female, a sexually active female, or a female undergoing fertility treatments.

8. The method of claim 1, wherein delivering comprises antibody or antibody fragment administration, or genetic delivery with an RNA or DNA sequence or vector encoding the antibody or antibody fragment.

9. The method of claim 1, wherein the subject is a pregnant female and the method comprises protecting the health of a placenta and/or fetus of the pregnant a subject infected with or at risk of infection with Rift Valley Fever Virus.

10. The method of claim 5, wherein said mutated Fc portion is a LALA, LALA PG, N297, GASD/ALIE, DHS, YTE or LS mutation.

11. The method of claim 5, wherein said glycan modification is an enzymatic or chemical addition or removal of glycans or results from expression in a cell line engineered with a defined glycosylating pattern.

* * * * *